(12) United States Patent
Moneo Ocaña et al.

(10) Patent No.: US 11,590,129 B2
(45) Date of Patent: Feb. 28, 2023

(54) COMBINATION THERAPY WITH AN ANTITUMOR ALKALOID

(71) Applicant: PHARMA MAR, S.A., Madrid (ES)

(72) Inventors: Victoria Moneo Ocaña, Madrid (ES); Gema Santamaría Núñez, Madrid (ES); Luis Francisco García Fernández, Madrid (ES); Carlos María Galmarini, Madrid (ES); María José Guillén Navarro, Madrid (ES); Pablo Manuel Avilés Marín, Madrid (ES)

(73) Assignee: PHARMA MAR, S.A., Madrid (ES)

( * ) Notice: Subject to any disclaimer, the term of this patent is extended or adjusted under 35 U.S.C. 154(b) by 0 days.

(21) Appl. No.: 15/824,551

(22) Filed: Nov. 28, 2017

(65) Prior Publication Data

US 2018/0078551 A1    Mar. 22, 2018

Related U.S. Application Data

(63) Continuation of application No. 13/884,874, filed as application No. PCT/EP2011/069976 on Nov. 11, 2011.

(30) Foreign Application Priority Data

Nov. 12, 2010 (EP) .................................. 10382300

(51) Int. Cl.
| | | |
|---|---|---|
| *A61K 31/4995* | (2006.01) | |
| *A61K 31/513* | (2006.01) | |
| *A61K 31/519* | (2006.01) | |
| *A61K 31/69* | (2006.01) | |
| *A61K 31/7068* | (2006.01) | |
| *A61K 45/06* | (2006.01) | |
| *A61K 38/15* | (2006.01) | |
| *A61K 33/243* | (2019.01) | |
| *A61K 31/337* | (2006.01) | |
| *A61K 31/4164* | (2006.01) | |
| *A61K 31/4188* | (2006.01) | |
| *A61K 31/4375* | (2006.01) | |
| *A61K 31/55* | (2006.01) | |
| *A61K 31/704* | (2006.01) | |
| *A61P 11/00* | (2006.01) | |
| *A61P 35/00* | (2006.01) | |

(52) U.S. Cl.
CPC ........ *A61K 31/4995* (2013.01); *A61K 31/337* (2013.01); *A61K 31/4164* (2013.01); *A61K 31/4188* (2013.01); *A61K 31/4375* (2013.01); *A61K 31/513* (2013.01); *A61K 31/519* (2013.01); *A61K 31/55* (2013.01); *A61K 31/69* (2013.01); *A61K 31/704* (2013.01); *A61K 31/7068* (2013.01); *A61K 33/243* (2019.01); *A61K 38/15* (2013.01); *A61K 45/06* (2013.01); *A61P 11/00* (2018.01); *A61P 35/00* (2018.01)

(58) Field of Classification Search
CPC ............ A61K 2300/00; A61K 31/4995; A61K 31/513; A61K 31/519; A61K 31/69; A61K 31/7068; A61K 38/15; A61K 31/337; A61K 31/4164; A61K 31/4188; A61K 31/4375; A61K 31/55; A61K 31/704; A61K 33/243; A61K 45/06; A61P 11/00; A61P 35/00
See application file for complete search history.

(56) References Cited

U.S. PATENT DOCUMENTS

| | | |
|---|---|---|
| 5,089,273 A | 2/1992 | Rinehart et al. |
| 5,149,804 A | 9/1992 | Rinehart et al. |
| 5,256,663 A | 10/1993 | Rinehart et al. |
| 5,478,932 A | 12/1995 | Rinehart et al. |
| 5,654,426 A | 8/1997 | Rinehart et al. |
| 5,721,362 A | 2/1998 | Corey et al. |
| 5,985,876 A | 11/1999 | Rinehart et al. |
| 6,124,292 A | 9/2000 | Corey |
| 6,124,293 A | 9/2000 | Rinehart et al. |
| 6,316,214 B1 | 11/2001 | Rinehart et al. |
| 6,348,467 B1 | 2/2002 | Corey |
| 6,686,470 B2 | 2/2004 | Danishefsky et al. |
| 6,867,334 B2 | 3/2005 | Rinehart et al. |

(Continued)

FOREIGN PATENT DOCUMENTS

| | | |
|---|---|---|
| EP | 0 309 477 | 11/1991 |
| EP | 10382300.1 | 11/2010 |

(Continued)

OTHER PUBLICATIONS

Arai, T. et al., "The Structure of a Novel Antitumor Antibiotic, Saframycin A", Experientia, vol. 36, pp. 1025-1027 (1980).

Arai, Tadashi et al., "Directed Biosynthesis of New Saframycin Derivatives with Resting Cells of Streptomyces lavendulae", Antimicrobial Agents and Chemotherapy, vol. 28, No. 1, pp. 5-11 (1985).

Arai, Tadashi et al., "Increased Production of Saframycin A and Isolation of Saframycin S", The Jounral of Antibiotics, vol. XXXIII, No. 9, pp. 951-960 (1980).

Arai, Tadashi et al., "Isoquinolineinones from Actinomycetes and Sponges", The Alkaloids Chemistry and Pharmacology, vol. XXI, pp. 56-100 (1983).

(Continued)

*Primary Examiner* — Kara R McMillian
(74) *Attorney, Agent, or Firm* — Ballard Spahr LLP

(57) ABSTRACT

The present invention relates to the combination of PM01183 with several anticancer drugs, in particular other anticancer drugs selected from antitumor platinum coordination complexes, antimetabolites, mitotic inhibitors, anticancer antibiotics, topoisomerase I and/or II inhibitors, proteasome inhibitors, histone deacetylase inhibitors, nitrogen mustard alkylating agents, nitrosourea alkylating agents, nonclassical alkylating agents, estrogen antagonists, androgen antagonists, mTOR inhibitors, tyrosine kinase inhibitors, and other agents selected from aplidine, ET-743, PM02734 and PM00104, and the use of these combinations in the treatment of cancer.

15 Claims, 62 Drawing Sheets

(56) References Cited

U.S. PATENT DOCUMENTS

| | | | | |
|---|---|---|---|---|
| 7,763,615 | B2 * | 7/2010 | Gallego | C07D 515/22 514/249 |
| 8,975,248 | B2 | 3/2015 | Zaknoen et al. | |
| 2003/0216397 | A1 | 11/2003 | Flores et al. | |
| 2004/0019056 | A1 | 1/2004 | Manzanares et al. | |
| 2004/0108086 | A1 * | 6/2004 | Takahashi | A61K 31/495 162/227 |
| 2005/0267140 | A1 * | 12/2005 | Miller | A61K 31/407 514/269 |
| 2007/0197517 | A1 | 8/2007 | Jani et al. | |
| 2009/0253685 | A1 | 10/2009 | Provost et al. | |
| 2018/0008602 | A1 * | 1/2018 | Moneo Ocana | A61K 31/4995 |

FOREIGN PATENT DOCUMENTS

| | | |
|---|---|---|
| JP | 59-225189 | 12/1984 |
| JP | 60-84288 | 3/1985 |
| WO | WO 87/07610 | 12/1987 |
| WO | WO 92/09607 | 6/1992 |
| WO | WO 98/12198 | 3/1998 |
| WO | WO 98/46080 | 10/1998 |
| WO | WO 99/51238 | 10/1999 |
| WO | WO 99/58125 | 11/1999 |
| WO | WO 00/18233 | 4/2000 |
| WO | WO 00/69862 | 11/2000 |
| WO | WO 01/77115 | 10/2001 |
| WO | WO 01/87894 | 11/2001 |
| WO | WO 2005/049031 | 6/2005 |
| WO | WO 2009/140675 | 11/2009 |
| WO | PCT/EP2011/69976 | 11/2011 |

OTHER PUBLICATIONS

Arai, Tadashi et al., "New Antibiotics, Safraycins A, B, C, D and E", The Journal of Antibiotics, vol. XXX, No. 11, pp. 1015-1018 (1977).
Asaoka, Takemitsu et al., "A New Saframycin, Saframycin R", The Journal of Antibiotics, vol. XXXV, No. 12, pp. 1708-1710 (1982).
Aviles, et al., "Mechanism of action and antitumor activity of PM01183," AACR Annual Meeting, Abstract No. 2679, 1 page, Apr. 18-22, 2009, Denver, CO.
Aviles, et al., "Mechanism of action and antitumor activity of PM01183," Pharma Mar Grupo Zeltia, Poster corresponding to Abstract # 2679, Apr. 20, 2009.
Barton, Derek H.R. et al, "Synthesis and Properties of a Series of Sterically Hindered Guanidine Bases", Journal of the Chemical Society Perkin Transactions I, No. 9, pp. 2085-2090 (1982).
Brown, J.M., "NCI's Anticancer Drug Screening Program May Not Be Selecting for Clinically Active Compounds," Oncol. Res. 9(5):213-215 (1997).
Cable, Karl M. et al., "The Biosynthesis of Tuberin from Tyrosine and Glycine; Observations on the Stereochemistry Associated with the Conversion of Glycine through Methylenetetrahydrofolate into Methenyltetrahydrofolate", Journal of the Chemical Society Perkins Transactions I, No. 7, pp. 1593-1598 (1987).
Calabresi et al., "Chemotherapy of Neoplastic Diseases", Goodman & Gilman's The Pharmacological Basis of Therapeutics, 9th ed. New York: McGraw-Hill, 1996, pp. 1225-1229.
Calvo et al., "Lurbinectedin (PM01183) in Combination With Doxorubicin (Dox): Preliminary Results of a Phase IB Study," Europ. J. Canc., 49, Supplement 2, Sep. 1, 2013 (Abstract).
"Cancer" definition, http://www.medterms.com/script/main/art.asp?articlekey+2580, accessed Nov. 27, 2007.
Cecil Textbook of Medicine (Bennet, J.C. and Plum, F., eds.) 20th Edition, vol. 1, pp. 1004-1010 (1996).
Cecil Textbook of Medicine, 21st Edition (2000), Goldman & Bennett (Editors), W.B. Saunders Company (Publisher), Chapter 198, pp. 1060-1074.
Cooper, Raymond et al., "Structure of the Quinone Antibiotic EM5519 and the Behavior of Quinones in Fast Atom Bombardment Mass Spectrometry", The Journal of Antibiotics, vol. XXXVIII, No. 1, pp. 24-30 (1985).

Corey, E.J. et al., "Enantioselective Total Synthesis of Ecteinascidin 743", Journal of the American Chemical Society, vol. 118, No. 38, pp. 9202-9203 (1996).
Cuevas, Carmen et al., "Synthesis of Ecteinascidin ET-743 and Phthalascidin Pt-650 from Cyanosafracin B", Organic Letters, vol. 2, No. 16, pp. 2545-2548 (2000).
David-Cordonnier et al., "DNA And Non-DNA Targets In The Mechanism Of Action Of The Antitumor Drug Trabectedin", Chemistry & Biology, vol. 12, pp. 1201-1210, Nov. 2005.
Draetta, G. and Pagano, M., "Annual Reports in Medicinal Chemistry, vol. 31," Academic Press, San Diego, pp. 241-246 (1996).
Dorwald F. A. Side Reactions in Organic Synthesis, 2005, Wiley: VCH, Weinheim p. IX of Preface.
Eckhardt, S.G. et al., "Activity of ecteinascidin, a novel marine cytotoxic, against primary human tumor colony-forming units", Proceedings of the American Association for Cancer Research, vol. 37, #2791, pp. 409 (1996).
Faircloth, G. et al., "Ecteinascidin-743 (ET743): in vitro (IVT) and in vivo (INV) Results in Tumor Models", The European Journal of Cancer, vol. 32A, Supp. 1, #24 O, pp. S5 (1996).
Flam, Faye, "Chemical Prospectors Scour the Seas for Promising Drugs", Science, vol. 266, pp. 1324-1325 (1994).
Fregeau, Nancy Louise, "Biologically Active Compounds froma Clam and a Tunicate", Thesis, University of Illinois art Urbana-Champaign, 1992.
Frincke, James M. et al., "Antimicrobial Metabolites of the Sponge *Reniera* sp.", Journal of the American Chemical Society, vol. 104, pp. 265-269 (1982).
Fukuyama, Tohru et al., "Stereocontrolled Total Synthesis of (±)-Saframycin B", Journal of American Chemical Society, vol. 104, pp. 4957-4958 (1982).
Fukuyama, Tohru et al., "Total Synthesis of (±)-Saframycin A", Journal of American Chemical Society, vol. 112, pp. 3712-3713 (1990).
Galmarini et al., "Abstract 5499: Lurbinectedin (PM01183) Synergizes with Topoisomerase I Inhibitors in Vitro and in Vivo," Cancer Research, vol. 73, issue 8, supplement 1, Apr. 15, 2013 (Abstract).
Galmarini, "New Marine Anticancer Agents in Development," PharmaMar Grupo Zeltia, 28 pages, 6$^{th}$ European Spring Oncology Conference, Jun. 22-25, 2010.
Garcia-Rocha, M. et al., "Characterisation of antimitotic products from marine organisms that disorganize the microtubule network: ecteinascidin 743, isohomohalichondrin-B and LL-15", British Journal of Cancer, vol. 73, pp. 875-883 (1996).
Goldwasser, F, et al. "Characterization of ecteinascidin 743-induced DNA damages in cells", Proceedings of the American Association for Cancer Research, vol. 39, #4066, pp. 598 (1998).
Greene et al., Protective Groups in Organic Systems, 1999, Table of Contents for Chapters 2 and 7.
Guan, Yue et al., "Molecular and Crystal Structures of Ecteinascidins: Potent Antitumor Compounds from the Caribbean Tunicate Ecteinascidia Turbinata", Journal of Biomolecular Structure & Dynamics, vol. 10, No. 5, pp. 793-818 (1993).
Gulavita, Nanda K., et al., "Antimicrobial Constituents of a Sponge-Nudibranch Pair from Sri Lanka", Bioactive Compounds from Marine Organisms, Oxford & IBH Publishing Co. Pvt. Ltd., pp. 229-233 (1991).
Guillen et al., "In Vivo Combination Studies Of Pm01183 With Alkylating, Antimetabolites, Dna-Topoisomerase Inhibitors And Tubulin Binding Agents." Cancer Research, vol. 73, Supplement 1, Apr. 15, 2013 (Abstract).
Hande et al., "Topoisomerase II inhibitors," Update of Cancer Therapeutics, vol. 3, pp. 13-26, Mar. 25, 2008.
He, Hai-Yin et al., "Renieramycins E and F from the Sponge *Reniera* sp.: Reassignment of the Stereochemistry of the Renieramycins", The Journal of Organic Chemistry, vol. 54, No. 24, pp. 5822-5824 (1989).
Hendriks, H.R. et al., "High antitumor activity of ET743 in human tumor xenograft models", Proceedings of the American Association for Cancer Research, vol. 37, #2653, pp. 389 (1996).
Holt, Tom Grady, "The Isolation and Structural Characterization of the Ecteinascidins", Thesis, University of Illinois art Urbana-Champaign, 1986.

(56) References Cited

OTHER PUBLICATIONS

Ikeda, Yoshifumi et al., "Safracins, New Antitumor Antibiotics I. Producing Organism, Fermentation and Isolation", The Journal of Antibiotics, vol. XXXVI, No. 10, pp. 1279-1283 (1983).
Ikeda, Yoshifumi et al., "Safracins, New Antitumor Antibiotics I. Producing Organism, Fermentation and Isolation", The Journal of Antibiotics, vol. XXXVI, No. 10, pp. 1284-1289 (1983).
Internal Medicine, 4th Edition, Editor-in-Chief Jay Stein, (1994); Chapters 71-72, pp. 699-715.
Internal Medicine, 4th Edition, Editor-in-Chief Jay Stein, Chapters 71-72, pp. 699-729, 1994.
Ito, Yoichiro, "High-Speed Countercurrent Chromatography", Critical Reviews in Analytical Chemistry, vol. 17, No. 1, pp. 65-143 (1986).
"IUPAC Gold Book", http://goldbook.iupac.org/A00123.html, accessed Dec. 26, 2007.
Kania, "The first Enantioselective Total Synthesis of Dolabellatrienone and Ecteinascidin 743", Harvard University, Sep. 1997, pp. 1-225.
Koenig, Karl E., "The Applicability of Asymmetric Homogeneous Catalytic Hodrogenation", Asymmetric Synthesis, Ed. Morrison, Academic Press, Inc., Orlando, FL, vol. 5, pp. 71 (1985).
Kofron, William G. et al., "A Convenient Method for Estimation of Alkyllithium Concentrations", The Journal of Organic Chemistry, vol. 41, No. 10, pp. 1879-1880 (1976).
Kubo, Akinori et al., "Structure of Saframycin D, A New Dimeric Isoquinolinequinone Antibiotic", Chem. Pharm. Bull., vol. 35, No. 1, pp. 440-442 (1987).
Kuffel, M.J. et al., "Cytochrome P450 catalyzed metabolism of Ecteinascidin 743 by rat and human liver microsomes", Proceedings of the American Association for Cancer Research, vol. 38, #4003, pp. 596 (1997).
Larsen, et al., "The marine product Tryptamicidin shows activity toward platinum-resistant cells and attenuates nucleotide excision repair" Universite Pierre & Marie Curie Science A Paris, Inserm Institute National de la santé et de la recherche médicale, 20 pages, 31st EORTC-PAMM (Pharmacology and Molecular Mechanisms) Group Annual Winter Meeting held on Toulouse (France) on Jan. 27-30, 2010.
Leal, et al., "PM01183, a new DNA minor groove covalent binder with potent in vitro and in vivo anti-tumour activity," BJP British Journal of Pharmacology, 161, pp. 1099-1110, 2010.
Lighter, W. et al., "Biological Activities Exerted by Extracts of Ecteinascidia Turbinata", Food and Drugs from the Sea Proceedings, pp. 117-127 (1972).
Lown, J. William et al., "Molecular Mechanisms of Binding and Single-Strand Scission of Deoxyribonucleic Acid by the Antitumor Antibiotics Saframycins A and C", Biochemistry, vol. 21, No. 3, pp. 419-428 (1982).
Lown, J. William et al., "Structure and Confirmation of Saframycin R Determined by High Field H and C NMR and its Interactions with DNA in Soloution", The Journal of Antibiotics, vol. XXXVI, No. 9, pp. 1184-1194 (1983).
Martinez et al., "A New, More Efficient, and Effective Process for the Synthesis of a Key Pentacyclic Intermediate for Production of Ecteinascidin and Phthalascidin Antitumor Agents", Organic Letters, 2(7):993-996 (2000).
Martinez et al., "Enantioselective Synthesis of Saframycin A and Evaluation of Antitumor Activity Relative to Ecteinascidin/Saframycin Hybirds", Organic Letters, 1(7):75-77 (1999).
Martinez, Eduardo J. et al., "Phthalascidin, a synthetic antitumor agent with potency and mode of action comparable to ecteinascidin 743", Chemistry, vol. 96, pp. 3496-3501 (1999).
Messersmith et al., Cancer Chemother. Pharmacol., vol. 63, pp. 181-188, 2008.
Mikami, Yuzuru et al., "Structural Studies on Minor Components of Saframycin Group Antibiotics Saframycins F, G and H", The Journal of Antibiotics, vol. XLI, No. 6, pp. 734-740 (1988).

Minotti et al., "Anthracyclines: Molecular Advances And Pharmacologic Developments In Antitumor Activity And Cardiotoxicity," Pharmacol. Rev., vol. 56, No. 2, pp. 185-229, Jun. 1, 2004.
Mirsalis, J.C. et al., "Toxicity of Ecteinascidin 743 in female Fischer-344 rats administered i.v. in a multiple-dose regimen", Proceedings of the American Association for Cancer Research, vol. 38, #2073, pp. 309 (1997).
Moneo, et al., "PM01183 is a novel compound that binds DNA and displays cytotoxic effect in vitro and in vivo in human cancer cell lines," AACR Annual Meeting, Abstract No. 4525, 1 page, Apr. 18-22, 2009, Denver, CO.
Moore, B.M. et al., "The NMR model of an ecteinascidin 743-DNA adduct", Proceedings of the American Association for Cancer Research, vol. 38, #2105, pp. 314 (1997).
Morales, Jose Javier, "Marine Natural Products Chemistry of a Caribbean Tunicate and a Palau Sponge", University of Illinois art Urbana-Champaign, 1999.
Myers et al., "A Concise, Stereocontrolled Syntheis of (−)-Saframycin A by the Directed Condensation of ∝-Amino Aldehyde Precursors", J. Am. Chem. Soc., 121:10828-10829 (1999).
Nakagawa, Masako et al., "Total Synthesis of (−)-Eudistomin L and (—)-Debromoeudistomin L", Journal of the American Chemical Society, vol. 111, No. 7, pp. 2721-2722 (1989).
Parulekar, A.H. et al., "Bioactivity and Chemical Ecology of Some Interdial Animals" Bioactivity and Chemical Ecology, pp. 29-35, 1991.
Pommier, "Topoisomerase I Inhibitors: Camptothecins and Beyond," Nature Rev. Cancer, vol. 6, pp. 789-802, Oct. 1, 2006.
Pommier, Yves et al., "DNA Sequence- and Structure-Selective Alkylation of Guanine N2 in the DNA Minor Groove by Ecteinascidin 743, a Potent Antitumor Compound from the Caribbean Tunicate Ecteinascidia Turbinata", Biochemistry, vol. 35, pp. 13303-13309 (1996).
Pretsch et al., Tables of Spectral Data for Structure Determination of Organic Compounds, pp. H125 (1983).
Ratain, et al., "First-in-man phase I study of PM01183 using an accelerated titration design," Poster Session—Natural products, new cytotoxics, clinical trials, 434, pp. 137-138, Nov. 18, 2010.
Ratain, et al., "PM01183 clinical and pharmacokinetic (PK) preliminary results of the first-in-man phase I study following an accelerated titration design," Pharma Mar Grupo Zeltia, Nov. 18, 2010, 1 page.
Reid, Joel M. et al., "Preclinical pharmacology of ecteinascidin 729, a marine natural product with potent antitumor activity", Cancer Chemotherapy and Pharmacology, vol. 38, No. 4, pp. 329-334 (1996).
Remers, William A., "Saframycins, Renieramycins, and Safracins", The Chemistry of Antitumor Antibiotics, vol. 2, pp. 93-119 (1988).
Rinehart et al., "Novel Bioactive Natural Products from Marine Organisms", Topics in Pharmaceutical Sciences 1989, pp. 613-626, D.D. Breimer, D.J.A. Cromwelin, K.K. Midha, Eds., Amsterdam Medical Press B.V. Noordwijk, The Netherlands (1989).
Rinehart, Kenneth L. et al., "Applications of High-Resolution Tandem FAB Mass Spectrometry", Biological Mass Spectrometry, eds. Burlingame et al., Elsevier Amsterdam, pp. 233-258 (1990).
Rinehart, Kenneth L. et al., "Bioactive Compounds from Aquatic and Terrestrial Sources", Journal of Natural Products, vol. 53, No. 4, pp. 771-792 (1990).
Rinehart, Kenneth L. et al., "Biologically active natural products", Pure and Applied Chemistry, vol. 62, No. 7, pp. 1277-1280 (1990).
Rinehart, Kenneth L. et al., "Ecteinascidins 729, 743, 759A, 759B, and 770: Potent Antitumor Agents from the Caribbean Tunicate Exteinascidia Turbinata", The Journal of Organic Chemistry, vol. 55, No. 15, pp. 4512-4515 (1990).
Rinehart, Kenneth L., "Antitumor Compounds from Tunicates", Medicinal Research Reviews, vol. 20, No. 1, pp. 1-27 (2000).
Paz, "Antitumor Antibiotics," Anticancer Therapeutics, Chapter 8, Jan. 1, 2008.
Saito, Naoki et al., "Synthesis of Saframycins. 3. Preparation of a Key Tricyclic Lactam Intermediate to Saframycin A", The Journal of Organic Chemistry, vol. 54, No. 22, pp. 5391-5395 (1989).
Sakai, et al., Proceedings of the National Academy of Sciences of the United States of America (1992), 89(23), 11456-60.

(56) References Cited

OTHER PUBLICATIONS

Sakai, Ryuichi, "Biologically Active Compounds from Tunicates and a Sponge", Thesis, University of Illinois art Urbana-Champaign, 1991.
Sakai, Ryuichi et al., "Additional antitumor ecteinascidins from a Caribbean tunicate: Crystal structures and activities in vivo", Proceedings of the National Academy of Sciences, vol. 89, No. 23, pp. 11456-11460 (1992).
Sakai, Ryuichi et al., "Ecteinascidins: Putative Biosynthetic Precursors and Absolute Stereochemistry", Journal of the American Chemical Society, vol. 118, No. 38, pp. 9017-9023 (1996).
Scaife et al., "Antimetabolites In Cancer Therapy," Anticancer Therapeutics, Chapter 7, Jan. 1, 2008.
Schmidt at al., "Mitotic Drug Targets And The Development Of Novel Anti-Mitotic Anticancer Drugs," Drug Resistance Updates, vol. 10, pp. 162-181, Aug. 1, 2007.
Seaman and Hurley, "Molecular Basis for the DNA Sequence Selectivity of Ecteinascidin 736 and 743: Evidence for the Dominant Role of Direct Readout via Hydrogen Bonding", J. Am. Chem. Soc., vol. 120, pp. 13028-13041, Dec. 3, 1998.
Shamma, Maurice et al., Carbon-13 NMR Shift Assignments of Amines and Alkaloids, pp. 206 (1979).
Soares et al., "The DNA damage response to monofunctional anticancer DNA binders", Drug Discovery Today: Disease Models, vol. 9, No. 2,pp. e59-e67, Jun. 2012.
Soares, et al., "The marine-derived product PM01183 shows activity toward platinum-resistant cells and attenuates nucleotide excision repair," Abstract to Poster Session—DNA repair and inhibitors, 522, pp. 166-167, Nov. 19, 2010.
Soares, et al., "The marine product PM01183 (Tryptamicidin) shows activity toward platinum-resistant cells and attenuates nucleotide excision repair" 22nd EORTC-NCI-AACR Molecular Targets and Cancer Therapeutics, Universite Pierre & Marie Curie Science A Paris, Inserm Institute National de la santé et de la recherche médicale, Poster presentation, 1 page, Nov. 19, 2010.
Soares, et al., "The marine products yondelis and tryptamicidin (PM01183) show activity toward platinum-resistant cells and attenuates nucleotide excision repair," EORTC PAMM-Group Winter Meeting, Toulouse, 1 page, Jan. 28-30, 2010.
Soares et al., "Trabectedin and Its C Subunit Modified Analogue PM01183 Attenuate Nucleotide Excision Repair and Show Activity towards Platinum-Resistant Cells", Molecular Cancer Therapeutics, vol. 10, No. 8, pp. 1481-1489,May 27, 2011.
Sparidans Rolf W. et al., "Search for metabolites of ecteinascidin 743, a novel, marine-derived anti-cancer agent, in man." Anti-Cancer Drugs, vol. 12, pp. 653-666, 2001.
Still, W. Clark et al., "Rapid Chromatographic Technique for Preparative Separations with Moderate Resolution", Journal of Organic Chemistry, vol. 43, No. 14, pp. 2923-2925 (1978).
Takahaski, Katsuhiro et al., "Microbial Conversion of Saframycin A to 25-Dihydrosaframycin A and 21-Decyano-25-Dihydrosaframycin A (25-Dihydrosaframycin B) and Their Biological Activities", The Journal of Antibiotics, vol. XXXV, No. 2, pp. 196-202 (1982).
Takahaski, Katsuhiro, "New Antibiotics, Saframycins A, B, C, D and E", The Journal of Antibiotics, vol. XXX, No. 11, pp. 1015-1018 (1977).
Takahashi et al., "Preclinical Investigations of PM01183 (Lurbinectedin) as a Single Agent or in Combination with other Anticancer Agents for Clear Cell Carcinoma of the Ovary", PLOS One, Mar. 17, 2016.
Takahashi et al., "Sequence-dependent Enhancement of Cytotoxicity Produced by Ecteinascidin 743 (ET-743) with Doxorubicin or Paclitaxel in Soft Tissue Sarcoma Cells", Clinical Cancer Research, vol. 7, pp. 3251-3257, Oct. 2001.
Takahashi et al., "Sequence-dependent Synergistic Cytotoxicity of Ecteinascidin-743 and Paclitaxel in Human Breast Cancer Cell Lines in Vitro and in Vivo", Cancer Research, vol. 62, pp. 6909-6915, Dec. 1, 2002.
Tourneau et al., "Mtorci Inhibitors: Is Temsirolimus In Renal Cancer Telling Us How They Really Work?" Brit. J. Canc., vol. 99, pp. 1197-1203, Sep. 16, 2008.

Trowitzsch-Kienast, Wolfram et al., "Isolierung und Strukturauflclarung der Saframycine Mx 1 und Mx 2, neue antitumor-aktive Antibiotika aus Myxococcus xanthus", Liebigs Ann. Chem., vol. XXXV, pp. 475-481 (1988).
Valeri, et al., "Development of an in vitro model for the simultaneous study of the efficacy and hematotoxicity of antileukemic compounds," ScienceDirect, Toxicology Letters 199, pp. 317-322, 2010.
Valoti et al. Clin. Cancer Res. 4(8): 1977-83 (1998).
Witten, Jane L. et al., "Structures of Two Cockroach Neuropeptides Assigned by Fast Atom bombardment Mass Spectrometry", Biochemical and Biophysical Research Communications, vol. 124, No. 2, pp. 350-358 (1984).
Wright, Amy E. et al., "Antitumor Tetrahydroisoquinoline Alkaloids from the Colonial Ascidian Ecteinascidia Turbinata", The Journal of Organic Chemistry, vol. 55, No. 15, pp. 4508-4512 (1990).
Yazawa, Katsukiyo et al., "Bioconversions of Saframycin A Specific to some Genera of Actinomycetes", The Journal of Antibiotics, vol. XXXV, No. 7, pp. 915-917 (1982).
Yazawa, Katsukiyo et al., "Isolation and Structural Elucidation of New Saframycins Y3, Yd-1, Yd-2, Ad-1, Y2b and Y2b-d", The Journal of Antibiotics, vol. XXXIX, No. 12, pp. 1639-1650 (1986).
Zmijewski, Milton J., Jr. et al., "The in vitro Interaction of Naphthyridinomycin with Deoxyribonucleic Acids", Chemico-Biological Interactions, vol. 52, No. 3, pp. 361-375 (1985).
Cassier et al., "Trabectedin and Its Potential in the Treatment of Soft Tissue Sarcoma," Therapeutics and Clinical Risk Management, 4(1), pp. 109-116, 2008.
Christinat et al., "Role of Trabectedin in the Treatment of Soft Tissue Sarcoma," Onco Targets and Therapy, 2, pp. 105-113, 2009.
Gore et al., "Phase I Combination Study of Trabectedin (T) and Capecitabine (C) in Patients with Advanced Malignancies," J. of Clinical Oncology, 24(18S), 2079, 2008 ASCO Annual Meeting Proceedings (Post-Meeting edition).
Von Mehren et al., "A Phase I Study of the Safety and Pharmacokinetics of Trabectedin in Combination with Pegylated Liposomal Doxorubicin in Patients with Advanced Malignancies," Annals of Oncoloy, 19, pp. 1802-1809, 2008.
Scotlandi et al., "Effectiveness of Ecteinascidin-743 Against Drug-Sensitive and Resistant Bone Tumor Cells," Clinical Cancer Research, 8, pp. 3893-3903, 2002.
Sessa et al., "Phase I Clinical and Pharmacokinetic Study of Trabectedin and Doxorubicin in Advanced Soft Tissue Sarcoma and Breast Cancer," European Journal of Cancer, 45, pp. 1153-1161, 2009.
**D'Incalci et al., "A Review of Trabectedin (ET-743): A Unique Mechanism of Action," Mol Cancer Ther; (2010) 9(8), pp. 2157-2163.
**Erba et al., "The Unique Biological Features of the Marine Product YondelisTM (ET-743, Trabectedin) Are Shared by its Analog ET-637, Which Lacks the C Ring," Oncology Research, (2004) vol. 14, pp. 579-587.
**Meco et al., "Effective combination of ET-743 and doxorubicin in sarcoma: preclinical studies," Cancer Cehmother. Pharmacol., (2003) 52, pp. 131-138.
**Moore et al., "Sequencing evaluation of ET-743 combinations with standard chemotherapy agents against a panel of human tumor cell lines," Clinical Cancer Research, vol. 6, Abstract 504 (Nov. 2000) along with Table A.
**Vincenzi et al., "Wide-spectrum characterization of trabectedin: biology, clinical activity and future perspectives," Pharmacogenomics, (2010) 11(6), pp. 865-878.
International Search Report (dated May 18, 2012) and Written Opinion (dated May 12, 2012) by the International Searching Authority for International Application No. PCT/EP2011/069976, filed on Nov. 11, 2011 (Applicant—Pharma Mar, S.A.) (25 Pages).
International Preliminary Report on Patentability dated May 14, 2013 by the International Preliminary Examining Authority for International Application No. PCT/EP2011/069976, filed on Nov. 11, 2011 (Applicant—Pharma Mar, S.A.) (18 pages).
US, U.S. Appl. No. 13/884,874, filed Jun. 4, 2013, Ocaña.
US, U.S. Appl. No. 15/711,478, filed Sep. 21, 2017, Ocaña.
US, U.S. Appl. No. 15/824,506, filed Nov. 28, 2017, Ocaña.

(56) References Cited

OTHER PUBLICATIONS

Cuevas et al, Anticancer Agents from Natural Products, Second Edition, CRC Press, 2012, "Ecteinascidin-473 (Yondelis), Aplidin, and Irvalec", Chapter 12, pp. 291-310.
Cuevas et al, Drug Discovery from Natural Products, Section 1, Chapter 1, "Semisynthesis Approach of Ecteinascidin 473 (ET-473, Yondelis)", Sep. 13, 2012, p. 5-12, https://doi.org/10.1039/9781849734950.
Bray F, et al. Global cancer statistics 2018: GLOBOCAN estimates of incidence and mortality worldwide for 36 cancers in 185 countries. CA Cancer J Clin (2018) 68 (6): 394-424.
Simos D, et al. Third-line chemotherapy in small-cell lung cancer: an international analysis. Clin Lung Cancer (2014) 15 (2): 110-8.
Puglisi M, et al. Treatment options for small cell lung cancer—do we have more choice? Br J Cancer (2010) 102 (4): 629-38.
Slotman B, et al. Prophylactic cranial irradiation in extensive small-cell lung cancer. N Engl J Med (2007) 357 (7): 664-72.
Pelayo Alvarez M, et al. Chemotherapy versus best supportive care for extensive small cell lung cancer. Cochrane Database Syst Rev (2013) 11: CD001990.
Sundstrom S, et al. Cisplatin and etoposide regimen is superior to cyclophosphamide, epirubicin, and vincristine regimen in small-cell lung cancer: results from a randomized phase III trial with 5 years' follow-up. J Clin Oncol (2002) 20 (24): 4665-72.
Hurwitz JL, et al. New advances in the second-line treatment of small cell lung cancer. Oncologist (2009) 14 (10): 986-94.
Fischer B, et al. Current status of clinical trials for small cell lung cancer. Rev Recent Clin Trials (2008) 3 (1): 40-61.
Topotecan United Kingdom Summary of Product Characteristics (PP-PFE-GBR-2780 / Jul. 2020).
Dingemans AC, et al. Small-cell lung cancer: ESMO Clinical Practice Guidelines for diagnosis, treatment and follow-up. Ann Oncol (2021) 32 (7): 839-53.
NCCN Clinical Practice Guidelines in Oncology. Small Cell Lung Cancer. Version 2.2022—Nov. 24, 2021. https://www.nccn.org/professionals/physician_gls/pdf/sclc.pdf.
Von Pawel J, et al. Topotecan versus cyclophosphamide, doxorubicin, and vincristine for the treatment of recurrent small-cell lung cancer. J Clin Oncol (1999) 17 (2): 658-67.
Von Pawel J, et al. Phase II comparator study of oral versus intravenous topotecan in patients with chemosensitive small-cell lung cancer. J Clin Oncol (2001) 19 (6): 1743-9.
O' Brien ME, et al. Phase III trial comparing supportive care alone with supportive care with oral topotecan in patients with relapsed small-cell lung cancer. J Clin Oncol (2006) 24 (34): 5441-7.
Eckardt JR, et al. Phase III study of oral compared with intravenous topotecan as second-line therapy in small-cell lung cancer. J Clin Oncol (2007) 25 (15): 2086-92.
Von Pawel J, et al. Randomized phase III trial of amrubicin versus topotecan as second-line treatment for patients with small-cell lung cancer. J Clin Oncol (2014) 32 (35): 4012-9.
Evans TL, et al. Cabazitaxel Versus Topotecan in Patients with Small-Cell Lung Cancer with Progressive Disease During or After First-Line Platinum-Based Chemotherapy. J Thorac Oncol (2015) 10 (8): 1221-8.
Reck M, et al. Efficacy and safety of nivolumab (nivo) monotherapy versus chemotherapy (chemo) in recurrent small cell lung cancer (SCLC): Results from CheckMate 331. Ann Oncol (2018) 29 (Suppl 10): x39-x43. 10.1093/annonc/mdy511.
Pujol JL, et al. A Randomized Non-Comparative Phase II Study of Anti-Programmed Cell Death-Ligand 1 Atezolizumab or Chemotherapy as Second-Line Therapy in Patients With Small Cell Lung Cancer: Results From the IFCT-1603 Trial. J Thorac Oncol (2019) 14 (5): 903-13.
Chou TC. Drug combination studies and their synergy quantification using the Chou-Talalay method. Cancer Res. Jan. 15, 2010;70(2):440-6. doi: 10.1158/0008-5472.CAN-09-1947. Epub Jan. 12, 2010. PMID: 20068163.

Chou TC, Talalay P. Quantitative analysis of dose-effect relationships: the combined effects of multiple drugs or enzyme inhibitors. Adv Enzyme Regul 1984;22:27-55.
Chou TC, Talalay P. Analysis of combined drug effects: a new look at a very old problem. Trends in Pharm Sci 4, 1983, 450-454. doi: 10.1016/0165-6147(83)90490-X.
Tallarida RJ. Quantitative methods for assessing drug synergism. Genes Cancer. Nov. 2011;2(11):1003-8. doi: 10.1177/1947601912440575. PMID: 22737266; PMCID: PMC3379564.
Jonsson et al., Differential Activity of topotecan, irinotecan and SN-38 in fresh human tumor cells but no in cell lines, European Journal of Cancer, 36, 2000, pp. 2120-2127.
Chou T. Relationships between inhibition constants and fractional inhibition in enzyme-catalyzed reactions with different numbers of reactants, different reaction mechanisms, and different types and mechanisms of inhibition. Mol Pharmacol. Mar. 1974;10(2):235-47. PMID: 4212316.
Willis, Michael, Response to Non-Final Office Action filed in related U.S. Appl. No. 10/416,086, response filed Aug. 23, 2005, pp. 1-7.
Willis, Michael, Response to Final Office Action with Notice of Appeal filed in related U.S. Appl. No. 10/416,086, Notice of Appeal filed May 17, 2006, pp. 1-16.
Lee, Wan Chieh, Response to Non-Final Office Action filed in related U.S. Appl. No. 10/416,086, Response to Non-Final Office Action filed on Aug. 9, 2007, pp. 1-190.
Willis, Michael, Response to Final Office Action with Notice of Appeal filed in related U.S. Appl. No. 10/416,086, Response to Final Office Action filed on Apr. 4, 2008, pp. 1-20.
Fetterolf, Brandon J., Examiner Interview Summary issued for related U.S. Appl. No. 10/416,086, Interview Summary dated May 7, 2008, pp. 1-2.
Willis, Michael, Response to Non-Final Office Action in related U.S. Appl. No. 10/416,086, Response to Non-Final Office Action filed on Sep. 2, 2008, pp. 1-23.
Shah et al. The relevance of drug sequence in combination chemotherapy, Drug resistance update (2000), 3, 335-356.
Perez-Ruixo et al, Population Pharmacokinetic Meta-Analysis of trabectedin in cancer patients, Clin. Pharmacokinet, 2007,46, 867-884.
Fernandez-Teruel, Population-Pharmacokinetic and covariate analysis of lurbinectedin (PM01183) a new RNA polymerase II inhibitor, in pooled phase I/II trials in patients with cancer, Clinical Pharmacokinetics, 2019, 58, 363-374.
Erba et al., Ascites interferes with the activity of lurbinectedin and trabectedin: Potential role of their binding to alpha 1-acid glycoprotein, Biochem. Pharmacol. (2017).
Allavena et al., Effects of the Anti-Tumor Agents Trabectedin and Lurbinectedin on Immune Cells of the Tumor Microenvironment, Front. Oncol. 12:851790.
A.I. Vengerovsky, Farmakologicheskaya nesovmestimost [Pharmacological incompatibility], Bulleten Sibirskoi meditsiny [Bulletin of Siberian Medicine], 2003, No. 3, pp. 49-56.
Riccardi et al., "Combination of trabectedin and irinotecan is highly effective in a human rhabdomyosarcoma xenograft", Anti-Cancer Drugs 2005, 16, 811-815.
Bria et al., "Gemcitabine-based combinations for inoperable pancreatic cancer: Have we made real progress? A meta-analysis of 20 phase 3 trials", Cancer 2007, 110(3), 525-533.
Saulnier et al., "Discovery of a Fluoroindolo[2,3-a]carbazole Clinical Candidate with Broad Spectrum Antitumor Activity in Preclinical Tumor Models Superior to the Marketed Oncology Drug, CPT-11." Journal of Medicinal Chemistry 2005, 48(7), 2258-2261.
Ren et al., "NB-506, an indolocarbazole topoisomerase I inhibitor, binds preferentially to triplex DNA." FEBS Letters 2000, 470(3), 355-359.
Li et al., "Characterization of ARC-111 as a Novel Topoisomerase I-Targeting Anticancer Drug." Cancer Research 2003, 63(23), 8400-8407.
Bredberg et al., "Ciprofloxacin-induced inhibition of topoisomerase II in human lymphoblastoid cells." Antimicrobial Agents and Chemotherapy 1991, 35(3), 448-450.

(56) References Cited

OTHER PUBLICATIONS

Nitiss et al., "Targeting DNA topoisomerase II in cancer chemotherapy." Nature reviews. Cancer. 2009, 9(5), 338-350.
Office Action for Russian Application No. 2018102080 dated Aug. 26, 2021, 20 pages.
Office Action for Russian Application No. 2018102080 dated Apr. 12, 2021, 18 pages.

\* cited by examiner

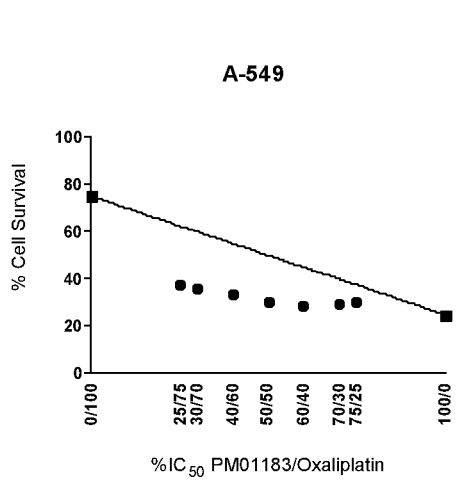
Figure 1
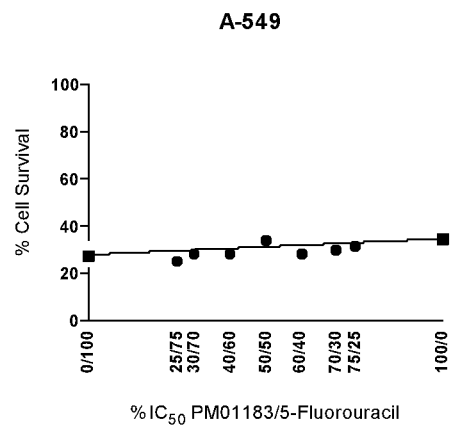
Figure 2
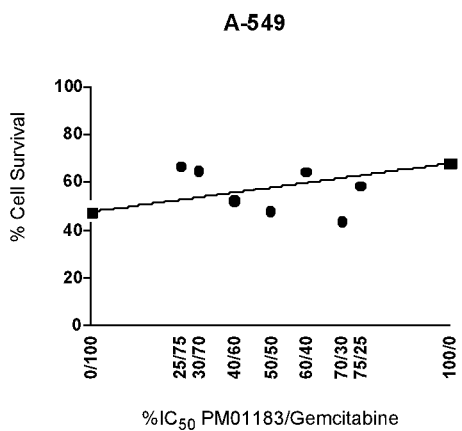
Figure 3
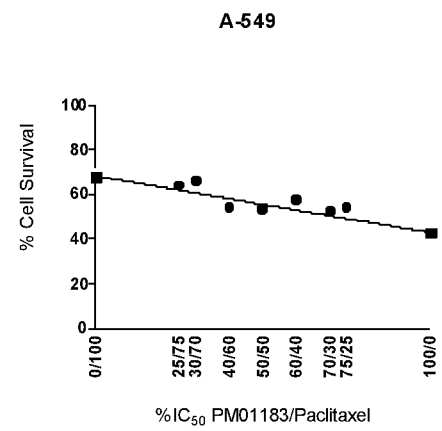
Figura 4
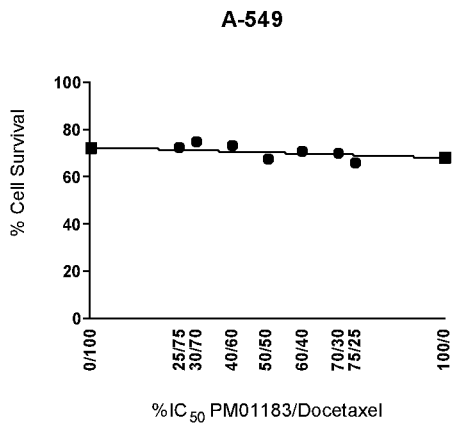
Figure 5
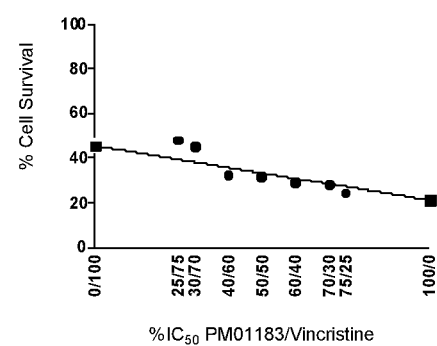
Figure 6

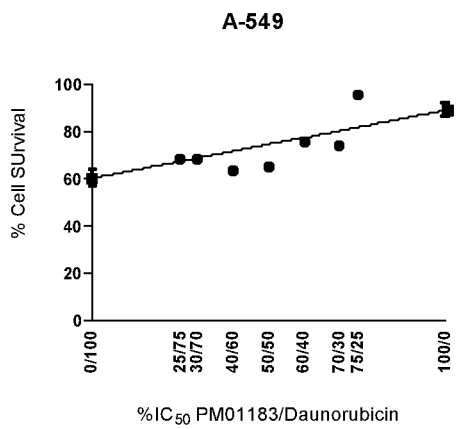
Figure 7
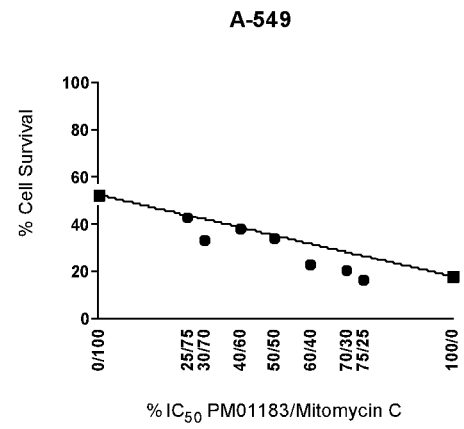
Figure 8
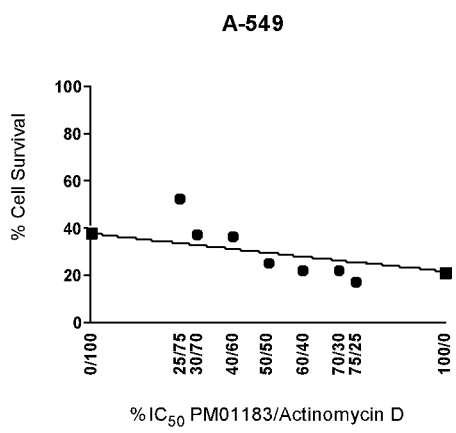
Figure 9
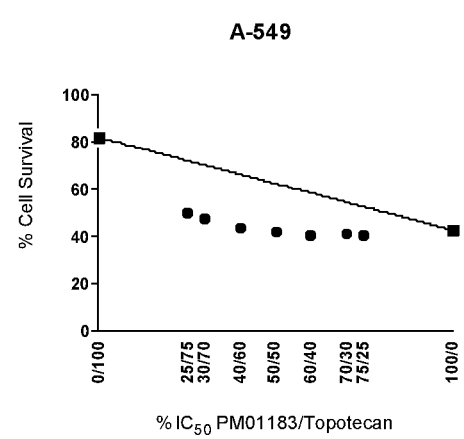
Figura 10
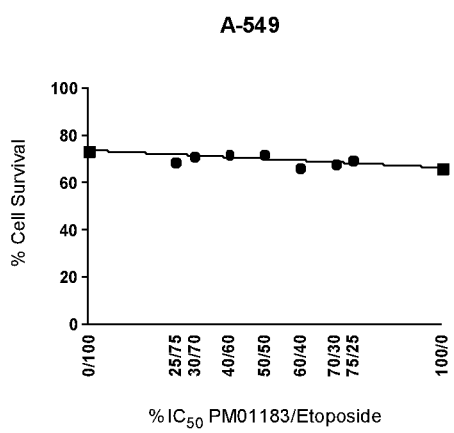
Figure 11
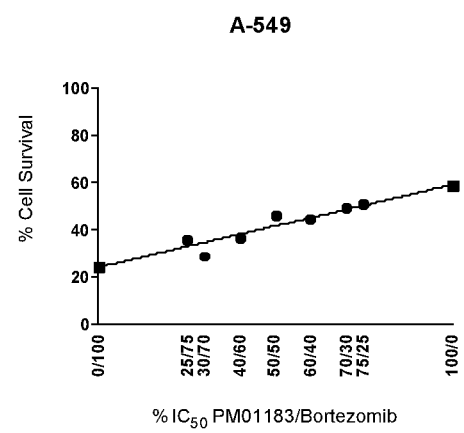
Figure 12

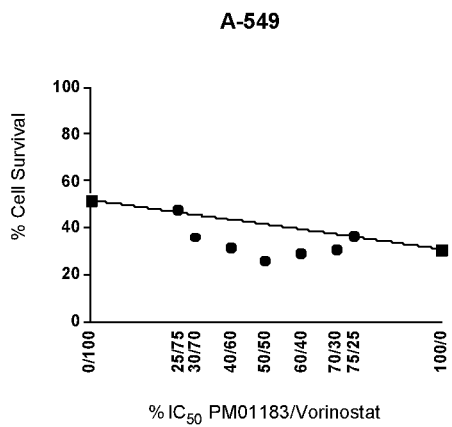
Figure 13
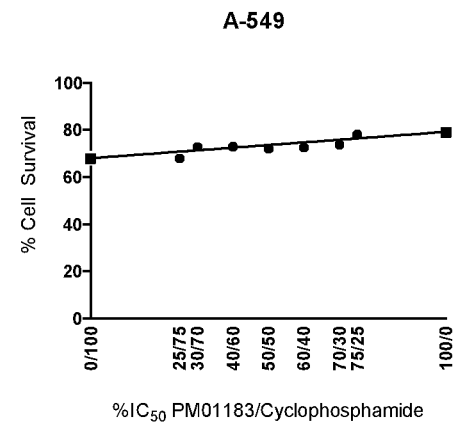
Figure 14
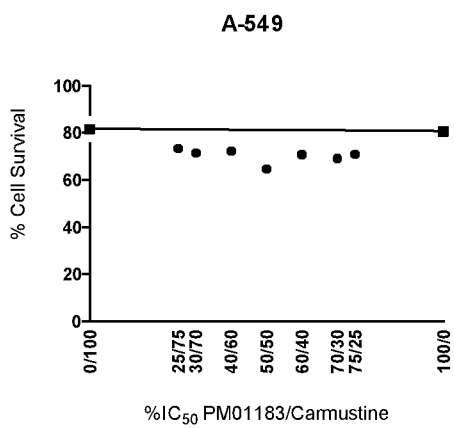
Figure 15
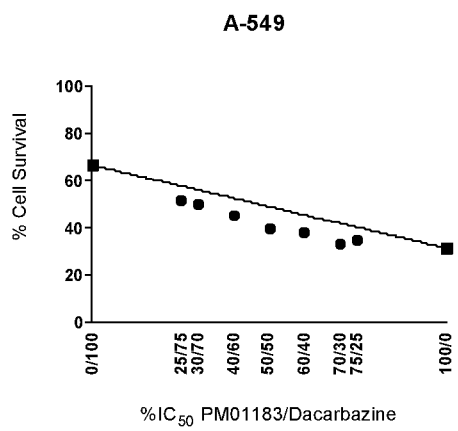
Figura 16
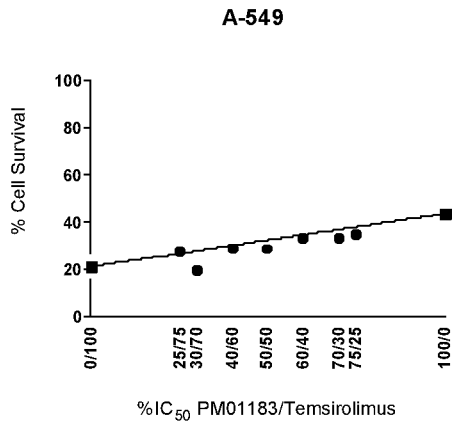
Figure 17
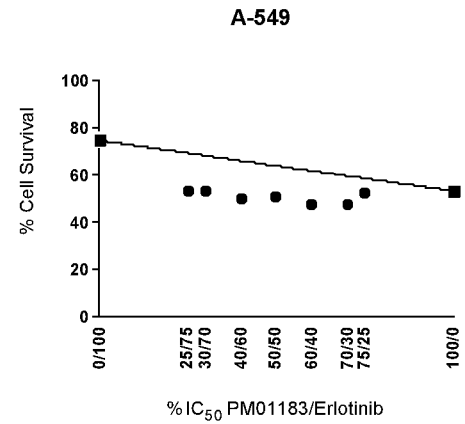
Figure 18

COMBINATION THERAPY WITH AN ANTITUMOR ALKALOID

FIELD OF THE INVENTION

The present invention relates to the combination of PM01183 with other anticancer drugs, in particular other anticancer drugs selected from antitumor platinum coordination complexes, antimetabolites, mitotic inhibitors, anticancer antibiotics, topoisomerase I and/or II inhibitors, proteasome inhibitors, histone deacetylase inhibitors, nitrogen mustard alkylating agents, nitrosourea alkylating agents, nonclassical alkylating agents, estrogen antagonists, androgen antagonists, mTOR inhibitors, tyrosine kinase inhibitors, and other agents selected from aplidine, ET-743, PM02734, and PM00104 and the use of these combinations in the treatment of cancer.

BACKGROUND OF THE INVENTION

Cancer develops when cells in a part of the body begin to grow out of control. Although there are many kinds of cancer, they all arise from out-of-control growth of abnormal cells. Cancer cells can invade nearby tissues and can spread through the bloodstream and lymphatic system to other parts of the body. There are several main types of cancer. Carcinoma is a malignant neoplasm, which is an uncontrolled and progressive abnormal growth, arising from epithelial cells. Epithelial cells cover internal and external surfaces of the body, including organs, lining of vessels, and other small cavities. Sarcoma is cancer arising from cells in bone, cartilage, fat, muscle, blood vessels, or other connective or supportive tissue. Leukemia is cancer that arises in blood-forming tissue such as the bone marrow, and causes large numbers of abnormal blood cells to be produced and enter the bloodstream. Lymphoma and multiple myeloma are cancers that arise from cells of the immune system.

In addition, cancer is invasive and tends to infiltrate the surrounding tissues and give rise to metastases. It can spread directly into surrounding tissues and also may be spread through the lymphatic and circulatory systems to other parts of the body.

Many treatments are available for cancer, including surgery and radiation for localised disease, and chemotherapy. However, the efficacy of available treatments for many cancer types is limited, and new, improved forms of treatment showing clinical benefits are needed. This is especially true for those patients presenting with advanced and/or metastatic disease and for patients relapsing with progressive disease after having been previously treated with established therapies which become ineffective or intolerable due to acquisition of resistance or to limitations in administration of the therapies due to associated toxicities.

Since the 1950s, significant advances have been made in the chemotherapeutic management of cancer. Unfortunately, more than 50% of all cancer patients either do not respond to initial therapy or experience relapse after an initial response to treatment and ultimately die from progressive metastatic disease. Thus, the ongoing commitment to the design and discovery of new anticancer agents is critically important.

Chemotherapy, in its classic form, has been focused primarily on killing rapidly proliferating cancer cells by targeting general cellular metabolic processes, including DNA, RNA, and protein biosynthesis. Chemotherapy drugs are divided into several groups based on how they affect specific chemical substances within cancer cells, which cellular activities or processes the drug interferes with, and which specific phases of the cell cycle the drug affects. The most commonly used types of chemotherapy drugs include: DNA-alkylating drugs (such as cyclophosphamide, ifosfamide, cisplatin, carboplatin, dacarbazine), antimetabolites (5-fluorouracil, capecitabine, 6-mercaptopurine, methotrexate, gemcitabine, cytarabine, fludarabine), mitotic inhibitors (such as paclitaxel, docetaxel, vinblastine, vincristine), anticancer antibiotics (such as daunorubicin, doxorubicin, epirubicin, idarubicin, mitoxantrone), topoisomerase I and/or II inhibitors (such as topotecan, irinotecan, etoposide, teniposide), and hormone therapy (such as tamoxifen, flutamide).

The ideal antitumor drug would kill cancer cells selectively, with a wide index relative to its toxicity towards non-cancer cells and it would also retain its efficacy against cancer cells, even after prolonged exposure to the drug. Unfortunately, none of the current chemotherapies with these agents posses an ideal profile. Most posses very narrow therapeutic indexes and, in addition, cancerous cells exposed to slightly sublethal concentrations of a chemotherapeutic agent may develop resistance to such an agent, and quite often cross-resistance to several other antitumor agents.

PM01183, also known as tryptamicidin, is a synthetic alkaloid which is currently in clinical trials for the treatment of cancer, and has the following chemical structure:

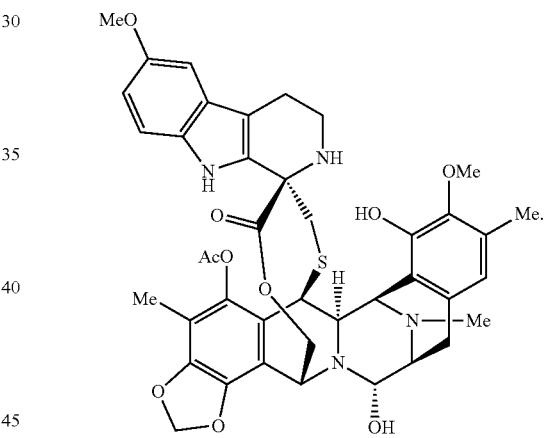

PM01183 has demonstrated a highly potent in vitro activity against solid and non-solid tumour cell lines as well as a significant in vivo activity in several xenografted human tumor cell lines in mice, such as those for breast, kidney and ovarian cancer.

PM01183 exerts its anticancer effects through the covalent modification of guanines in the DNA minor groove that eventually give rise to DNA double-strand break, S-phase arrest and apoptosis in cancer cells. Further information regarding this compound can be found in WO 03/01427; 100th AACR Annual Meeting, Apr. 18-22, 2009, Denver, Colo., Abstract Nr. 2679 and Abstract Nr. 4525; and Leal J F M et al. Br. J. Pharmacol. 2010, 161, 1099-1110.

Since cancer is a leading cause of death in animals and humans, several efforts have been and are still being undertaken in order to obtain a therapy active and safe to be administered to patients suffering from a cancer. The problem to be solved by the present invention is to provide anticancer therapies that are useful in the treatment of cancer.

SUMMARY OF THE INVENTION

The present invention establishes that PM01183 potentiates the antitumor activity of other anticancer agents, in particular other anticancer drugs selected from antitumor platinum coordination complexes, antimetabolites, mitotic inhibitors, anticancer antibiotics, topoisomerase I and/or II inhibitors, proteasome inhibitors, histone deacetylase inhibitors, nitrogen mustard alkylating agents, nitrosourea alkylating agents, nonclassical alkylating agents, estrogen antagonists, androgen antagonists, mTOR inhibitors, tyrosine kinase inhibitors, and other agents selected from aplidine, ET-743, PM02734 and PM00104. Therefore PM01183 and said other anticancer agents can be successfully used in combination therapy for the treatment of cancer.

Thus, this invention is directed to pharmaceutical compositions, kits, methods for the treatment of cancer using these combination therapies and uses of both drugs in the treatment of cancer and in the manufacture of medicaments for combination therapies.

In accordance with one aspect of this invention, we provide effective combination therapies for the treatment of cancer based on PM01183, or a pharmaceutically acceptable salt thereof, and using another anticancer drug as defined above.

In another embodiment, the invention is directed to PM01183, or a pharmaceutically acceptable salt thereof, for use in the treatment of cancer comprising administering a therapeutically effective amount of PM01183, or a pharmaceutical acceptable salt thereof, in combination with a therapeutically effective amount of another anticancer drug.

In another embodiment, the invention encompasses a method of treating cancer comprising administering to a patient in need of such treatment a therapeutically effective amount of PM01183, or a pharmaceutically acceptable salt thereof, and a therapeutically effective amount of another anticancer drug.

In another aspect, the invention encompasses a method of increasing or potentiating the therapeutic efficacy of an anticancer drug in the treatment of cancer, which comprises administering to a patient in need thereof a therapeutically effective amount of PM01183, or a pharmaceutically acceptable salt thereof, in conjunction with this other anticancer drug.

In another embodiment, the invention encompasses the use of PM01183, or a pharmaceutically acceptable salt thereof, for the manufacture of a medicament for the treatment of cancer by combination therapy employing PM01183, or a pharmaceutically acceptable salt thereof, with another anticancer drug.

In a further aspect, the invention encompasses a pharmaceutical composition comprising PM01183, or a pharmaceutically acceptable salt thereof, and/or another anticancer drug, and a pharmaceutically acceptable carrier, to be used in combination therapy for the treatment of cancer.

The invention also encompasses a kit for use in the treatment of cancer which comprises a dosage form of PM01183, or a pharmaceutically acceptable salt thereof, and/or a dosage form of another anticancer drug, and instructions for the use of both drugs in combination.

In one preferred aspect, the present invention is concerned with synergistic combinations of PM01183, or a pharmaceutically acceptable salt thereof, with another anticancer drug.

BRIEF DESCRIPTION OF THE FIGURES

FIG. 1-20. In vitro activity data of PM01183 in combination with oxaliplatin, 5-fluorouracil, gemcitabine, paclitaxel, docetaxel, vincristine, daunorubicin, mitomycin C, actinomycin D, topotecan, etoposide, bortezomib, vorinostat, cyclophosphamide, carmustine, dacarbazine, temsirolimus, erlotinib, ET-743 and PM00104 respectively against A549 cells.

DETAILED DESCRIPTION OF THE INVENTION

Figure 19:
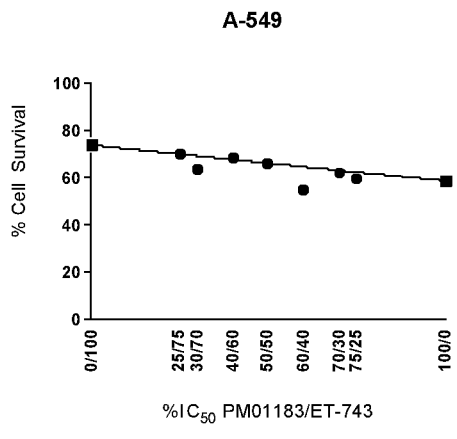

We surprisingly found that PM01183 greatly enhances the anticancer activity of other anticancer drugs when these anticancer drugs are combined with PM01183. Thus, the present invention is directed to provide an efficacious treatment of cancer based on the combination of PM01183, or a pharmaceutically acceptable salt thereof, with another anticancer drug.

In the present application, by "cancer" it is meant to include tumors, neoplasias, and any other malignant disease having as cause malignant tissue or cells.

The term "treating", as used herein, unless otherwise indicated, means reversing, alleviating, or inhibiting the progress of the disease or condition to which such term applies, or one or more symptoms of such disorder or condition. The term "treatment", as used herein, unless otherwise indicated, refers to the act of treating as "treating" is defined immediately above.

The term "combination" as used throughout the specification, is meant to encompass the administration to a patient suffering from cancer of the referred therapeutic agents in the same or separate pharmaceutical formulations, and at the same time or at different times. If the therapeutic agents are administered at different times they should be administered sufficiently close in time to provide for the potentiating or synergistic response to occur.

As mentioned above, PM01183 is a synthetic alkaloid, having the following structure:

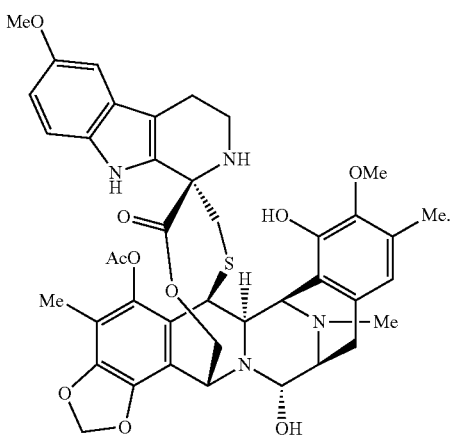 [SMILES: COc1ccc2[nH]c3c(c2c1)CCN[C@]31CS[C@@H]2c3c(OC(C)=O)c(C)c4c(c3[C@H](COC1=O)N1[C@@H]2[C@H]2c3c(cc(C)c(OC)c3O)C[C@@H]([C@@H]1O)N2C)OCO4]

The term "PM01183" is intended here to cover any pharmaceutically acceptable salt, solvate, hydrate, prodrug, or any other compound which, upon administration to the patient is capable of providing (directly or indirectly) the compound as described herein. The preparation of salts, solvates, hydrates, and prodrugs can be carried out by methods known in the art.

Pharmaceutically acceptable salts can be synthesized from the parent compound, which contains a basic or acidic moiety, by conventional chemical methods. Generally, such salts are, for example, prepared by reacting the free acid or base forms of these compounds with a stoichiometric amount of the appropriate base or acid in water or in an organic solvent or in a mixture of the two. Generally, nonaqueous media like ether, ethyl acetate, ethanol, isopropanol or acetonitrile are preferred. Examples of the acid addition salts include mineral acid addition salts such as, for example, hydrochloride, hydrobromide, hydroiodide, sulphate, nitrate, phosphate, and organic acid addition salts such as, for example, acetate, trifluoroacetate, maleate, fumarate, citrate, oxalate, succinate, tartrate, malate, mandelate, methanesulphonate and p-toluenesulphonate. Examples of the alkali addition salts include inorganic salts such as, for example, sodium, potassium, calcium and ammonium salts, and organic alkali salts such as, for example, ethylenediamine, ethanolamine, N,N-dialkylenethanolamine, triethanolamine and basic aminoacids salts.

Any compound that is a prodrug of PM01183 is within the scope and spirit of the invention. The term "prodrug" is used in its broadest sense and encompasses those derivatives that are converted in vivo to PM01183. The prodrug can hydrolyze, oxidize, or otherwise react under biological conditions to provide PM01183. Examples of prodrugs include, but are not limited to, derivatives and metabolites of PM01183 that include biohydrolyzable moeities such as biohydrolyzable amides, biohydrolyzable esters, biohydrolyzable carbamates, biohydrolyzable carbonates, biohydrolyzable ureides, and biohydrolyzable phosphate analogues. Prodrugs can typically be prepared using well-known methods, such as those described by Burger in "Medicinal Chemistry and Drug Discovery" 6th ed. (Donald J. Abraham ed., 2001, Wiley) and "Design and Applications of Prodrugs" (H. Bundgaard ed., 1985, Harwood Academic Publishers).

In addition, any drug referred to herein may be in amorphous form or crystalline form either as free compound or as solvates (e.g. hydrates) and it is intended that both forms are within the scope of the present invention. Methods of solvation are generally known within the art.

Moreover, PM01183 for use in accordance with the present invention may be prepared following the synthetic process such as the one disclosed in WO 03/014127, which is incorporated herein by reference.

Pharmaceutical compositions of PM01183, or of a pharmaceutically acceptable salt thereof, that can be used include solutions, suspensions, emulsions, lyophilised compositions, etc., with suitable excipients for intravenous administration. Preferably, PM01183 may be supplied and stored as a sterile lyophilized product, comprising PM01183 and excipients in a formulation adequate for therapeutic use. For further guidance on pharmaceutical compositions of PM01183, or a pharmaceutically acceptable salt thereof, see for example the formulations described in WO 2006/046079, which is incorporated herein by reference.

Administration of PM01183, or a pharmaceutically acceptable salt thereof, or pharmaceutical compositions comprising the compound is preferably by intravenous infusion. Infusion times of up to 72 hours can be used, more preferably between 1 and 24 hours, with either about 1 hour or about 3 hours most preferred. Short infusion times which allow treatment to be carried out without an overnight stay in hospital are especially desirable. However, infusion may be around 24 hours or even longer if required.

Preferably the administration of PM01183 is performed in cycles. In a preferred administration schedule an intravenous infusion of PM01183 is given to the patients the first week of each cycle and the patients are allowed to recover for the remainder of the cycle. The preferred duration of each cycle is of either 3 or 4 weeks. Multiple cycles can be given as needed. Administration of PM01183, or a pharmaceutically acceptable salt thereof, by intravenous infusion during about 1 hour once every 3 weeks is the most preferred administration schedule, although other protocols can be devised as variations.

In the present invention, particularly preferred is the combination of PM01183, or a pharmaceutically acceptable salt thereof, with another anticancer drug selected from antitumor platinum coordination complexes, antimetabolites, mitotic inhibitors, anticancer antibiotics, topoisomerase I and/or II inhibitors, proteasome inhibitors, histone deacetylase inhibitors, nitrogen mustard alkylating agents, nitrosourea alkylating agents, nonclassical alkylating agents, estrogen antagonists, androgen antagonists, mTOR inhibitors, tyrosine kinase inhibitors, and other agents selected from aplidine, ET-743, PM02734 and PM00104 in the treatment of cancer.

Particularly preferred cancer types are those selected from lung cancer, sarcoma, malignant melanoma, bladder carcinoma, prostate cancer, pancreas carcinoma, thyroid cancer, gastric carcinoma, ovarian cancer, hepatoma (also known as liver cancer), breast cancer, colorectal cancer, kidney cancer, esophageal cancer, neuroblastoma, brain cancer, cervical cancer, anal cancer, testicular cancer, leukemia, multiple myeloma and lymphoma.

In a preferred embodiment, the invention is directed to the combination of PM01183, or a pharmaceutically acceptable salt thereof, with an antitumor platinum coordination complex in the treatment of cancer, and more particularly in the treatment of a cancer selected from lung cancer, sarcoma, malignant melanoma, prostate cancer, pancreas carcinoma, gastric carcinoma, ovarian cancer, hepatoma, breast cancer, colorectal cancer, kidney cancer, brain cancer and lymphoma. This chemotherapeutic group includes, but is not limited to cisplatin, oxaliplatin, carboplatin, triplatin tetranitrate (BBR3464), satraplatin, tetraplatin, ormiplatin, iproplatin, nedaplatin and lobaplatin. Particularly preferred is the combination of PM01183, or a pharmaceutically acceptable salt thereof, with cisplatin, oxaliplatin, carboplatin, triplatin tetranitrate, satraplatin, tetraplatin, ormiplatin, iproplatin, nedaplatin and lobaplatin, and even more preferred is the combination with cisplatin and oxaliplatin in the treatment of cancer, and more particularly in the treatment of a cancer selected from lung cancer, sarcoma, malignant melanoma, prostate cancer, pancreas carcinoma, gastric carcinoma, ovarian cancer, hepatoma, breast cancer, colorectal cancer, kidney cancer and brain cancer.

In another preferred embodiment, the invention is directed to the combination of PM01183, or a pharmaceutically acceptable salt thereof, with an antimetabolite in the treatment of cancer, and more particularly in the treatment of a cancer selected from lung cancer, sarcoma, malignant melanoma, bladder carcinoma, prostate cancer, pancreas carcinoma, gastric carcinoma, ovarian cancer, hepatoma, breast cancer, colorectal cancer, kidney cancer, esophageal cancer, brain cancer, anal cancer, leukaemia and lymphoma. This chemotherapeutic group includes, but is not limited to 5-fluorouracil, gemcitabine, cytarabine, capecitabine, decitabine, floxuridine, fludarabine, aminopterin, methotrexate, pemetrexed, raltitrexed, cladribine, clofarabine, mercaptopurine, pentostatin, and thioguanine. Particularly preferred is the combination of PM01183, or a pharmaceutically acceptable salt thereof, with 5-fluorouracil, gemcitabine, cytarabine, capecitabine, decitabine, floxuridine, fludarabine, aminopterin, methotrexate, pemetrexed, raltitrexed, cladribine, clofarabine, mercaptopurine, pentostatin, and thioguanine, and even more preferred is the combination with 5-fluorouracil, gemcitabine, cytarabine and methotrexate in the treatment of cancer, and more particularly in the treatment of a cancer selected from lung cancer, sarcoma, malignant melanoma, prostate cancer, pancreas carcinoma, gastric carcinoma, ovarian cancer, hepatoma, breast cancer, colorectal cancer, kidney cancer, brain cancer, leukemia and lymphoma.

In another preferred embodiment, the invention is directed to the combination of PM01183, or a pharmaceutically acceptable salt thereof, with a mitotic inhibitor in the treatment of cancer, and more particularly in the treatment of a cancer selected from lung cancer, sarcoma, prostate cancer, gastric carcinoma, ovarian cancer, hepatoma, breast cancer, colorectal cancer, kidney cancer, brain cancer, leukemia and lymphoma. This chemotherapeutic group includes, but is not limited to paclitaxel, docetaxel, vinblastine, vincristine, vindesine, and vinorelbine. Particularly preferred is the combination of PM01183, or a pharmaceutically acceptable salt thereof, with paclitaxel, docetaxel, vinblastine, vincristine, vindesine, and vinorelbine, and even more preferred is the combination with paclitaxel, docetaxel, vincristine and vinorelbine in the treatment of cancer, and more particularly in the treatment of a cancer selected from lung cancer, sarcoma, prostate cancer, gastric carcinoma, ovarian cancer, hepatoma, breast cancer, colorectal cancer, kidney cancer and brain cancer.

In another preferred embodiment, the invention is directed to the combination of PM01183, or a pharmaceutically acceptable salt thereof, with an anticancer antibiotic in the treatment of cancer, and more particularly in the treatment of lung cancer, sarcoma, malignant melanoma, bladder carcinoma, prostate cancer, pancreas carcinoma, thyroid cancer, gastric carcinoma, ovarian cancer, hepatoma, breast cancer, colorectal cancer, kidney cancer, neuroblastoma, brain cancer, anal cancer, testicular cancer, leukemia, multiple myeloma and lymphoma. This chemotherapeutic group includes, but is not limited to daunorubicin, doxorubicin, epirubicin, idarubicin, mitoxantrone, pixantrone, valrubicin, mitomycin C, bleomycin, actinomycin A and mithramycin. Particularly preferred is the combination of PM01183, or a pharmaceutically acceptable salt thereof, with daunorubicin, doxorubicin, epirubicin, idarubicin, mitoxantrone, pixantrone, valrubicin, mitomycin C, bleomycin, actinomycin D and mithramycin, and even more preferred is the combination with daunorubicin, doxorubicin, mitomycin C and actinomycin D in the treatment of cancer, and more particularly in the treatment of lung cancer, sarcoma, malignant melanoma, prostate cancer, pancreas carcinoma, gastric carcinoma, ovarian cancer, hepatoma, breast cancer, colorectal cancer, kidney cancer, brain cancer, leukemia and lymphoma.

In another preferred embodiment, the invention is directed to the combination of PM01183, or a pharmaceutically acceptable salt thereof, with a topoisomerase I and/or II inhibitor in the treatment of cancer, and more particularly in the treatment of lung cancer, sarcoma, malignant melanoma, prostate cancer, pancreas carcinoma, gastric carcinoma, ovarian cancer, hepatoma, breast cancer, colorectal cancer, kidney cancer, neuroblastoma, brain cancer, cervical cancer, testicular cancer, leukemia and lymphoma. This chemotherapeutic group includes, but is not limited to topotecan, SN-38, irinotecan, camptothecin, rubitecan, etoposide, amsacrine and teniposide. Particularly preferred is the combination of PM00104, or a pharmaceutically acceptable salt thereof, with topotecan, SN-38, irinotecan, camptothecin, rubitecan, etoposide, amsacrine and teniposide, and even more preferred is the combination with topotecan, irinotecan and etoposide in the treatment of cancer, and more particularly in the treatment of lung cancer, sarcoma, malignant melanoma, prostate cancer, pancreas carcinoma, gastric carcinoma, ovarian cancer, hepatoma, breast cancer, colorectal cancer, kidney cancer, and brain cancer.

In another preferred embodiment, the invention is directed to the combination of PM01183, or a pharmaceutically acceptable salt thereof, with a proteosome inhibitor in the treatment of cancer, and more particularly in the treatment of lung cancer, prostate cancer, pancreas carcinoma, gastric carcinoma, hepatoma, colorectal cancer, brain cancer, multiple myeloma and lymphoma. This chemotherapeutic group includes, but is not limited to bortezomib, disulfiram, epigallocatechin gallate, and salinosporamide A. Particularly preferred is the combination of PM01183, or a pharmaceutically acceptable salt thereof, with bortezomib, disulfiram, epigallocatechin gallate, and salinosporamide A, and even more preferred is the combination with bortezomib in the treatment of cancer, and more particularly in the treatment of lung cancer, prostate cancer, pancreas carcinoma, gastric carcinoma, hepatoma, colorectal cancer and brain cancer.

In another preferred embodiment, the invention is directed to the combination of PM01183, or a pharmaceutically acceptable salt thereof, with a histone deacetylase inhibitor in the treatment of cancer, and more particularly in the treatment of lung cancer, sarcoma, prostate cancer, pancreas carcinoma, gastric carcinoma, ovarian cancer, breast cancer, colorectal cancer, kidney cancer, brain cancer and lymphoma. This chemotherapeutic group includes, but is not limited to romidepsin, panobinostat, vorinostat, mocetinostat, belinostat, entinostat, resminostat, PCI-24781, AR-42, CUDC-101, and valproic acid. Particularly preferred is the combination of PM01183, or a pharmaceutically acceptable salt thereof, with romidepsin, panobinostat, vorinostat, mocetinostat, belinostat, entinostat, resminostat, PCI-24781, AR-42, CUDC-101, and valproic acid, and even more preferred is the combination with vorinostat in the treatment of cancer, and more particularly in the treatment of lung cancer, sarcoma, prostate cancer, pancreas carcinoma, gastric carcinoma, ovarian cancer, breast cancer, colorectal cancer, kidney cancer and brain cancer.

In another preferred embodiment, the invention is directed to the combination of PM01183, or a pharmaceutically acceptable salt thereof, with a nitrogen mustard alkylating agent in the treatment of cancer, and more particularly in the treatment of lung cancer, sarcoma, bladder carcinoma, gastric carcinoma, ovarian cancer, hepatoma, breast cancer, colorectal cancer, kidney cancer, leukemia, multiple myeloma and lymphoma. This chemotherapeutic group includes, but is not limited to melphalan, ifosfamide, chlorambucil, cyclophosphamide, mechlorethamine, uramustine, estramustine and bendamustine. Particularly preferred is the combination of PM01183, or a pharmaceutically acceptable salt thereof, with melphalan, ifosfamide, chlorambucil, cyclophosphamide, mechlorethamine, uramustine, estramustine and bendamustine, and even more preferred is the combination with cyclophosphamide in the treatment of cancer, and more particularly in the treatment of lung cancer, sarcoma, gastric carcinoma, ovarian cancer, hepatoma, breast cancer, colorectal cancer and kidney cancer.

In another preferred embodiment, the invention is directed to the combination of PM01183, or a pharmaceutically acceptable salt thereof, with a nitrosourea alkylating agent in the treatment of cancer, and more particularly in the treatment of lung cancer, ovarian cancer, breast cancer, brain cancer, multiple myeloma and lymphoma. This chemotherapeutic group includes, but is not limited to lomustine, semustine, carmustine, fotemustine and streptozotocin. Particularly preferred is the combination of PM01183, or a pharmaceutically acceptable salt thereof, with lomustine, semustine, carmustine, fotemustine and streptozotocin, and even more preferred is the combination with carmustine in the treatment of cancer, and more particularly in the treatment of lung cancer, ovarian cancer and breast cancer.

In another preferred embodiment, the invention is directed to the combination of PM01183, or a pharmaceutically acceptable salt thereof, with a nonclassical alkylating agent in the treatment of cancer, and more particularly in the treatment of lung cancer, sarcoma, malignant melanoma, pancreas carcinoma, gastric carcinoma, ovarian cancer, breast cancer, colorectal cancer, kidney cancer, brain cancer, leukemia and lymphoma. This chemotherapeutic group includes, but is not limited to procarbazine, dacarbazine, temozolomide and altretamine. Particularly preferred is the combination of PM01183, or a pharmaceutically acceptable salt thereof, with procarbazine, dacarbazine, temozolomide and altretamine, and even more preferred is the combination with dacarbazine and tezolomide in the treatment of lung cancer, sarcoma, malignant melanoma, gastric carcinoma, ovarian cancer, breast cancer, colorectal cancer, kidney cancer and brain cancer.

In another preferred embodiment, the invention is directed to the combination of PM01183, or a pharmaceutically acceptable salt thereof, with an estrogen antagonist in the treatment of cancer, and more particularly in the treatment of breast cancer. This chemotherapeutic group includes, but is not limited to toremifene, fulvestrant, tamoxifen and nafoxidine. Particularly preferred is the combination of PM01183, or a pharmaceutically acceptable salt thereof, with toremifene, fulvestrant, tamoxifen and nafoxidine, and even more preferred is the combination with tamoxifen in the treatment of breast cancer.

In another preferred embodiment, the invention is directed to the combination of PM01183, or a pharmaceutically acceptable salt thereof, with an androgen antagonist in the treatment of cancer, and more particularly in the treatment of prostate cancer. This chemotherapeutic group includes, but is not limited to bicalutamide, flutamide, MDV3100 and nilutamide. Particularly preferred is the combination of PM01183, or a pharmaceutically acceptable salt thereof, with bicalutamide, flutamide, MDV3100 and nilutamide, and even more preferred is the combination with flutamide in the treatment of prostate cancer.

In another preferred embodiment, the invention is directed to the combination of PM01183, or a pharmaceutically acceptable salt thereof, with a mTOR inhibitor in the treatment of cancer, and more particularly in the treatment of lung cancer, sarcoma, malignant melanoma, prostate cancer, pancreas carcinoma, gastric carcinoma, ovarian cancer, breast cancer, colorectal cancer, kidney cancer and brain cancer. This chemotherapeutic group includes, but is not limited to sirolimus, temsirolimus, everolimus, ridaforolimus, KU-0063794 and WYE-354. Particularly preferred is the combination of PM01183, or a pharmaceutically acceptable salt thereof, with sirolimus, temsirolimus, everolimus, ridaforolimus, KU-0063794 and WYE-354, and even more preferred is the combination with temsirolimus in the treatment of lung cancer, sarcoma, malignant melanoma, prostate cancer, pancreas carcinoma, gastric carcinoma, ovarian cancer, breast cancer, colorectal cancer and brain cancer.

In another preferred embodiment, the invention is directed to the combination of PM01183, or a pharmaceutically acceptable salt thereof, with a tyrosine kinase inhibitor in the treatment of cancer, and more particularly in the treatment of a cancer selected from lung cancer, sarcoma, prostate cancer, pancreas carcinoma, gastric carcinoma, ovarian cancer, hepatoma, breast cancer, colorectal cancer, kidney cancer and brain cancer. This chemotherapeutic group includes, but is not limited to erlotinib, sorafenib, axitinib, bosutinib, cediranib, crizotinib, dasatinib, gefitinib, imatinib, canertinib, lapatinib, lestaurtinib, neratinib, nilotinib, semaxanib, sunitinib, vatalanib and vandetanib. Particularly preferred is the combination of PM01183, or a pharmaceutically acceptable salt thereof, with erlotinib, sorafenib, axitinib, bosutinib, cediranib, crizotinib, dasatinib, gefitinib, imatinib, canertinib, lapatinib, lestaurtinib, neratinib, nilotinib, semaxanib, sunitinib, vatalanib and vandetanib, and even more preferred is the combination with erlotinib in the treatment of cancer, and more particularly in the treatment of a cancer selected from lung cancer, sarcoma, prostate cancer, pancreas carcinoma, gastric carcinoma, ovarian cancer, hepatoma, breast cancer, colorectal cancer, kidney cancer and brain cancer.

In another preferred embodiment, the invention is directed to the combination of PM01183, or a pharmaceutically acceptable salt thereof, with aplidine in the treatment of cancer, and more particularly in the treatment of a cancer selected from sarcoma, gastric carcinoma, ovarian cancer, colorectal cancer, kidney cancer, brain cancer and leukemia.

In another preferred embodiment, the invention is directed to the combination of PM01183, or a pharmaceutically acceptable salt thereof, with ET-743 (trabectedin) in the treatment of cancer, and more particularly in the treatment of a cancer selected from lung cancer, sarcoma, malignant melanoma, prostate cancer, pancreas carcinoma, gastric carcinoma, ovarian cancer, hepatoma, breast cancer, kidney cancer, leukemia and lymphoma.

In another preferred embodiment, the invention is directed to the combination of PM01183, or a pharmaceutically acceptable salt thereof, with PM02734 in the treatment of cancer, and more particularly in the treatment of a cancer selected from sarcoma, malignant melanoma, prostate cancer, pancreas carcinoma, gastric carcinoma, ovarian cancer, breast cancer, colorectal cancer, kidney cancer, brain cancer, leukemia and lymphoma.

PM02734 ((4S)-MeHex-D-Val-L-Thr-L-Val-D-Val-D-Pro-L-Orn-D-allo-Ile-cyclo(D-allo-Thr-D-allo-Ile-D-Val-L-Phe-Z-Dhb-L-Val)) is a synthetic depsipeptide related to the family of kahalalide compounds, which is currently in clinical trials for the treatment of cancer. This compound is the subject of WO 2004/035613 and has the following structure:

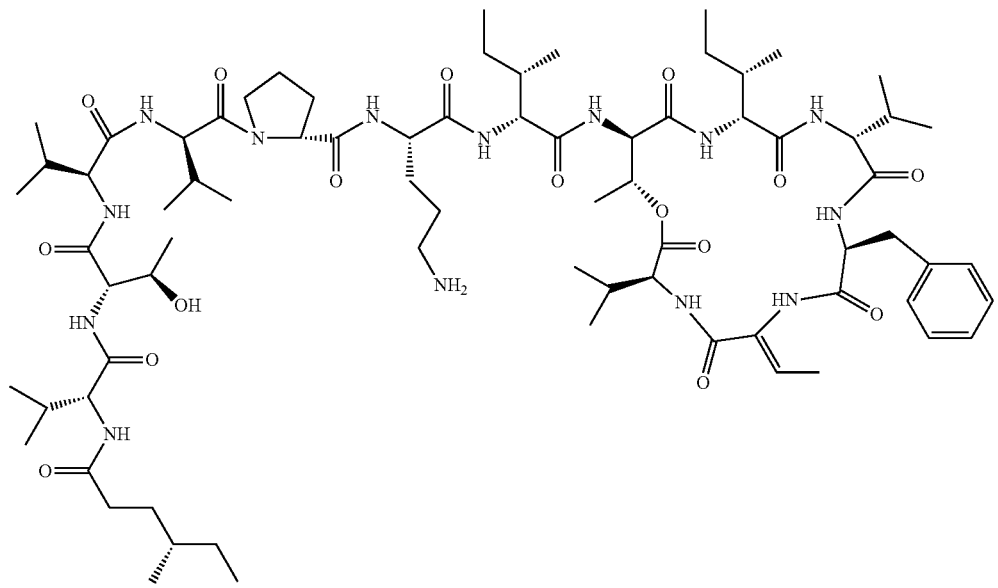 [SMILES: C/C=C1\NC(=O)[C@H](Cc2ccccc2)NC(=O)[C@@H](C(C)C)NC(=O)[C@@H]([C@@H](C)CC)NC(=O)[C@H](NC(=O)[C@H](NC(=O)[C@H](CCCN)NC(=O)[C@H]2CCCN2C(=O)[C@H](NC(=O)[C@@H](NC(=O)[C@@H](NC(=O)[C@H](NC(=O)CC[C@@H](C)CC)C(C)C)[C@@H](C)O)C(C)C)C(C)C)[C@@H](C)CC)[C@@H](C)OC(=O)[C@H](C(C)C)NC1=O]

In another preferred embodiment, the invention is directed to the combination of PM01183, or a pharmaceutically acceptable salt thereof, with PM00104 in the treatment of cancer, and more particularly in the treatment of a cancer selected from lung cancer, sarcoma, malignant melanoma, prostate cancer, pancreas carcinoma, gastric carcinoma, ovarian cancer, hepatoma, breast cancer, kidney cancer, leukemia and lymphoma.

PM00104 is a synthetic alkaloid related to jorumycin and renieramycins, and also to safracin and saframycin compounds, which is currently in clinical trials for the treatment of cancer, and has the following structure:

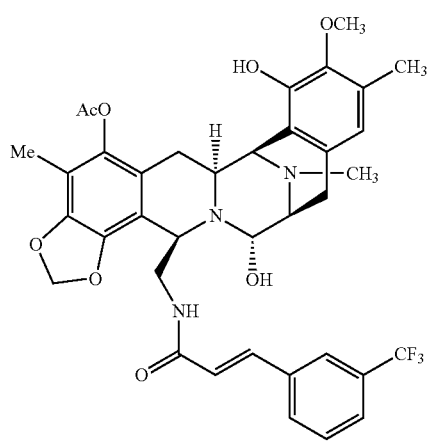 [SMILES: COc1c(C)cc2c(c1O)[C@@H]1[C@@H]3Cc4c(OC(C)=O)c(C)c5c(c4[C@H](CNC(=O)/C=C/c4cccc(C(F)(F)F)c4)N3[C@@H](O)[C@H](C2)N1C)OCO5]

For further details on PM00104 see WO 01/87894.

The invention includes any pharmaceutically acceptable salt of any drug referred to herein, which can be synthesized from the parent compound by conventional chemical methods as disclosed before.

In one embodiment, the invention relates to synergistic combinations employing PM01183, or a pharmaceutically acceptable salt thereof, and another anticancer drug selected from the list of drugs given above. An indication of synergism can be obtained by testing the combinations and analyzing the results, for example by the Chou-Talalay method or by any other suitable method, such as those provided in the Examples section.

The possible favorable outcomes for synergism include 1) increasing the efficacy of the therapeutic effect, 2) decreasing the dosage but increasing or maintaining the same efficacy to avoid toxicity, 3) minimizing or slowing down the development of drug resistance, and 4) providing selective synergism against target (or efficacy synergism) versus host (or toxicity antagonism). Accordingly, in a combination of two chemotherapeutic agents having synergism, the treatment regimen will be different of those in which the combination of the two drugs shows only an additive effect. In this regard, if there is synergism less dosage of one or both of the agents (compared with the amounts used in single therapy) may be required to obtain the same or even a greater efficacy, and the possible toxic side effects may be reduced or even avoided. Alternatively, if the dosage of both drugs in the combination is the same as those when given alone (as single agents), an increase in efficacy of the combination can be expected. Therefore, the existence of synergism in a given drug combination will modify the length of the treatment and/or the treatment regimen.

In another embodiment, the invention relates to a method of increasing or potentiating the therapeutic efficacy of an anticancer drug selected from the list of drugs given above in the treatment of cancer, which comprises administering to a patient in need thereof a therapeutically effective amount of PM01183, or a pharmaceutically acceptable salt thereof, in conjunction with this other anticancer drug. An indication of increase or potentiation of the therapeutic efficacy can be obtained by testing the combinations and analyzing the results, for example the tumor growth inhibition. This tumor growth inhibition can be assessed by comparing the mean tumor volume of the treatment combining the two drugs (PM01183 and the other drug) with those of the other drug monotherapy treatment. In this regard, increase or potentiation of the therapeutic efficacy is determined when the response of the combination therapy is greater than the best response of the most active drug administered as single agent (monotherapy) on the same schedule and dose as used in the combination therapy. This aspect of the invention is further illustrated in the Examples section, specifically in Examples 13-19.

In another aspect, the invention is directed to the use of PM01183, or a pharmaceutically acceptable salt thereof, for the manufacture of a medicament for the treatment of cancer by combination therapy employing PM01183, or a pharmaceutically acceptable salt thereof, with another anticancer drug selected from the list of drugs given above.

In a further aspect, the invention is directed to a method for the treatment of cancer comprising administering to a patient in need of such treatment a therapeutically effective amount of PM01183, or pharmaceutically acceptable salt thereof, in combination with a therapeutically effective amount of another anticancer drug selected from the list of drugs given above.

In another aspect, the invention is directed to PM01183, or a pharmaceutically acceptable salt thereof, for use in the treatment of cancer comprising administering a therapeutically effective amount of PM01183, or a pharmaceutical acceptable salt thereof, in combination with a therapeutically effective amount of another anticancer drug selected from the list of drugs given above.

According to the present invention, PM01183, or a pharmaceutically acceptable salt thereof, and the other anticancer drug may be provided in the same medicament or as separate medicaments for administration at the same time or at different times. Preferably, PM01183, or a pharmaceutically acceptable salt thereof, and the other anticancer drug are provided as separate medicaments for administration at different times. When administered separately and at different times, either PM01183, or a pharmaceutically acceptable salt thereof, or the other anticancer drug, may be administered first. In addition, both drugs can be administered in the same day or at different days, and they can be administered using the same schedule or at different schedules during the treatment cycle. Additionally, the administration of both drugs can be done by using the same route of administration or different routes. For instance, both drugs can be administered by intravenous administration or, alternatively, one drug can be administered orally and the other one by intravenous administration.

Thus, the pharmaceutical compositions of the present invention may comprise all the components (drugs) in a single pharmaceutically acceptable formulation or, alternatively, the components may be formulated separately and administered in combination with one another. Various pharmaceutically acceptable formulations well known to those of skill in the art can be used in the present invention. Moreover, selection of an appropriate formulation for use in the present invention can be performed by those skilled in the art by taking into account the route of administration and the solubility characteristics of the components of the composition.

The correct dosage of both drugs in combination will vary according to the particular formulation, the mode of application, and the particular site, patient and tumour being treated. Other factors like age, body weight, sex, diet, time of administration, rate of excretion, condition of the patient, other drug combinations, reaction sensitivities and severity of the disease shall be taken into account. Administration can be carried out continuously or periodically within the maximum tolerated dose.

The combination of the invention may be used alone or in combination with one or more of a variety of anticancer agents or supportive care agents.

In addition, depending on the type of tumor and the development stage of the disease, anticancer effects of the treatments of the present invention include, but are not limited to, inhibition of tumor growth, tumor growth delay, regression of tumor, shrinkage of tumor, increased time to regrowth of tumor on cessation of treatment, slowing of disease progression, and prevention of metastasis. It is expected that when a treatment of the present invention is administered to a patient, such as a human patient, in need of such treatment, said treatment will produce an effect, as measured by, for example, the extent of the anticancer effect, the response rate, the time to disease progression, or the survival rate. In particular, the treatments of the invention are suited for human patients, especially those who are relapsing or refractory to previous chemotherapy. First line therapy is also envisaged.

In another aspect, the present invention is directed to a kit for use in the treatment of cancer, comprising a supply of PM01183, or a pharmaceutically acceptable salt thereof, in dosage units for at least one cycle, and printed instructions for the use of PM01183, or a pharmaceutically acceptable salt thereof, with another anticancer drug selected from the list of drugs given above in combination.

In a related aspect, the present invention is directed to a kit for use in the treatment of cancer, comprising a supply of PM01183, or a pharmaceutically acceptable salt thereof, in dosage units for at least one cycle, a supply of another anticancer drug selected from the list of drugs given above in dosage units for at least one cycle, and printed instructions for the use of both drugs in combination.

In another aspect, the present invention also provides a pharmaceutical composition comprising PM01183, or a pharmaceutically acceptable salt thereof, and a pharmaceutically acceptable carrier or excipient, for use in combination with another anticancer drug selected from the list of drugs given above in the treatment of cancer.

In a further aspect, the present invention also provides a pharmaceutical composition comprising PM01183, or a pharmaceutically acceptable salt thereof, another anticancer drug selected from the list of drugs given above, and a pharmaceutically acceptable carrier. This pharmaceutical composition is preferable for use in the treatment of cancer.

In another aspect, the invention further provides for the use of PM01183, or a pharmaceutically acceptable salt thereof, in the preparation of a composition for use in combination with another anticancer drug selected from the list of drugs given above in the treatment of cancer.

In another aspect, the invention further provides for the use of PM01183, or a pharmaceutically acceptable salt thereof, for the treatment of cancer, in combination therapy with another anticancer drug selected from the list of drugs given above.

In one embodiment, cancer cells are contacted, or otherwise treated, with a combination of PM01183, or a pharmaceutically acceptable salt thereof, and another anticancer drug selected from the list of drugs given above. The cancer cells are preferably human and include carcinoma cells, sarcoma cells, leukemia cells, lymphoma cells, and myeloma cells. More preferably, the cancer cells are cells of lung cancer, sarcoma, malignant melanoma, bladder carcinoma, prostate cancer, pancreas carcinoma, thyroid cancer, gastric carcinoma, ovarian cancer, hepatoma, breast cancer, colorectal cancer, kidney cancer, esophageal cancer, neuroblastoma, brain cancer, cervical cancer, anal cancer, testicular cancer, leukemia, multiple myeloma and lymphoma. In addition, the combination provides a synergistic inhibitory effect against the cancer cells, particularly against the human cancer cells mentioned above.

For example, the combination inhibits proliferation or survival of contacted cancer cells. A lower level of proliferation or survival of the contacted cancer cells compared to the non-contacted cancer cells supports the combination of PM01183, or a pharmaceutically acceptable salt thereof, and another anticancer drug selected from the list of drugs given above as being effective for treating a patient with cancer.

In another aspect, the invention provides for a method for inhibiting the growth of cancer cells comprising contacting said cancer cells with an effective amount of PM01183, or a pharmaceutically acceptable salt thereof, in combination with another anticancer drug selected from the list of drugs given above.

In another aspect, the invention provides for a method for inhibiting the growth of cancer cells comprising contacting said cancer cells with a synergistic combination of PM01183, or a pharmaceutically acceptable salt thereof, and another anticancer drug selected from the list of drugs given above, wherein said combination provides improved inhibition against cancer cell growth as compared to (i) PM01183, or a pharmaceutically acceptable salt thereof, in the absence of the other anticancer drug, or (ii) the other anticancer drug in the absence of PM01183.

In another aspect, the invention provides for a pharmaceutical composition comprising a synergistic combination of PM01183, or a pharmaceutically acceptable salt thereof, and another anticancer drug selected from the list of drugs given above for inhibiting the growth of cancer cells, wherein said combination provides improved inhibition against cancer cell growth as compared to (i) PM01183, or a pharmaceutically acceptable salt thereof, in the absence of the other anticancer drug, or (ii) the other anticancer drug in the absence of PM01183.

In another embodiment, the combination of PM01183, or a pharmaceutically acceptable salt thereof, and another anticancer drug selected from the list of drugs given above inhibits tumor growth or reduces the size of a tumor in vivo. In particular, the combination inhibits in vivo growth and/or reduces the size of carcinoma, sarcoma, leukemia, lymphoma, and myeloma. Preferably, the combination inhibits in vivo tumor growth of lung, sarcoma, malignant melanoma, bladder, prostate, pancreas, thyroid, gastric, ovarian, hepatoma, breast, colorectal, kidney, esophageal, neuroblastoma, brain, cervical, anal, testicular, leukemia, multiple myeloma and lymphoma tumours.

For example, these combinations inhibit tumor growth or reduce the size of human cancer xenografts, particularly human gastric, pancreas, sarcoma, lung, colorectal and ovary tumors xenografts, in animal models. A reduced growth or reduced size of human cancer xenografts in animal models administered with these combinations further supports the combination of PM01183, or a pharmaceutically acceptable salt thereof, and another anticancer drug selected from the list of drugs given above as being effective for treating a patient with cancer.

Therefore, in another aspect, the invention provides for a method for reducing the size of a tumor, comprising administering an effective amount of PM01183, or a pharmaceutically acceptable salt thereof, in combination with another anticancer drug selected from the list of drugs given above.

In another aspect, the invention provides for a method for inhibiting tumor growth, comprising administering an effective amount of PM01183, or a pharmaceutically acceptable salt thereof, in combination with another anticancer drug selected from the list of drugs given above.

The following examples further illustrate the invention. These examples should not be interpreted as a limitation of the scope of the invention.

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value.

EXAMPLES

Example 1. In Vitro Studies to Determine the Effect of PM01183 in Combination with Chemotherapeutic Agents on Human Lung Carcinoma Cell Lines The objective of this study was to determine the ability of PM01183 to potentiate the antitumor activity of chemotherapeutic agents used in the treatment of lung carcinoma.

The following agents were evaluated in combination with PM01183: oxaliplatin, carmustine, cyclophosphamide, mytomicin C (stock solutions of these compounds prepared in sterile double distilled water and stored at −20° C.), 5-fluorouracil (5-FU), gemcitabine, paclitaxel, docetaxel, vincristine, daunorubicin, actinomycin D, topotecan, etoposide, bortezomib, vorinostat, dacarbazine, temsirolimus, erlotinib, ET-743 and PM00104 (stock solutions of these compounds prepared in pure DMSO and stored at −20° C.). Additional serial dilutions were prepared in serum-free culture medium to achieve a final 4× concentration. Aliquots of 50 μL of each diluted compound were added per well.

A549 was the human lung carcinoma cell line selected for this assay. A549 cells were maintained in Dulbecco's modified Eagle's medium (DMEM) supplemented with 10% Fetal Bovine Serum (FBS), 2 mM L-glutamine and 100 units/mL of Penicillin-Streptomycin, at 37° C., 5% CO2 and 95% humidity.

The screening was performed in two parts:
a. In the first set of assays, $IC_{50}$ values were determined for each drug in A549 cells after 72 hours of drug exposure. Briefly, cells were harvested and seeded in 96 well microtiter plates at a density of 5,000 cells in 150 μL of culture medium and incubated for 24 hours in drug-free medium before treatment with vehicle alone or test compounds for 72 h.

The cytotoxic effect was measured by the MTT reduction assay, in which 3-(4,5-Dimethylthiazol-2-yl)-2,5-diphenyltetrazolium bromide, a tetrazole, which is reduced to purple formazan in the mitochondria of living cells, was used. MTT (50 μL of 1 mg/mL stock solution) was added to the wells and incubated for 8 hours at 37° C. until formazan crystals were formed. After gently removing the culture medium, DMSO was added to dissolve the insoluble purple formazan product into a colored solution. The absorbance of the wells was quantified by measuring the optical density at 540 nm. Results were expressed as percentage of control cell growth. The 1050 values (concentration of drug that produces a 50% inhibition of cell growth) used for the combination studies were calculated using Prism v5.02 software (GraphPad). The results were expressed as molar concentration and represented the average of 2-4 independent assays.

The $IC_{50}$ values (72 hours drug exposure) of each individual agent for the A549 tumor cell line are shown in table 1.

TABLE 1

| IC$_{50}$ values in molar concentration (M) for each of the agent | | | | | |
|---|---|---|---|---|---|
| Compound | IC$_{50}$ (M) | Compound | IC$_{50}$ (M) | Compound | IC$_{50}$ (M) |
| PM01183 | 3.60E−09 | Oxaliplatin | 9.00E−04 | 5-FU | 9.23E−05 |
| Gemcitabine | 2.80E−10 | Paclitaxel | 4.00E−08 | Docetaxel | 3.00E−09 |
| Vincristine | 2.50E−07 | Daunorubicin | 3.55E−07 | Mitomycin C | 2.49E−04 |
| Actinomycin D | 4.70E−09 | Topotecan | 8.00E−07 | Etoposide | 7.82E−07 |
| Bortezomib | 3.10E−09 | Vorinostat | 6.81E−06 | Cyclophosphamide | 1.00E−03 |
| Carmustine | 1.00E−03 | Dacarbazine | 6.00E−04 | Temsirolimus | 3.29E−06 |
| Erlotinib | 1.00E−05 | ET-743 | 2.25E−08 | PM00104 | 7.00E−09 | b. In a second set of assays, A549 human tumor cells were incubated with PM01183 in combination with each of the agents mentioned above. The previously obtained $IC_{50}$ values were used as starting concentrations for each compound (100% concentration). Arbitrary dilutions, as percentage of the initial $IC_{50}$ value (100%, 75%, 70%, 60%, 50%, 40%, 30%, 25%, and 0%), were performed for each pair of compounds and tested in combined complementary (opposite concentrations) dose-response curves as follows:

| IC$_{50}$ of PM01183 | IC$_{50}$ of Agent |
|---|---|
| 100% | 0% |
| 75% | 25% |
| 70% | 30% |
| 60% | 40% |
| 50% | 50% |
| 40% | 60% |
| 30% | 70% |
| 25% | 75% |
| 0% | 100% |

As a visual aid, response values were plotted on a scatter plot with dose ratios given on the x-axis and % response values on the y-axis. A horizontal line was drawn between the two endpoint response values (E.g. between the response values for 100% IC$_{50}$ PM01183 and 100% IC$_{50}$ standard chemotherapeutic agent). In cases where response values at the two endpoints were approximately equivalent, points lying above or below this predicted line of additivity could be interpreted as representing antagonistic or synergistic drug interaction, respectively.

The in vitro combinations of each drug with PM01183 have the potential to be synergistic, additive or antagonistic. Synergistic cytotoxicity to tumor cells is an optimal effect and implies that the combination of PM01183 with another drug is more effective than either drug alone.

Figure 20:
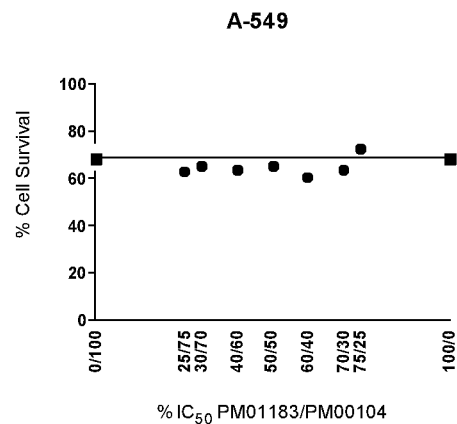

According to this assay, it was found that in A549 human lung carcinoma cell line:
a. The combination of PM01183 with oxaliplatin exhibited strong synergism (FIG. 1).
b. The combination of PM0183 with 5-fluorouracil (FIG. 2) and PM01183 with gemcitabine (FIG. 3) showed synergism at almost all dose ratios.
c. The combination of PM01183 with paclitaxel showed synergism (FIG. 4) at the 50/50-40/60 dose ratios, while the combination of PM01183 with docetaxel showed synergism (FIG. 5) at the 75/25 and 50/50 dose ratios, and the combination of PM01183 with vincristine exhibited synergism (FIG. 6) at almost all dose ratios.
d. The combination of PM01183 with daunorubicin (FIG. 7), PM01183 with mitomycin C (FIG. 8), and PM01183 with actinomycin D (FIG. 9) exhibited synergism at almost all dose ratios.
e. The combination of PM01183 with topotecan showed strong synergism (FIG. 10), while the combination of PM01183 with etoposide showed synergism (FIG. 11) at the 60/40 and 25/75 dose ratios.
f. The combination of PM01183 with bortezomib showed synergism (FIG. 12) at the 40/60-30/70 dose ratios.
g. The combination of PM01183 with vorinostat (FIG. 13) showed strong synergism at almost all dose ratios.

h. The combination of PM01183 with cyclophosphamide (FIG. 14) showed synergism at almost all dose ratios.
i. The combination of PM01183 with carmustine exhibited strong synergism (FIG. 15).
j. The combination of PM01183 with dacarbazine showed strong synergism (FIG. 16).
k. The combinations of PM01183 with temsirolimus showed synergism (FIG. 17) at almost all dose ratios.
l. The combination of PM01183 with erlotinib showed strong synergism (FIG. 18).
m. The combination of PM01183 with ET-743 showed synergism (FIG. 19) at the 75/25-60/40 and 30/70 dose ratios.
n. The combination of PM01183 with PM00104 (FIG. 20) showed synergism at almost all dose ratios.

Example 2. In Vitro Studies to Determine the Effect of PM01183 in Combination with Chemotherapeutic Agents on Human Sarcoma Cell Lines The objective of this study was to determine the ability of PM01183 to potentiate the antitumor activity of chemotherapeutic agents used in the treatment of sarcoma.

The following agents were evaluated in combination with PM01183: cisplatin, oxaliplatin, cyclophosphamide, mytomicin C (stock solutions of these compounds prepared in sterile double distilled water and stored at −20° C.), gemcitabine, docetaxel, vincristine, vinorelbine, daunorubicin, cytarabine, actinomycin D, topotecan, etoposide, vorinostat, dacarbazine, temsirolimus, erlotinib, aplidine, PM02734, ET-743 and PM00104 (stock solutions of these compounds prepared in pure DMSO and stored at −20° C.). Additional serial dilutions were prepared in serum-free culture medium to achieve a final 4× concentration. Aliquots of 50 µL of each diluted compound were added per well.

A673 was the human rhabdomyosarcoma cell line selected for this assay. A673 cells were maintained in Dulbecco's modified Eagle's medium (DMEM) supplemented with 10% Fetal Bovine Serum (FBS), 2 mM L-glutamine and 100 units/mL of Penicillin-Streptomycin, at 37° C., 5% CO2 and 95% humidity.

The screening was performed in two parts as disclosed in example 1:
a. In the first set of assays, $IC_{50}$ values were determined for each drug after 72 hours of drug exposure in the A673 tumor cell line.

The $IC_{50}$ values (72 hours drug exposure) of each individual agent for the A673 tumor cell line were calculated by using the same methodology disclosed in example 1 and are shown in table 2.

b. In a second set of assays, A673 human tumor cells were incubated with PM01183 in combination with each of the agents mentioned above in the same combination of unique $IC_{50}$ concentrations as those described in example 1.

Cell culture and cell plating were performed as described before and the cytotoxic effect was measured by the MTT Assay as disclosed in example 1.

Figure 21:
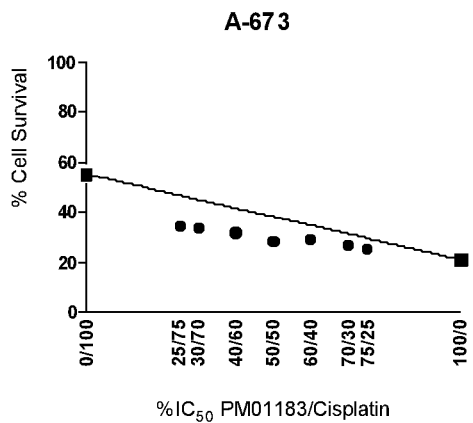
FIG. 21-41. In vitro activity data of PM01183 in combination with cisplatin, oxaliplatin, cytarabine, gemcitabine, docetaxel, vincristine, vinorelbine, daunorubicin, mitomycin C, actinomycin D, topotecan, etoposide, vorinostat, cyclophosphamide, dacarbazine, temsirolimus, erlotinib, aplidine, ET-743, PM02734 and PM00104 respectively against A673 cells.
Figure 22:
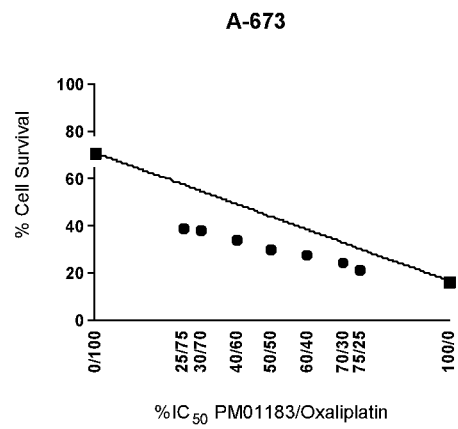
Figure 23:
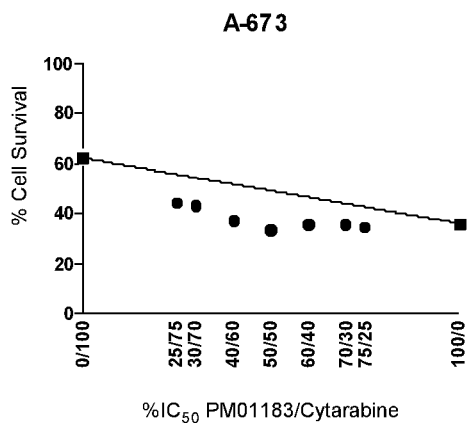
Figure 24:
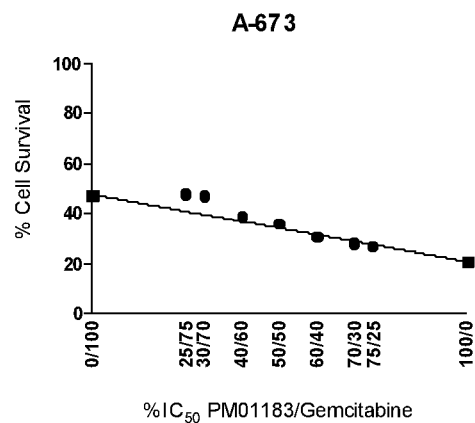
Figure 25:
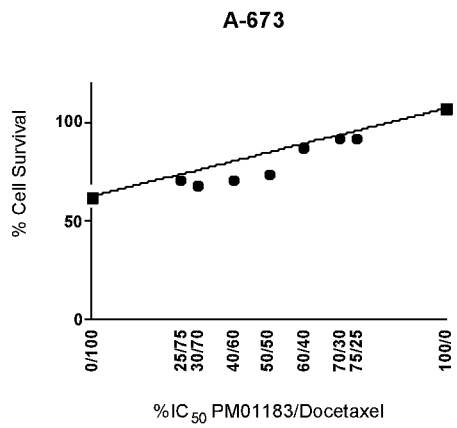
Figure 26:
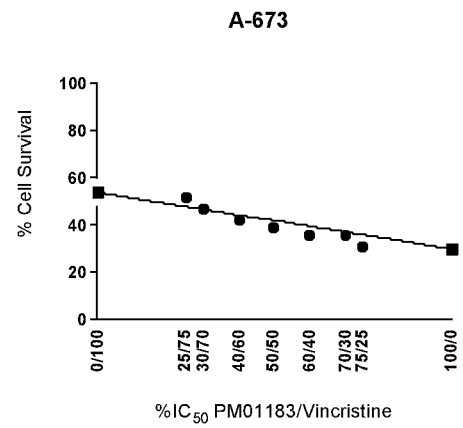
Figure 27:
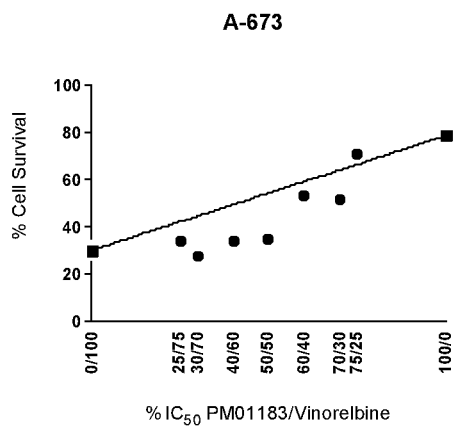
Figure 28:
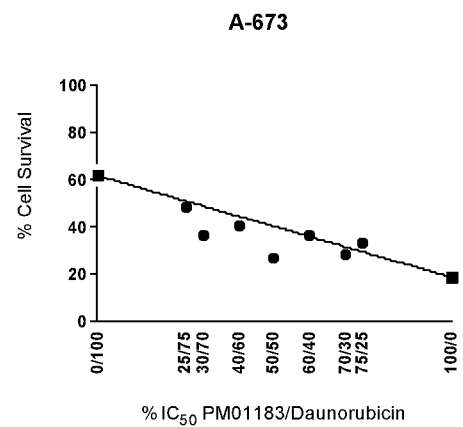
Figure 29:
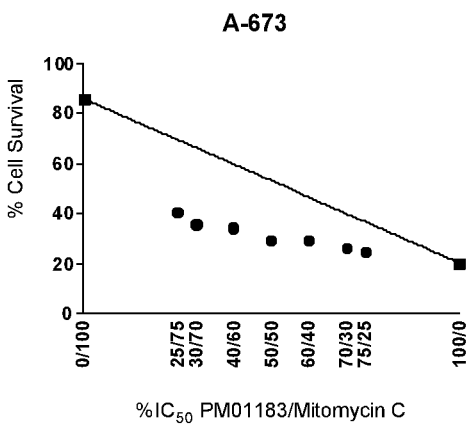
Figure 30:
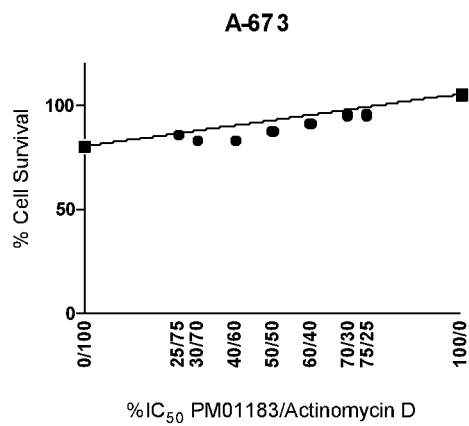
Figure 31:
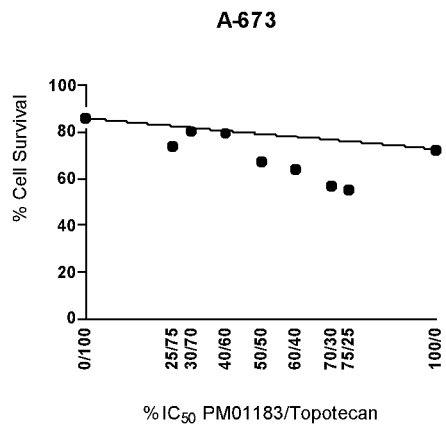
Figure 32:
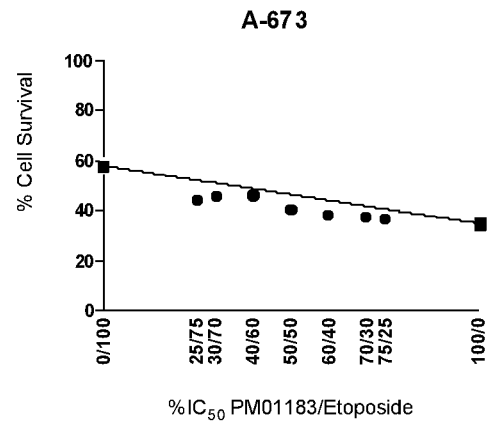
Figure 33:
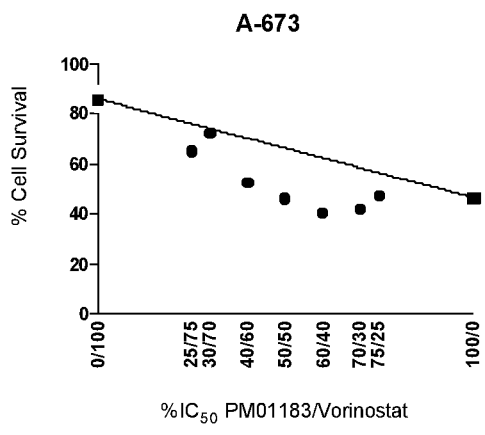
Figure 34:
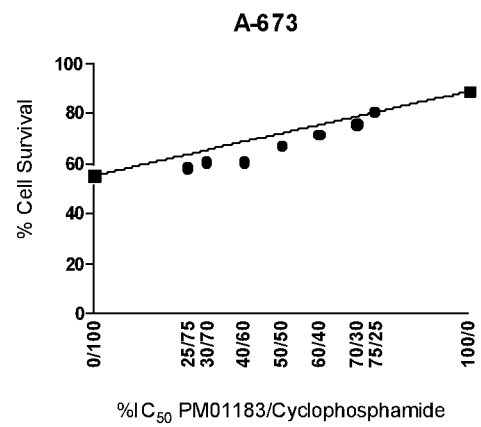
Figure 35:
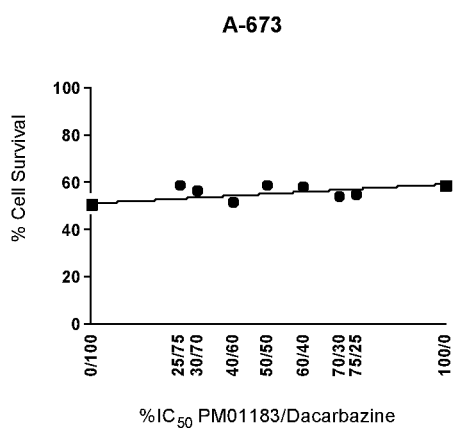
Figure 36:
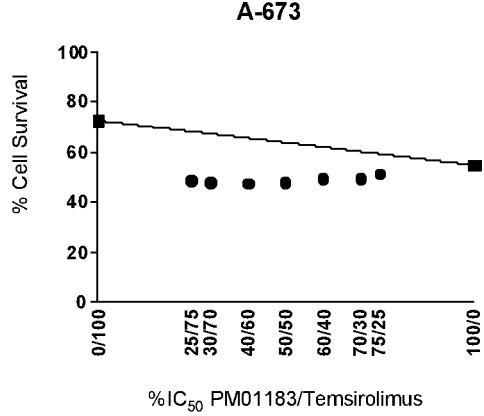
Figure 37:
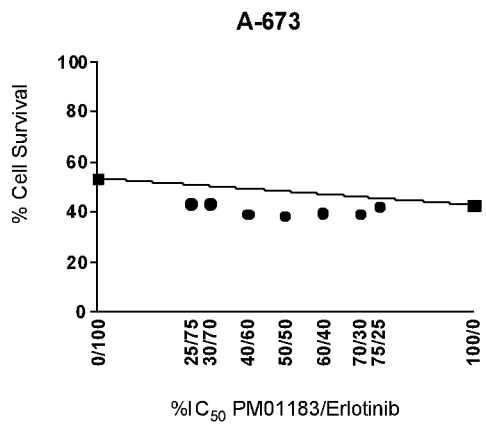
Figure 38:
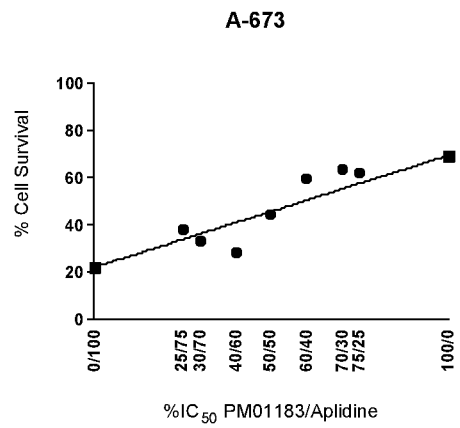
Figure 39:
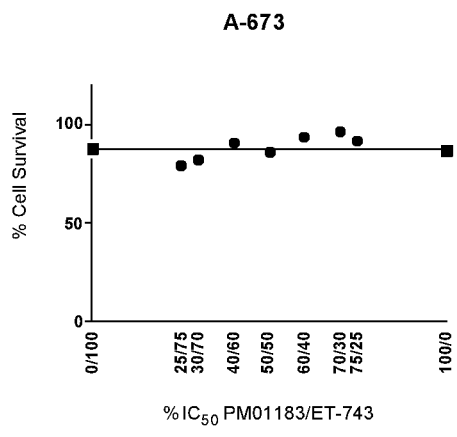
Figure 40:
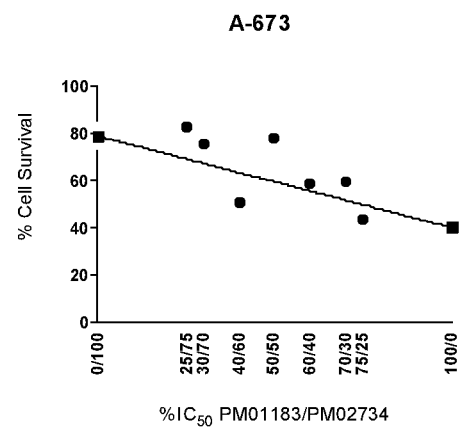
Figure 41:
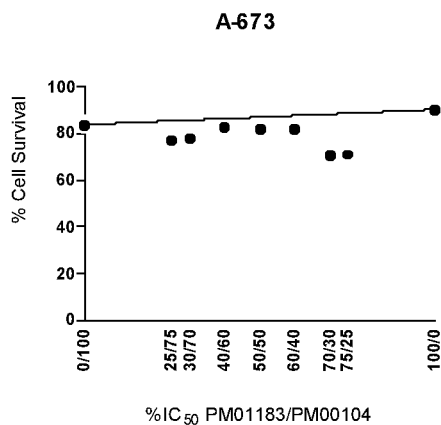

According to this assay, it was found that in A673 human sarcoma cell line:
a. The combination of PM01183 with cisplatin (FIG. 21) and PM01183 with oxaliplatin (FIG. 22) exhibited strong synergism.
b. The combination of PM01183 with cytarabine exhibited strong synergism (FIG. 23), while the combination of PM01183 with gemcitabine showed synergism (FIG. 24) at the 75/25-70/30 dose ratios.
c. The combination of PM01183 with docetaxel (FIG. 25), PM01183 with vincristine (FIG. 26) and PM01183 with vinorelbine (FIG. 27) showed synergism at almost all dose ratios.
d. The combination of PM01183 with daunorubicin (FIG. 28) and PM01183 with actinomycin D (FIG. 30) showed synergism at almost all dose ratios, while the combination of PM01183 with mitomycin C (FIG. 29) exhibited strong synergism.
e. The combination of PM01183 with topotecan (FIG. 31) and PM01183 with etoposide (FIG. 32) exhibited strong synergism at almost all dose ratios.
f. The combination of PM01183 with vorinostat (FIG. 33) showed strong synergism.
g. The combination of PM01183 with cyclophosphamide (FIG. 34) showed synergism at almost all dose ratios.
h. The combination of PM01183 with dacarbazine showed synergism (FIG. 35) at the 75/25-70/30 and 40/60 dose ratios.
i. The combinations of PM01183 with temsirolimus showed strong synergism (FIG. 36).
j. The combination of PM01183 with erlotinib exhibited strong synergism (FIG. 37).
k. The combination of PM01183 with aplidine showed synergism (FIG. 38) at the 50/50-30/70 dose ratios.
l. The combination of PM01183 with ET-743 (FIG. 39) showed synergism at the 30/70-25/75 dose ratios.
m. The combination of PM01183 with PM02734 (FIG. 40) showed synergism at the 75/25 and 40/60 dose ratios.
n. The combination of PM01183 with PM00104 exhibited synergism (FIG. 41).

TABLE 2

| $IC_{50}$ values in molar concentration (M) for each of the agent | | | | | |
|---|---|---|---|---|---|
| Compound | $IC_{50}$ (M) | Compound | $IC_{50}$ (M) | Compound | $IC_{50}$ (M) |
| PM01183 | 2.20E−09 | Cisplatin | 3.03−05 | Oxaliplatin | 7.80E−05 |
| Cytarabine | 1.97E−07 | Gemcitabine | 4.34E−10 | Docetaxel | 6.50E−10 |
| Vincristine | 8.60E−09 | Vinorelbine | 5.00E−08 | Daunorubicin | 5.20E−07 |
| Mitomycin C | 2.99E−06 | Actinomycin D | 9.56E−10 | Topotecan | 2.40E−08 |
| Etoposide | 1.55E−06 | Vorinostat | 2.16E−06 | Cyclophosphamide | 1.00E−03 |
| Dacarbazine | 3.00E−04 | Temsirolimus | 1.00E−06 | Erlotinib | 5.00E−05 |
| Aplidine | 2.16E−09 | ET-743 | 1.90E−09 | PM02734 | 3.60E−06 |
| PM00104 | 3.00E−09 | | | | |

Example 3. In Vitro Studies to Determine the Effect of PM01183 in Combination with Chemotherapeutic Agents on Human Malignant Melanoma Cell Lines The objective of this study was to determine the ability of PM01183 to potentiate the antitumor activity of chemotherapeutic agents used in the treatment of malignant melanoma.

The following agents were evaluated in combination with PM01183: cisplatin, mytomicin C (stock solutions of these compounds prepared in sterile double distilled water and stored at −20° C.), 5-fluorouracil, doxorubicin, daunorubicin, cytarabine, topotecan, irinotecan, methotrexate, etoposide, dacarbazine, temsirolimus, PM02734, ET-743 and PM00104 (stock solutions of these compounds prepared in pure DMSO and stored at −20° C.). Additional serial dilutions were prepared in serum-free culture medium to achieve a final 4× concentration. Aliquots of 50 μL of each diluted compound were added per well.

SK-MEL-2 was the human melanoma cell line selected for this assay. SK-MEL-2 cells were maintained in Minimum Essential Medium Eagle (MEME) supplemented with 10% Fetal Bovine Serum (FBS), 2 mM L-glutamine and 100 units/mL of Penicillin-Streptomycin, at 37° C., 5% CO2 and 95% humidity.

The screening was performed in two parts as disclosed in example 1:

a. In the first set of assays, $IC_{50}$ values were determined for each drug after 72 hours of drug exposure in the SK-MEL-2 tumor cell line.

The $IC_{50}$ values (72 hours drug exposure) of each individual agent for the SK-MEL-2 tumor cell line were calculated by using the same methodology disclosed in example 1 and are shown in table 3.

TABLE 3

$IC_{50}$ values in molar concentration (M) for each of the agent

| Compound | $IC_{50}$ (M) | Compound | $IC_{50}$ (M) | Compound | $IC_{50}$ (M) |
| --- | --- | --- | --- | --- | --- |
| PM01183 | 2.00E−09 | Cisplatin | 1.60E−04 | 5-FU | 7.00E−04 |
| Cytarabine | 3.89E−06 | Methotrexate | 1.00E−04 | Daunorubicin | 1.77E−07 |
| Doxorubicin | 3.00E−07 | Mitomycin C | 9.00E−07 | Topotecan | 4.37E−07 |
| Irinotecan | 1.80E−05 | Etoposide | 2.89E−06 | Dacarbazine | 6.30E−04 |
| Temsirolimus | 5.00E−05 | ET-743 | 2.00E−09 | PM02734 | 1.76E−06 |
| PM00104 | 2.00E−09 | | | | | b. In a second set of assays, SK-MEL-2 tumor cells were incubated with PM01183 in combination with each of the agents mentioned above in the same combination of unique $IC_{50}$ concentrations as those described in example 1.

Cell culture and cell plating were performed as described before and the cytotoxic effect was measured by the MTT Assay as disclosed in example 1.

Figure 42:
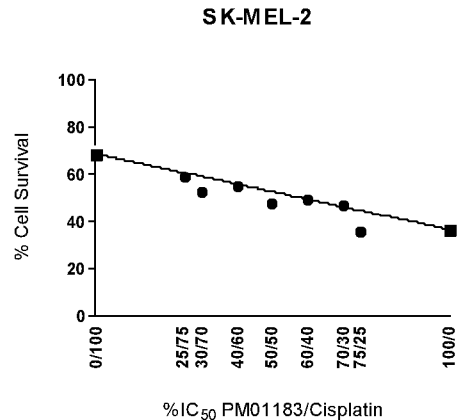
FIG. 42-56. In vitro activity data of PM01183 in combination with cisplatin, 5-fluorouracil, cytarabine, methotrexate, daunorubicin, doxorubicin, mitomycin C, topotecan, irinotecan, etoposide, dacarbazine, temsirolimus, ET-743, PM02734 and PM00104 respectively against SK-MEL-2 cells.
Figure 43:
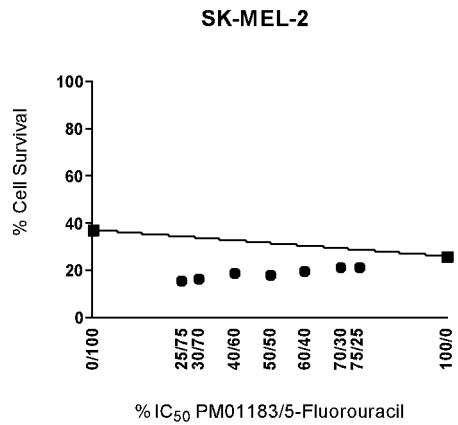
Figure 44:
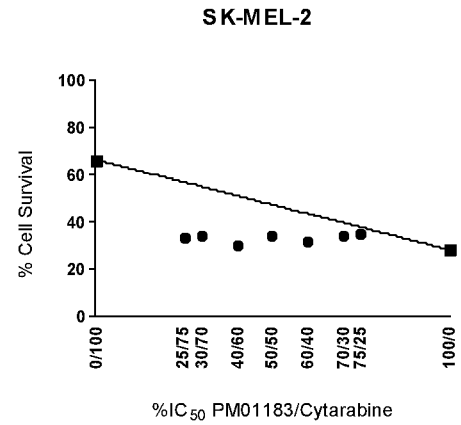
Figure 45:
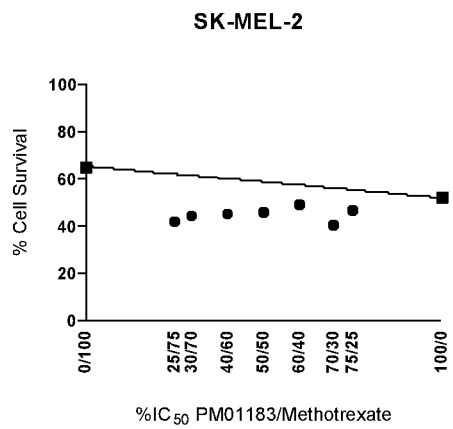
Figure 46:
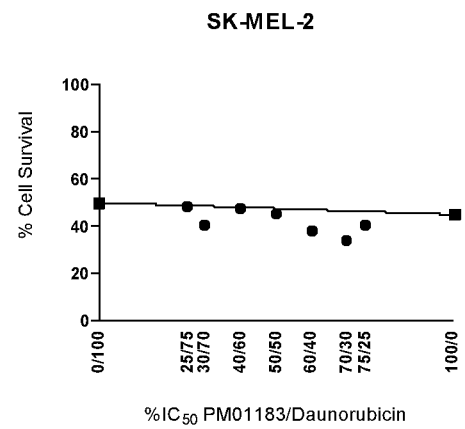
Figure 47:
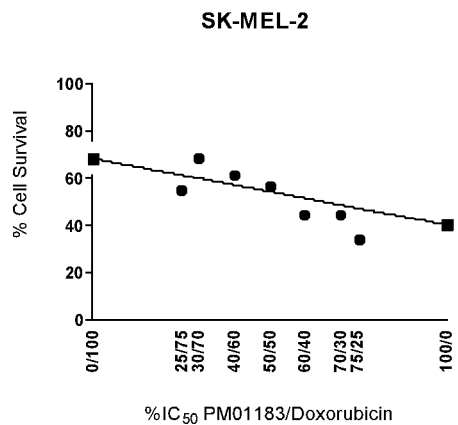
Figure 48:
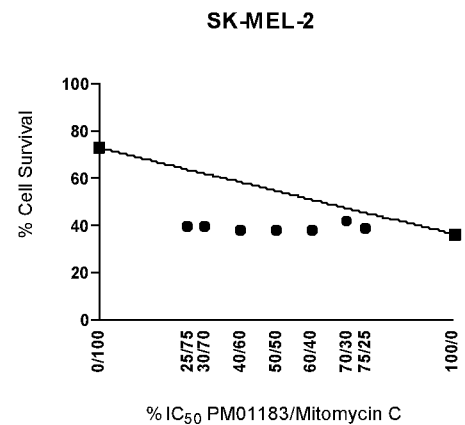
Figure 49:
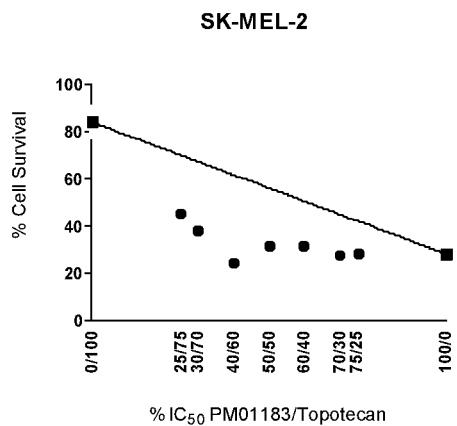
Figure 50:
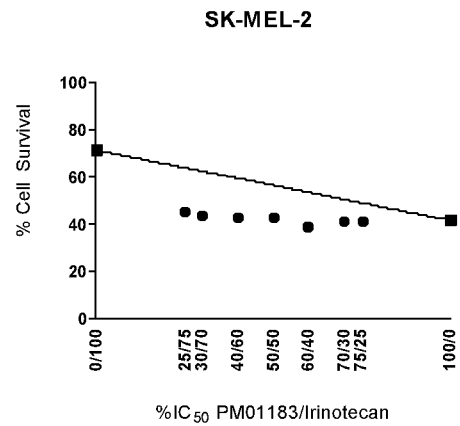
Figure 51:
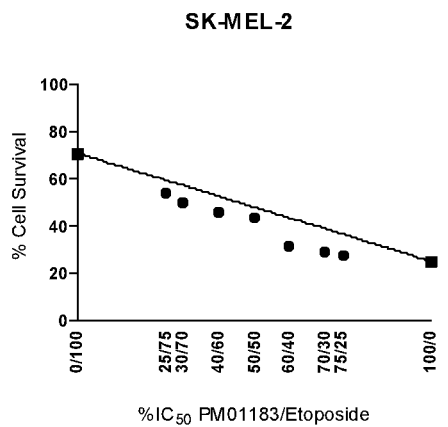
Figure 52:
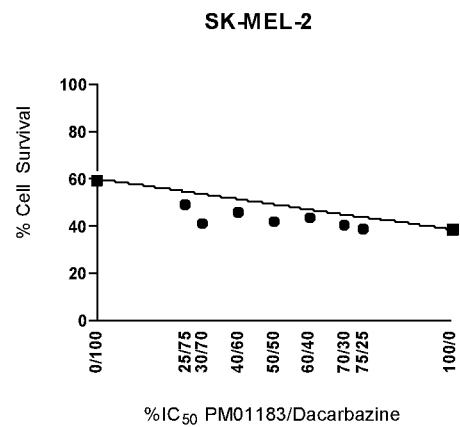
Figure 53:
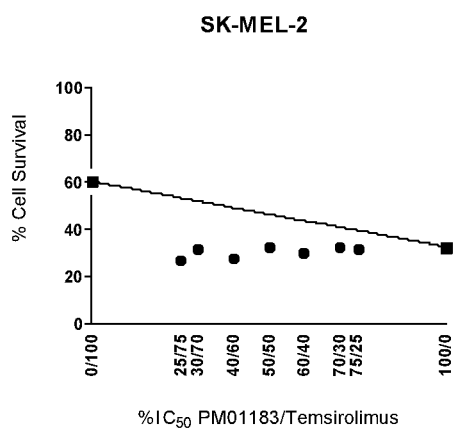
Figure 54:
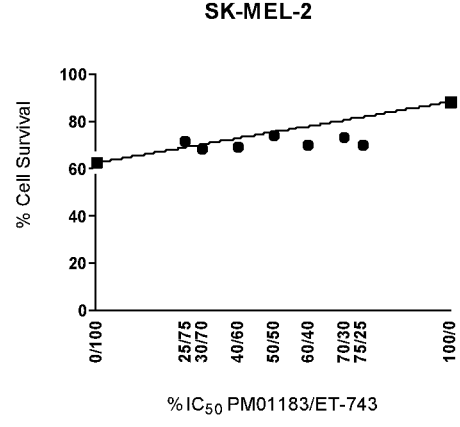
Figure 55:
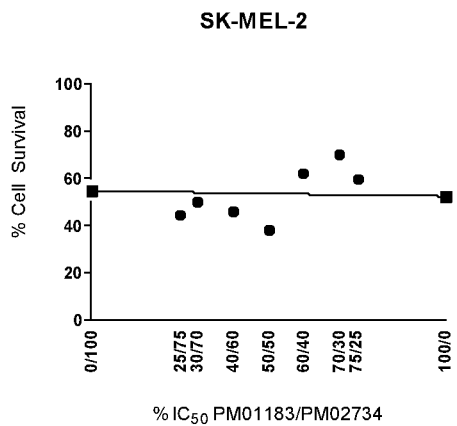
Figure 56:
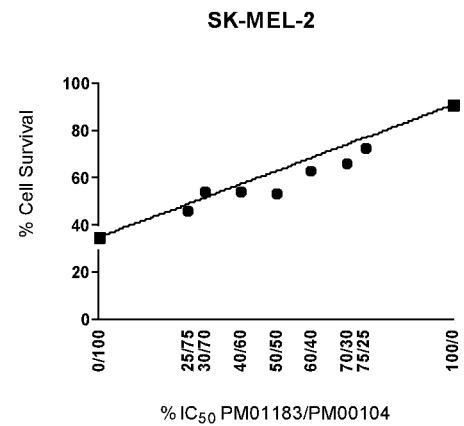

According to this assay, it was found that in SK-MEL-2 human melanoma cell line:

a. The combination of PM01183 with cisplatin (FIG. 42) showed synergism at the 75/25, 50/50 and 30/70 dose ratios.
b. The combination of PM01183 with 5-fluorouracil (FIG. 43), PM01183 with cytarabine (FIG. 44), and PM01183 with methotrexate (FIG. 45) exhibited strong synergism.
c. The combination of PM01183 with daunorubicin (FIG. 46) and PM01183 with doxorubicin (FIG. 47) showed synergism at almost all dose ratios, while the combination of PM01183 with mitomycin C (FIG. 48) exhibited strong synergism.
d. The combination of PM01183 with topotecan (FIG. 49), PM01183 with irinotecan (FIG. 50), and PM01183 with etoposide (FIG. 51) exhibited synergism and even strong synergism in some dose ratios.
e. The combination of PM01183 with dacarbazine showed synergism (FIG. 52).
f. The combinations of PM01183 with temsirolimus showed strong synergism (FIG. 53).
g. The combination of PM01183 with ET-743 (FIG. 54) showed synergism at almost all dose ratios.
h. The combination of PM01183 with PM02734 (FIG. 55) showed synergism at the 25/75-50/50 dose ratios.
i. The combination of PM01183 with PM00104 (FIG. 56) exhibited synergism at almost all dose ratios.

Example 4. In Vitro Studies to Determine the Effect of PM01183 in Combination with Chemotherapeutic Agents on Human Prostate Carcinoma Cell Lines The objective of this study was to determine the ability of PM01183 to potentiate the antitumor activity of chemotherapeutic agents used in the treatment of prostate cancer.

The following agents were evaluated in combination with PM01183: cisplatin, oxaliplatin, mytomicin C (stock solutions of these compounds prepared in sterile double distilled water and stored at −20° C.), 5-fluorouracil, gemcitabine, docetaxel, paclitaxel, vinorelbine, daunorubicin, cytarabine, doxorubicin, actinomycin D, topotecan, irinotecan, methotrexate, etoposide, vorinostat, temsirolimus, bortezomib, erlotinib, flutamide, PM02734, ET-743 and PM00104 (stock solutions of these compounds prepared in pure DMSO and stored at −20° C.). Additional serial dilutions were prepared in serum-free culture medium to achieve a final 4× concentration. Aliquots of 50 μL of each diluted compound were added per well.

PC-3 was the human prostate adenocarcinoma cell line selected for this assay. PC-3 cells were maintained in Roswell Park Memorial Institute medium (RPMI) supplemented with 10% Fetal Bovine Serum (FBS), 2 mM L-glutamine and 100 units/mL of Penicillin-Streptomycin, at 37° C., 5% CO2 and 95% humidity.

The screening was performed in two parts as disclosed in example 1:

a. In the first set of assays, $IC_{50}$ values were determined for each drug after 72 hours of drug exposure in the PC-3 tumor cell line.

The $IC_{50}$ values (72 hours drug exposure) of each individual agent for the PC-3 tumor cell line were calculated by using the same methodology disclosed in example 1 and are shown in table 4.

TABLE 4

$IC_{50}$ values in molar concentration (M) for each of the agent

| Compound | $IC_{50}$ (M) | Compound | $IC_{50}$ (M) | Compound | $IC_{50}$ (M) |
| --- | --- | --- | --- | --- | --- |
| PM01183 | 2.60E−09 | Cisplatin | 1.10E−04 | Oxaliplatin | 1.71E−04 |
| 5-FU | 1.00E−03 | Cytarabine | 4.00E−05 | Gemcitabine | 4.00E−07 |
| Methotrexate | 1.20E−04 | Docetaxel | 1.86E−08 | Paclitaxel | 9.00E−08 |
| Vinorelbine | 1.00E−05 | Daunorubicin | 1.15E−06 | Doxorubicin | 1.48E−06 |
| Mitomycin C | 1.00E−05 | Actinomycin D | 1.00E−08 | Topotecan | 6.33E−07 |

TABLE 4-continued

IC$_{50}$ values in molar concentration (M) for each of the agent

| Compound | IC$_{50}$ (M) | Compound | IC$_{50}$ (M) | Compound | IC$_{50}$ (M) |
|---|---|---|---|---|---|
| Irinotecan | 7.00E−05 | Etoposide | 4.80E−05 | Bortezomib | 8.00E−07 |
| Vorinostat | 3.90E−06 | Flutamide | 4.90E−05 | Temsirolimus | 5.00E−07 |
| Erlotinib | 2.33E−04 | ET-743 | 8.00E−09 | PM02734 | 5.40E−07 |
| PM00104 | 7.10E−09 | | | | | b. In a second set of assays, PC-3 human tumor cells were incubated with PM01183 in combination with each of the agents mentioned above in the same combination of unique IC$_{50}$ concentrations as those described in example 1.

Cell culture and cell plating were performed as described before and the cytotoxic effect was measured by the MTT Assay as disclosed in examples 1.

Figure 57:
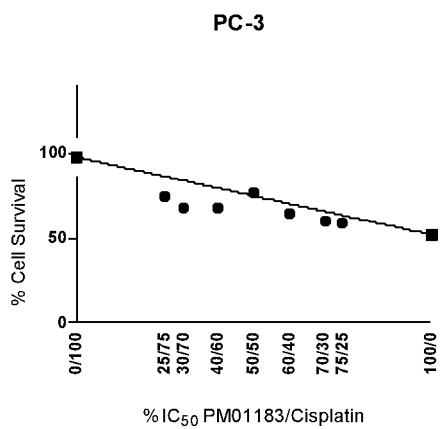
FIG. 57-80. In vitro activity data of PM01183 in combination with cisplatin, oxaliplatin, 5-fluorouracil, cytarabine, gemcitabine, methotrexate, docetaxel, paclitaxel, vinorelbine, daunorubicin, doxorubicin, mitomycin C, actinomycin D, topotecan, irinotecan, etoposide, bortezomib, vorinostat, flutamide, temsirolimus, erlotinib, ET-743, PM02734 and PM00104 respectively against PC-3 cells.
Figure 58:
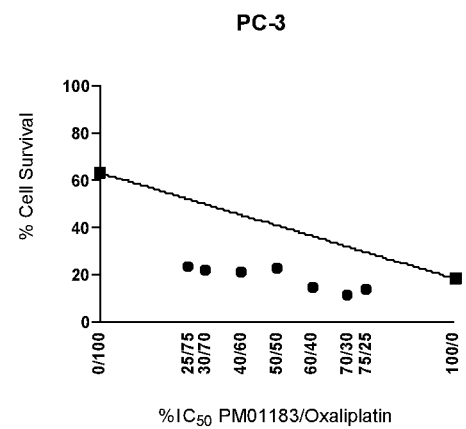
Figure 59:
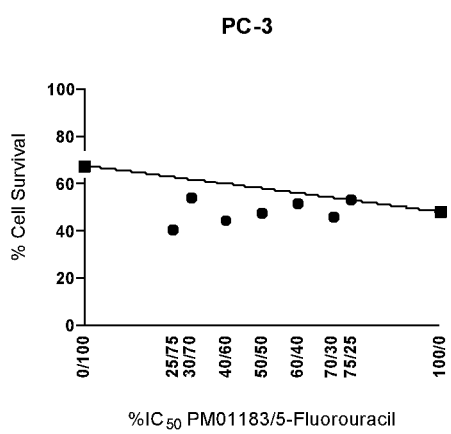
Figure 60:
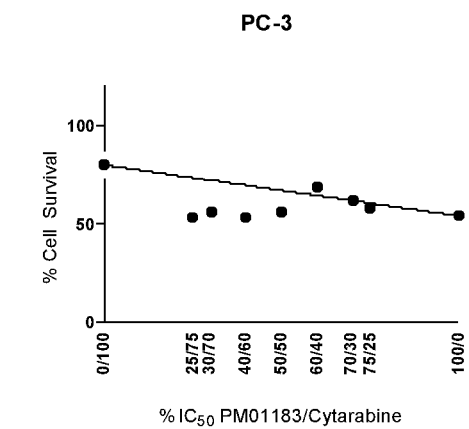
Figure 61:
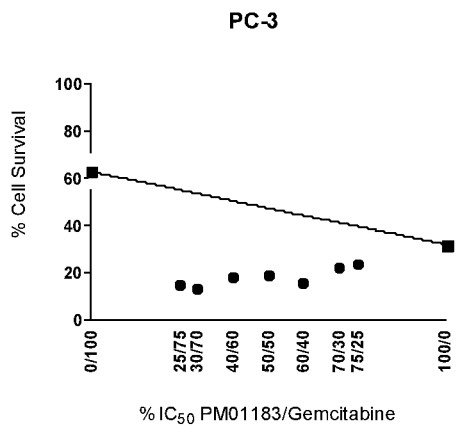
Figure 62:
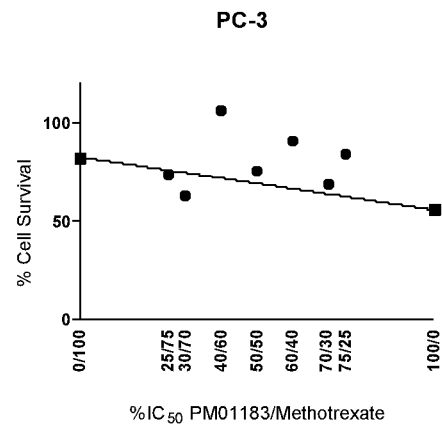
Figure 63:
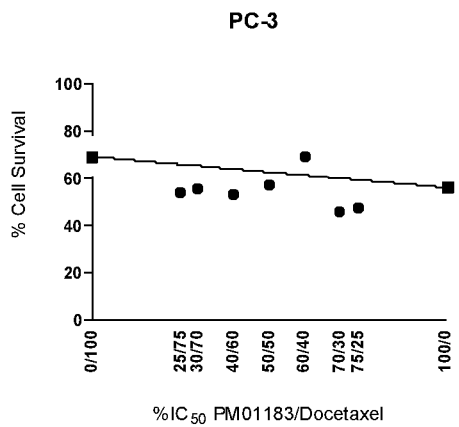
Figure 64:
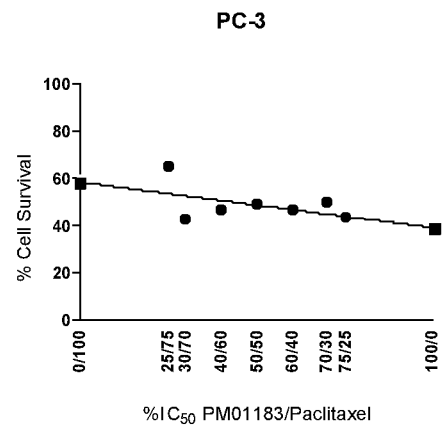
Figure 65:
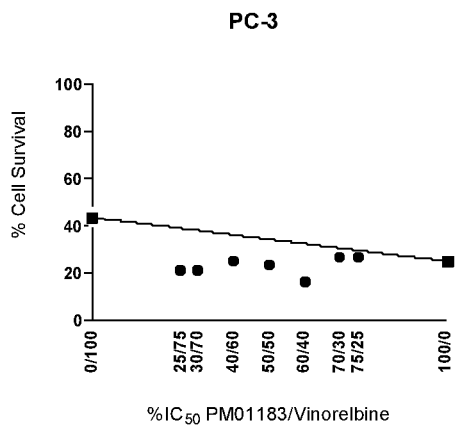
Figure 66:
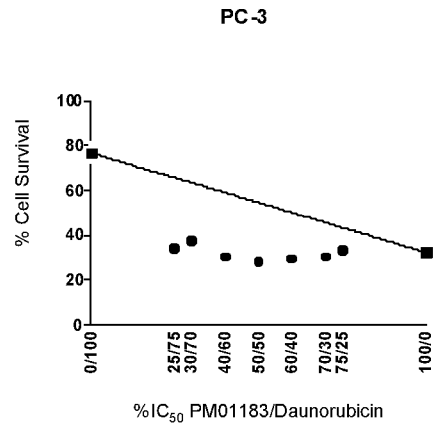
Figure 67:
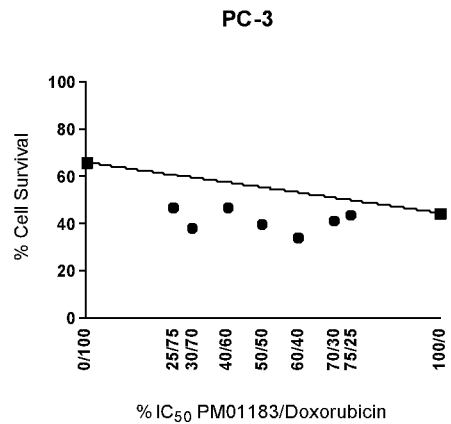
Figure 68:
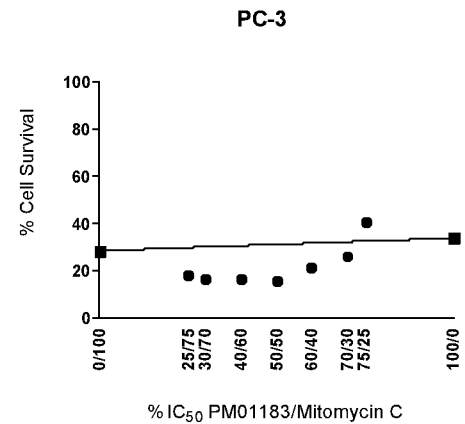
Figure 69:
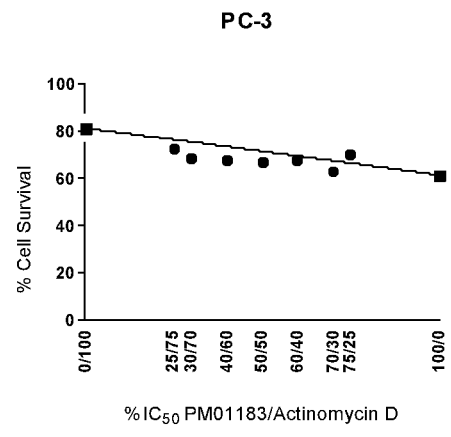
Figure 70:
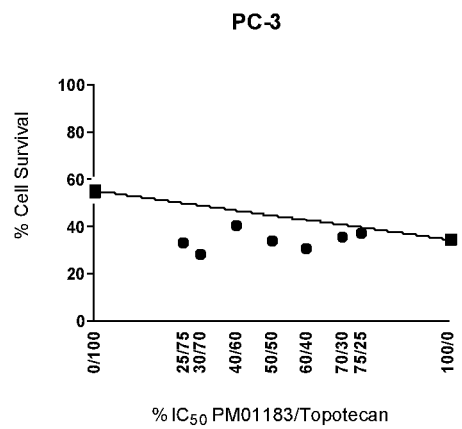
Figure 71:
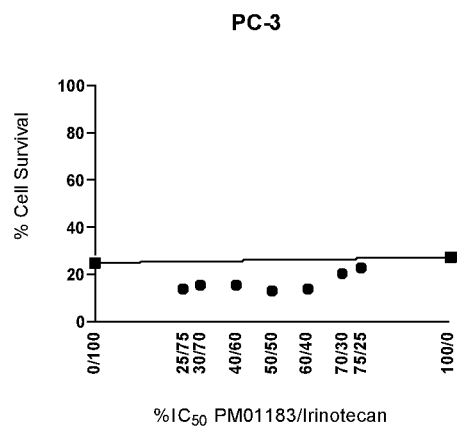
Figure 72:
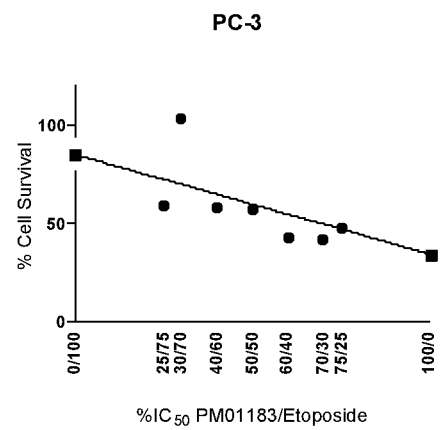
Figure 73:
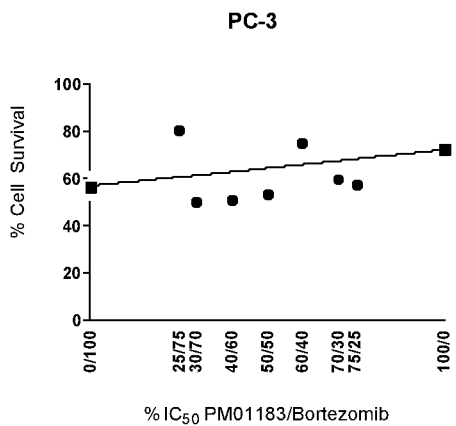
Figure 74:
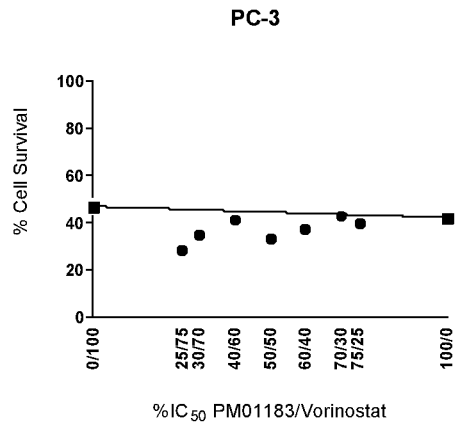
Figure 75:
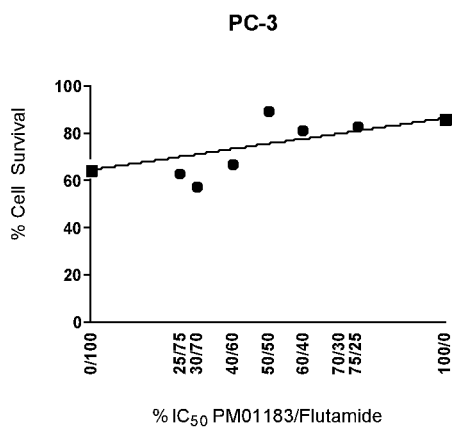
Figure 76:
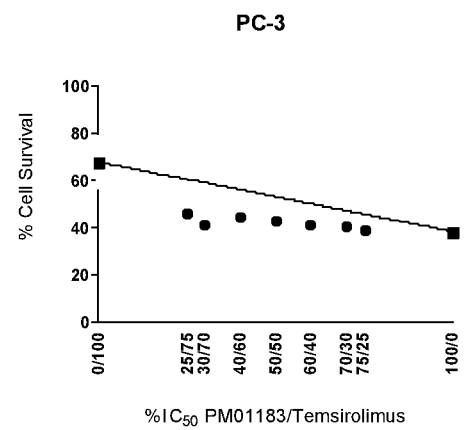
Figure 77:
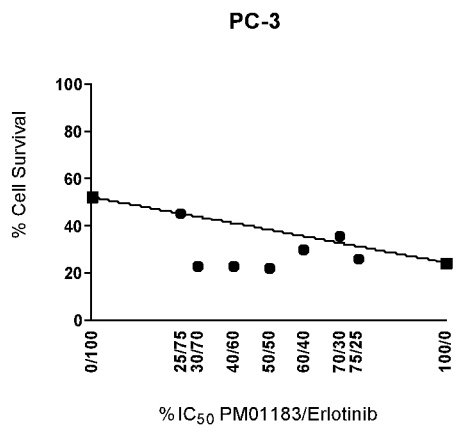
Figure 78:
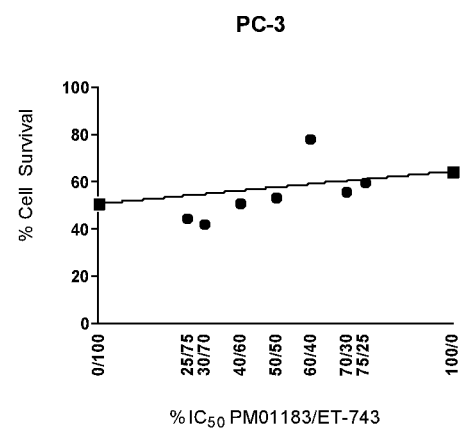
Figure 79:
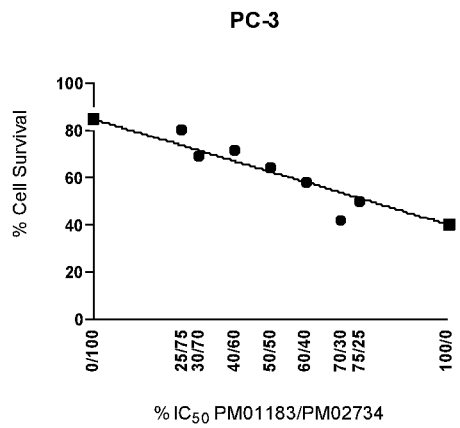
Figure 80:
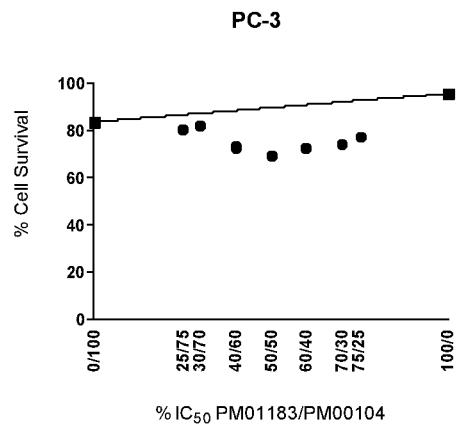

According to this assay it was found that in PC-3 human prostate cancer cell line:

a. The combination of PM01183 with cisplatin (FIG. 57) showed synergism at almost all dose ratios, while the combination of PM01183 with oxaliplatin (FIG. 58) exhibited strong synergism.

b. The combination of PM01183 with 5-fluorouracil (FIG. 59) and PM01183 with cytarabine (FIG. 60) exhibited synergism at almost all dose ratios, and the combination of PM01183 with gemcitabine exhibited strong synergism (FIG. 61). Finally, the combination of PM01183 with methotrexate showed synergism (FIG. 62) at the 30/70-25/75 dose ratios.

c. The combination of PM01183 with docetaxel showed synergism (FIG. 63) at almost all dose ratios, while the combination of PM01183 with paclitaxel (FIG. 64) showed synergism at the 40/60-30/70 dose ratios. The combination of PM01183 with vinorelbine (FIG. 65) showed strong synergism.

d. The combination of PM01183 with daunorubicin (FIG. 66) and PM01183 with doxorubicin (FIG. 67) exhibited strong synergism. The combination of PM01183 with mitomycin C (FIG. 68) and PM01183 with actinomycin D (FIG. 69) showed synergism at almost all dose ratios.

e. The combination of PM01183 with topotecan (FIG. 70) and PM01183 with irinotecan (FIG. 71) exhibited strong synergism, while the combination of PM01183 with etoposide (FIG. 72) showed synergism at almost all dose ratios.

f. The combination of PM01183 with bortezomib (FIG. 73) showed synergism at almost all dose ratios.

g. The combination of PM01183 with vorinostat (FIG. 74) showed synergism.

h. The combination of PM01183 with flutamide (FIG. 75) showed synergism at the 40/60-25/75 dose ratios.

i. The combination of PM01183 with temsirolimus exhibited strong synergism (FIG. 76).

j. The combination of PM01183 with erlotinib (FIG. 77) showed synergism at almost all dose ratios.

k. The combination of PM01183 with ET-743 (FIG. 78) showed synergism at almost all dose ratios.

l. The combination of PM01183 with PM02734 (FIG. 79) showed synergism at the 75/25-70/30 and 30/70 dose ratios.

m. The combination of PM01183 with PM00104 exhibited strong synergism (FIG. 80).

Example 5. In Vitro Studies to Determine the Effect of PM01183 in Combination with Chemotherapeutic Agents on Human Pancreas Carcinoma Cell Lines The objective of this study was to determine the ability of PM01183 to potentiate the antitumor activity of chemotherapeutic agents used in the treatment of pancreatic carcinoma.

The following agents were evaluated in combination with PM01183: cisplatin, oxaliplatin, (stock solutions of these compounds prepared in sterile double distilled water and stored at −20° C.), gemcitabine, daunorubicin, cytarabine, doxorubicin, actinomycin D, topotecan, irinotecan, methotrexate, etoposide, vorinostat, temsirolimus, bortezomib, erlotinib, PM02734, ET-743 and PM00104 (stock solutions of these compounds prepared in pure DMSO and stored at −20° C.). Additional serial dilutions were prepared in serum-free culture medium to achieve a final 4× concentration. Aliquots of 50 μL of each diluted compound were added per well.

PANC-1 was the human pancreatic carcinoma cell line selected for this assay. PANC-1 cells were maintained in Roswell Park Memorial Institute medium (RPMI) supplemented with 10% Fetal Bovine Serum (FBS), 2 mM L-glutamine and 100 units/mL of Penicillin-Streptomycin, at 37° C., 5% CO2 and 95% humidity.

The screening was performed in two parts as disclosed in example 1:

a. In the first set of assays, IC$_{50}$ values were determined for each drug after 72 hours of drug exposure in the PANC-1 tumor cell line.

The IC$_{50}$ values (72 hours drug exposure) of each individual agent for the PANC-1 tumor cell line were calculated by using the same methodology disclosed in example 1 and are shown in table 5.

TABLE 5

IC$_{50}$ values in molar concentration (M) for each of the agent

| Compound | IC$_{50}$ (M) | Compound | IC$_{50}$ (M) | Compound | IC$_{50}$ (M) |
|---|---|---|---|---|---|
| PM01183 | 2.80E−09 | Cisplatin | 1.47E−04 | Oxaliplatin | 1.84E−04 |
| Cytarabine | 9.00E−05 | Gemcitabine | 1.00E−06 | Methotrexate | 1.00E−05 |
| Daunorubicin | 8.69E−07 | Doxorubicin | 3.45E−06 | Actinomycin D | 2.20E−08 |
| Topotecan | 4.37E−06 | Irinotecan | 9.00E−05 | Etoposide | 1.00E−05 |
| Bortezomib | 4.16E−07 | Vorinostat | 6.05E−06 | Temsirolimus | 1.00E−05 |
| Erlotinib | 4.16E−07 | ET-743 | 2.10E−08 | PM02734 | 9.00E−06 |
| PM00104 | 7.89E−09 | | | | | b. In a second set of assays, PANC-1 human tumor cells were incubated with PM01183 in combination with each of the agents mentioned above in the same combination of unique IC$_{50}$ concentrations as those described in example 1.

Cell culture and cell plating were performed as described before and the cytotoxic effect was measured by the MTT Assay as disclosed example 1.

Figure 81:
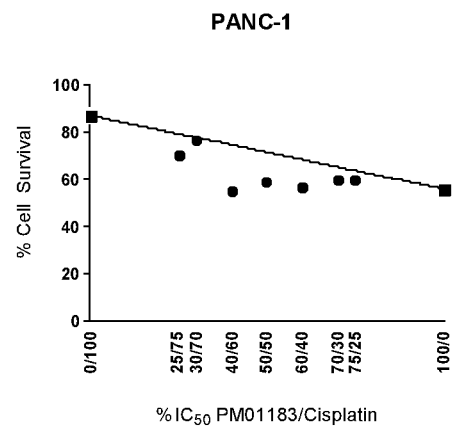
FIG. 81-98. In vitro activity data of PM01183 in combination with cisplatin, oxaliplatin, cytarabine, gemcitabine, methotrexate, daunorubicin, doxorubicin, actinomycin D, topotecan, irinotecan, etoposide, bortezomib, vorinostat, temsirolimus, erlotinib, ET-743, PM02734 and PM00104 respectively against PANC-1 cells.
Figure 82:
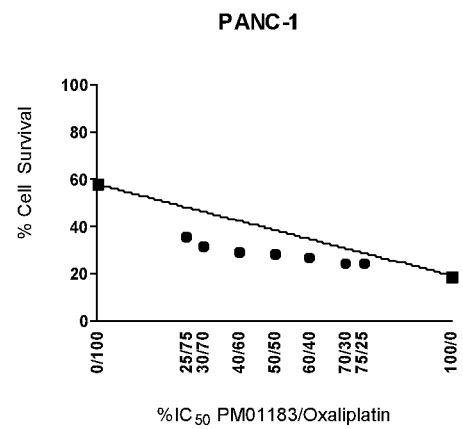
Figure 83:
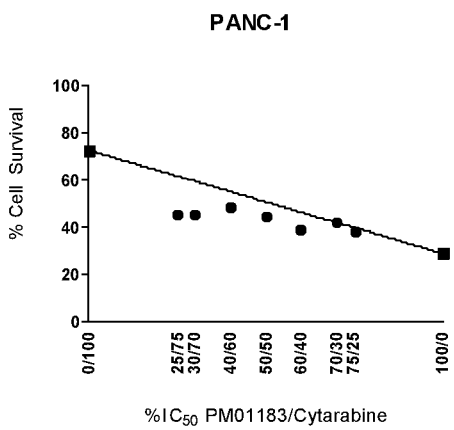
Figure 84:
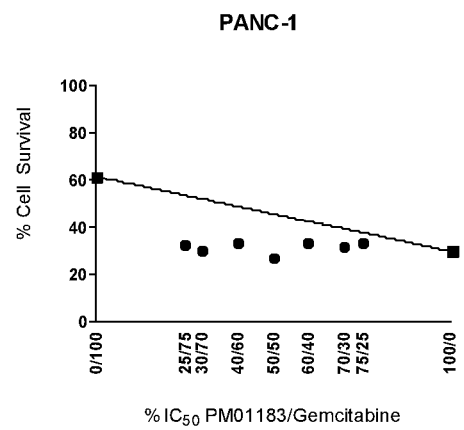
Figure 85:
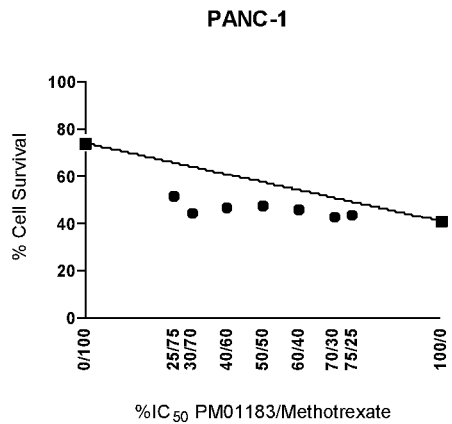
Figure 86:
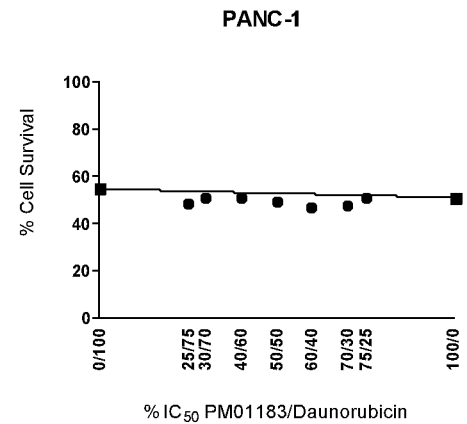
Figure 87:
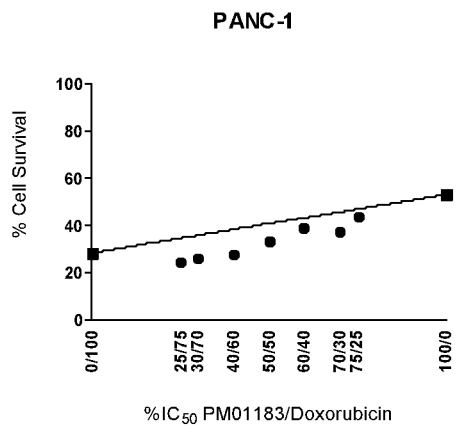
Figure 88:
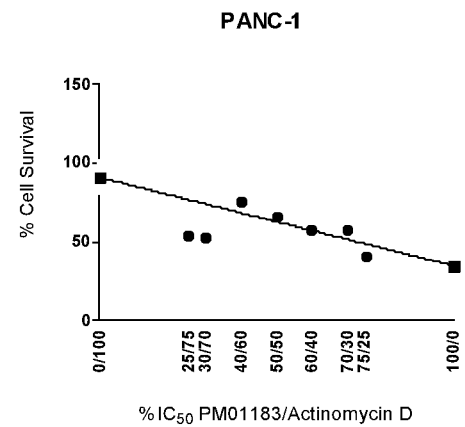
Figure 89:
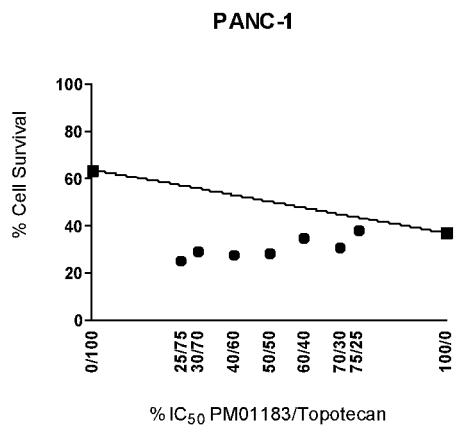
Figure 90:
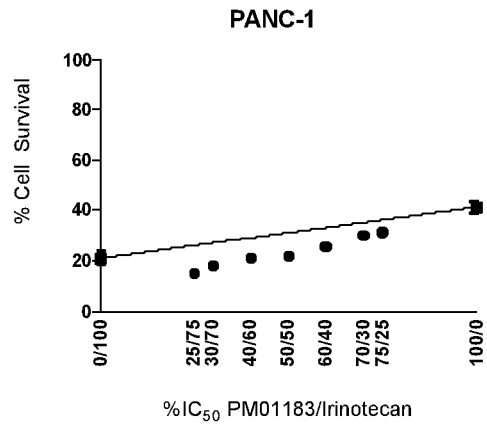
Figure 91:
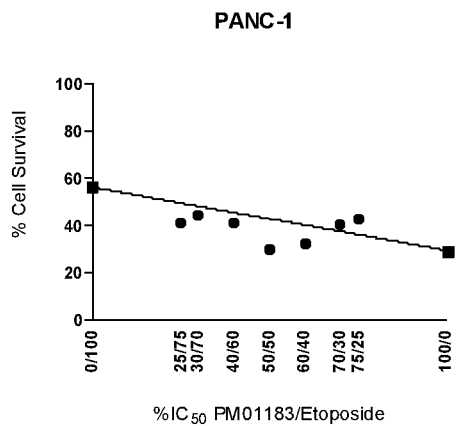
Figure 92:
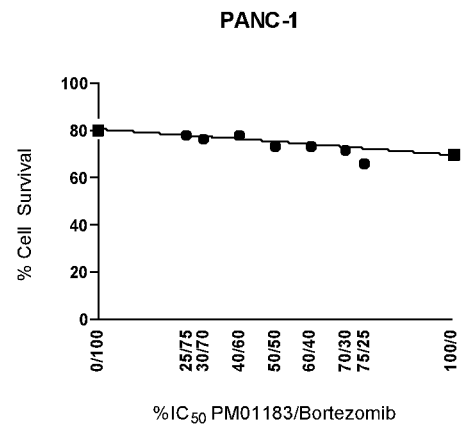
Figure 93:
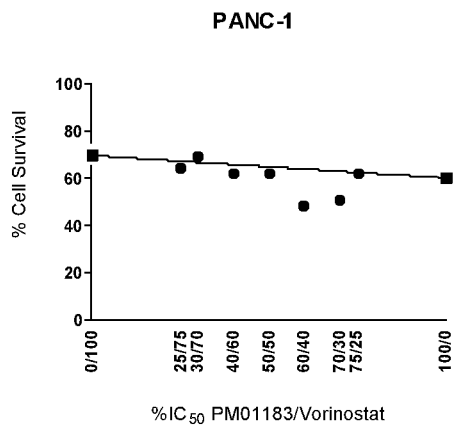
Figure 94:
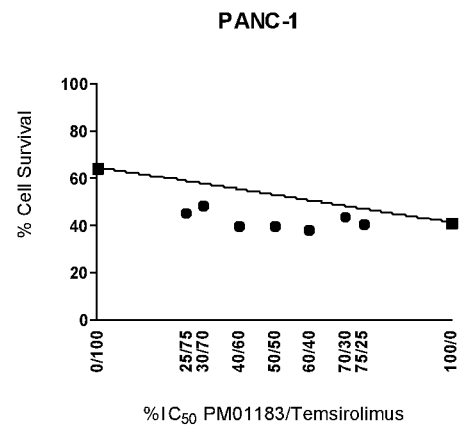
Figure 95:
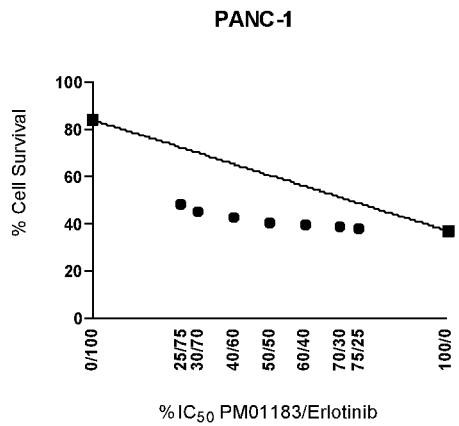
Figure 96:
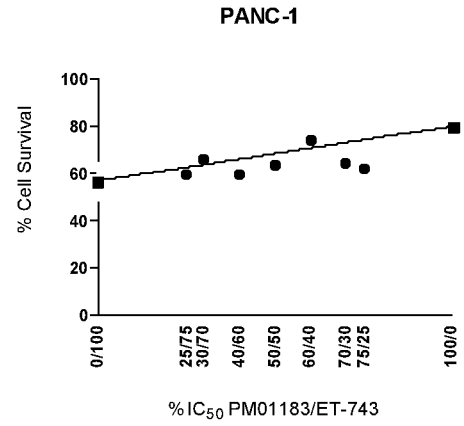
Figure 97:
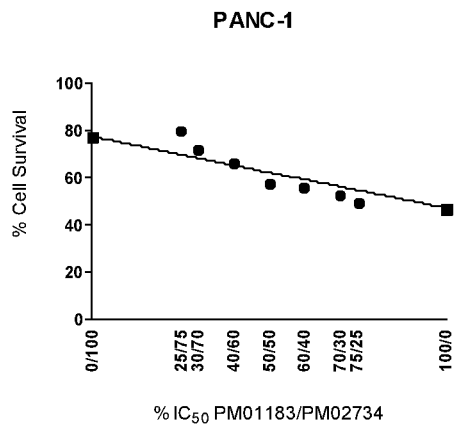
Figure 98:
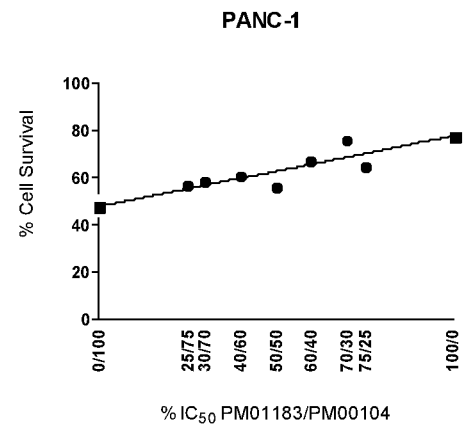

According to this assay it was found that in PANC-1 human pancreas carcinoma cell line:

a. The combination of PM01183 with cisplatin (FIG. 81) and PM01183 with oxaliplatin (FIG. 82) exhibited strong synergism.

b. The combination of PM01183 with cytarabine (FIG. 83) showed synergism at almost all dose ratios, while the combination of PM01183 with gemcitabine (FIG. 84) and PM01183 with methotrexate (FIG. 85) exhibited strong synergism.

c. The combination of PM01183 with daunorubicin (FIG. 86) and PM01183 with doxorubicin (FIG. 87) exhibited synergism, while the combination of PM01183 with actinomycin D (FIG. 88) showed synergism at the 75/25 and 30/70-25/75 dose ratios.

d. The combination of PM01183 with topotecan (FIG. 89) and PM01183 with irinotecan (FIG. 90) exhibited strong synergism, while the combination of PM01183 with etoposide (FIG. 91) showed synergism at almost all dose ratios.

e. The combination of PM01183 with bortezomib (FIG. 92) showed synergism at the 75/25-70/30 and 50/50 dose ratios.

f. The combination of PM01183 with vorinostat (FIG. 93) showed synergism at almost all dose ratios.

g. The combination of PM01183 with temsirolimus exhibited strong synergism (FIG. 94).

h. The combination of PM01183 with erlotinib exhibited strong synergism (FIG. 95).

i. The combination of PM01183 with ET-743 (FIG. 96) showed synergism at almost all dose ratios.

j. The combination of PM01183 with PM02734 (FIG. 97) showed synergism at almost all dose ratios.

k. The combination of PM01183 with PM00104 showed synergism (FIG. 98) at the 75/25 and 50/50 dose ratios.

Example 6. In Vitro Studies to Determine the Effect of PM01183 in Combination with Chemotherapeutic Agents on Human Gastric Carcinoma Cell Lines The objective of this study was to determine the ability of PM01183 to potentiate the antitumor activity of chemotherapeutic agents used in the treatment of gastric cancer.

The following agents were evaluated in combination with PM01183: cisplatin, oxaliplatin, cyclophosphamide (stock solutions of these compounds prepared in sterile double distilled water and stored at −20° C.), 5-fluorouracil, gemcitabine, paclitaxel, vincristine, vinorelbine, daunorubicin, dacarbazine, cytarabine, doxorubicin, actinomycin D, topotecan, irinotecan, methotrexate, etoposide, vorinostat, temsirolimus, bortezomib, erlotinib, aplidine, PM02734, ET-743 and PM00104 (stock solutions of these compounds prepared in pure DMSO and stored at −20° C.). Additional serial dilutions were prepared in serum-free culture medium to achieve a final 4× concentration. Aliquots of 50 µL of each diluted compound were added per well.

HGC-27 was the human gastric carcinoma cell line selected for this assay. HGC-27 cells were maintained in Iscove's modified Dulbeco's medium (IDMD) supplemented with 10% Fetal Bovine Serum (FBS), 2 mM L-glutamine and 100 units/mL of Penicillin-Streptomycin, at 37° C., 5% CO2 and 95% humidity.

The screening was performed in two parts as disclosed in example 1:

a. In the first set of assays, $IC_{50}$ values were determined for each drug after 72 hours of drug exposure in the HGC-27 tumor cell line.

The $IC_{50}$ values (72 hours drug exposure) of each individual agent for the HGC-27 tumor cell line were calculated by using the same methodology disclosed in example 1 and are shown in table 6.

TABLE 6

| IC$_{50}$ values in molar concentration (M) for each of the agent ||||||
|---|---|---|---|---|---|
| Compound | IC$_{50}$ (M) | Compound | IC$_{50}$ (M) | Compound | IC$_{50}$ (M) |
| PM01183 | 8.50E−10 | Cisplatin | 8.00E−05 | Oxaliplatin | 1.06E−04 |
| 5-FU | 1.00E−05 | Cytarabine | 5.00E−05 | Gemcitabine | 5.34E−10 |
| Methotrexate | 3.30E−08 | Paclitaxel | 5.00E−09 | Vincristine | 1.25E−08 |
| Vinorelbine | 6.50E−08 | Daunorubicin | 3.72E−07 | Doxorubicin | 5.40E−08 |
| Actinomycin D | 3.74E−09 | Topotecan | 8.08E−07 | Irinotecan | 4.00E−06 |
| Etoposide | 2.90E−06 | Bortezomib | 5.60E−09 | Vorinostat | 1.20E−06 |
| Cyclophosphamide | 1.00E−03 | Dacarbazine | 3.46E−04 | Temsirolimus | 1.50E−07 |
| Erlotinib | 7.50E−06 | Aplidine | 9.00E−09 | ET-743 | 5.80E−09 |
| PM02734 | 9.50E−07 | PM00104 | 3.20E−09 | | | b. In a second set of assays, HGC-27 human tumor cells were incubated with PM01183 in combination with each of the agents mentioned above in the same combination of unique $IC_{50}$ concentrations as those described in example 1.

Cell culture and cell plating were performed, as described before and the cytotoxic effect was measured by the MTT Assay, as disclosed in example 1.

Figure 99:
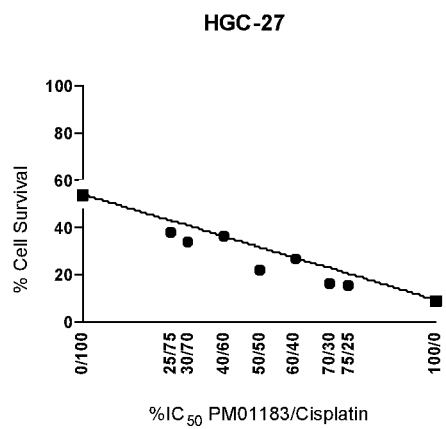
FIG. 99-123. In vitro activity data of PM01183 in combination with cisplatin, oxaliplatin, 5-fluorouracil, cytarabine, gemcitabine, methotrexate, paclitaxel, vincristine, vinorelbine, daunorubicin, doxorubicin, actinomycin D, topotecan, irinotecan, etoposide, bortezomib, vorinostat, cyclophosphamide, dacarbazine, temsirolimus, erlotinib, aplidine, ET-743, PM02734 and PM00104 respectively against HGC-27 cells.
Figure 100:
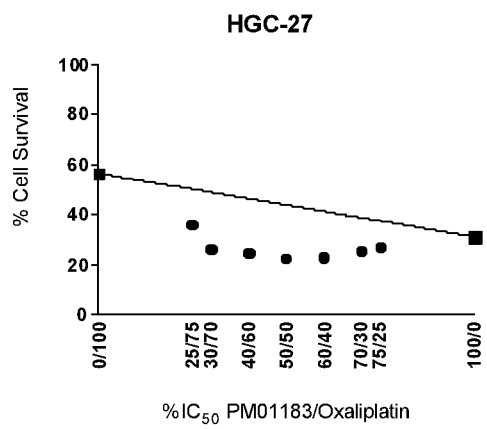
Figure 101:
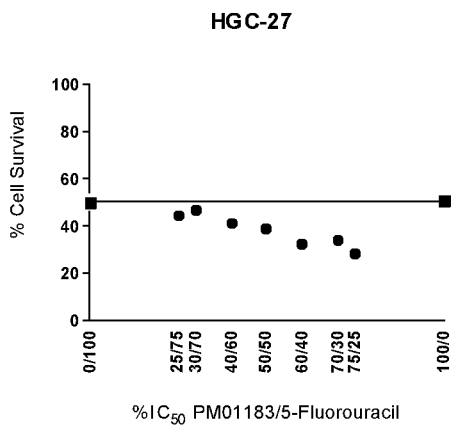
Figure 102:
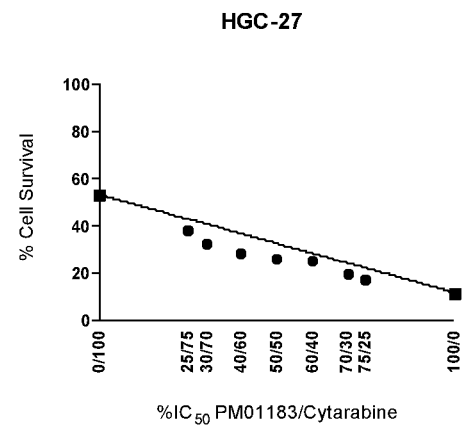
Figure 103:
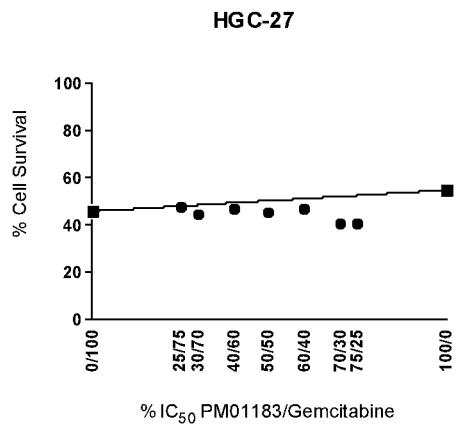
Figure 104:
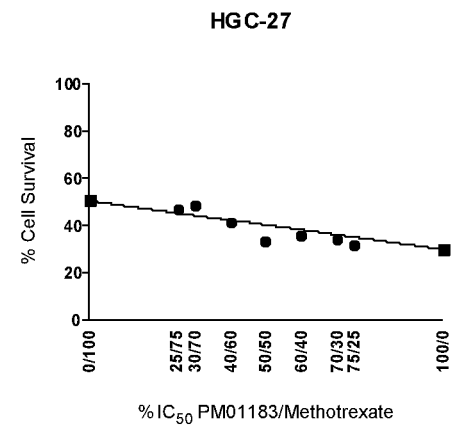
Figure 105:
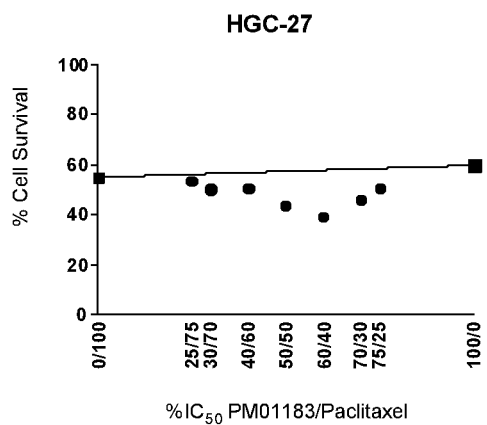
Figure 106:
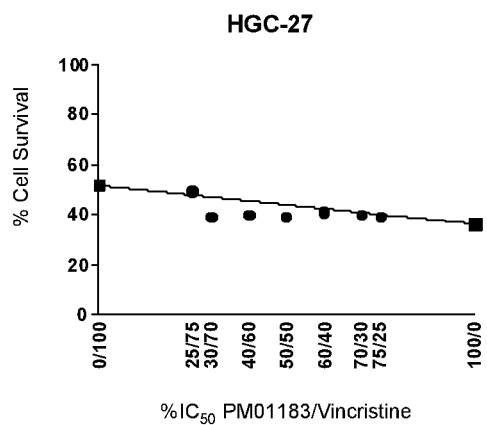
Figure 107:
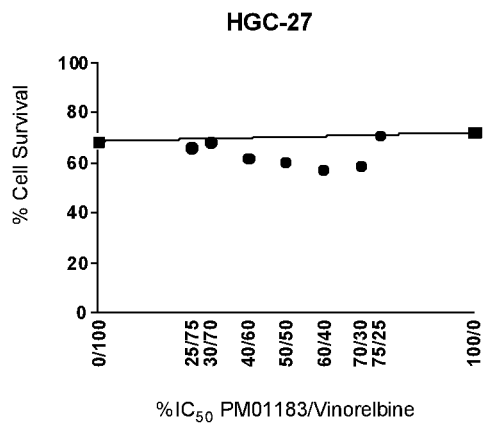
Figure 108:
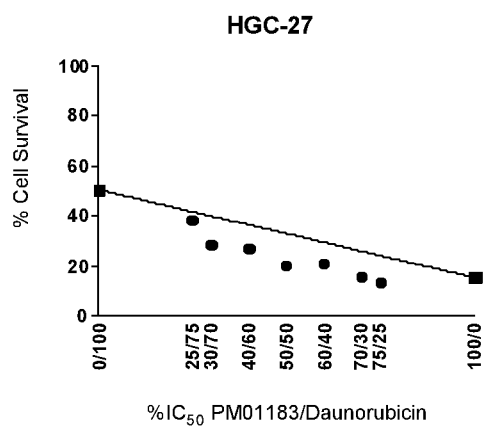
Figure 109:
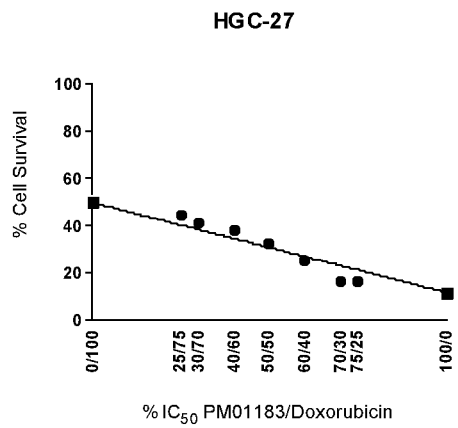
Figure 110:
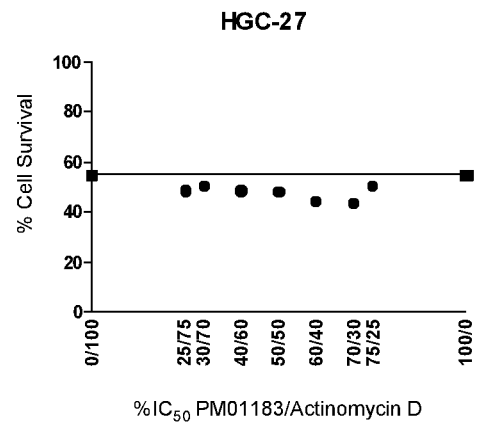
Figure 111:
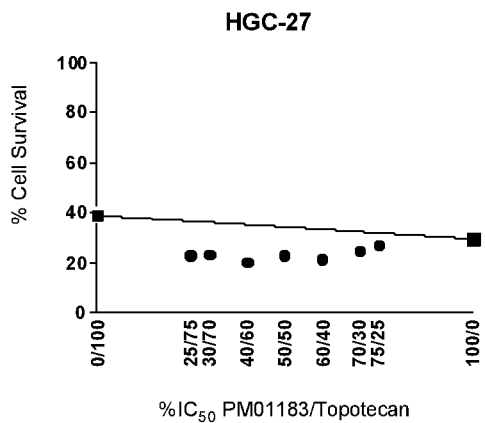
Figure 112:
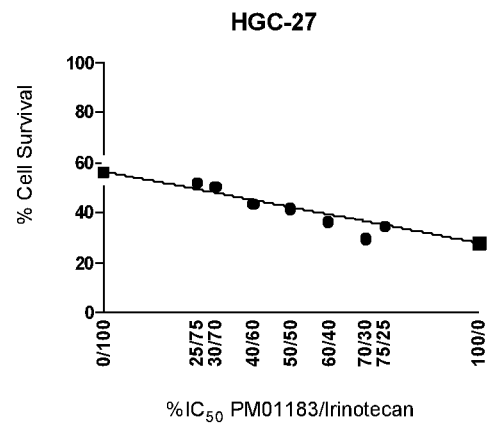
Figure 113:
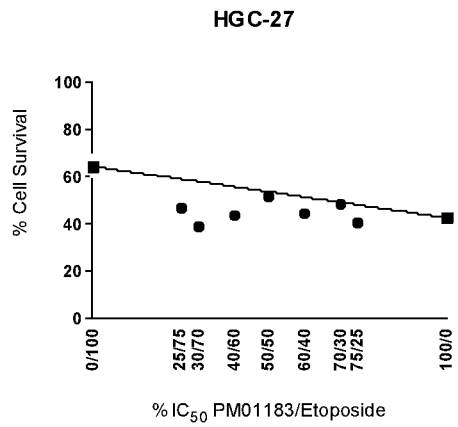
Figure 114:
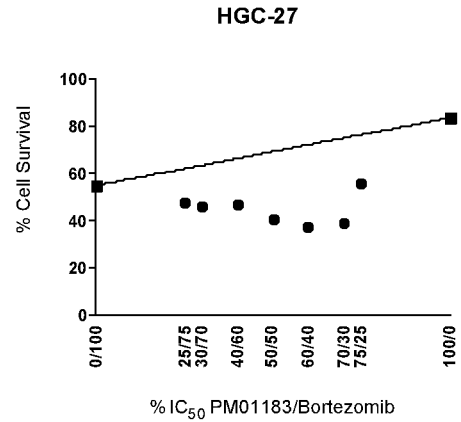
Figure 115:
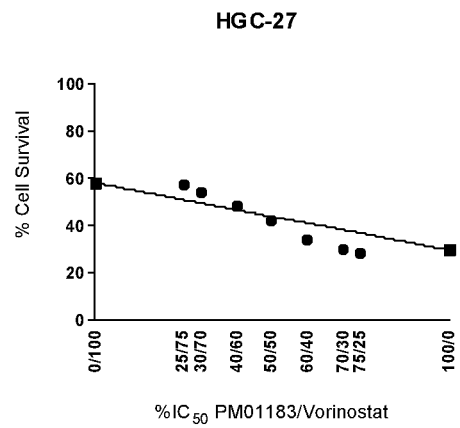
Figure 116:
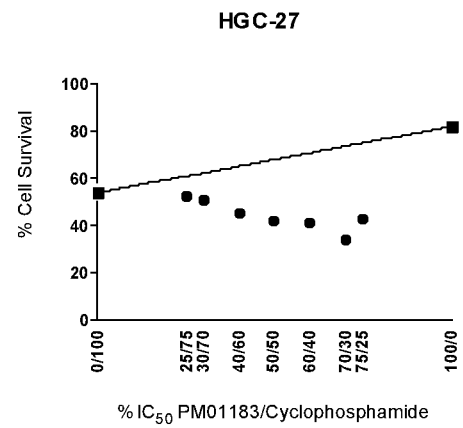
Figure 117:
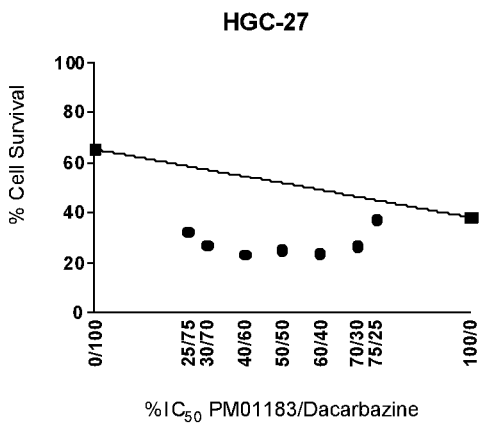
Figure 118:
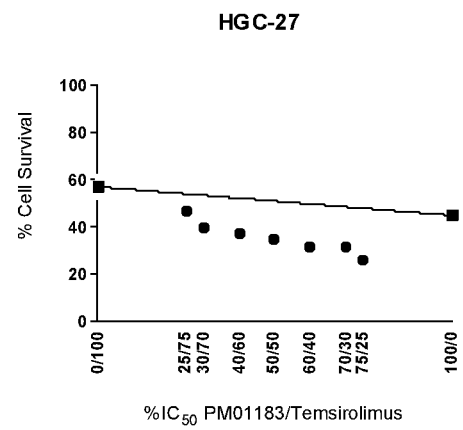
Figure 119:
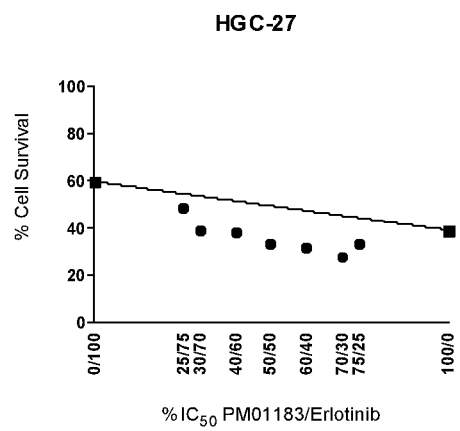
Figure 120:
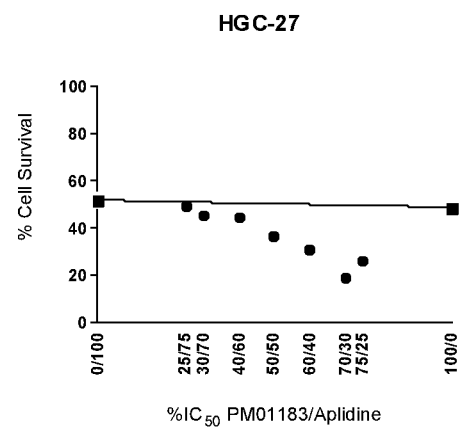
Figure 121:
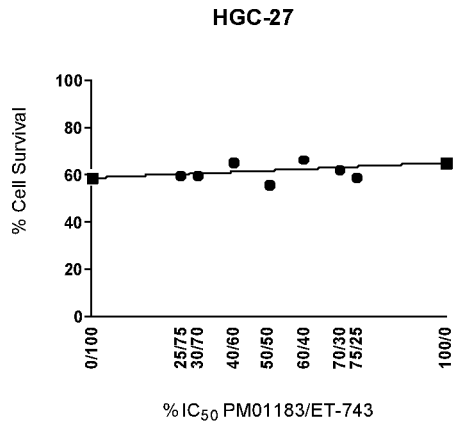
Figure 122:
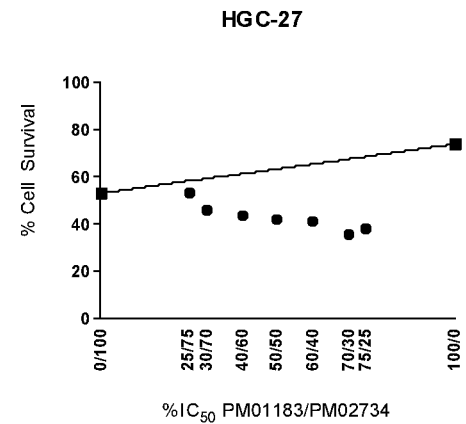
Figure 123:
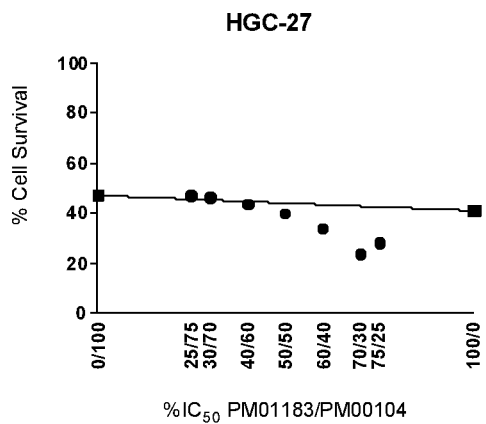

According to this assay it was found that in HGC-27 human gastric carcinoma cell line:

a. The combination of PM01183 with cisplatin (FIG. 99) showed synergism at almost all dose ratios, while the combination of PM01183 with oxaliplatin (FIG. 100) exhibited strong synergism.

b. The combination of PM01183 with 5-fluorouracil (FIG. 101) and PM01183 with cytarabine (FIG. 102) exhibited synergism, even being strong in some dose ratios. The combination of PM01183 with gemcitabine (FIG. 103) and PM01183 with methotrexate (FIG. 104) showed synergism at almost all dose ratios.

c. The combination of PM01183 with paclitaxel exhibited strong synergism (FIG. 105). The combination of PM01183 with vincristine (FIG. 106) and PM01183 with vinorelbine (FIG. 107) showed synergism at almost all dose ratios.

d. The combination of PM01183 with daunorubicin (FIG. 108) and PM01183 with actinomycin D (FIG. 110) exhibited strong synergism. The combination of PM01183 with doxorubicin (FIG. 109) exhibited synergism at the 75/25-60/40 dose ratios.

e. The combination of PM01183 with topotecan exhibited strong synergism (FIG. 111). The combination of PM01183 with irinotecan (FIG. 112) showed synergism at the 70/30-60/40 and 40/60 dose ratios, while the combination of PM01183 with etoposide (FIG. 113) showed synergism at almost all dose ratios.

f. The combination of PM01183 with bortezomib exhibited strong synergism (FIG. 114).

g. The combination of PM01183 with vorinostat (FIG. 115) showed synergism at almost all dose ratios.

h. The combination of PM01183 with cyclophosphamide exhibited strong synergism (FIG. 116).

i. The combination of PM01183 with dacarbazine exhibited strong synergism (FIG. 117).

j. The combination of PM01183 with temsirolimus exhibited strong synergism (FIG. 118).

k. The combination of PM01183 with erlotinib exhibited strong synergism (FIG. 119).

l. The combination of PM01183 with aplidine showed strong synergism (FIG. 120).

m. The combination of PM01183 with ET-743 (FIG. 121) showed synergism at the 50/50 and 75/25 dose ratios.

n. The combination of PM01183 with PM02734 exhibited strong synergism (FIG. 122).

o. The combination of PM01183 with PM00104 (FIG. 123) showed synergism at almost all dose ratios.

Example 7. In Vitro Studies to Determine the Effect of PM01183 in Combination with Chemotherapeutic Agents on Human Ovarian Carcinoma Cell Lines The objective of this study was to determine the ability of PM01183 to potentiate the antitumor activity of chemotherapeutic agents used in the treatment of ovarian cancer.

The following agents were evaluated in combination with PM01183: cisplatin, oxaliplatin, cyclophosphamide, carmustine, mytomicin C (stock solutions of these compounds prepared in sterile double distilled water and stored at $-20°$ C.), 5-fluorouracil, gemcitabine, docetaxel, paclitaxel, vincristine, vinorelbine, daunorubicin, dacarbazine, cytarabine, doxorubicin, actinomycin D, topotecan, irinotecan, methotrexate, etoposide, vorinostat, temsirolimus, erlotinib, aplidine, PM02734, ET-743 and PM00104 (stock solutions of these compounds prepared in pure DMSO and stored at $-20°$ C.). Additional serial dilutions were prepared in serum-free culture medium to achieve a final 4× concentration. Aliquots of 50 µL of each diluted compound were added per well.

IGROV-1 was the human ovarian adenocarcinoma cell line selected for this assay. IGROV-1 cells were maintained in Roswell Park Memorial Institute medium (RPMI) supplemented with 10% Fetal Bovine Serum (FBS), 2 mM L-glutamine and 100 units/mL of Penicillin-Streptomycin, at 37° C., 5% CO2 and 95% humidity.

The screening was performed in two parts as disclosed in example 1:

a. In the first set of assays, $IC_{50}$ values were determined for each drug after 72 hours of drug exposure in the IGROV-1 tumor cell line.

The $IC_{50}$ values (72 hours drug exposure) of each individual agent for the IGROV-1 tumor cell line were calculated by using the same methodology disclosed in example 1 and are shown in table 7.

Cell culture and cell plating were performed as described before and the cytotoxic effect was measured by the MTT Assay as disclosed in example 1.

Figure 124:
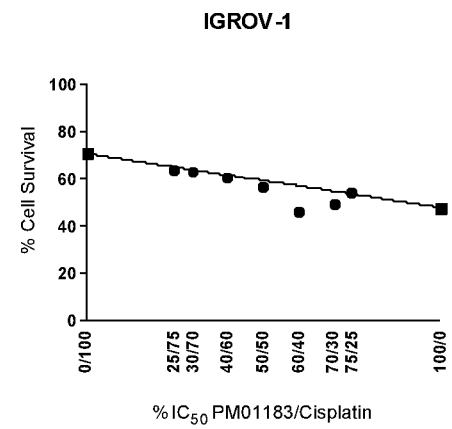
FIG. 124-150. In vitro activity data of PM01183 in combination with cisplatin, oxaliplatin, 5-fluorouracil, cytarabine, gemcitabine, methotrexate, docetaxel, paclitaxel, vincristine, vinorelbine, daunorubicin, doxorubicin, actinomycin D, mitomycin C, topotecan, irinotecan, etoposide, vorinostat, cyclophosphamide, carmustine, dacarbazine, temsirolimus, erlotinib, aplidine, ET-743, PM02734 and PM00104 respectively against IGROV-1 cells.
Figure 125:
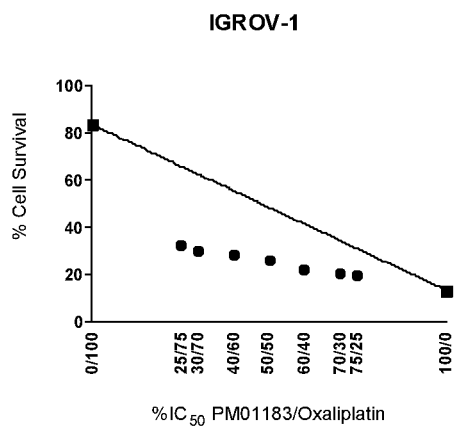
Figure 126:
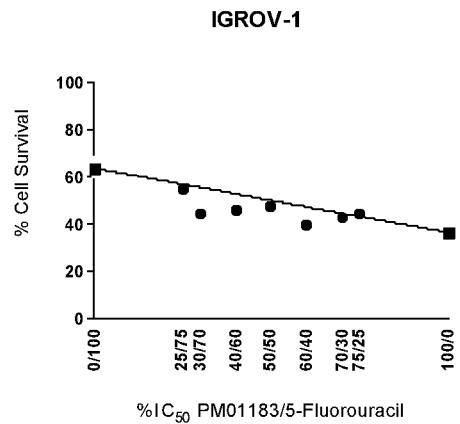
Figure 127:
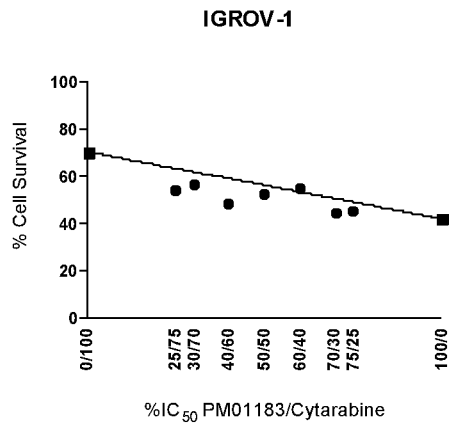
Figure 128:
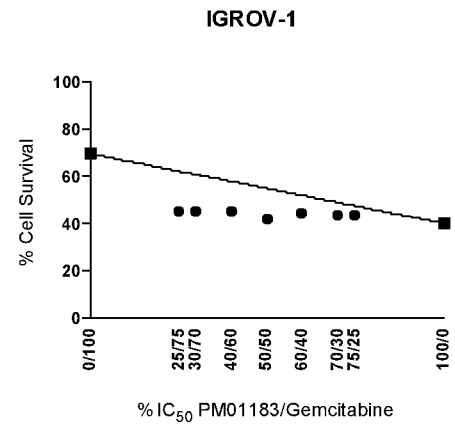
Figure 129:
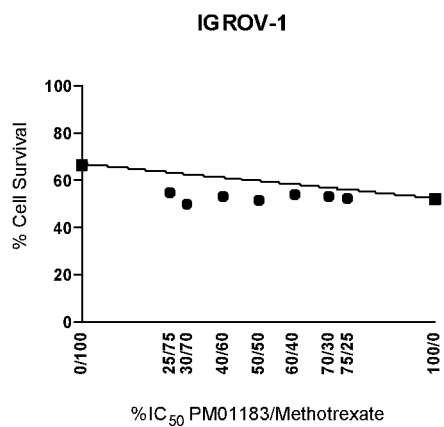
Figure 130:
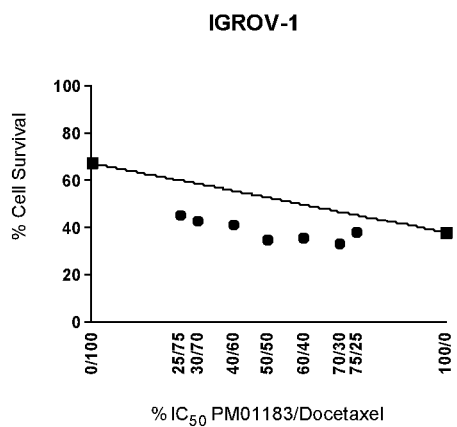
Figure 131:
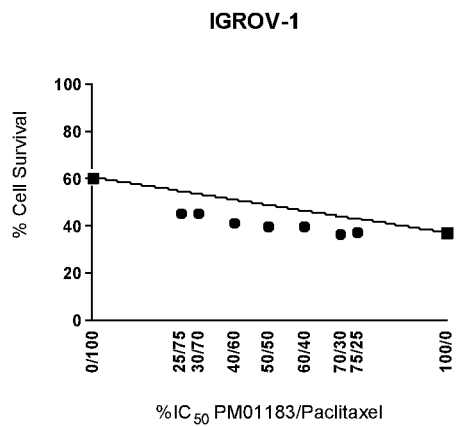
Figure 132:
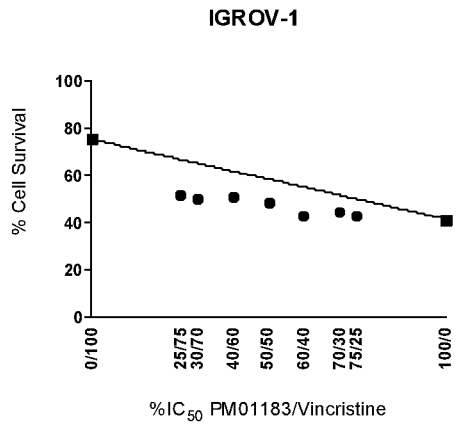
Figure 133:
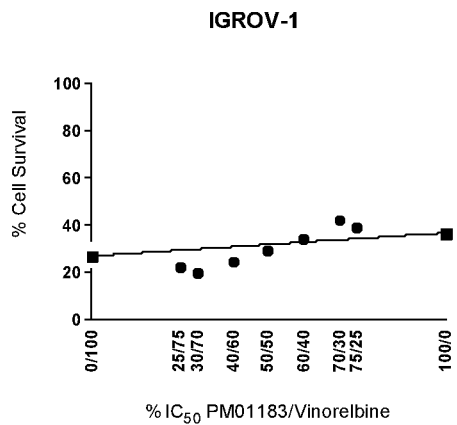
Figure 134:
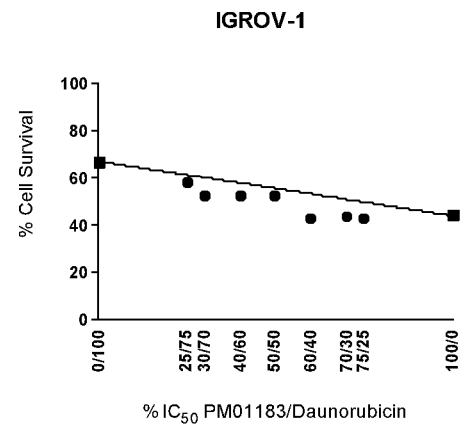
Figure 135:
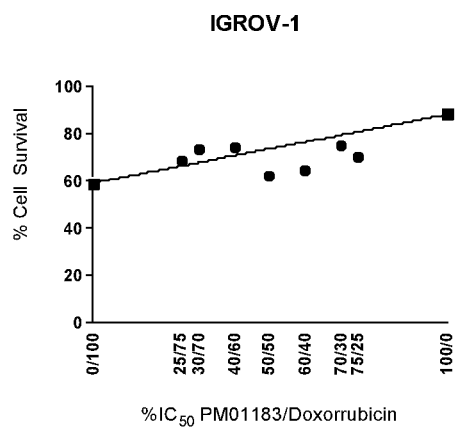
Figure 136:
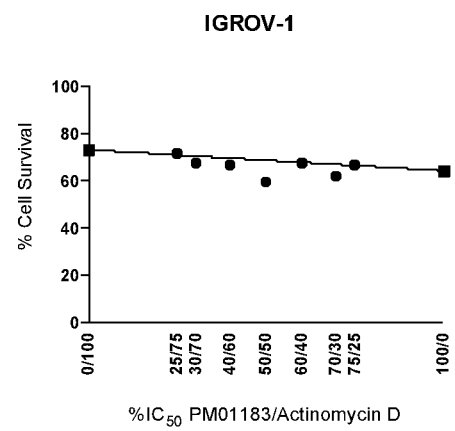
Figure 137:
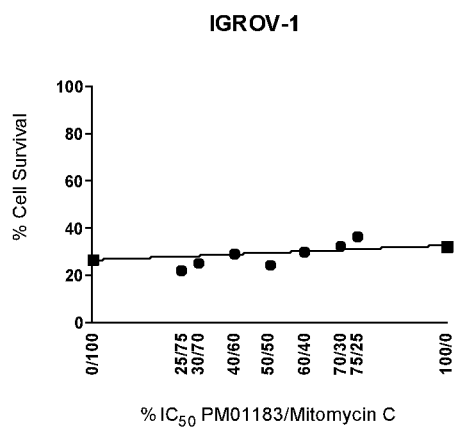
Figure 138:
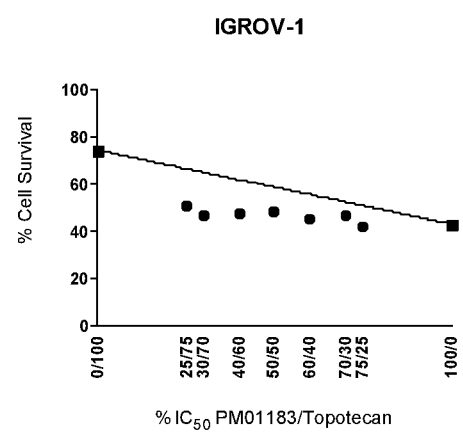
Figure 139:
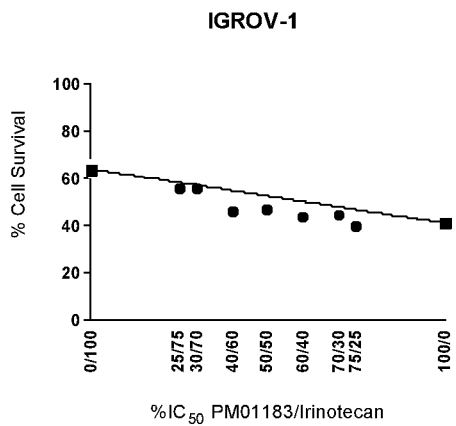
Figure 140:
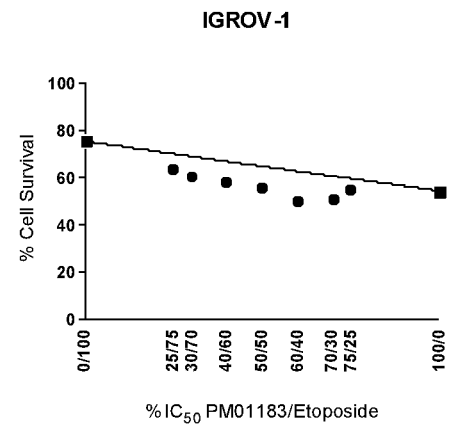
Figure 141:
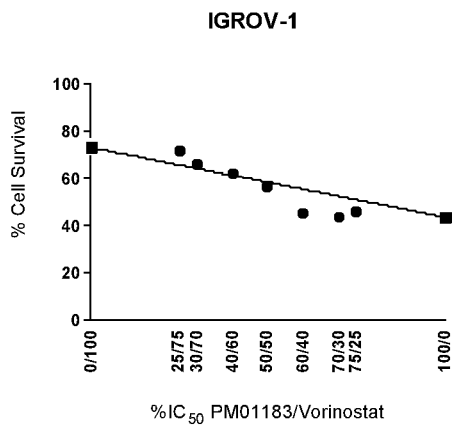
Figure 142:
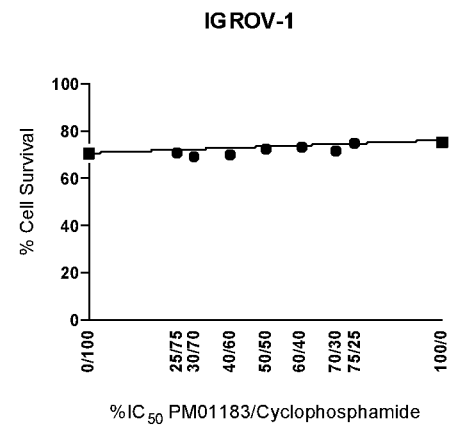
Figure 143:
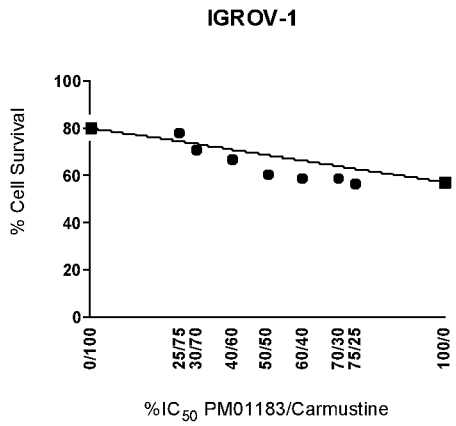
Figure 144:
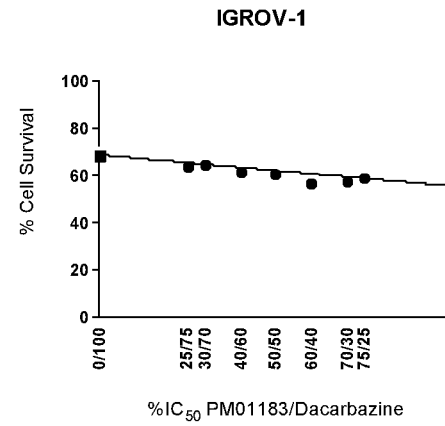
Figure 145:
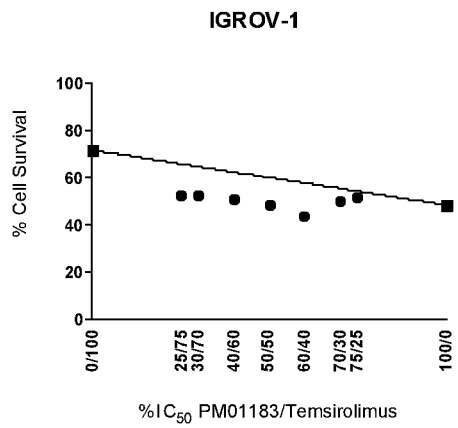
Figure 146:
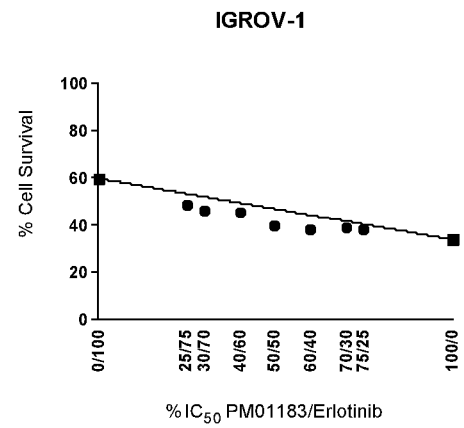
Figure 147:
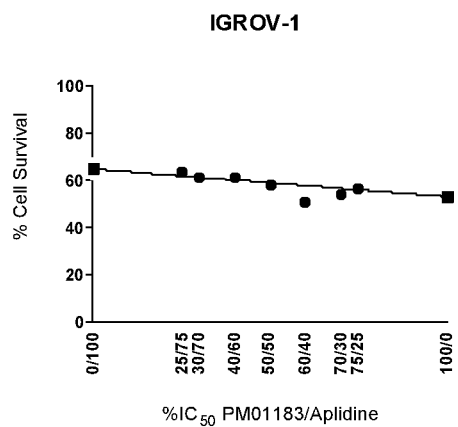

According to this assay it was found that in IGROV-1 human ovarian carcinoma cell line:

a. The combination of PM01183 with cisplatin (FIG. 124) showed synergism at almost all dose ratios, while the combination of PM01183 with oxaliplatin exhibited strong synergism (FIG. 125).

b. The combination of PM01183 with 5-fluorouracil (FIG. 126) and PM01183 with cytarabine (FIG. 127) showed synergism at almost all dose ratios. The combination of PM01183 with gemcitabine (FIG. 128) and PM01183 with methotrexate (FIG. 129) exhibited synergism.

c. The combination of PM01183 with docetaxel (FIG. 130), PM01183 with paclitaxel (FIG. 131), and PM01183 with vincristine (FIG. 132) exhibited strong synergism, while the combination of PM01183 with vinorelbine (FIG. 133) showed synergism at almost all dose ratios.

d. The combination of PM01183 with daunorubicin (FIG. 134) exhibited synergism. The combination of PM01183 with doxorubicin (FIG. 135) and PM01183 with actinomycin D (FIG. 136) exhibited synergism at almost all dose ratios, while the combination of PM01183 with mitomycin C (FIG. 137) showed synergism at the 50/50 and 30/70-25/75 dose ratios.

e. The combination of PM01183 with topotecan (FIG. 138), PM01183 with irinotecan (FIG. 139), and PM01183 with etoposide (FIG. 140) exhibited synergism.

f. The combination of PM01183 with vorinostat (FIG. 141) showed synergism at almost all dose ratios.

g. The combination of PM01183 with cyclophosphamide (FIG. 142) showed synergism at almost all dose ratios.

h. The combination of PM01183 with carmustine (FIG. 143) exhibited synergism at almost all dose ratios.

i. The combination of PM01183 with dacarbazine (FIG. 144) showed synergism at almost all dose ratios.

j. The combination of PM01183 with temsirolimus exhibited synergism (FIG. 145).

k. The combination of PM01183 with erlotinib exhibited synergism (FIG. 146).

l. The combination of PM01183 with aplidine (FIG. 147) showed synergism at the 70/30-60/40 dose ratios.

TABLE 7

Figure 148:
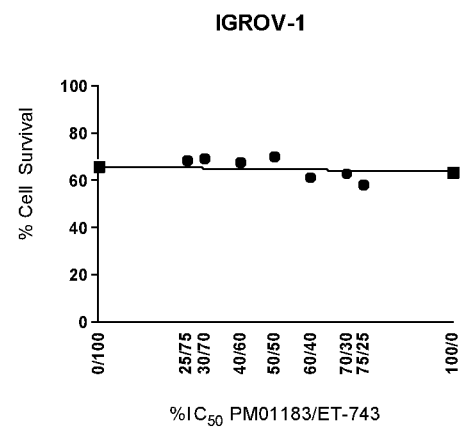
Figure 149:
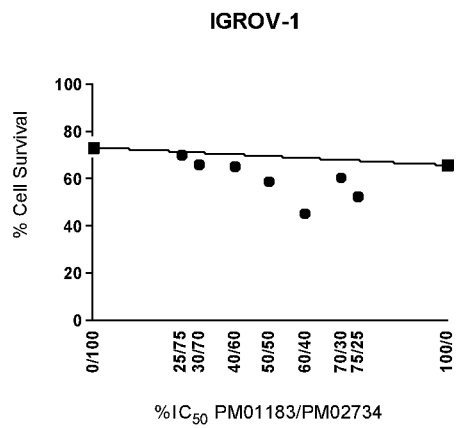
Figure 150:
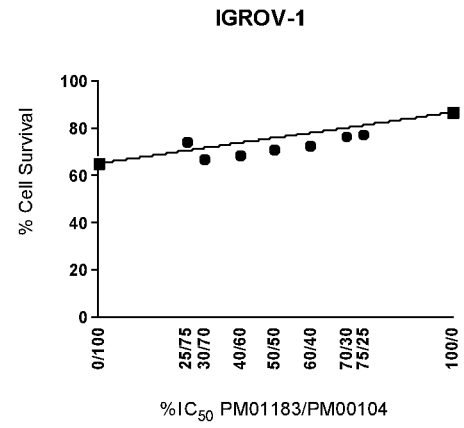

| $IC_{50}$ values in molar concentration (M) for each of the agent | | | | | |
|---|---|---|---|---|---|
| Compound | $IC_{50}$ (M) | Compound | $IC_{50}$ (M) | Compound | $IC_{50}$ (M) |
| PM01183 | 3.20E−09 | Cisplatin | 7.00E−05 | Oxaliplatin | 8.50E−06 |
| 5-FU | 9.00E−05 | Cytarabine | 1.17E−05 | Gemcitabine | 6.34E−09 |
| Methotrexate | 1.00E−04 | Docetaxel | 5.01E−08 | Paclitaxel | 9.50E−08 |
| Vincristine | 3.79E−07 | Vinorelbine | 1.39E−06 | Daunorubicin | 3.55E−07 |
| Doxorubicin | 2.59E−07 | Actinomycin D | 3.29E−09 | Mitomycin C | 3.00E−06 |
| Topotecan | 3.00E−07 | Irinotecan | 1.00E−05 | Etoposide | 3.06E−06 |
| Vorinostat | 2.88E−06 | Carmustine | 7.12E−04 | Cyclophosphamide | 1.00E−03 |
| Dacarbazine | 3.98E−04 | Temsirolimus | 1.27E−07 | Erlotinib | 7.91E−06 |
| Aplidine | 1.50E−09 | ET-743 | 6.45E−09 | PM02734 | 3.33E−07 |
| PM00104 | 3.30E−09 | | | | | b. In a second set of assays, IGROV-1 human tumor cells were incubated with PM01183 in combination with each of the agents mentioned above in the same combination of unique $IC_{50}$ concentrations as those described in example 1.

m. The combination of PM01183 with ET-743 (FIG. 148) showed synergism at the 75/25-60/40 dose ratios.

n. The combination of PM01183 with PM02734 exhibited strong synergism (FIG. 149).

o. The combination of PM01183 with PM00104 (FIG. 150) showed synergism at almost all dose ratios.

Example 8. In Vitro Studies to Determine the Effect of PM01183 in Combination with Chemotherapeutic Agents on Human Hepatocellular Carcinoma Cell Lines The objective of this study was to determine the ability of PM01183 to potentiate the antitumor activity of chemotherapeutic agents used in the treatment of hepatocellular cancer.

The following agents were evaluated in combination with PM01183: cisplatin, oxaliplatin, cyclophosphamide (stock solutions of these compounds prepared in sterile double distilled water and stored at −20° C.), 5-fluorouracil, gemcitabine, paclitaxel, docetaxel, vincristine, vinorelbine, daunorubicin, cytarabine, doxorubicin, topotecan, irinotecan, methotrexate, etoposide, bortezomib, erlotinib, ET-743 and PM00104 (stock solutions of these compounds prepared in pure DMSO and stored at −20° C.). Additional serial dilutions were prepared in serum-free culture medium to achieve a final 4× concentration. Aliquots of 50 μL of each diluted compound were added per well.

HepG2 was the human hepatocellular liver carcinoma cell line selected for this assay. HepG2 cells were maintained in Minimum Essential Medium Eagle (MEME) supplemented with 10% Fetal Bovine Serum (FBS), 2 mM L-glutamine and 100 units/mL of Penicillin-Streptomycin, at 37° C., 5% CO2 and 95% humidity.

The screening was performed in two parts as disclosed in example 1:
a. In the first set of assays, $IC_{50}$ values were determined for each drug after 72 hours of drug exposure in the HepG2 tumor cell line.

The $IC_{50}$ values (72 hours drug exposure) of each individual agent for the HepG2 tumor cell line were calculated by using the same methodology disclosed in example 1 and are shown in table 8.

TABLE 8

$IC_{50}$ values in molar concentration (M) for each of the agent

| Compound | $IC_{50}$ (M) | Compound | $IC_{50}$ (M) | Compound | $IC_{50}$ (M) |
|---|---|---|---|---|---|
| PM01183 | 2.50E-09 | Cisplatin | 5.00E-05 | Oxaliplatin | 2.80E-05 |
| 5-FU | 4.50E-06 | Cytarabine | 2.06E-05 | Gemcitabine | 5.34E-09 |
| Methotrexate | 3.96E-08 | Docetaxel | 5.00E-07 | Paclitaxel | 5.70E-08 |
| Vincristine | 6.00E-08 | Vinorelbine | 1.02E-06 | Daunorubicin | 3.00E-07 |
| Doxorubicin | 2.00E-07 | Topotecan | 1.00E-06 | Irinotecan | 1.00E-06 |
| Etoposide | 1.04E-05 | Bortezomib | 3.90E-07 | Cyclophosphamide | 1.00E-03 |
| Erlotinib | 8.60E-06 | ET-743 | 7.21E-09 | PM00104 | 3.00E-09 | b. In a second set of assays, HepG2 human tumor cells were incubated with PM01183 in combination with each of the agents mentioned above in the same combination of unique $IC_{50}$ concentrations as those described in example 1.

Cell culture and cell plating were performed as described before and the cytotoxic effect was measured by the MTT Assay as disclosed in example 1.

Figure 151:
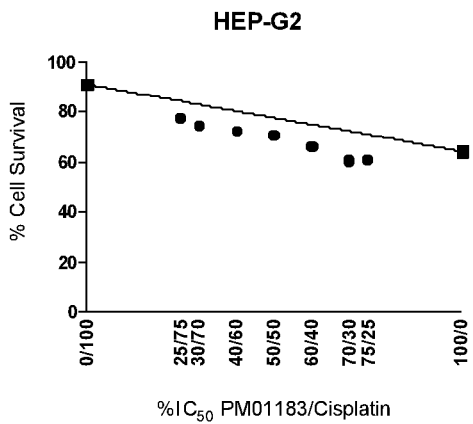
FIG. 151-170. In vitro activity data of PM01183 in combination with cisplatin, oxaliplatin, 5-fluorouracil, cytarabine, gemcitabine, methotrexate, docetaxel, paclitaxel, vincristine, vinorelbine, daunorubicin, doxorubicin, topotecan, irinotecan, etoposide, bortezomib, cyclophosphamide, erlotinib, ET-743 and PM00104 respectively against HEP-G2 cells.
Figure 152:
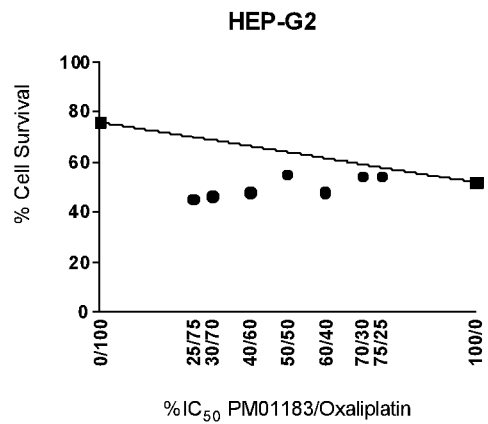
Figure 153:
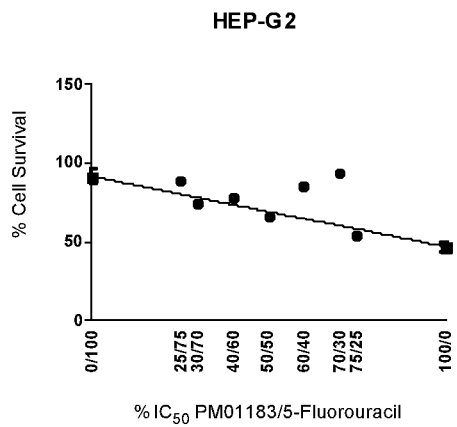
Figure 154:
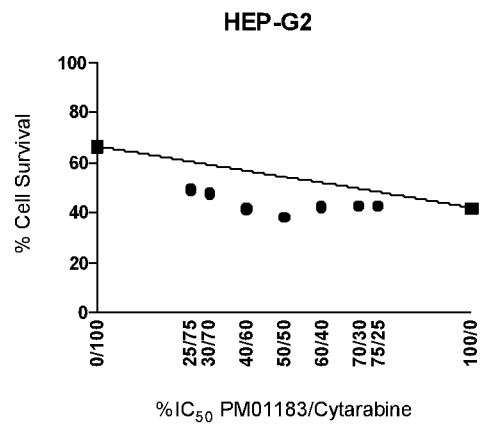
Figure 155:
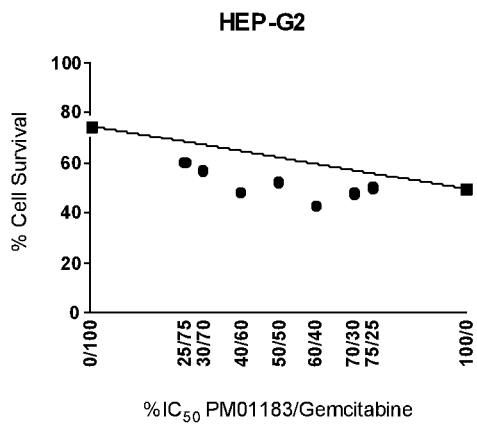
Figure 156:
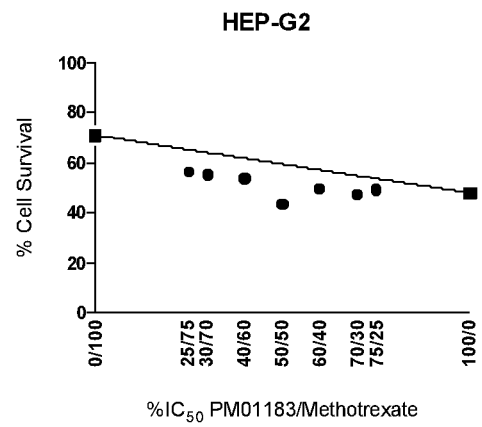
Figure 157:
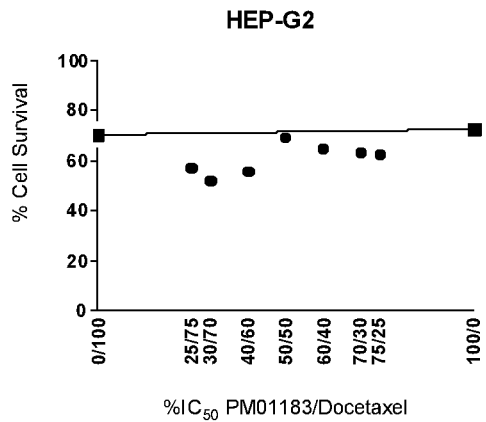
Figure 158:
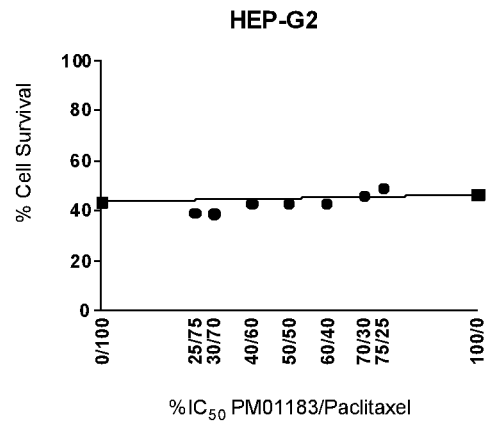
Figure 159:
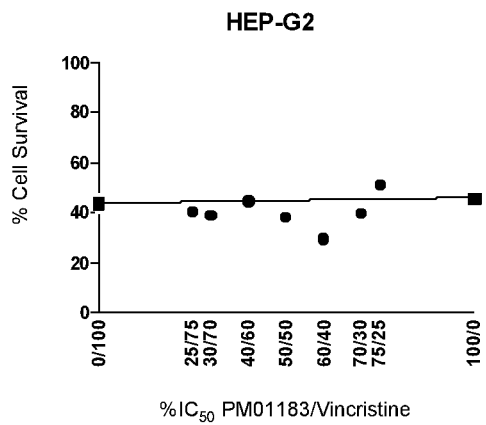
Figure 160:
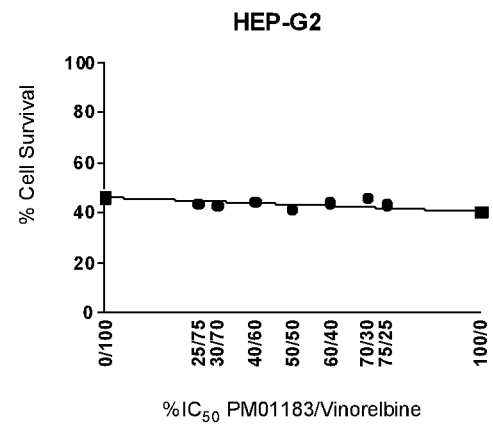
Figure 161:
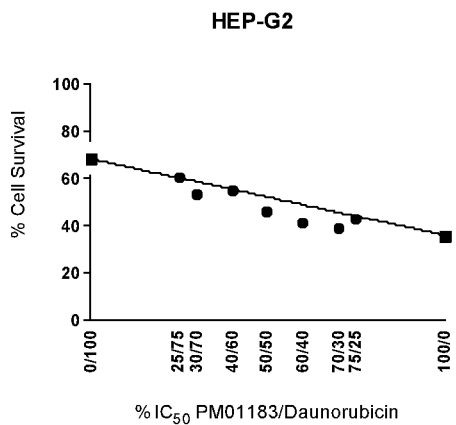
Figure 162:
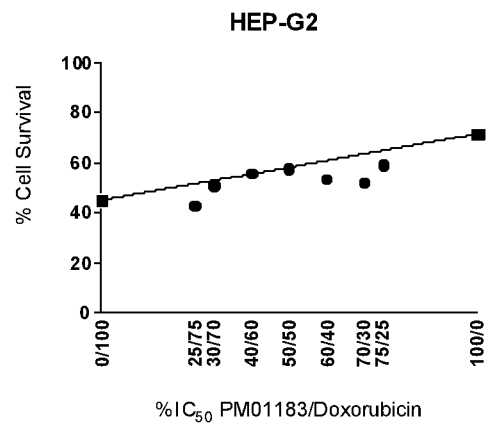
Figure 163:
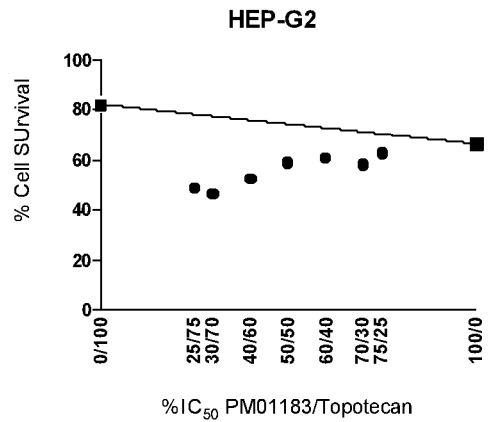
Figure 164:
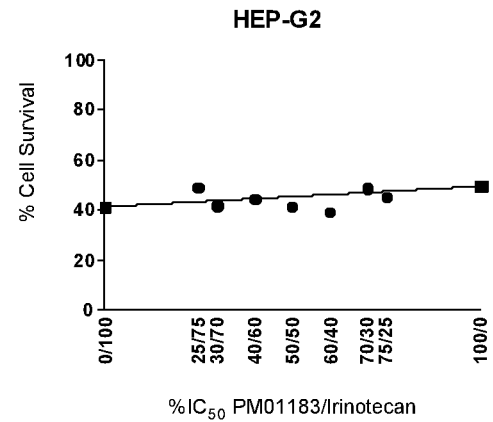
Figure 165:
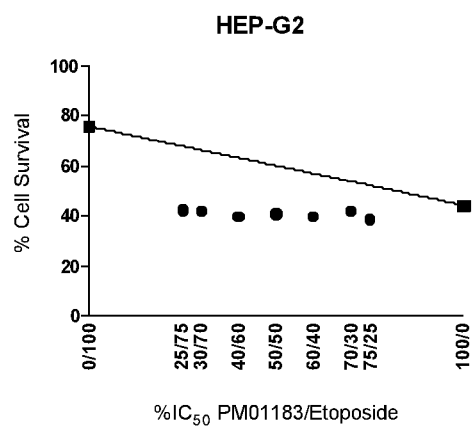
Figure 166:
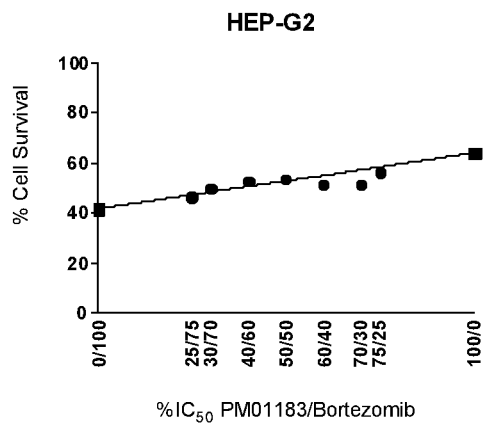
Figure 167:
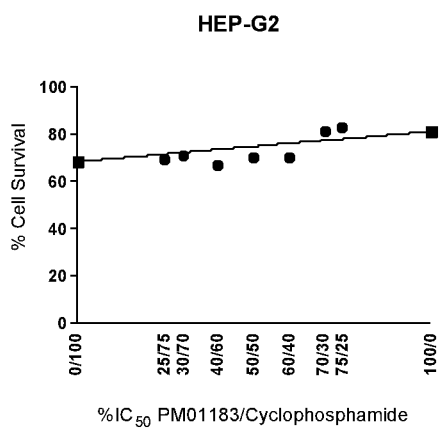
Figure 168:
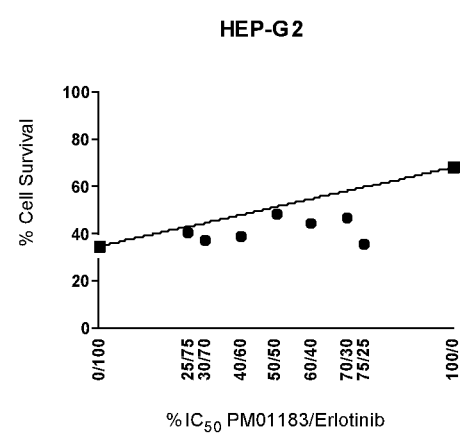
Figure 169:
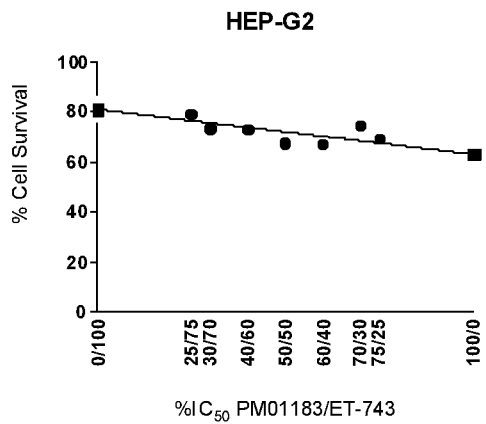
Figure 170:
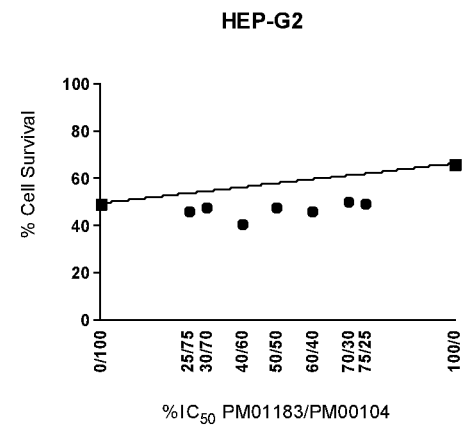

According to this assay it was found that in HepG2 human hepatocellular cell line:
a. The combination of PM01183 with cisplatin (FIG. 151) and PM01183 with oxaliplatin (FIG. 152) exhibited strong synergism.

b. The combination of PM01183 with 5-fluorouracil (FIG. 153) showed synergism at the 75/25, 50/50 and 30/70 dose ratios. The combination of PM01183 with cytarabine (FIG. 154), PM01183 with gemcitabine (FIG. 155) and PM01183 with methotrexate (FIG. 156) exhibited strong synergism.
c. The combination of PM01183 with docetaxel (FIG. 157) exhibited strong synergism. The combination of PM01183 with paclitaxel (FIG. 158) and PM01183 with vincristine (FIG. 159) showed synergism at almost all dose ratios, while the combination of PM01183 with vinorelbine (FIG. 160) showed synergism at the 50/50 and 30/70-25/75 dose ratios.
d. The combination of PM01183 with daunorubicin (FIG. 161) and PM01183 with doxorubicin (FIG. 162) showed synergism at almost all dose ratios.
e. The combination of PM01183 with topotecan (FIG. 163) and PM01183 with etoposide (FIG. 165) exhibited strong synergism. The combination of PM01183 with irinotecan (FIG. 164) showed synergism at almost all dose ratios.
f. The combination of PM01183 with bortezomib (FIG. 166) showed synergism at the 75/25-60/40 dose ratios.
g. The combination of PM01183 with cyclophosphamide (FIG. 167) showed synergism at almost all dose ratios.
h. The combination of PM01183 with erlotinib (FIG. 168) exhibited strong synergism.
i. The combination of PM01183 with ET-743 (FIG. 169) showed synergism at the 60/40-50/50 dose ratios.
j. The combination of PM01183 with PM00104 (FIG. 170) exhibited strong synergism.

Example 9. In Vitro Studies to Determine the Effect of PM01183 in Combination with Chemotherapeutic Agents on Human Breast Carcinoma Cell Lines The objective of this study was to determine the ability of PM01183 to potentiate the antitumor activity of chemotherapeutic agents used in the treatment of breast cancer.

The following agents were evaluated in combination with PM01183: cisplatin, oxaliplatin, cyclophosphamide, carmustine, mytomicin C (stock solutions of these compounds prepared in sterile double distilled water and stored at −20° C.), 5-fluorouracil, gemcitabine, paclitaxel, docetaxel, vincristine, vinorelbine, daunorubicin, dacarbazine, cytarabine, doxorubicin, actinomycin D, topotecan, irinotecan, methotrexate, etoposide, vorinostat, temsirolimus, erlotinib, tamoxifen, PM02734, ET-743 and PM00104 (stock solutions of these compounds prepared in pure DMSO and stored at −20° C.). Additional serial dilutions were prepared in serum-free culture medium to achieve a final 4× concentration. Aliquots of 50 μL of each diluted compound were added per well.

MDA-MB-231 was the human breast adenocarcinoma cell line selected for this assay. MDA-MB-231 cells were maintained in Dulbecco's modified Eagle's medium (DMEM) supplemented with 10% Fetal Bovine Serum (FBS), 2 mM L-glutamine and 100 units/mL of Penicillin-Streptomycin, at 37° C., 5% CO2 and 95% humidity.

The screening was performed in two parts as disclosed in example 1:
a. In the first set of assays, $IC_{50}$ values were determined for each drug after 72 hours of drug exposure in the MDA-MB-231 tumor cell line.

The $IC_{50}$ values (72 hours drug exposure) of each individual agent for the MDA-MB-231 tumor cell line were calculated by using the same methodology disclosed in example 1 and are shown in table 9.

TABLE 9

IC$_{50}$ values in molar concentration (M) for each of the agent

| Compound | IC$_{50}$ (M) | Compound | IC$_{50}$ (M) | Compound | IC$_{50}$ (M) |
|---|---|---|---|---|---|
| PM01183 | 3.50E−09 | Cisplatin | 1.53E−04 | Oxaliplatin | 1.08E−04 |
| 5-FU | 9.00E−05 | Cytarabine | 9.57E−06 | Gemcitabine | 8.50E−09 |
| Methotrexate | 5.94E−06 | Docetaxel | 2.50E−09 | Paclitaxel | 8.50E−09 |
| Vincristine | 5.00E−08 | Vinorelbine | 1.20E−05 | Daunorubicin | 3.70E−07 |
| Doxorubicin | 6.00E−07 | Actinomycin D | 4.54E−10 | Mitomycin C | 2.00E−06 |
| Topotecan | 1.66E−07 | Irinotecan | 8.50E−06 | Etoposide | 4.80E−06 |
| Vorinostat | 1.70E−06 | Cyclophosphamide | 1.00E−03 | Carmustine | 9.00E−04 |
| Dacarbazine | 1.92E−05 | Tamoxifen | 1.30E−05 | Temsirolimus | 1.20E−05 |
| Erlotinib | 1.00E−04 | ET-743 | 2.00E−09 | PM02734 | 2.80E−06 |
| PM00104 | 1.00E−09 | | | | | b. In a second set of assays, MDA-MB-231 human tumor cells were incubated with PM01183 in combination with each of the agents mentioned above in the same combination of unique IC$_{50}$ concentrations as those described in example 1.

Cell culture and cell plating were performed as described before and the cytotoxic effect was measured by the MTT Assay as disclosed in example 1.

Figure 171:
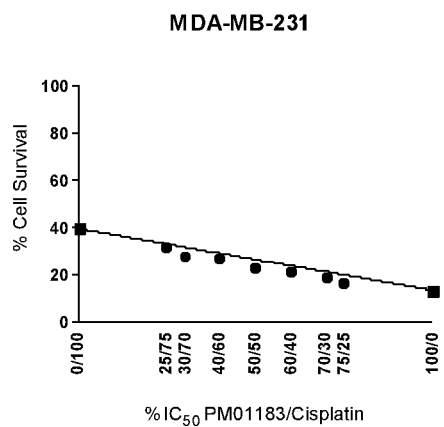
FIG. 171-197. In vitro activity data of PM01183 in combination with cisplatin, oxaliplatin, 5-fluorouracil, cytarabine, gemcitabine, methotrexate, docetaxel, paclitaxel, vincristine, vinorelbine, daunorubicin, doxorubicin, actinomycin D, mitomycin C, topotecan, irinotecan, etoposide, vorinostat, cyclophosphamide, carmustine, dacarbazine, tamoxifen, temsirolimus, erlotinib, ET-743, PM02734 and PM00104 respectively against MDA-MB-231 cells.
Figure 172:
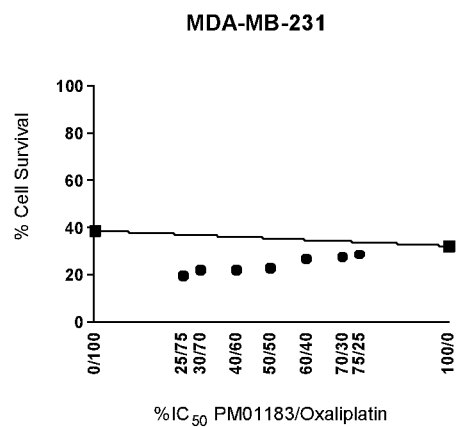
Figure 173:
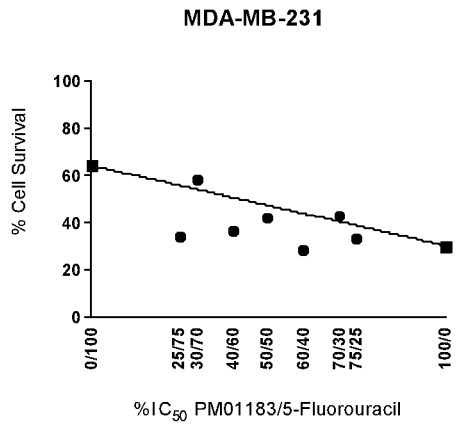
Figure 174:
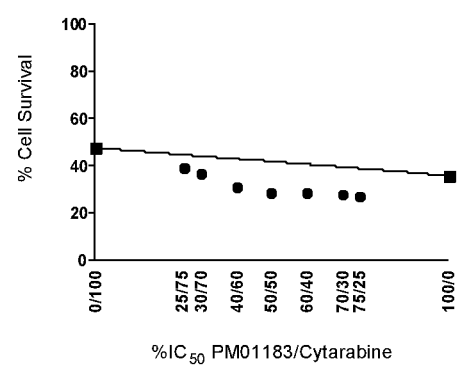
Figure 175:
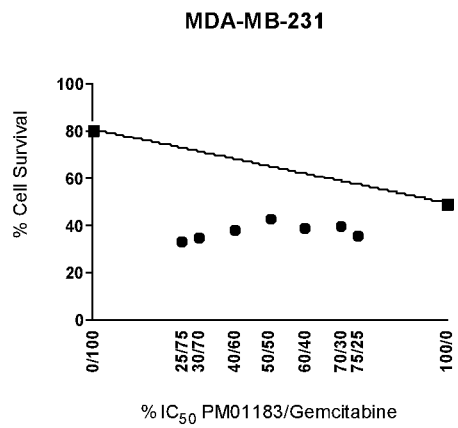
Figure 176:
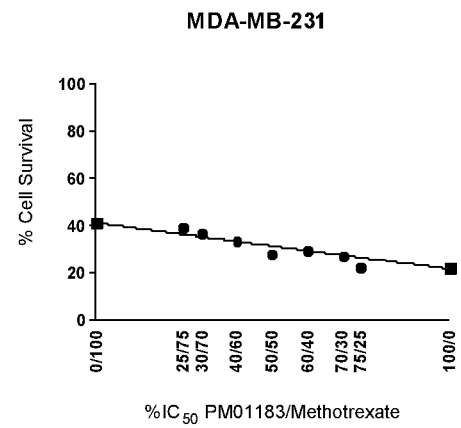
Figure 177:
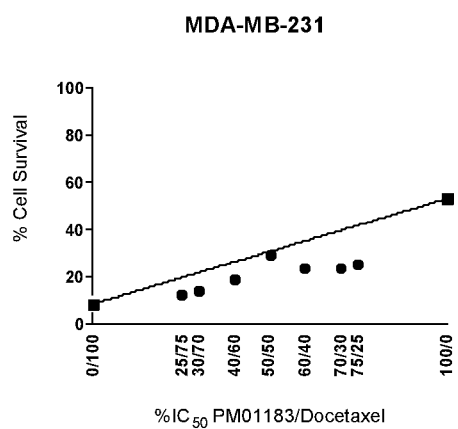
Figure 178:
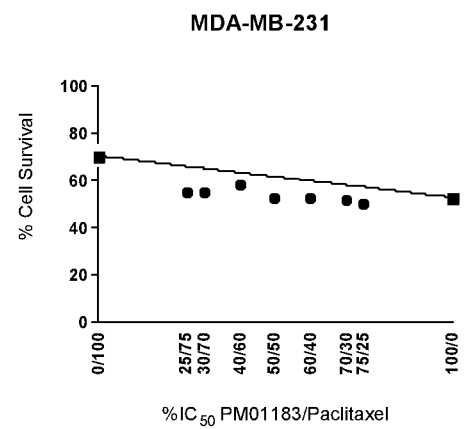
Figure 179:
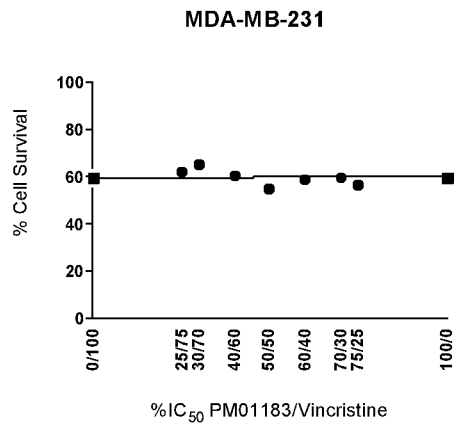
Figure 180:
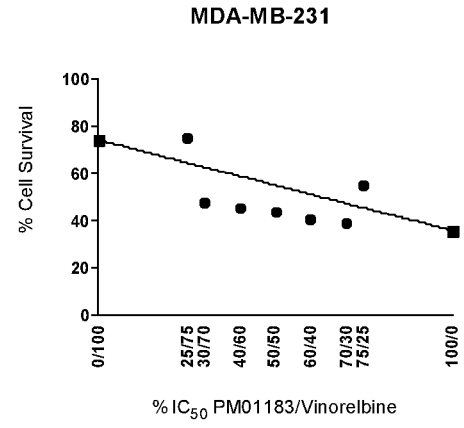
Figure 181:
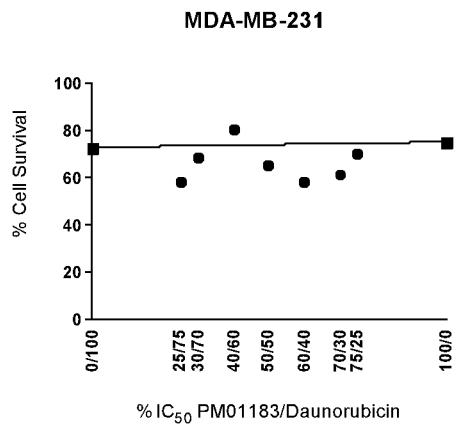
Figure 182:
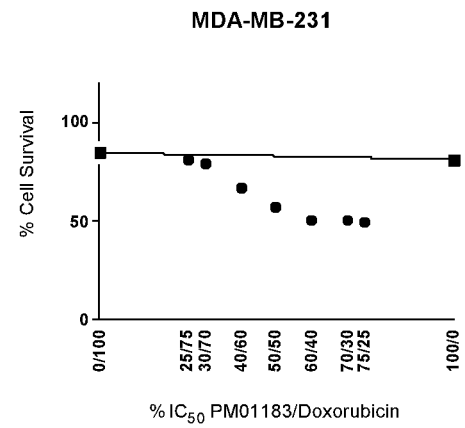
Figure 183:
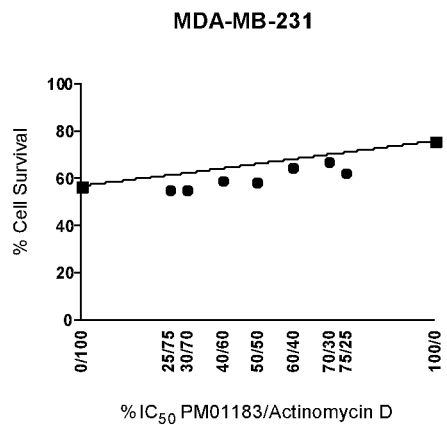
Figure 184:
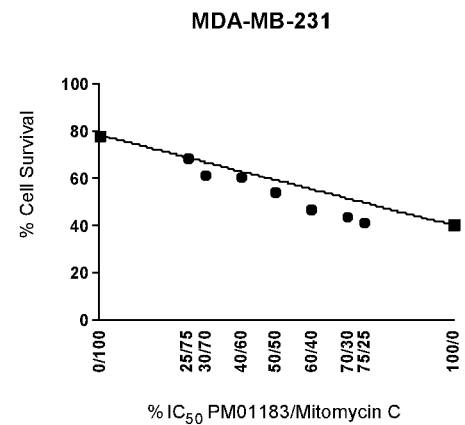
Figure 185:
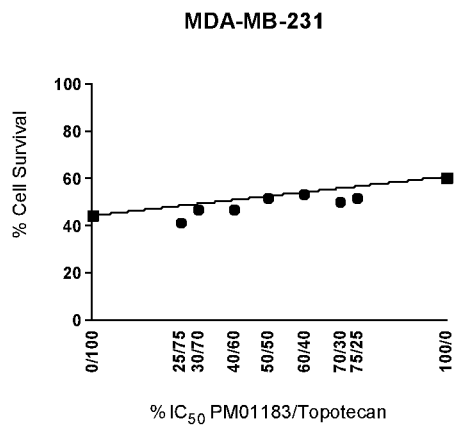
Figure 186:
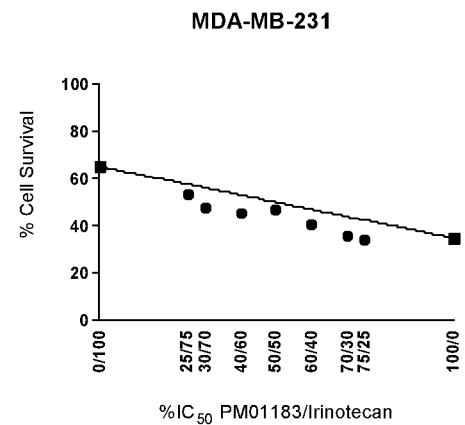
Figure 187:
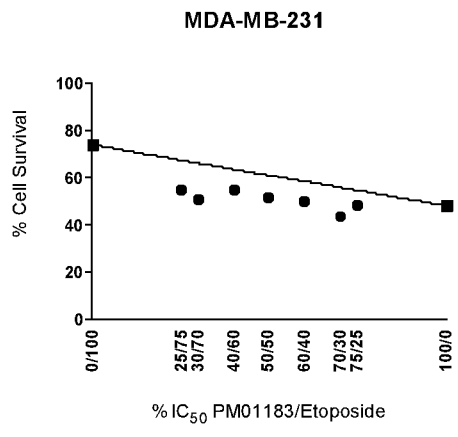
Figure 188:
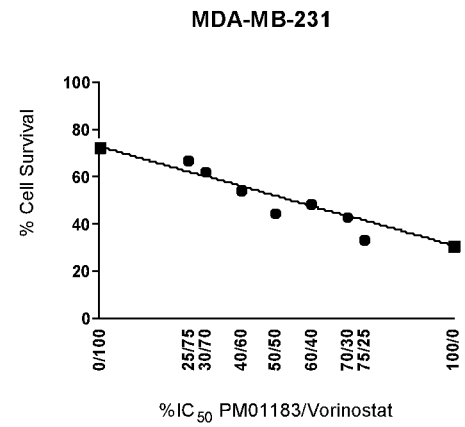
Figure 189:
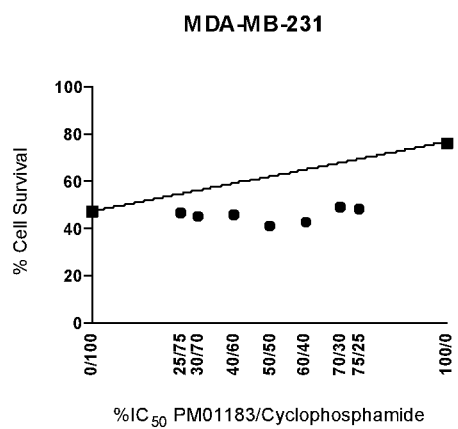
Figure 190:
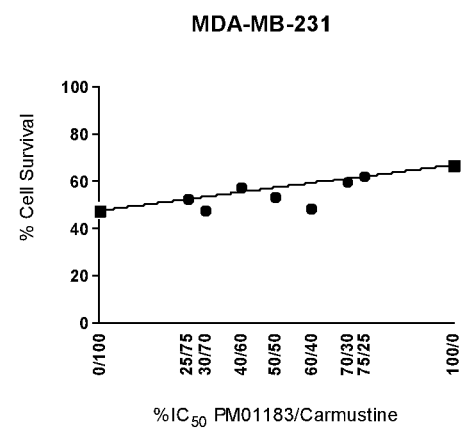
Figure 191:
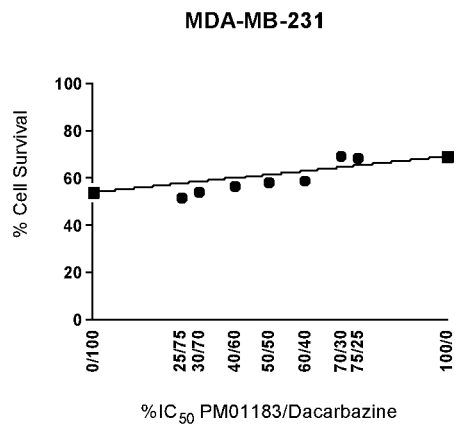
Figure 192:
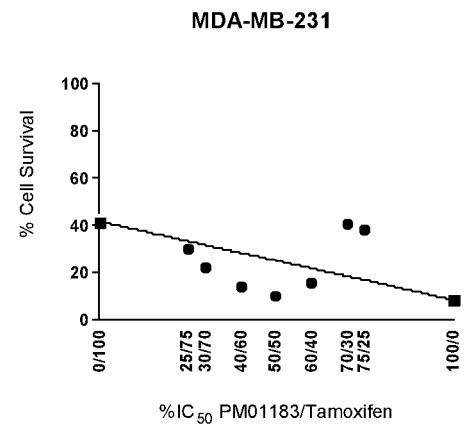
Figure 193:
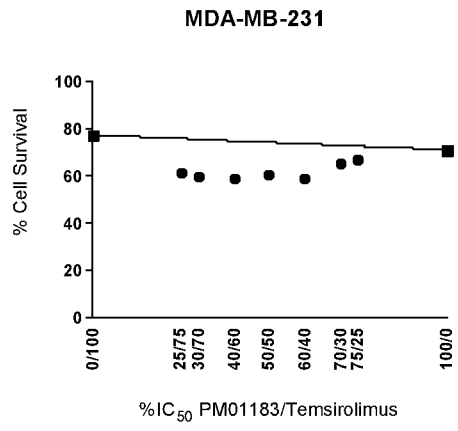
Figure 194:
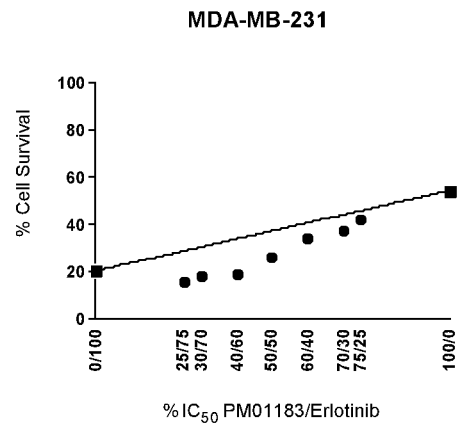
Figure 195:
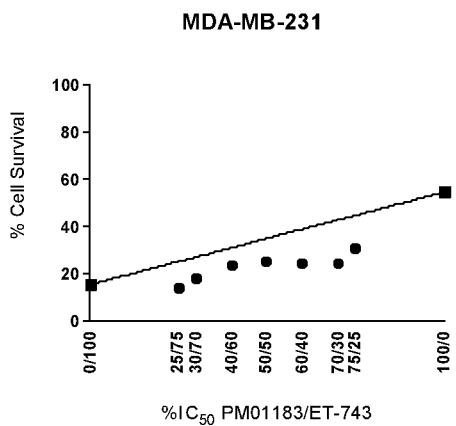
Figure 196:
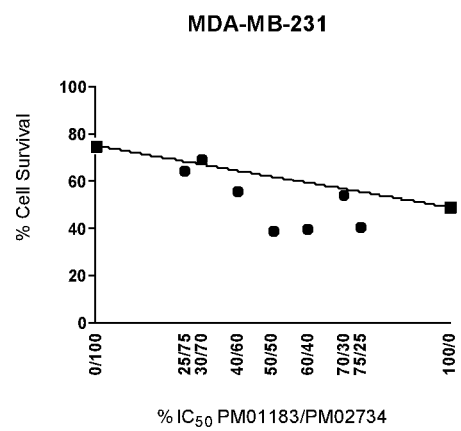
Figure 197:
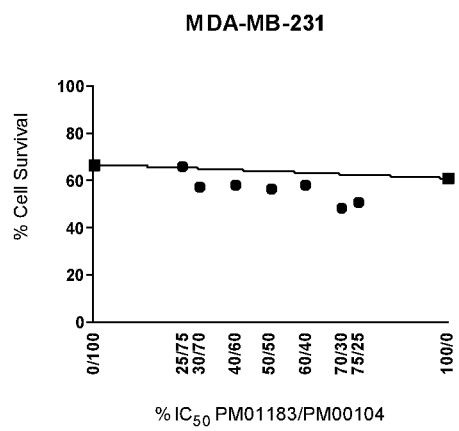

According to this assay it was found that in MDA-MB-231 human breast carcinoma cell line:
a. The combination of PM01183 with cisplatin (FIG. 171) and PM01183 with oxaliplatin (FIG. 172) exhibited synergism.
b. The combination of PM01183 with 5-fluorouracil (FIG. 173) showed synergism at almost all dose ratios. The combination of PM01183 with cytarabine (FIG. 174) and PM01183 with gemcitabine (FIG. 175) exhibited strong synergism, while the combination of PM01183 with methotrexate (FIG. 176) showed synergism at the 75/25-70/30 and 50/50 dose ratios.
c. The combination of PM01183 with docetaxel (FIG. 177) and PM01183 with paclitaxel (FIG. 178) exhibited synergism. The combination of PM01183 with vincristine (FIG. 179) showed synergism at the 75/25 and 50/50 dose ratios, while the combination of PM01183 with vinorelbine (FIG. 180) showed synergism at almost all dose ratios.
d. The combination of PM01183 with daunorubicin (FIG. 181) and PM01183 with mitomycin C (FIG. 184) exhibited synergism at almost all dose ratios. The combination of PM01183 with doxorubicin (FIG. 182) exhibited strong synergism and the combination of PM01183 with actinomycin D (FIG. 183) exhibited synergism.
e. The combination of PM01183 with topotecan (FIG. 185) showed synergism at almost all dose ratios. The combination of PM01183 with irinotecan (FIG. 186) and PM01183 with etoposide (FIG. 187) exhibited synergism.
f. The combination of PM01183 with vorinostat (FIG. 188) showed synergism at 75/25 and 50/50-40/60 dose ratios.
g. The combination of PM01183 with cyclophosphamide (FIG. 189) exhibited strong synergism.
h. The combination of PM01183 with carmustine (FIG. 190) exhibited synergism at almost all dose ratios.
i. The combination of PM01183 with dacarbazine (FIG. 191) showed synergism at almost all dose ratios.
j. The combination of PM01183 with tamoxifen (FIG. 192) showed synergism at almost all dose ratios k. The combination of PM01183 with temsirolimus exhibited strong synergism (FIG. 193).
l. The combination of PM01183 with erlotinib exhibited strong synergism (FIG. 194).
m. The combination of PM01183 with ET-743 exhibited strong synergism (FIG. 195).
n. The combination of PM01183 with PM02734 (FIG. 196) exhibited synergism at almost all dose ratios.
o. The combination of PM01183 with PM00104 (FIG. 197) showed synergism at almost all dose ratios.

Example 10. In Vitro Studies to Determine the Effect of PM01183 in Combination with Chemotherapeutic Agents on Human Colorectal Carcinoma Cell Lines The objective of this study was to determine the ability of PM01183 to potentiate the antitumor activity of chemotherapeutic agents used in the treatment of colorectal cancer.

The following agents were evaluated in combination with PM01183: cisplatin, oxaliplatin, cyclophosphamide, mytomicin C (stock solutions of these compounds prepared in sterile double distilled water and stored at −20° C.), 5-fluorouracil, gemcitabine, docetaxel, vinorelbine, daunorubicin, dacarbazine, cytarabine, doxorubicin, actinomycin D, topotecan, irinotecan, etoposide, vorinostat, bortezomib, temsirolimus, erlotinib, PM02734 and aplidine (stock solutions of these compounds prepared in pure DMSO and stored at −20° C.). Additional serial dilutions were prepared in serum-free culture medium to achieve a final 4× concentration. Aliquots of 50 μL of each diluted compound were added per well.

HT-29 was the human colon adenocarcinoma cell line selected for this assay. HT-29 cells were maintained in Dulbecco's modified Eagle's medium (DMEM) supplemented with 10% Fetal Bovine Serum (FBS), 2 mM L-glutamine and 100 units/mL of Penicillin-Streptomycin, at 37° C., 5% CO2 and 95% humidity.

The screening was performed in two parts as disclosed in example 1:
a. In the first set of assays, IC$_{50}$ values were determined for each drug after 72 hours of drug exposure in the HT-29 tumor cell line.

The IC$_{50}$ values (72 hours drug exposure) of each individual agent for the HT-29 tumor cell line were calculated by using the same methodology disclosed in example 1 and are shown in table 10.

TABLE 10

IC$_{50}$ values in molar concentration (M) for each of the agent

| Compound | IC$_{50}$ (M) | Compound | IC$_{50}$ (M) | Compound | IC$_{50}$ (M) |
|---|---|---|---|---|---|
| PM01183 | 3.70E−09 | Cisplatin | 2.20E−04 | Oxaliplatin | 1.03E−04 |
| 5-FU | 9.00E−06 | Cytarabine | 7.80E−06 | Gemcitabine | 4.00E−07 |
| Docetaxel | 3.20E−10 | Vinorelbine | 3.00E−08 | Daunorubicin | 5.32E−07 |
| Doxorubicin | 9.00E−07 | Actinomycin D | 3.27E−09 | Mitomycin C | 2.00E−06 |

TABLE 10-continued

IC$_{50}$ values in molar concentration (M) for each of the agent

| Compound | IC$_{50}$ (M) | Compound | IC$_{50}$ (M) | Compound | IC$_{50}$ (M) |
|---|---|---|---|---|---|
| Topotecan | 3.28E−07 | Irinotecan | 9.00E−06 | Etoposide | 5.44E−06 |
| Bortezomib | 6.15E−09 | Vorinostat | 2.76E−06 | Cyclophosphamide | 1.00E−03 |
| Dacarbazine | 2.47E−05 | Temsirolimus | 3.50E−06 | Erlotinib | 2.56E−05 |
| Aplidine | 1.76E−09 | PM02734 | 2.14E−07 | | | b. In a second set of assays, HT-29 human tumor cells were incubated with PM01183 in combination with each of the agents mentioned above in the same combination of unique IC$_{50}$ concentrations as those described in example 1.

Cell culture and cell plating were performed as described before and the cytotoxic effect was measured by the MTT Assay as disclosed in example 1.

Figure 198:
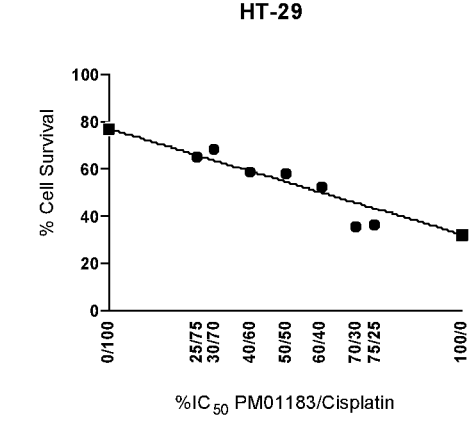
FIG. 198-219. In vitro activity data of PM01183 in combination with cisplatin, oxaliplatin, 5-fluorouracil, cytarabine, gemcitabine, docetaxel, vinorelbine, daunorubicin, doxorubicin, actinomycin D, mitomycin C, topotecan, irinotecan, etoposide, bortezomib, vorinostat, cyclophosphamide, dacarbazine, temsirolimus, erlotinib, aplidine and PM02734 respectively against HT-29 cells.
Figure 199:
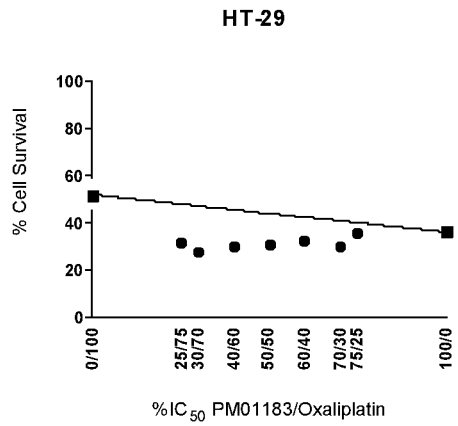
Figure 200:
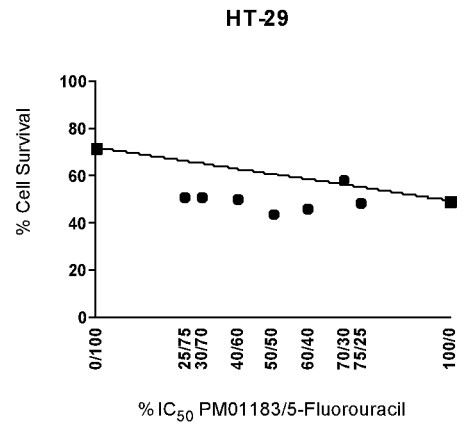
Figure 201:
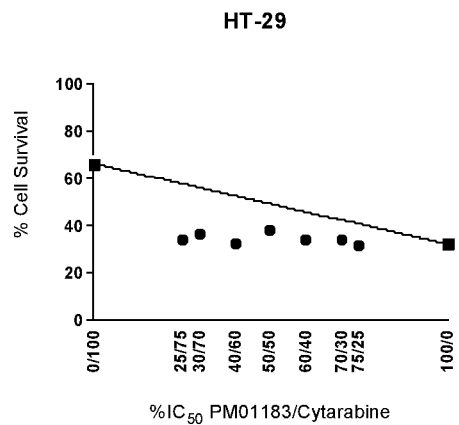
Figure 202:
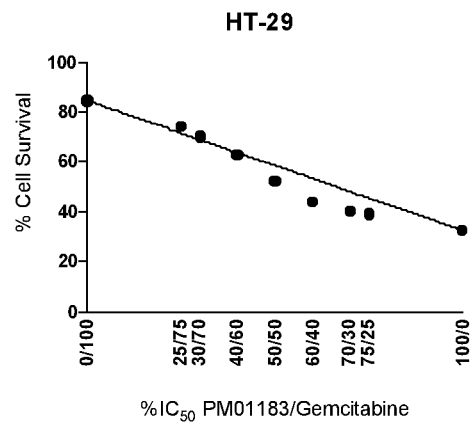
Figure 203:
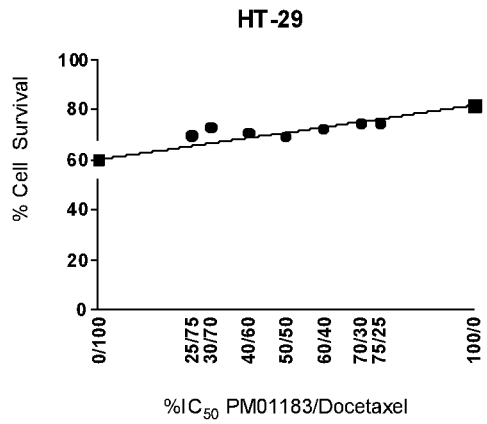
Figure 204:
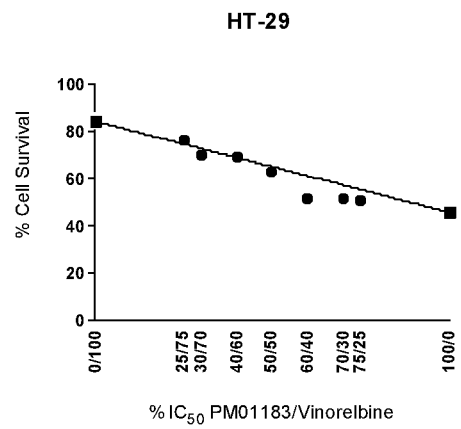
Figure 205:
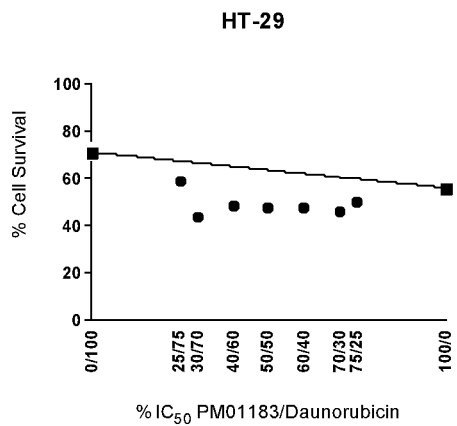
Figure 206:
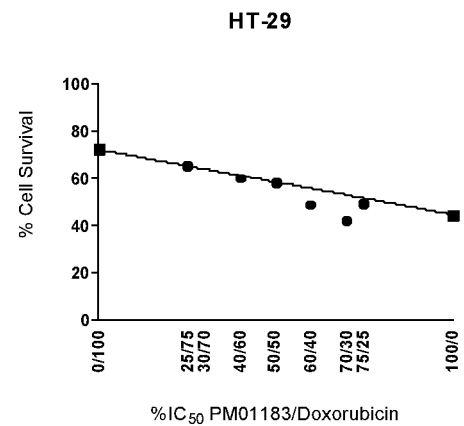
Figure 207:
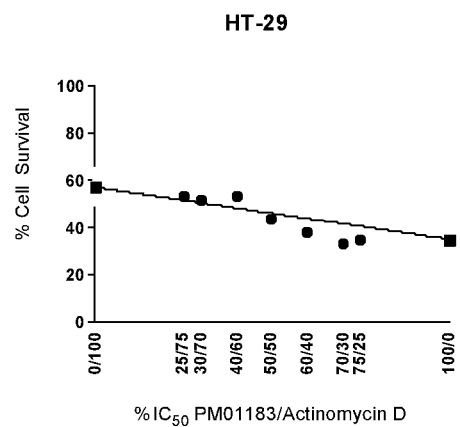
Figure 208:
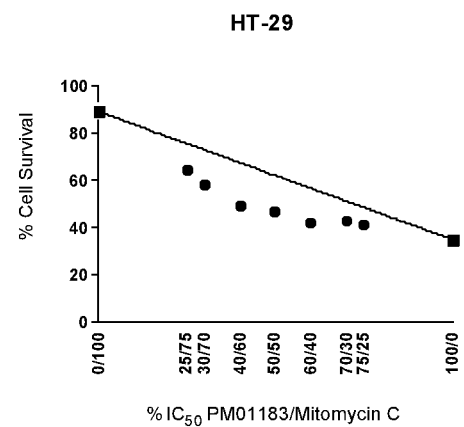
Figure 209:
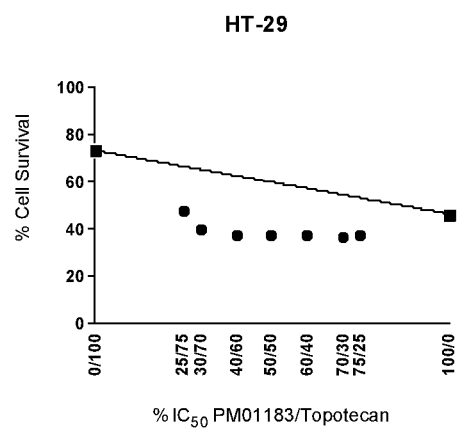
Figure 210:
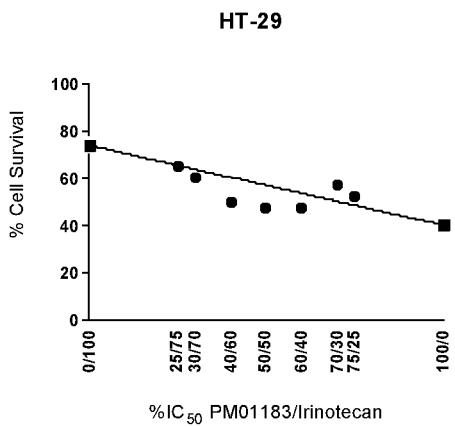
Figure 211:
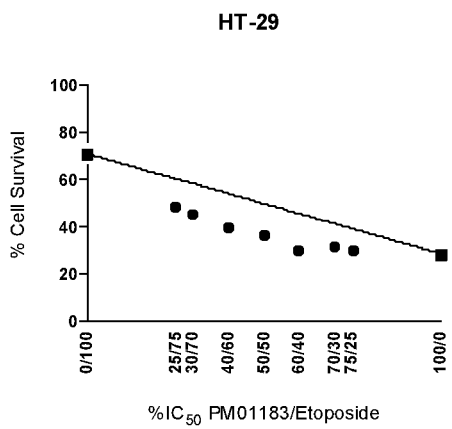
Figure 212:
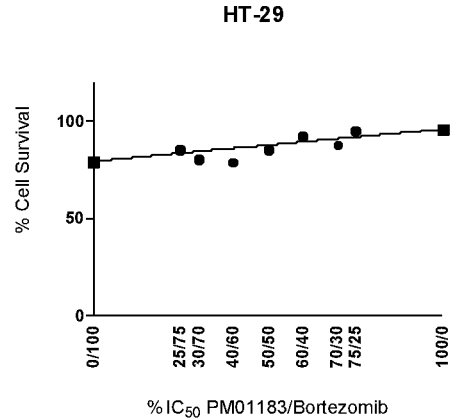
Figure 213:
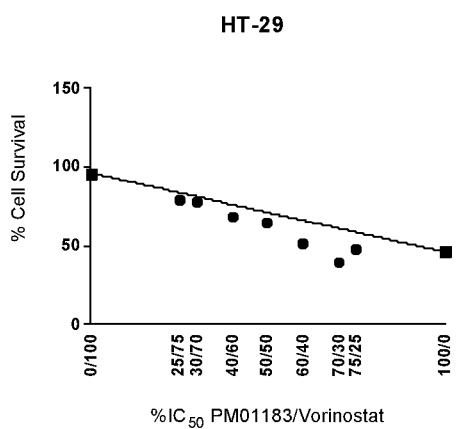
Figure 214:
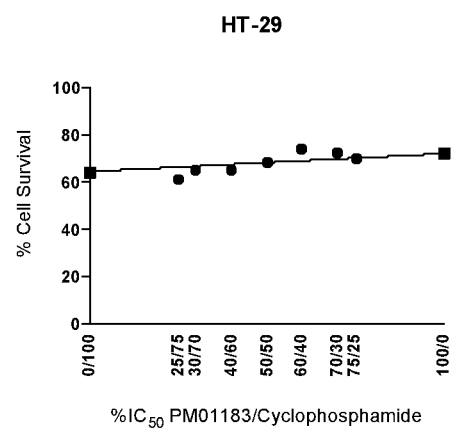
Figure 215:
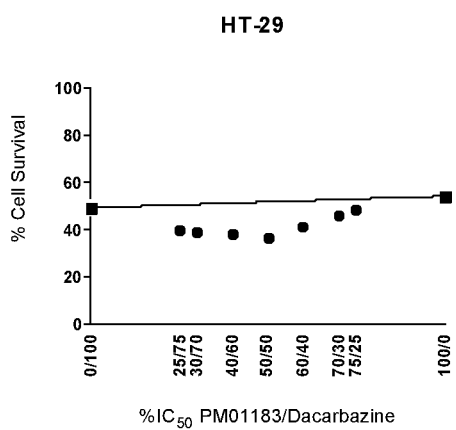
Figure 216:
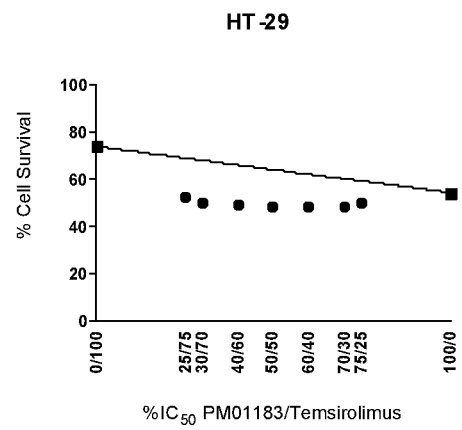
Figure 217:
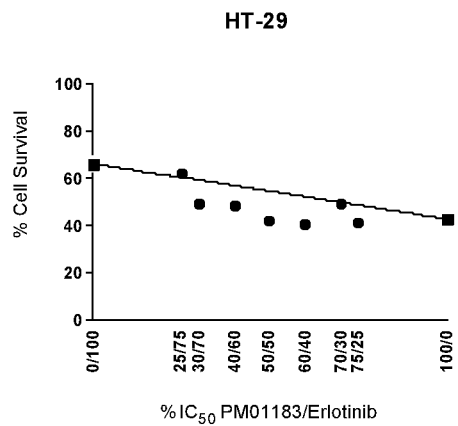
Figure 218:
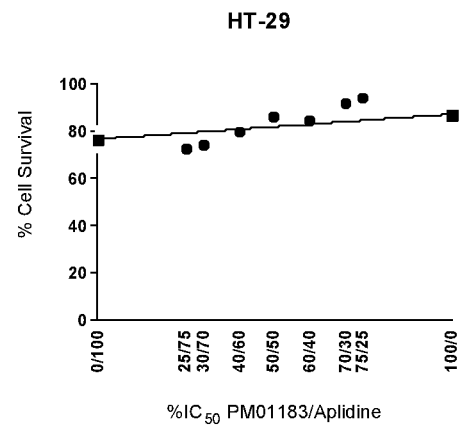
Figure 219:
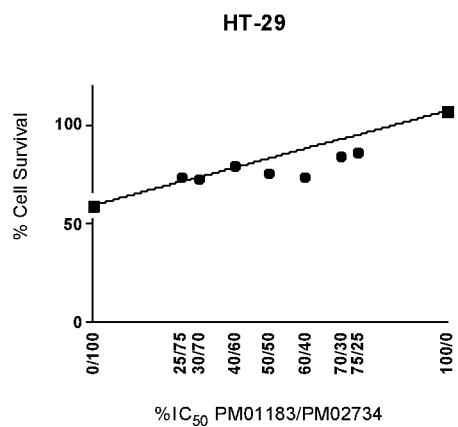

According to this assay it was found that in HT-29 human colorectal carcinoma cell line:

a. The combination of PM01183 with cisplatin (FIG. 198) showed synergism at the 75/25-70/30 dose ratios, while the combination of PM01183 with oxaliplatin (FIG. 199) exhibited strong synergism.

b. The combination of PM01183 with 5-fluorouracil (FIG. 200) and PM01183 with gemcitabine (FIG. 202) showed synergism at almost all dose ratios, and the combination of PM01183 with cytarabine (FIG. 201) exhibited strong synergism.

c. The combination of PM01183 with docetaxel (FIG. 203) exhibited synergism at the 50/50 and 75/25 dose ratios, while the combination of PM01183 with vinorelbine (FIG. 204) showed synergism at almost all dose ratios.

d. The combination of PM01183 with daunorubicin (FIG. 205) and PM01183 with mitomycin C (FIG. 208) exhibited strong synergism. The combination of PM01183 with doxorubicin (FIG. 206) and PM01183 with actinomycin D (FIG. 207) showed synergism at almost all dose ratios.

e. The combination of PM01183 with topotecan (FIG. 209) and PM01183 with etoposide (FIG. 211) exhibited strong synergism. The combination of PM01183 with irinotecan (FIG. 210) showed synergism at almost all dose ratios.

f. The combination of PM01183 with bortezomib (FIG. 212) showed synergism at almost all dose ratios.

g. The combination of PM01183 with vorinostat (FIG. 213) exhibited synergism.

h. The combination of PM01183 with cyclophosphamide (FIG. 214) showed synergism at the 40/60-25/75 dose ratios.

i. The combination of PM01183 with dacarbazine (FIG. 215) exhibited strong synergism.

j. The combination of PM01183 with temsirolimus exhibited strong synergism (FIG. 216).

k. The combination of PM01183 with erlotinib showed synergism at almost all dose ratios (FIG. 217).

l. The combination of PM01183 with aplidine (FIG. 218) showed synergism at the 40/60-25/75 dose ratios.

m. The combination of PM01183 with PM02734 (FIG. 219) showed synergism at almost all dose ratios.

Example 11. In Vitro Studies to Determine the Effect of PM01183 in Combination with Chemotherapeutic Agents on Human Kidney Carcinoma Cell Lines The objective of this study was to determine the ability of PM01183 to potentiate the antitumor activity of chemotherapeutic agents used in the treatment of kidney cancer.

The following agents were evaluated in combination with PM01183: cisplatin, cyclophosphamide, mytomicin C (stock solutions of these compounds prepared in sterile double distilled water and stored at −20° C.), 5-fluorouracil, gemcitabine, methotrexate, docetaxel, vincristine, vinorelbine, daunorubicin, dacarbazine, cytarabine, doxorubicin, actinomycin D, topotecan, irinotecan, etoposide, vorinostat, erlotinib, PM02734, ET-743, PM00104 and aplidine (stock solutions of these compounds prepared in pure DMSO and stored at −20° C.). Additional serial dilutions were prepared in serum-free culture medium to achieve a final 4× concentration. Aliquots of 50 μL of each diluted compound were added per well.

RXF-393 was the human kidney carcinoma cell line selected for this assay. RXF-393 cells were maintained in Roswell Park Memorial Institute medium (RPMI) supplemented with 10% Fetal Bovine Serum (FBS), 2 mM L-glutamine and 100 units/mL of Penicillin-Streptomycin, at 37° C., 5% CO2 and 95% humidity.

The screening was performed in two parts as disclosed in example 1:

a. In the first set of assays, IC$_{50}$ values were determined for each drug after 72 hours of drug exposure in the RXF-393 tumor cell line.

The IC$_{50}$ values (72 hours drug exposure) of each individual agent for the RXF-393 tumor cell line were calculated by using the same methodology disclosed in example 1 and are shown in table 11.

TABLE 11

IC$_{50}$ values in molar concentration (M) for each of the agent

| Compound | IC$_{50}$ (M) | Compound | IC$_{50}$ (M) | Compound | IC$_{50}$ (M) |
|---|---|---|---|---|---|
| PM01183 | 5.00E−09 | Cisplatin | 6.67E−05 | 5-FU | 3.00E−04 |
| Cytarabine | 5.00E−05 | Gemcitabine | 5.00E−07 | Methotrexate | 1.75E−04 |
| Docetaxel | 5.94E−10 | Vincristine | 1.73E−08 | Vinorelbine | 8.50E−06 |
| Daunorubicin | 6.20E−07 | Doxorubicin | 8.00E−07 | Actinomycin D | 7.09E−10 |
| Mitomycin C | 9.00E−06 | Topotecan | 3.93E−07 | Irinotecan | 1.40E−05 |
| Etoposide | 2.00E−05 | Vorinostat | 4.10E−06 | Cyclophosphamide | 1.00E−03 |
| Dacarbazine | 7.94E−04 | Erlotinib | 4.80E−06 | Aplidine | 1.50E−09 |
| ET-743 | 9.60E−09 | PM02734 | 5.00E−06 | PM00104 | 5.40E−09 | b. In a second set of assays, RXF-393 human tumor cells were incubated with PM01183 in combination with each of the agents mentioned above in the same combination of unique IC$_{50}$ concentrations as those described in example 1.

Cell culture and cell plating were performed as described before and the cytotoxic effect was measured by the MTT Assay as disclosed in example 1.

Figure 220:
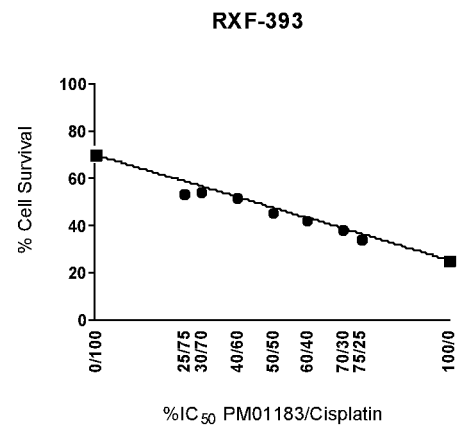
FIG. 220-242. In vitro activity data of PM01183 in combination with cisplatin, 5-fluorouracil, cytarabine, gemcitabine, methotrexate, docetaxel, vincristine, vinorelbine, daunorubicin, doxorubicin, actinomycin D, mitomycin C, topotecan, irinotecan, etoposide, vorinostat, cyclophosphamide, dacarbazine, erlotinib, aplidine, ET-743, PM02734 and PM00104 respectively against RXF-393 cells.
Figure 221:
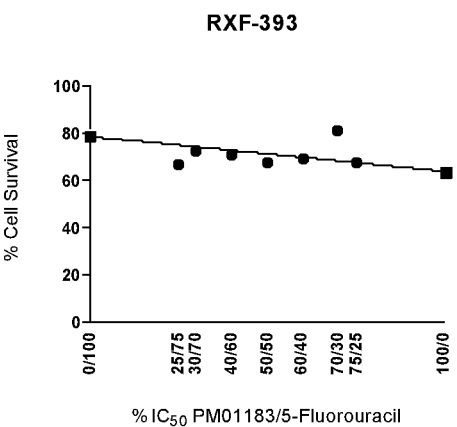
Figure 222:
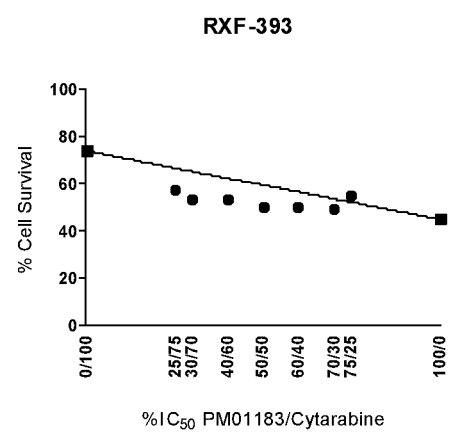
Figure 223:
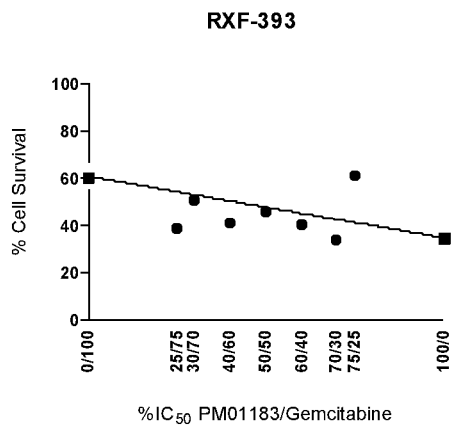
Figure 224:
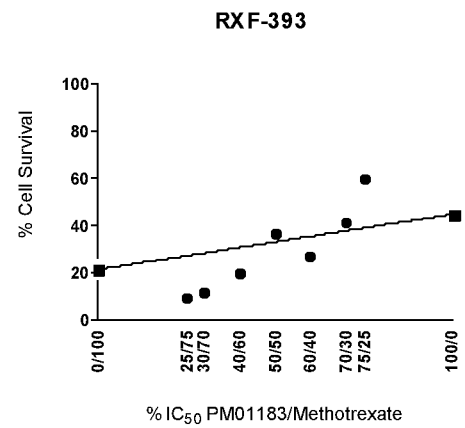
Figure 225:
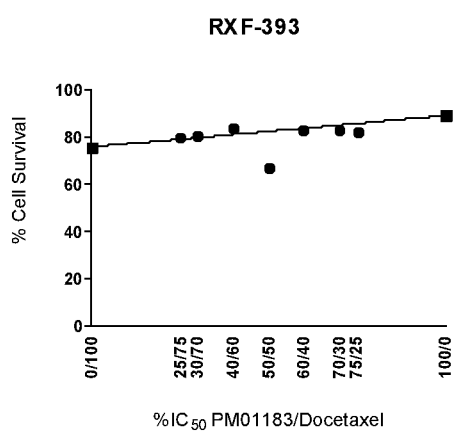
Figure 226:
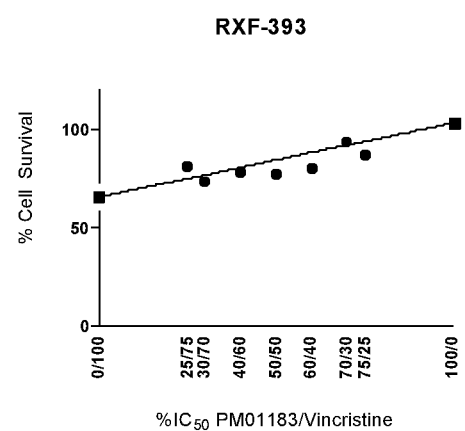
Figure 227:
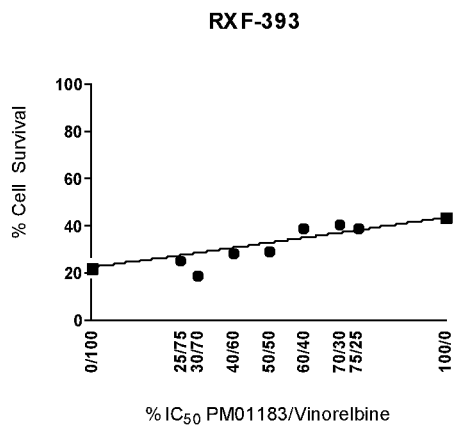
Figure 228:
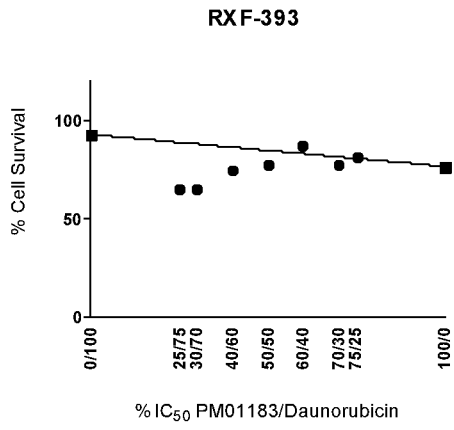
Figure 229:
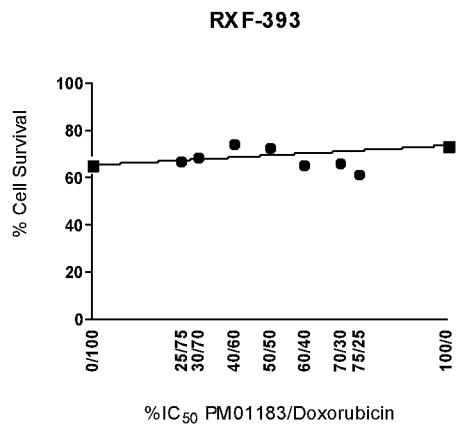
Figure 230:
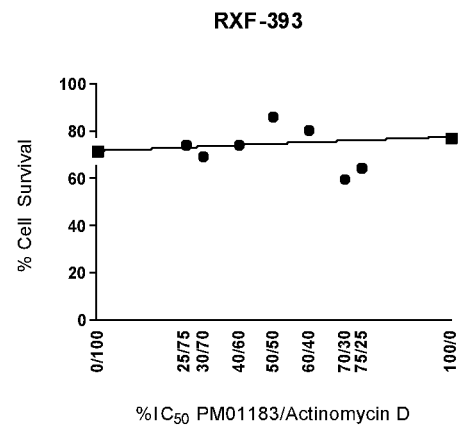
Figure 231:
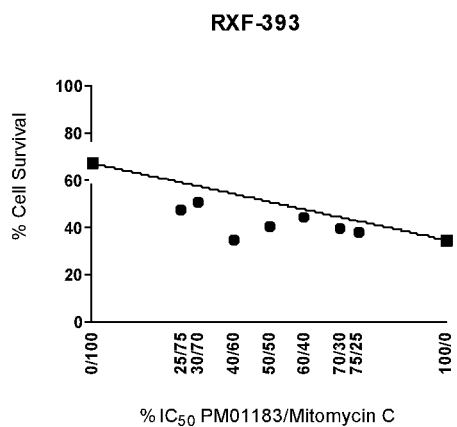
Figure 232:
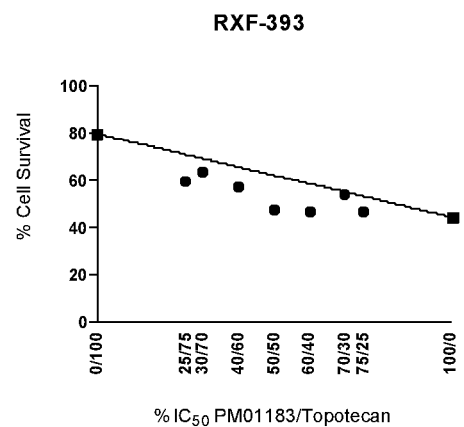
Figure 233:
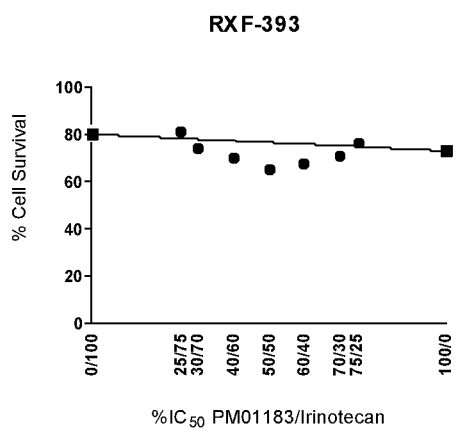
Figure 234:
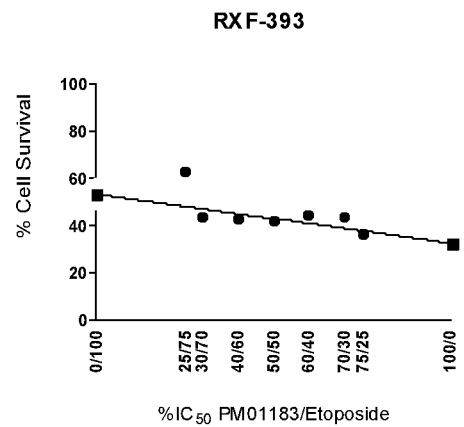
Figure 235:
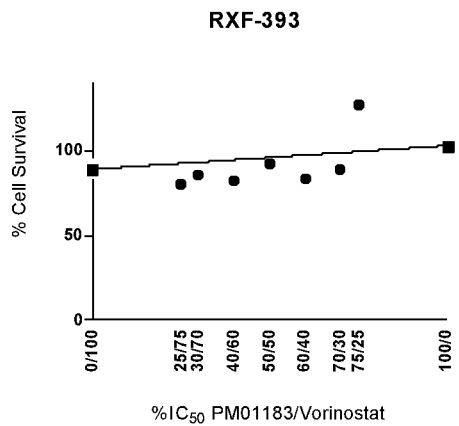
Figure 236:
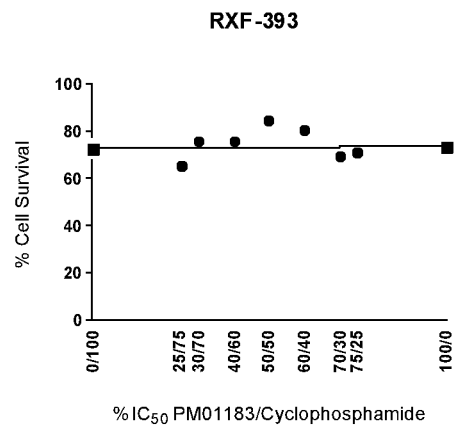
Figure 237:
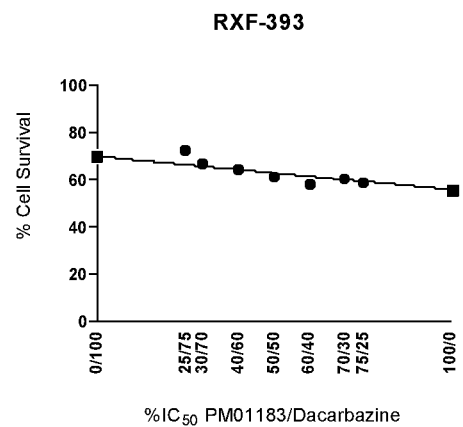
Figure 238:
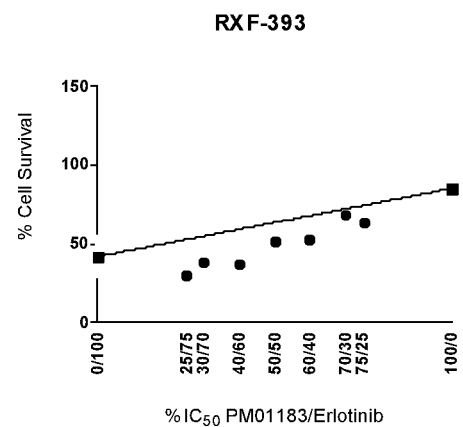
Figure 239:
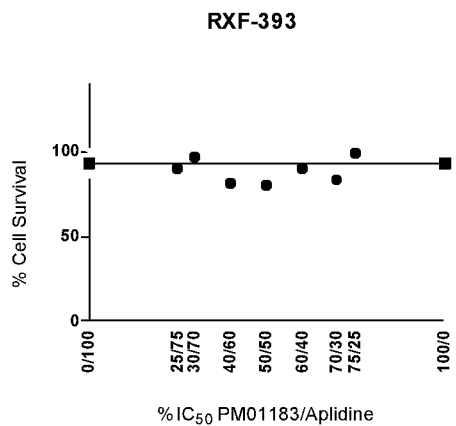
Figure 240:
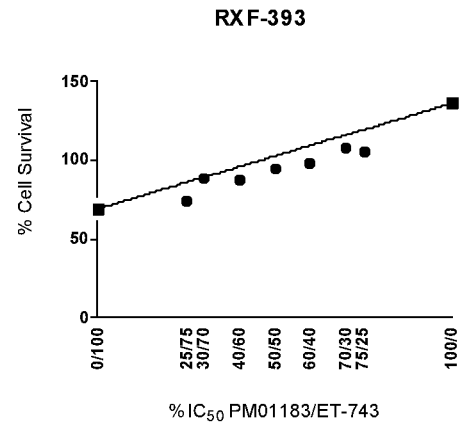
Figure 241:
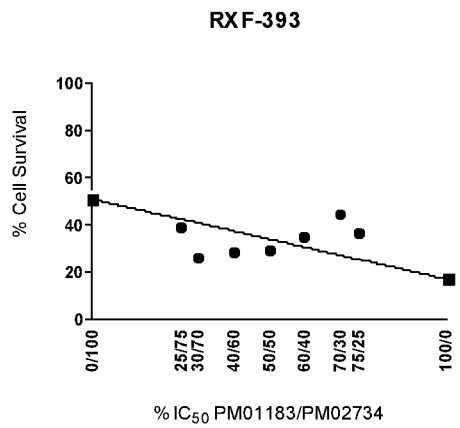
Figure 242:
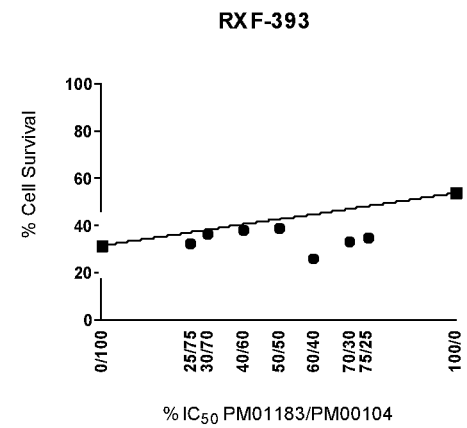

According to this assay it was found that in RXF-393 human kidney carcinoma cell line:

a. The combination of PM01183 with cisplatin (FIG. 220) showed synergism at almost all dose ratios.

b. The combination of PM01183 with 5-fluorouracil (FIG. 221), PM01183 with cytarabine (FIG. 222), PM01183 with gemcitabine (FIG. 223), and PM01183 with methotrexate (FIG. 224) showed synergism at almost all dose ratios.

c. The combination of PM01183 with docetaxel (FIG. 225), PM01183 with vincristine (FIG. 226) and PM01183 with vinorelbine (FIG. 227) showed synergism at almost all dose ratios.

d. The combination of PM01183 with daunorubicin (FIG. 228) showed synergism at almost all dose ratios. The combination of PM01183 with doxorubicin (FIG. 229) showed synergism at the 75/25-60/40 dose ratios, while the combination of PM01183 with actinomycin D (FIG. 230) showed synergism at the 75/25-70/30 and 30/70 dose ratios. The combination of PM01183 with mitomycin C (FIG. 231) exhibited strong synergism.

e. The combination of PM01183 with topotecan (FIG. 232) exhibited strong synergism. The combination of PM01183 with irinotecan (FIG. 233) showed synergism at almost all dose ratios, while the combination of PM01183 with etoposide (FIG. 234) showed synergism at the 75/25 and 40/60-30/70 dose ratios.

f. The combination of PM01183 with vorinostat (FIG. 235) showed synergism at almost all dose ratios.

g. The combination of PM01183 with cyclophosphamide (FIG. 236) showed synergism at the 75/25-70/30 and 25/75 dose ratios.

h. The combination of PM01183 with dacarbazine (FIG. 237) showed synergism at the 60/40-50/50 dose ratios.

i. The combination of PM01183 with erlotinib exhibited strong synergism (FIG. 238).

j. The combination of PM01183 with aplidine (FIG. 239) showed synergism at almost all dose ratios.

k. The combination of PM01183 with ET-743 (FIG. 240) showed synergism at almost all dose ratios.

l. The combination of PM01183 with PM02734 (FIG. 241) showed synergism at almost all dose ratios.

m. The combination of PM01183 with PM00104 (FIG. 242) exhibited strong synergism.

Example 12. In Vitro Studies to Determine the Effect of PM01183 in Combination with Chemotherapeutic Agents on Human Glioblastoma Cell Lines The objective of this study was to determine the ability of PM01183 to potentiate the antitumor activity of chemotherapeutic agents used in the treatment of glioblastoma.

The following agents were evaluated in combination with PM01183: cisplatin, oxaliplatin (stock solutions of these compounds prepared in sterile double distilled water and stored at −20° C.), 5-fluorouracil, gemcitabine, docetaxel, vincristine, daunorubicin, dacarbazine, doxorubicin, topotecan, irinotecan, methotrexate, etoposide, vorinostat, temsirolimus, bortezomib erlotinib, PM02734, ET-743 and aplidine (stock solutions of these compounds prepared in pure DMSO and stored at −20° C.). Additional serial dilutions were prepared in serum-free culture medium to achieve a final 4× concentration. Aliquots of 50 µL of each diluted compound were added per well.

U87-MG was the human glioblastoma cell line selected for this assay. U87-MG cells were maintained in Minimum Essential Medium Eagle (MEME) supplemented with 10% Fetal Bovine Serum (FBS), 2 mM L-glutamine and 100 units/mL of Penicillin-Streptomycin, at 37° C., 5% CO2 and 95% humidity.

The screening was performed in two parts as disclosed in example 1:

a. In the first set of assays, $IC_{50}$ values were determined for each drug after 72 hours of drug exposure in the U87-MG tumor cell line.

The $IC_{50}$ values (72 hours drug exposure) of each individual agent for the U87-MG tumor cell line were calculated by using the same methodology disclosed in example 1 and are shown in table 12.

TABLE 12

$IC_{50}$ values in molar concentration (M) for each of the agent

| Compound | $IC_{50}$ (M) | Compound | $IC_{50}$ (M) | Compound | $IC_{50}$ (M) |
|---|---|---|---|---|---|
| PM01183 | 4.50E−09 | Cisplatin | 4.40E−05 | Oxaliplatin | 1.90E−04 |
| 5-FU | 1.00E−03 | Gemcitabine | 4.50E−07 | Methotrexate | 5.00E−05 |
| Docetaxel | 1.00E−07 | Vincristine | 1.00E−07 | Daunorubicin | 2.84E−07 |
| Doxorubicin | 3.00E−07 | Topotecan | 7.50E−07 | Irinotecan | 7.54E−06 |
| Etoposide | 1.85E−05 | Bortezomib | 4.00E−07 | Vorinostat | 1.60E−05 |
| Dacarbazine | 7.00E−04 | Temsirolimus | 3.50E−06 | Erlotinib | 1.49E−04 |
| Aplidine | 3.80E−09 | ET-743 | 5.00E−09 | PM02734 | 4.08E−06 | b. In a second set of assays, U87-MG human tumor cells were incubated with PM01183 in combination with each of the agents mentioned above in the same combination of unique $IC_{50}$ concentrations as those described in example 1.

Cell culture and cell plating were performed as described before and the cytotoxic effect was also measured by the MTT Assay as disclosed in example 1.

Figure 243:
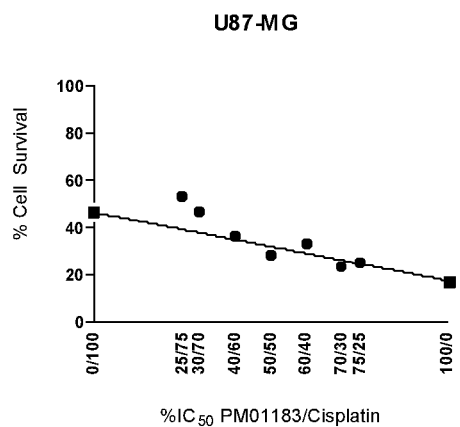
FIG. 243-262. In vitro activity data of PM01183 in combination with cisplatin, oxaliplatin, 5-fluorouracil, gemcitabine, methotrexate, docetaxel, vincristine, daunorubicin, doxorubicin, topotecan, irinotecan, etoposide, bortezomib, vorinostat, dacarbazine, temsirolimus, erlotinib, aplidine, ET-743 and PM02734 respectively against U87-MG cells.
Figure 244:
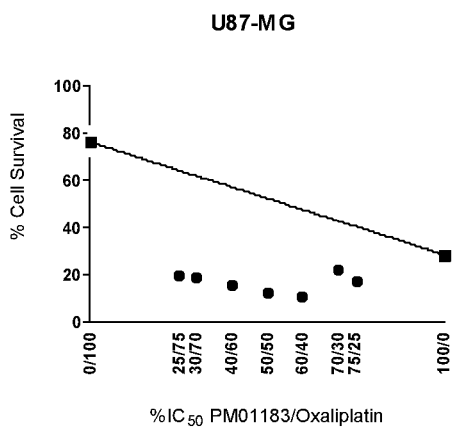
Figure 245:
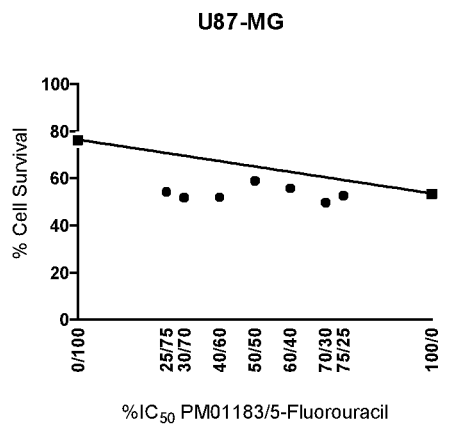
Figure 246:
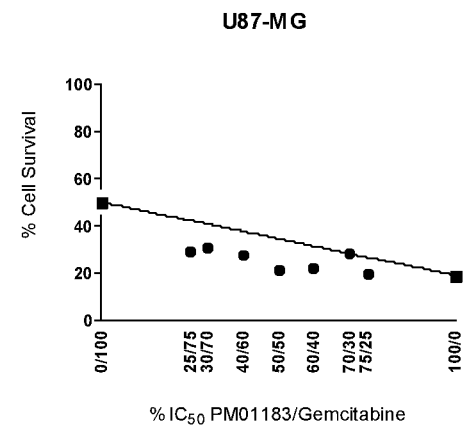
Figure 247:
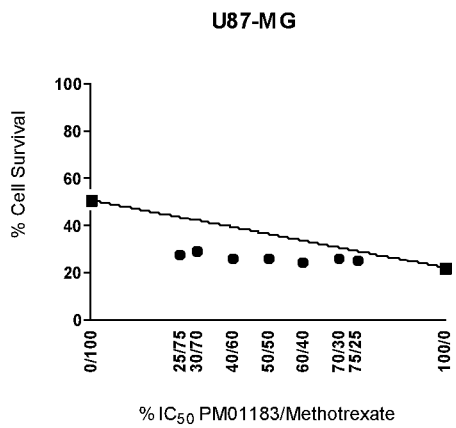
Figure 248:
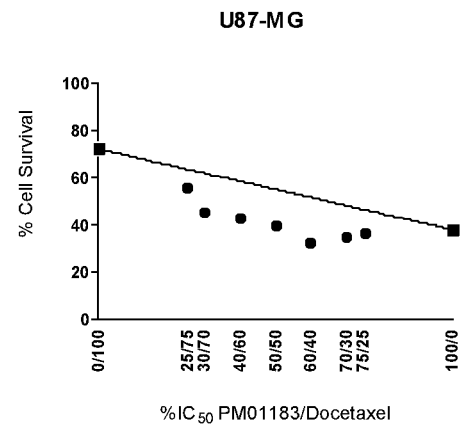
Figure 249:
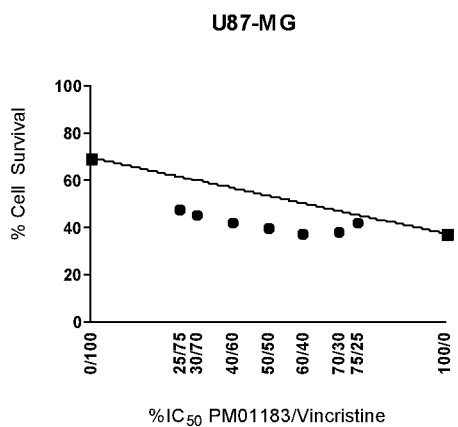
Figure 250:
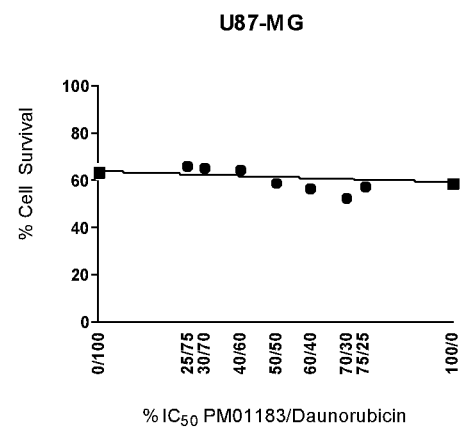
Figure 251:
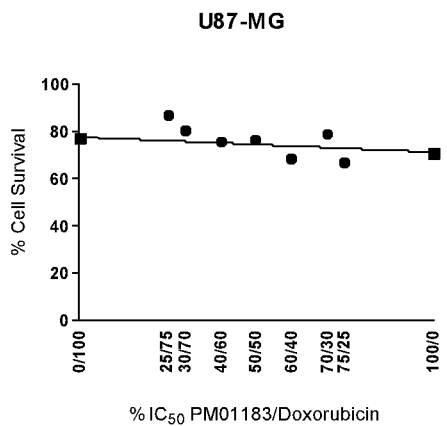
Figure 252:
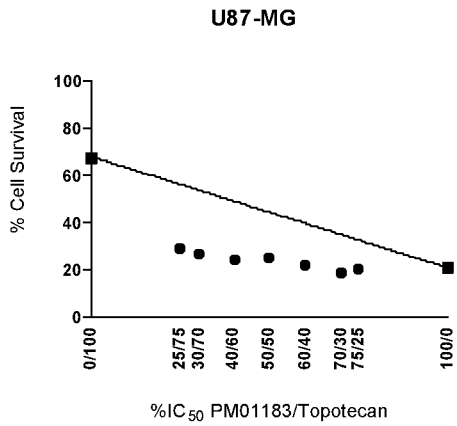
Figure 253:
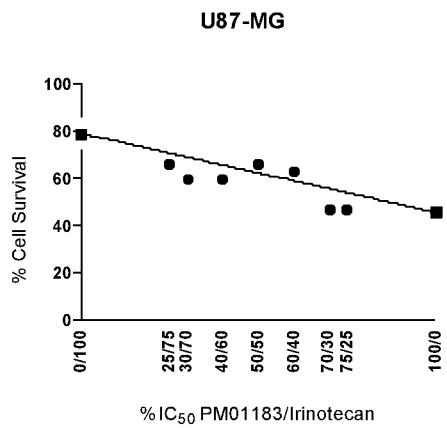
Figure 254:
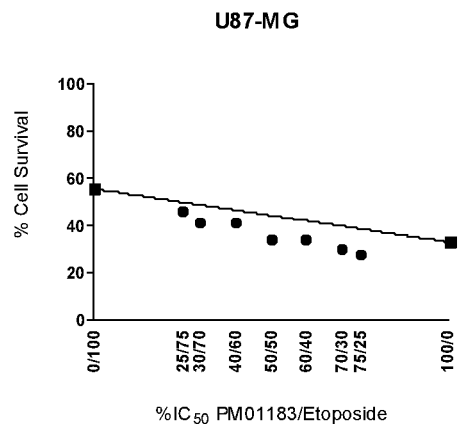
Figure 255:
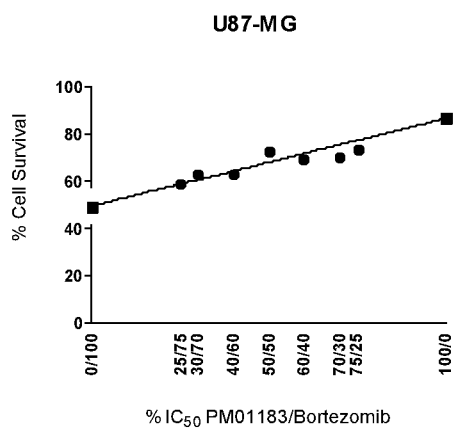
Figure 256:
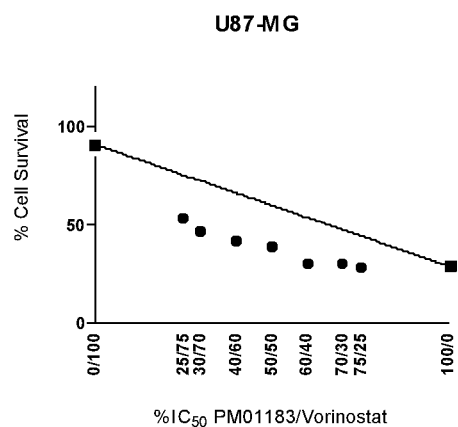
Figure 257:
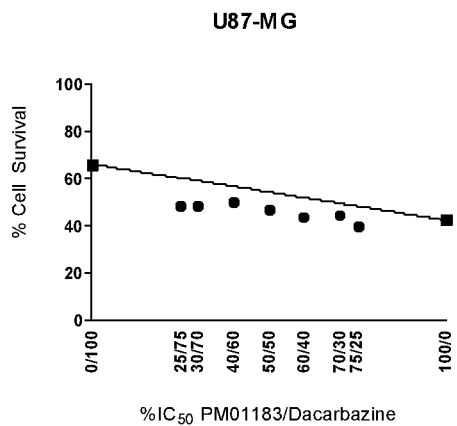
Figure 258:
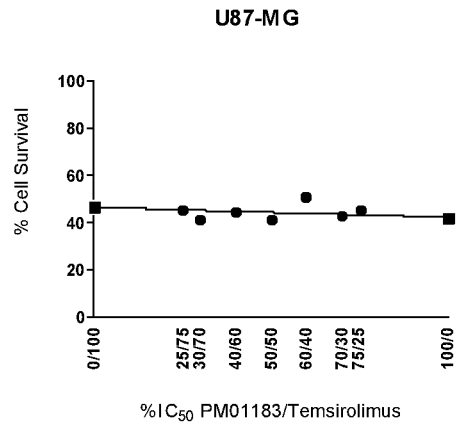
Figure 259:
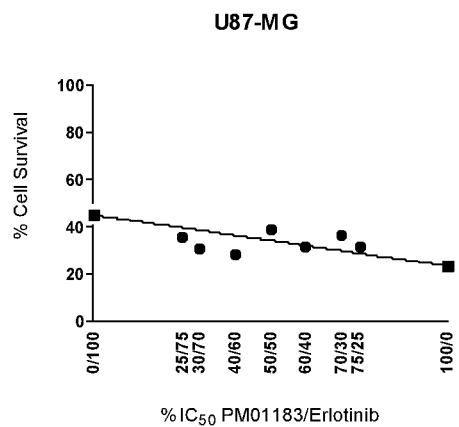
Figure 260:
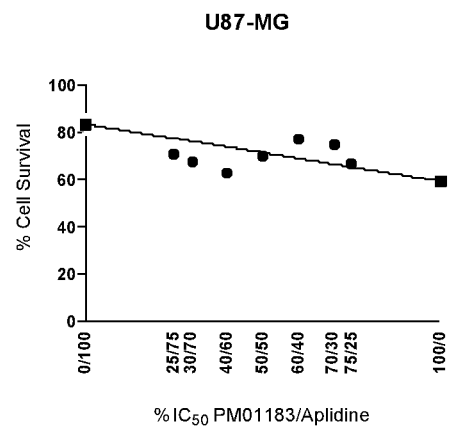
Figure 261:
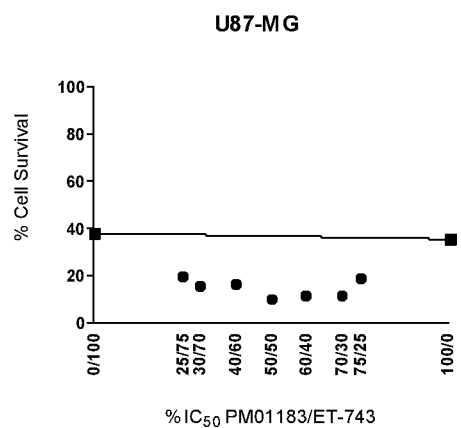
Figure 262:
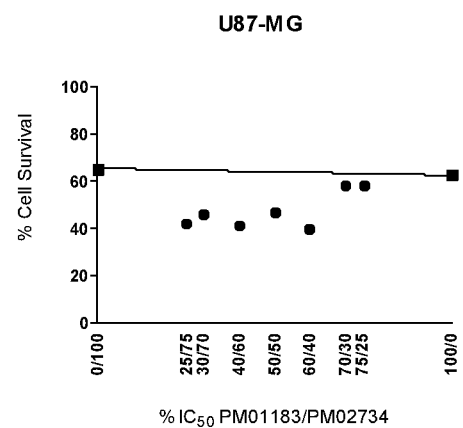

According to this assay it was found that in U87-MG human glioblastoma cell line:

a. The combination of PM01183 with cisplatin (FIG. 243) showed synergism at the 70/30 and 50/50 dose ratios, while the combination of PM01183 with oxaliplatin (FIG. 244) exhibited strong synergism.

b. The combination of PM01183 with 5-fluorouracil (FIG. 245) and PM01183 with methotrexate (FIG. 247) exhibited synergism. The combination of PM01183 with gemcitabine (FIG. 246) showed synergism at almost all dose ratios.

c. The combination of PM01183 with docetaxel (FIG. 248) and PM01183 with vincristine (FIG. 249) exhibited strong synergism.

d. The combination of PM01183 with daunorubicin (FIG. 250) showed synergism at almost all dose ratios, while the combination of PM01183 with doxorubicin (FIG. 251) showed synergism at the 75/25 and 60/40 dose ratios.

e. The combination of PM01183 with topotecan (FIG. 252) and PM01183 with etoposide (FIG. 254) showed strong synergism. The combination of PM01183 with irinotecan (FIG. 253) showed synergism at almost all dose ratios.

f. The combination of PM01183 with bortezomib (FIG. 255) showed synergism at almost all dose ratios.

g. The combination of PM01183 with vorinostat (FIG. 256) exhibited strong synergism.

h. The combination of PM01183 with dacarbazine (FIG. 257) exhibited synergism.

i. The combination of PM01183 with temsirolimus (FIG. 258) showed synergism at the 50/50 and 30/70 dose ratios.

j. The combination of PM01183 with erlotinib (FIG. 259) showed synergism at the 40/60-25/75 dose ratios.

k. The combination of PM01183 with aplidine (FIG. 260) showed synergism at the 50/50-25/75 dose ratios.
m. The combination of PM01183 with ET-743 (FIG. 261) exhibited strong synergism.
l. The combination of PM01183 with PM02734 (FIG. 262) showed strong synergism.

Example 13. In Vivo Studies to Determine the Effect of PM01183 in Combination with Paclitaxel, Vinorelbine and Doxorubicin in Human Ovarian Tumor Xenografts The aim of these studies was to evaluate the ability of PM01183 to potentiate the antitumor activity of paclitaxel, vinorelbine and doxorubicin by using a xenograft model of human ovarian carcinoma.

Female athymic nude mice (Harlan Laboratories Models, S.L. (Barcelona, Spain) were utilized for all experiments. Animals were housed in individually ventilated cages, up to ten per cage in a 12-hour light-dark cycle at 21-23° C. and 40-60% humidity. The mice were allowed free access to irradiated standard rodent diet and sterilized water. Animals were acclimated for at least 5 days prior to tumor implantation with a tumor cell suspension.

The tumor model used in these studies was A2780 cell line, which was obtained from the European Collection of Cell Cultures (ECACC no. 93112519).

A2780 cells were grown at 37° C. with 5% $CO_2$ in RPMI-1640 medium. Each animal was subcutaneously implanted on the right flank, using 26G needle and a 1 cc syringe, with $1 \times 10^7$ A2780 cells (from in vitro passage 5 in PM01183 and doxorubicin and PM01183 and vinorelbine studies; and passage 9 in PM01183 and paclitaxel study), in 0.05 mL suspension of 50% Matrigel and 50% serum free medium, without antibiotics.

Tumor measurements were determined by using digital caliper (Fowler Sylvac, S235PAT). The formula to calculate volume for a prolate ellipsoid was used to estimate tumor volume ($mm^3$) from 2-dimensional tumor measurements: Tumor volume ($mm^3$)=$[L \times W^2] \div 2$, where L is the length and it is the longest diameter in mm, and W is the width and it is the shortest diameter in mm of a tumor. Assuming unit density, volume was converted to weight (i.e., 1 $mm^3$=1 mg). Tumor volume and animal body weights were measured 2-3 times per week starting form the first day of treatment (Day 0).

Treatment tolerability was assessed by monitoring body weight evolution, clinical signs as well as evidences of local damage in the injection site.

When tumors reached a volume of about 195 $mm^3$ in the study of PM01183 with paclitaxel, a volume of about 158 $mm^3$ in the study of PM01183 with vinorelbine and a volume of about 163.5 $mm^3$ in the study of PM01183 with doxorubicin, the mice were randomly allocated into the treatments and control groups (N=5-7/group) based on body weight and tumor volumen measurements by using NewLab Oncology Software (version 2.25.06.00).

PM01183 was provided in the form of vials of lyophilized PM01183 cake which was reconstituted with water for infusion to a concentration of 0.2 mg/mL. The PM01183 stock solution was further diluted in 5% glucose solution for injection to the dosing formulation concentrations. Doxorubicin was provided in the form of a solid powder containing Doxorubicin HCl, which was reconstituted in 0.9% saline solution. Vinorelbine was provided as a solution prepared by diluting the product with 0.9% saline solution. Paclitaxel was provided in the form of a solution prepared by diluting the product with 5% glucose solution for injection to the target final concentration.

In these experiments, PM01183 and paclitaxel, PM01183 and vinorelbine and PM01183 and doxorubicin treatments, as well as placebo, were intravenously administered once per week up to 2 consecutive weeks on Days 0 and 7. Dose level groups were administered either as single agents or in combination.

Comparison of the median tumor volume in the treatment groups (T) to the median tumor volume in the control group (T/C×100%) was used for evaluation of the antitumor efficacy. In addition, potentiation was determined when the response of the combination group was greater than the best response of the most active agent administered as single agent (monotherapy) on the same schedule and dose as those used in the combination therapy.

Finally, the combination index (CI), that quantitatively measures the degree of drug interactions, was obtained from the fractions affected by the treatment, Fa (defined as 1 −T/C) for each experimental group at the last measurement day (Day 10 for PM01183 and paclitaxel combination study, and PM01183 and doxorubicin study, and Day 9 for PM01183 and vinorelbine study) using the median-effect principle (Chou T. C. Pharmacol. Rev. 2006, 58, 621-681).

Figure 263:
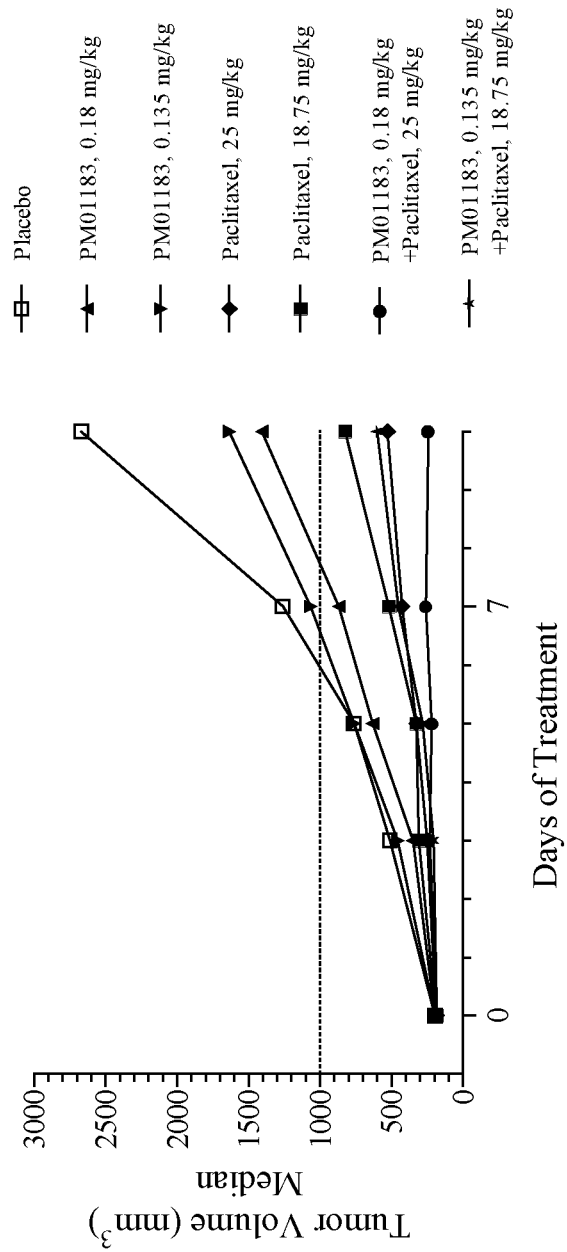
FIG. 263. Tumor volume evaluation of A2780 tumors in mice treated with placebo, PM01183, paclitaxel and PM01183 plus paclitaxel.

Table 13 reports the % T/C values obtained with PM01183 and paclitaxel both administered as single agents and in combination for each dose level, and FIG. 263 shows the tumor volume evaluation of A2780 tumors in mice treated with placebo, PM01183, paclitaxel, and the corresponding combinations for the groups dosed at the two highest ratios.

TABLE 13

| Group | Dose | Test materials | % T/C on day 0 | 3 | 5 | 7 | 10 |
|---|---|---|---|---|---|---|---|
| G01 (Control group) | 10 ml/kg | Placebo | — | — | — | — | — |
| G02 | 0.18 mg/kg | PM01183 | 101.6 | 68.9 | 83.1 | 69.1 | 52.8 |
| G03 | 0.135 mg/kg | PM01183 | 101.2 | 89.9 | 99.8 | 84.5 | 61.2 |
| G04 | 0.09 mg/kg | PM01183 | 94.2 | 88.5 | 114.1 | 103.3 | 88.0 |
| G05 | 0.045 mg/kg | PM01183 | 94.0 | 91.1 | 99.6 | 88.0 | 73.1 |
| G06 | 25 mg/kg | Paclitaxel | 95.3 | 49.3 | 42.9 | 34.0 | 19.8 |
| G07 | 18.75 mg/kg | Paclitaxel | 95.0 | 60.4 | 43.2 | 41.5 | 31.1 |
| G08 | 12.5 mg/kg | Paclitaxel | 96.2 | 62.5 | 73.9 | 62.5 | 50.8 |
| G09 | 6.25 mg/kg | Paclitaxel | 94.3 | 60.2 | 79.7 | 81.3 | 59.2 |
| G10 | 0.18 mg/kg 25 mg/kg | PM01183 Paclitaxel | 93.3 | 45.9 | 28.8 | 20.9 | 9.2 |
| G11 | 0.135 mg/kg 18.75 mg/kg | PM01183 Paclitaxel | 93.4 | 40.5 | 37.1 | 36.0 | 22.6 |
| G12 | 0.09 mg/kg 12.5 mg/kg | PM01183 Paclitaxel | 96.5 | 64.3 | 67.7 | 73.2 | 49.0 |
| G13 | 0.045 mg/kg 6.25 mg/kg | PM01183 Paclitaxel | 96.2 | 78.6 | 89.1 | 91.1 | 77.2 |

Placebo: lyophilised cake containing 100 mg Sucrose + Potassium dihydrogen phosphate 6.8 mg + Phosphoric acid q.s. pH 3.8-4.5, which was reconstituted with 1 mL of water for infusion.

Figure 264:
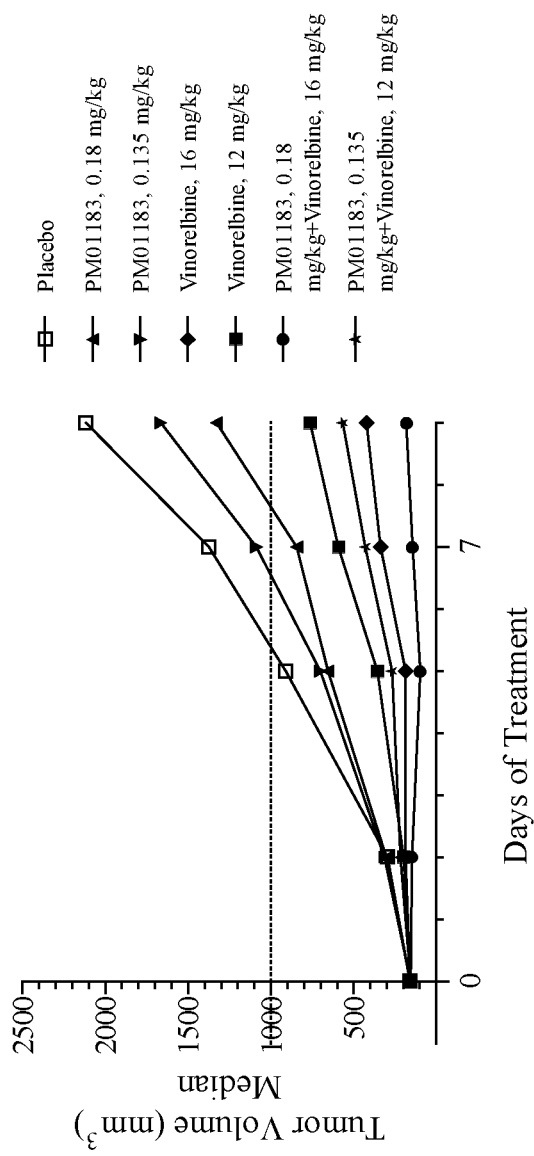
FIG. 264. Tumor volume evaluation of A2780 tumors in mice treated with placebo, PM01183, vinorelbine and PM01183 plus vinorelbine.

Table 14 reports the % T/C values obtained with PM01183 and vinorelbine both administered as single agents and in combination for each dose level, and FIG. 264 shows the tumor volume evaluation of A2780 tumors in mice treated with placebo, PM01183, vinorelbine, and the corresponding combinations for the groups dosed at the two highest ratios.

TABLE 14

| Group | Dose | Test materials | % T/C on day 0 | 2 | 5 | 7 | 9 |
|---|---|---|---|---|---|---|---|
| G01 (Control group) | 10 ml/kg | Placebo | — | — | — | — | — |
| G02 | 0.18 mg/kg | PM01183 | 98.9 | 101.6 | 72.2 | 61.3 | 62.8 |
| G03 | 0.135 mg/kg | PM01183 | 98.3 | 105.3 | 77.2 | 79.1 | 78.7 |
| G04 | 0.09 mg/kg | PM01183 | 98.0 | 88.6 | 61.2 | 87.6 | 94.5 |
| G05 | 0.045 mg/kg | PM01183 | 97.8 | 107.5 | 93.6 | 92.5 | 97.1 |
| G06 | 16.0 mg/kg | Vinorelbine | 99.0 | 62.5 | 20.8 | 24.5 | 20.0 |
| G07 | 12.0 mg/kg | Vinorelbine | 97.4 | 67.2 | 39.1 | 43.0 | 36.1 |
| G08 | 8.0 mg/kg | Vinorelbine | 97.6 | 79.5 | 45.0 | 54.2 | 47.9 |
| G09 | 4.0 mg/kg | Vinorelbine | 97.2 | 88.6 | 69.3 | 81.7 | 77.3 |
| G10 | 0.18 mg/kg PM01183 16.0 mg/kg Vinorelbine | | 97.3 | 50.1 | 10.9 | 10.6 | 8.6 |
| G11 | 0.135 mg/kg PM01183 12.0 mg/kg Vinorelbine | | 97.2 | 74.0 | 29.6 | 31.2 | 26.8 |
| G12 | 0.09 mg/kg PM01183 8.0 mg/kg Vinorelbine | | 96.8 | 69.3 | 48.3 | 56.5 | 49.8 |
| G13 | 0.045 mg/kg PM01183 4.0 mg/kg Vinorelbine | | 97.1 | 85.6 | 61.7 | 74.2 | 81.6 |

Placebo: as disclosed in table 13.

Figure 265:
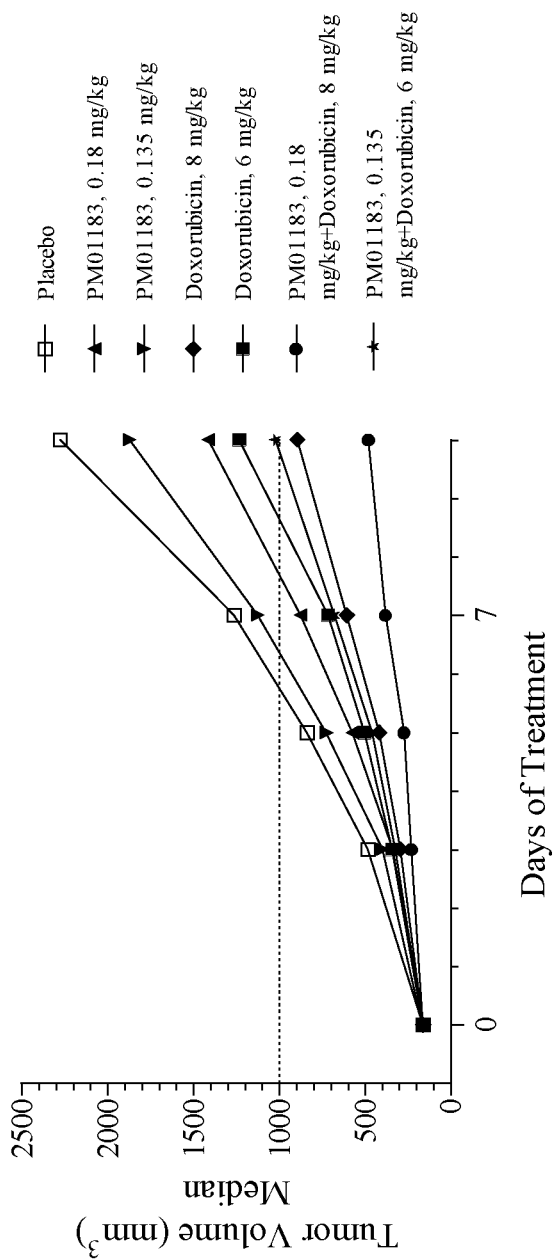
FIG. 265. Tumor volume evaluation of A2780 tumors in mice treated with placebo, PM01183, doxorubicin and PM01183 plus doxorubicin.

Table 15 reports the % T/C values obtained with PM01183 and doxorubicin both administered as single agents and in combination for each dose level, and FIG. 265 shows the tumor volume evaluation of A2780 tumors in mice treated with placebo, PM01183, doxorubicin, and the corresponding combinations for the groups dosed at the two highest ratios.

TABLE 15

| Group | Dose | Test materials | % T/C on day 0 | 3 | 5 | 7 | 10 |
|---|---|---|---|---|---|---|---|
| G01 (Control group) | 10 ml/kg | Placebo | — | — | — | — | — |
| G02 | 0.18 mg/kg | PM01183 | 100.9 | 70.2 | 68.5 | 69.3 | 62.1 |
| G03 | 0.135 mg/kg | PM01183 | 102.2 | 82.4 | 86.6 | 89.2 | 82.4 |
| G04 | 0.09 mg/kg | PM01183 | 100.2 | 93.3 | 95.2 | 93.5 | 87.7 |
| G05 | 0.045 mg/kg | PM01183 | 100.1 | 98.2 | 98.6 | 97.7 | 90.0 |
| G06 | 8.0 mg/kg | Doxorubicin | 99.5 | 60.8 | 49.8 | 48.1 | 39.4 |
| G07 | 6.0 mg/kg | Doxorubicin | 99.4 | 71.0 | 60.3 | 56.8 | 54.3 |
| G08 | 4.0 mg/kg | Doxorubicin | 102.0 | 82.9 | 75.1 | 75.0 | 68.9 |
| G09 | 2.0 mg/kg | Doxorubicin | 99.8 | 91.5 | 93.1 | 94.2 | 86.2 |
| G10 | 0.18 mg/kg PM01183 8.0 mg/kg Doxorubicin | | 99.7 | 47.6 | 32.6 | 30.3 | 21.1 |
| G11 | 0.135 mg/kg PM01183 6.0 mg/kg Doxorubicin | | 100.6 | 67.0 | 54.9 | 53.9 | 44.9 |
| G12 | 0.09 mg/kg PM01183 4.0 mg/kg Doxorubicin | | 98.3 | 74.7 | 69.0 | 63.1 | 64.4 |
| G13 | 0.045 mg/kg PM01183 2.0 mg/kg Doxorubicin | | 98.1 | 83.1 | 86.6 | 78.1 | 79.2 |

Placebo: as disclosed in table 13.

According to these assays it was found that:

a. The combination treatment of PM01183 and paclitaxel was effective in the inhibition of the growth of the A2780 ovarian cells, resulting in a statistically significant (P<0.01) tumor reduction compared to the control group with T/C values of 9.2% and 22.6% (Day 10) in the two highly-dosed groups. Moreover, the combination of PM01183 and paclitaxel produced lower T/C values than the more active single agent in this experiment (paclitaxel at doses of 25 mg/kg and 18.75 mg/kg). Specifically, the TC (%) values of the combination (25 mg/kg paclitaxel+0.18 mg/kg PM01183) vs paclitaxel alone (25 mg/kg paclitaxel) were 28.8 vs 42.9 (day 5), 20.9 vs 34.0 (day 7), and 9.2 vs 19.8 (day 10), and the TC (%) values of the combination (18.75 mg/kg paclitaxel+0.135 mg/kg PM01183) vs paclitaxel alone (18.75 mg/kg paclitaxel) were 37.1 vs 43.2 (day 5), 36.0 vs 41.5 (day 7), and 22.6 vs 31.1 (day 10). Therefore, when PM01183 is combined with paclitaxel a potentiation of the antitumor activity is clearly observed.

Additionally, based on the median-effect principle, the combination of PM01183 and paclitaxel resulted in CI values less than 1 (at Fa higher than 0.8), indicating synergism in mice bearing ovarian A2780 xenografted tumors.

b. The combination treatment of PM01183 and vinorelbine was effective in the inhibition of the growth of the A2780 ovarian cells, resulting in a statistically significant (P<0.01) tumor reduction compared to the control group with T/C values of 8.6% and 26.8% (Day 9) in the two highly-dosed groups. Moreover, the combination of PM01183 and vinorelbine produced lower T/C values than the more active single agent in this experiment (vinorelbine at doses of 16 mg/kg and 12 mg/kg). Specifically, the TC (%) values of the combination (16 mg/kg vinorelbine+0.18 mg/kg PM01183) vs vinorelbine alone (16 mg/kg vinorelbine) were 10.9 vs 20.8 (day 5), 10.6 vs 24.5 (day 7), and 8.6 vs 20.0 (day 9), and the TC (%) values of the combination (12 mg/kg vinorelbine+0.135 mg/kg PM01183) vs vinorelbine alone (12 mg/kg vinorelbine) were 29.6 vs 39.1 (day 5), 31.2 vs 43 (day 7), and 26.8 vs 36.1 (day 9). Therefore, when PM01183 is combined with vinorelbine a potentiation of the antitumor activity is clearly observed.

Additionally, based on the median-effect principle, the combination of PM01183 and vinorelbine resulted in CI values of 0.75 (at Fa equal to 0.97), indicating synergism in mice bearing ovarian A2780 xenografted tumors.

c. The combination treatment of PM01183 and doxorubicin was effective in the inhibition of the growth of the A2780 ovarian cells, resulting in a statistically significant (P<0.01) tumor reduction compared to the control group with T/C values of 21.1% and 44.9% (Day 10) in the two highly-dosed groups. Moreover, the combination of PM01183 and doxorubicin produced lower T/C values than the more active single agent in this experiment (doxorubicin at a dose of 8 mg/kg). Specifically, the TC (%) values of the combination (8 mg/kg doxorubicin+0.18 mg/kg PM01183) vs doxorubicin alone (8 mg/kg doxorubicin) were 32.6 vs 49.8 (day 5), 30.3 vs 48.1 (day 7), and 21.1 vs 39.4 (day 10). Therefore, when PM01183 is combined with doxorubicin a potentiation of the antitumor activity is clearly observed.

Additionally, based on the median-effect principle, the combination of PM01183 and doxorubicin resulted in CI values less than 1 (at Fa higher than 0.8), indicating synergism in mice bearing ovarian A2780 xenografted tumors.

Example 14. In Vivo Studies to Determine the Effect of PM01183 in Combination with Cisplatin and 5-Fluorouracil in Human Gastric Tumor Xenografts The aim of these studies was to evaluate the ability of PM01183 to potentiate the antitumor activity of cisplatin and 5-fluorouracil by using a xenograft model of human gastric carcinoma.

Female athymic nude mice (Harlan Laboratories Models, S.L. (Barcelona, Spain) were utilized for all experiments. Animals were housed in individually ventilated cages, up to ten per cage in a 12-hour light-dark cycle at 21-23° C. and 40-60% humidity. The mice were allowed free access to irradiated standard rodent diet and sterilized water. Animals were acclimated for at least 5 days prior to tumor implantation with a tumor cell suspension.

The tumor model used in these studies was HGC-27 cell line, which was obtained from the European Collection of Cell Cultures (ECACC no. 94042256).

HGC-27 cells were grown at 37° C. with 5% $CO_2$ in Iscove's modified Dulbeco's medium (IDMD). Each animal was subcutaneously implanted on the right flank, using 26G needle and a 1 cc syringe, with $5 \times 10^6$ HGC-27 cells (from in vitro passage 4 in PM01183 and cisplatin study, and passage 6 in PM01183 and 5-fluorouracil study), in 0.05 mL suspension of 50% Matrigel and 50% serum free medium, without antibiotics.

Tumor measurements and treatment tolerability were performed and determined as disclosed in Example 13.

When tumors reached a volume of about 165.5 mm³ in the study of PM01183 with cisplatin and a volume of about 170 mm³ in the study of PM01183 with 5-fluorouracil, mice were randomly allocated into the treatments and control groups (N=5-7/group) based on body weight and tumor volumen measurements by using NewLab Oncology Software (version 2.25.06.00).

PM01183 was provided in the form of vials of lyophilized PM01183 cake which was reconstituted with water for infusion to a concentration of 0.2 mg/mL. The PM01183 stock solution was further diluted in 5% glucose solution for injection to the dosing formulation concentrations. Cisplatin and 5-fluorouracil were provided as solutions prepared by diluting the product with 0.9% saline solution for injection to the target final concentration.

In these experiments, PM01183 and cisplatin and PM01183 and 5-fluorouracil treatments, as well as placebo, were intravenously administered once per week up to 2 consecutive weeks on Days 0 and 7. Dose level groups were administered either as single agents or in combination.

Comparison of the median tumor volume in the treatment groups (T) to the median tumor volume in the control group (T/C×100%) was used for evaluation of the antitumor efficacy. In addition, potentiation and combination index (CI) were determined as disclosed in Example 13.

Figure 266:
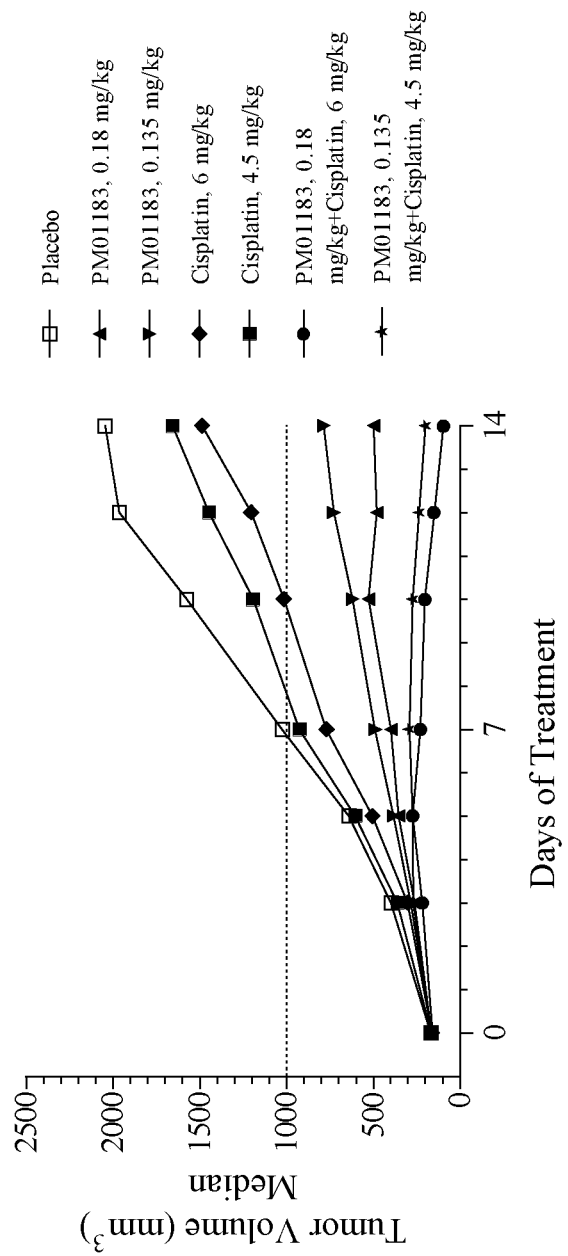
FIG. 266. Tumor volume evaluation of HGC-27 tumors in mice treated with placebo, PM01183, cisplatin and PM01183 plus cisplatin.

Table 16 reports the % T/C values obtained with PM01183 and cisplatin both administered as single agents and in combination for each dose level, and FIG. 266 shows the tumor volume evaluation of HGC-27 tumors in mice treated with placebo, PM01183, cisplatin, and the corresponding combinations for the groups dosed at the two highest ratios.

TABLE 16

| Group | Dose | Test materials | % T/C on day | | | | | | |
|---|---|---|---|---|---|---|---|---|---|
| | | | 0 | 3 | 5 | 7 | 10 | 12 | 14 |
| G01 (Control group) | 10 ml/kg | Placebo | — | — | — | — | — | — | — |
| G02 | 0.18 mg/kg | PM01183 | 99.6 | 65.9 | 55.6 | 38.7 | 33.5 | 24.3 | 24.3 |
| G03 | 0.135 mg/kg | PM01183 | 97.9 | 71.6 | 59.9 | 47.8 | 39.3 | 37.1 | 38.3 |
| G04 | 0.09 mg/kg | PM01183 | 98.6 | 67.5 | 67.9 | 66.1 | 70.2 | 60.3 | 65.0 |
| G05 | 0.045 mg/kg | PM01183 | 98.9 | 85.9 | 83.1 | 92.1 | 76.4 | 81.6 | 88.5 |
| G06 | 6.0 mg/kg | Cisplatin | 97.7 | 76.1 | 79.0 | 75.1 | 64.4 | 61.3 | 72.7 |
| G07 | 4.5 mg/kg | Cisplatin | 98.5 | 90.5 | 94.5 | 90.2 | 75.7 | 73.7 | 81.1 |
| G08 | 3.0 mg/kg | Cisplatin | 99.0 | 78.6 | 80.0 | 78.7 | 81.3 | 82.8 | 85.1 |
| G09 | 1.5 mg/kg | Cisplatin | 99.3 | 78.1 | 78.8 | 82.6 | 83.5 | 86.6 | 89.9 |
| G10 | 0.18 mg/kg PM01183 6.0 mg/kg Cisplatin | | 95.7 | 55.0 | 42.4 | 22.3 | 12.9 | 7.6 | 4.6 |
| G11 | 0.135 mg/kg PM01183 4.5 mg/kg Cisplatin | | 99.2 | 67.7 | 42.7 | 28.6 | 17.3 | 12.1 | 9.8 |
| G12 | 0.09 mg/kg PM01183 3.0 mg/kg Cisplatin | | 99.9 | 80.0 | 64.3 | 45.7 | 47.2 | 42.4 | 56.7 |
| G13 | 0.045 mg/kg PM01183 1.5 mg/kg Cisplatin | | 99.9 | 93.3 | 83.0 | 75.9 | 69.3 | 70.3 | 80.0 |

Placebo: as disclosed in table 13.

Figure 267:
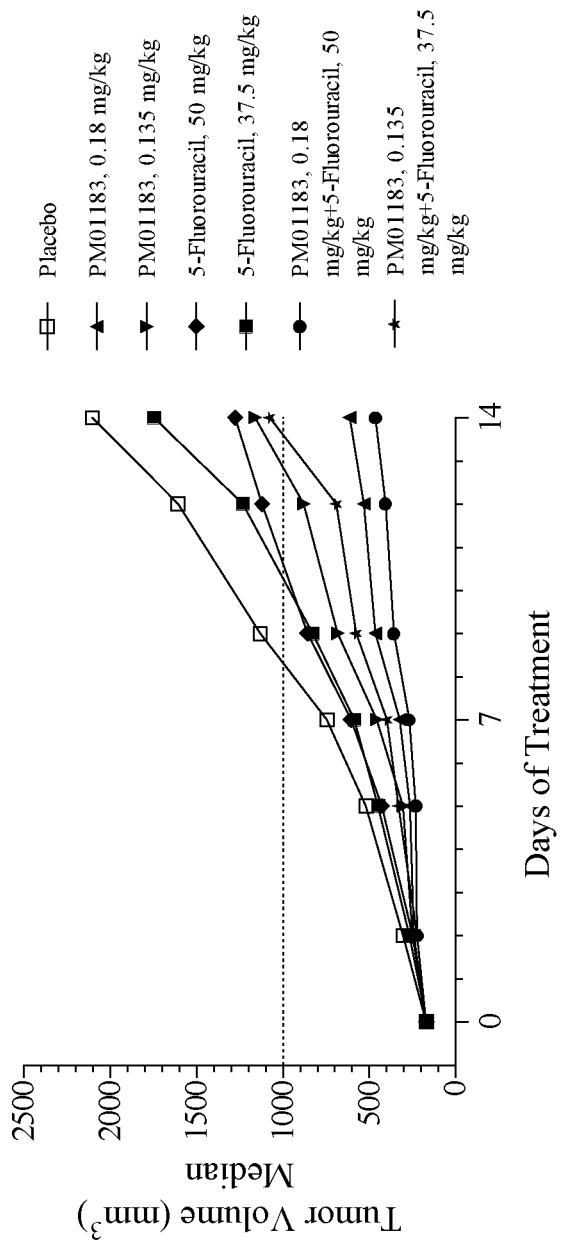
FIG. 267. Tumor volume evaluation of HGC-27 tumors in mice treated with placebo, PM01183, 5-fluorouracil and PM01183 plus 5-fluorouracil.
Figure 268:
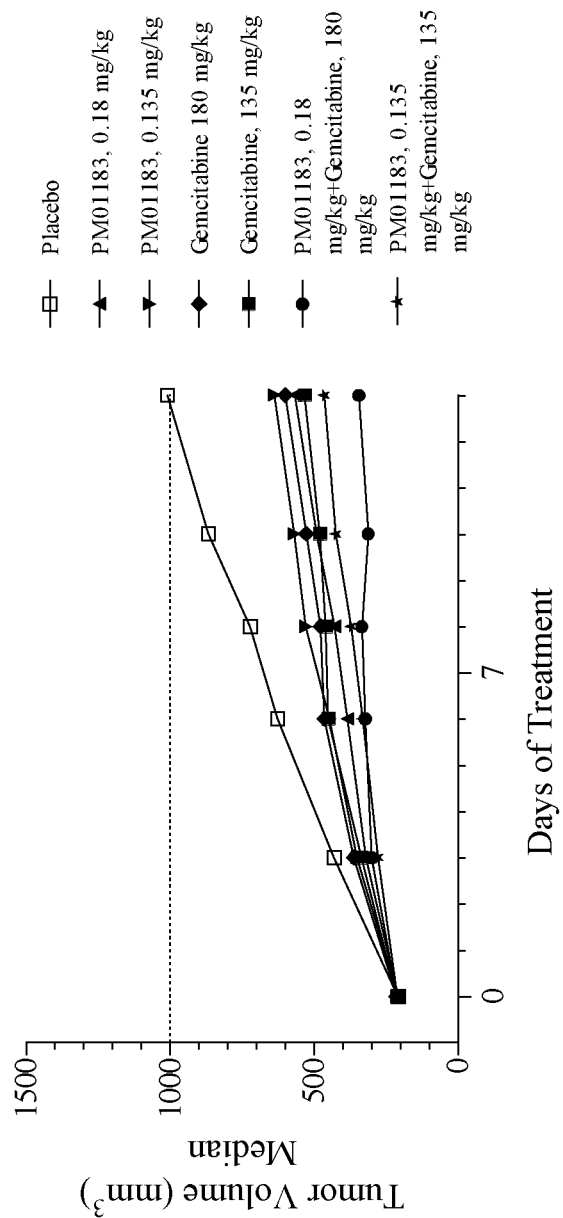
FIG. 268. Tumor volume evaluation of SW1990 tumors in mice treated with placebo, PM01183, gemcitabine and PM01183 plus gemcitabine.

Table 17 reports the % T/C values obtained with PM01183 and 5-fluorouracil both administered as single agents and in combination for each dose level, and FIG. 267 shows the tumor volume evaluation of HGC-27 tumors in mice treated with placebo, PM01183, 5-fluorouracil, and the corresponding combinations for the groups dosed at the two highest ratios.

TABLE 17

| Group | Dose | Test materials | % T/C on day | | | | | | |
|---|---|---|---|---|---|---|---|---|---|
| | | | 0 | 2 | 5 | 7 | 9 | 12 | 14 |
| G01 (Control group) | 10 ml/kg | Placebo | — | — | — | — | — | — | — |
| G02 | 0.18 mg/kg | PM01183 | 99.6 | 78.6 | 50.9 | 43.3 | 41.0 | 33.0 | 29.2 |
| G03 | 0.135 mg/kg | PM01183 | 100.2 | 81.5 | 58.7 | 61.4 | 60.2 | 54.6 | 55.1 |
| G04 | 0.09 mg/kg | PM01183 | 100.6 | 90.5 | 87.6 | 83.4 | 82.6 | 76.7 | 67.7 |
| G05 | 0.045 mg/kg | PM01183 | 99.9 | 84.3 | 103.2 | 104.6 | 103.5 | 101.6 | 85.0 |
| G06 | 50.0 mg/kg | 5-Fluorouracil | 100.3 | 81.2 | 82.3 | 81.1 | 75.6 | 69.6 | 60.7 |
| G07 | 37.5 mg/kg | 5-Fluorouracil | 99.4 | 86.9 | 86.9 | 78.6 | 73.2 | 76.7 | 83.1 |

TABLE 17-continued

| Group | Dose | Test materials | % T/C on day 0 | 2 | 5 | 7 | 9 | 12 | 14 |
|---|---|---|---|---|---|---|---|---|---|
| G08 | 25.0 mg/kg | 5-Fluorouracil | 100.6 | 89.8 | 97.0 | 111.4 | 102.6 | 93.9 | 82.8 |
| G09 | 12.5 mg/kg | 5-Fluorouracil | 100.7 | 81.7 | 101.3 | 102.8 | 98.6 | 90.5 | 83.8 |
| G10 | 0.18 mg/kg 50.0 mg/kg | PM01183 5-Fluorouracil | 99.6 | 73.0 | 44.2 | 35.9 | 31.5 | 25.3 | 22.0 |
| G11 | 0.135 mg/kg 37.5 mg/kg | PM01183 5-Fluorouracil | 100.8 | 73.4 | 63.5 | 53.1 | 50.6 | 42.8 | 51.1 |
| G12 | 0.09 mg/kg 25.0 mg/kg | PM01183 5-Fluorouracil | 99.6 | 95.8 | 97.7 | 98.9 | 90.0 | 74.7 | 69.9 |
| G13 | 0.045 mg/kg 12.5 mg/kg | PM01183 5-Fluorouracil | 99.5 | 80.6 | 87.3 | 88.5 | 99.3 | 87.1 | 84.2 |

Placebo: as disclosed in table 13.

According to these assays it was found that:
a. The combination treatment of PM01183 and cisplatin was effective in the inhibition of the growth of the HGC-27 gastric cells, resulting in a statistically significant (P<0.01) tumor reduction compared to the control group with T/C values of 4.6% and 9.8% (Day 14) in the two highly-dosed groups. Moreover, the combination of PM01183 and cisplatin produced lower T/C values than the more active single agent in this experiment (PM01183 at doses of 0.18 mg/kg and 0.135 mg/kg). Specifically, the TC (%) values of the combination (6 mg/kg cisplatin+0.18 mg/kg PM01183) vs PM01183 alone (0.18 mg/kg PM01183) were 12.9 vs 33.5 (day 10), 7.6 vs 24.3 (day 12), and 4.6 vs 24.3 (day 14), and the TC (%) values of the combination (4.5 mg/kg cisplatin+ 0.135 mg/kg PM01183) vs PM01183 alone (0.135 mg/kg PM01183) were 17.3 vs 39.3 (day 10), 12.1 vs 37.1 (day 12), and 9.8 vs 38.3 (day 14). Therefore, when PM01183 is combined with paclitaxel a potentiation of the antitumor activity is clearly observed.

Additionally, based on the median-effect principle, the combination of PM01183 and cisplatin resulted in CI values less than 1 (at Fa higher than 0.8), indicating synergism in mice bearing gastric HGC-27 xenografted tumors.

b. The combination treatment of PM01183 and 5-fluorouracil was effective in the inhibition of the growth of the HGC-27 gastric cells, resulting in a statistically significant (P<0.01) tumor reduction compared to the control group with T/C values of 22.0% and 51.1% (Day 14) in the two highly-dosed groups. Moreover, the combination of PM01183 and 5-fluorouracil produced lower T/C values than the more active single agent in this experiment (PM01183 at a dose of 0.18 mg/kg). Specifically, the TC (%) values of the combination (50 mg/kg 5-fluorouracil+0.18 mg/kg PM01183) vs PM01183 alone (0.18 mg/kg PM01183) were 35.9 vs 43.3 (day 7), 31.5 vs 41.0 (day 9), 25.3 vs 33.0 (day 12), and 22.0 vs 29.2 (day 14). Therefore, when PM01183 is combined with 5-fluorouracil a potentiation of the antitumor activity is clearly observed.

Additionally, based on the median-effect principle, the combination of PM01183 and 5-fluorouracil resulted in CI values of 0.78 (at Fa equal to 0.97), indicating moderate synergism in mice bearing gastric HGC-27 xenografted tumors.

Example 15. In Vivo Studies to Determine the Effect of PM01183 in Combination with Gemcitabine in Human Pancreatic Tumor Xenografts The aim of these studies was to evaluate the ability of PM01183 to potentiate the antitumor activity of gemcitabine by using a xenograft model of human pancreatic cancer.

Female athymic nude mice (Harlan Laboratories Models, S.L. (Barcelona, Spain) were utilized for all experiments. Animals were housed in individually ventilated cages, up to ten per cage in a 12-hour light-dark cycle at 21-23° C. and 40-60% humidity. The mice were allowed free access to irradiated standard rodent diet and sterilized water. Animals were acclimated for at least 5 days prior to tumor implantation with a tumor cell suspension.

The tumor model used in these studies was SW1990 cell line, which was obtained from the American Type Culture Collection (ATCC: CRL-2172™).

SW1990 cells were grown at 37° C. with 5% $CO_2$ in RPMI-1640 medium. Each animal was subcutaneously implanted on the right flank, using 26G needle and a 1 cc syringe, with $5 \times 10^6$ SW1990 cells, from in vitro passage 12, in 0.05 mL suspension of 50% Matrigel and 50% serum free medium, without antibiotics.

Tumor measurements and treatment tolerability were performed and determined as disclosed in Example 13.

When tumors reached a volume of about 210 $mm^3$ mice were randomly allocated into the treatments and control groups (N=5-7/group) based on body weight and tumor volumen measurements by using NewLab Oncology Software (version 2.25.06.00).

PM01183 was provided in the form of vials of lyophilized PM01183 cake which was reconstituted with water for infusion to a concentration of 0.2 mg/mL. The PM01183 stock solution was further diluted in 5% glucose solution for injection to the dosing formulation concentrations. Gemcitabine was provided as a solution prepared by reconstituting the product with 0.9% saline solution for injection to a concentration of 40 mg/ml stock solution. The gemcitabine stock solution was further diluted with 0.9% saline solution for injection to the target final concentration.

In these experiments, PM01183 and gemcitabine treatment, as well as placebo, were intravenously administered once per week up to 3 consecutive weeks on Days 0, 7 and 14. Dose level groups were administered either as single agents or in combination.

Comparison of the median tumor volume in the treatment groups (T) to the median tumor volume in the control group (T/C×100%) was used for evaluation of the antitumor efficacy. In addition, potentiation and combination index were determined as disclosed in Example 13.

Table 18 reports the % T/C values obtained with PM01183 and gemcitabine both administered as single agents and in combination for each dose level, and FIG. 26B shows the tumor volume evaluation of SW1990 tumors in mice treated with placebo, PM01183, gemcitabine, and the corresponding combinations for the groups dosed at the two highest ratios.

TABLE 18

| Group | Dose | Test materials | % T/C on day | | | | | |
|---|---|---|---|---|---|---|---|---|
| | | | 0 | 3 | 6 | 8 | 10 | 13 |
| G01 (Control group) | 10 ml/kg | Placebo | — | — | — | — | — | — |
| G02 | 0.18 mg/kg | PM01183 | 100.0 | 74.3 | 61.3 | 59.4 | 56.7 | 56.1 |
| G03 | 0.135 mg/kg | PM01183 | 99.6 | 81.3 | 71.0 | 73.1 | 65.6 | 63.1 |
| G04 | 0.09 mg/kg | PM01183 | 101.1 | 81.5 | 72.8 | 68.7 | 68.4 | 74.4 |
| G05 | 0.045 mg/kg | PM01183 | 100.2 | 83.6 | 82.8 | 93.3 | 82.9 | 88.1 |
| G06 | 180.0 mg/kg | Gemcitabine | 102.2 | 84.1 | 73.9 | 66.1 | 60.9 | 59.4 |
| G07 | 135.0 mg/kg | Gemcitabine | 102.3 | 78.3 | 71.9 | 63.7 | 55.4 | 52.7 |
| G08 | 90.0 mg/kg | Gemcitabine | 103.8 | 70.0 | 73.8 | 63.3 | 55.6 | 54.8 |
| G09 | 45.0 mg/kg | Gemcitabine | 102.3 | 85.5 | 70.3 | 70.5 | 63.3 | 64.8 |
| G10 | 0.18 mg/kg 180.0 mg/kg | PM01183 Gemcitabine | 102.1 | 69.7 | 51.2 | 46.2 | 36.0 | 34.1 |
| G11 | 0.135 mg/kg 135.0 mg/kg | PM01183 Gemcitabine | 100.4 | 64.6 | 52.8 | 51.5 | 48.9 | 46.0 |
| G12 | 0.09 mg/kg 90.0 mg/kg | PM01183 Gemcitabine | 98.2 | 83.2 | 64.4 | 59.7 | 50.6 | 49.6 |
| G13 | 0.045 mg/kg 45.0 mg/kg | PM01183 Gemcitabine | 97.7 | 81.6 | 70.9 | 68.8 | 65.9 | 65.7 |

| Group | Dose | Test materials | % T/C on day | | | | | |
|---|---|---|---|---|---|---|---|---|
| | | | 15 | 17 | 20 | 22 | 24 | 28 |
| G01 (Control group) | 10 ml/kg | Placebo | — | — | — | — | — | — |
| G02 | 0.18 mg/kg | PM01183 | 53.2 | 47.8 | 44.2 | 45.3 | 44.8 | 38.9 |
| G03 | 0.135 mg/kg | PM01183 | 56.3 | 56.7 | 56.9 | 56.5 | 53.0 | 51.7 |
| G04 | 0.09 mg/kg | PM01183 | 74.7 | 80.7 | 71.9 | 75.4 | 77.3 | 63.9 |
| G05 | 0.045 mg/kg | PM01183 | 92.6 | 86.5 | 85.1 | 84.5 | 85.8 | 85.4 |
| G06 | 180.0 mg/kg | Gemcitabine | 58.5 | 52.1 | 49.1 | 48.6 | 46.9 | 39.3 |
| G07 | 135.0 mg/kg | Gemcitabine | 54.8 | 51.2 | 49.5 | 48.7 | 49.8 | 49.5 |
| G08 | 90.0 mg/kg | Gemcitabine | 49.9 | 47.4 | 47.6 | 47.0 | 45.9 | 49.2 |
| G09 | 45.0 mg/kg | Gemcitabine | 63.1 | 58.5 | 58.7 | 57.3 | 65.2 | 59.3 |
| G10 | 0.18 mg/kg 180.0 mg/kg | PM01183 Gemcitabine | 34.7 | 31.6 | 31.7 | 28.0 | 26.0 | 22.7 |
| G11 | 0.135 mg/kg 135.0 mg/kg | PM01183 Gemcitabine | 42.4 | 38.2 | 36.6 | 34.6 | 31.5 | 25.8 |
| G12 | 0.09 mg/kg 90.0 mg/kg | PM01183 Gemcitabine | 47.4 | 46.0 | 43.8 | 49.1 | 46.0 | 42.9 |
| G13 | 0.045 mg/kg 45.0 mg/kg | PM01183 Gemcitabine | 57.9 | 59.9 | 55.9 | 54.9 | 52.1 | 50.5 |

Placebo: as disclosed in table 13.

According to this assay it was found that:
a. The combination treatment of PM01183 and gemcitabine was effective in the inhibition of the growth of the SW 1990 pancreatic cells, resulting in a statistically significant ($P<0.01$) tumor reduction compared to the control group with T/C values of 22.7% and 25.8% (Day 28) in the two highly-dosed groups. Moreover, the combination of PM01183 and gemcitabine produced lower T/C values than the more active single agent in this experiment (PM01183 at a dose of 0.18 mg/kg). Specifically, the TC (%) values of the combination (180 mg/kg gemcitabine+0.18 mg/kg PM01183) vs PM01183 alone (0.18 mg/kg PM01183) were 31.7 vs 44.2 (day 20), 28.0 vs 45.3 (day 22), 26.0 vs 44.8 (day 24), and 22.7 vs 38.9 (day 28). Therefore, when PM01183 is combined with gemcitabine a potentiation of the antitumor activity is clearly observed.

Additionally, based on the median-effect principle, the combination of PM01183 and gemcitabine resulted in CI values less than 1 (at Fa higher than 0.8), indicating synergism in mice bearing pancreatic SW 1990 xenografted tumors.

Example 16. In Vivo Studies to Determine the Effect of PM01183 in Combination with Temozolomide in Human Brain Tumor Xenografts The aim of these studies was to evaluate the ability of PM01183 to potentiate the antitumor activity of temozolomide by using a xenograft model of human brain tumor.

Female athymic nude mice (Harlan Laboratories Models, S.L. (Barcelona, Spain) were utilized for all experiments. Animals were housed in individually ventilated cages, up to ten per cage in a 12-hour light-dark cycle at 21-23° C. and 40-60% humidity. The mice were allowed free access to irradiated standard rodent diet and sterilized water. Animals were acclimated for at least 5 days prior to tumor implantation with a tumor cell suspension.

The tumor model used in these studies was U87-MG cell line, which was obtained from the American Type Culture Collection (ATCC HTB-14™).

U87-MG cells were grown at 37° C. with 5% $CO_2$ in Minimum Essential Medium Eagle (MEME). Each animal was subcutaneously implanted on the right flank, using 26G needle and a 1 cc syringe, with $5×10^6$ U87-MG cells, from in vitro passage 5, in 0.05 mL suspension of 50% Matrigel and 50% serum free medium, without antibiotics.

Tumor measurements and treatment tolerability were performed and determined as disclosed in Example 13.

When tumors reached a volume of about 139 mm³, mice were randomly allocated into the treatments and control groups (N=5-7/group) based on body weight and tumor volumen measurements by using NewLab Oncology Software (version 2.25.06.00).

PM01183 was provided in the form of vials of lyophilized PM01183 cake which was reconstituted with water for infusion to a concentration of 0.2 mg/mL. The PM01183 stock solution was further diluted in 5% glucose solution for injection to the dosing formulation concentrations. Temozolomide was provided as a solution prepared by diluting the product in DMSO 10% in 0.9% saline solution for injection to the target final concentration.

In these experiments, PM01183 and temozolomide treatments, as well as placebo, were administered as follows: PM01183, intravenously once per week up to 3 consecutive weeks, on Days 0, 7 and 14, temozolomide orally, in a daily basis during 8 consecutive days (Days 0 to 7), and placebo was administered following the same schedule as those provided for PM01183 and temozolomide. Dose level groups were administered either as single agents or in combination.

Comparison of the median tumor volume in the treatment groups (T) to the median tumor volume in the control group (T/C×100%) was used for evaluation of the antitumor efficacy. In addition, potentiation and combination index (CI) were determined as disclosed in Example 13.

Figure 269:
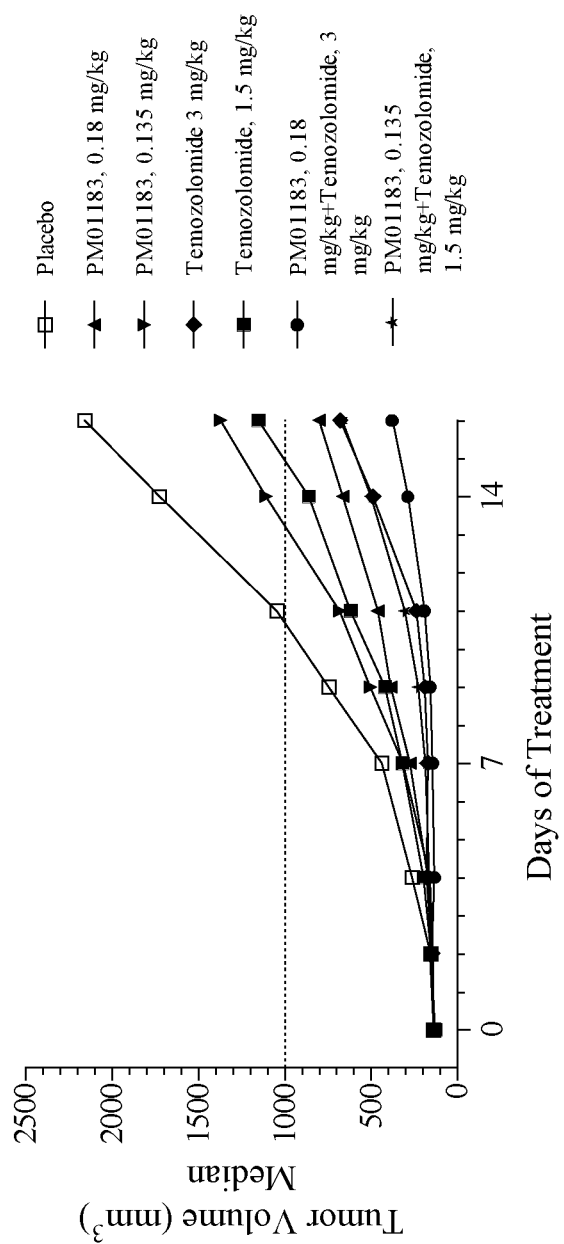
FIG. 269. Tumor volume evaluation of U87-MG tumors in mice treated with placebo, PM01183, temozolomide and PM01183 plus temozolomide.

Table 19 reports the % T/C values obtained with PM01183 and temozolomide both administered as single agents and in combination for each dose level, and FIG. 269 shows the tumor volume evaluation of U87-MG tumors in mice treated with placebo, PM01183, temozolomide, and the corresponding combinations for the groups dosed at the two highest ratios.

two highly-dosed groups. Moreover, the combination of PM01183 and temozolomide produced lower T/C values than the more active single agent in this experiment (temozolomide at doses of 3 mg/kg and 1.5 mg/kg).

Specifically, the TC (%) values of the combination (3 mg/kg temozolomide+0.18 mg/kg PM01183) vs temozolomide alone (3 mg/kg temozolomide) were 18.3 vs 22.9 (day 11), 16.6 vs 28.4 (day 14), and 17.4 vs 31.5 (day 16), and the TC (%) values of the combination (1.5 mg/kg temozolomide+0.135 mg/kg PM01183) vs temozolomide alone (1.5 mg/kg temozolomide) were 29.1 vs 59.3 (day 11), 29.0 vs 50.0 (day 14), and 30.9 vs 53.5 (day 16). Therefore, when PM01183 is combined with temozolomide a potentiation of the antitumor activity is clearly observed.

Additionally, based on the median-effect principle, the combination of PM01183 and temozolomide resulted in CI values less than 1 (at Fa higher than 0.8), indicating synergism in mice bearing brain U87-MG xenografted tumors.

Example 17. In Vivo Studies to Determine the Effect of PM01183 in Combination with Irinotecan in Human Lung Tumor Xenografts The aim of these studies was to evaluate the ability of PM01183 to potentiate the antitumor activity of iriniotecan by using a xenograft model of human lung cancer.

Female athymic nude mice (Harlan Laboratories Models, S.L. (Barcelona, Spain) were utilized for all experiments. Animals were housed in individually ventilated cages, up to ten per cage in a 12-hour light-dark cycle at 21-23° C. and 40-60% humidity. The mice were allowed free access to irradiated standard rodent diet and sterilized water. Animals were acclimated for at least 5 days prior to tumor implantation with a tumor cell suspension.

The tumor model used in these studies was H460 cell line, which was obtained from the American Type Culture Collection of Cell Cultures (ATCC ref. HTB-177™).

TABLE 19

| Group | Dose | Test materials | % T/C on day | | | | | | | |
|---|---|---|---|---|---|---|---|---|---|---|
| | | | 0 | 2 | 4 | 7 | 9 | 11 | 14 | 16 |
| G01 (Control group) | 10 ml/kg | Placebo | — | — | — | — | — | — | — | — |
| G02 | 0.18 mg/kg | PM01183 | 99.8 | 95.5 | 64.8 | 63.2 | 52.0 | 44.1 | 38.5 | 37.1 |
| G03 | 0.135 mg/kg | PM01183 | 98.5 | 90.5 | 61.2 | 71.3 | 67.7 | 65.3 | 64.2 | 63.6 |
| G04 | 0.09 mg/kg | PM01183 | 97.9 | 99.5 | 74.4 | 85.1 | 69.4 | 71.8 | 74.1 | 73.5 |
| G05 | 0.045 mg/kg | PM01183 | 98.2 | 101.0 | 80.4 | 83.8 | 78.8 | 77.7 | 76.7 | 82.5 |
| G06 | 3.0 mg/kg | Temozolomide | 97.1 | 95.5 | 67.3 | 39.4 | 25.3 | 22.9 | 28.4 | 31.5 |
| G07 | 1.5 mg/kg | Temozolomide | 94.1 | 96.9 | 75.6 | 73.0 | 56.5 | 59.3 | 50.0 | 53.5 |
| G08 | 1.0 mg/kg | Temozolomide | 98.2 | 100.2 | 65.1 | 81.2 | 55.0 | 63.5 | 73.1 | 75.0 |
| G09 | 0.75 mg/kg | Temozolomide | 97.7 | 98.9 | 76.3 | 77.3 | 64.4 | 63.1 | 62.8 | 72.7 |
| G10 | 0.18 mg/kg PM01183 3.0 mg/kg Temozolomide | | 97.8 | 95.0 | 50.9 | 33.1 | 21.0 | 18.3 | 16.6 | 17.4 |
| G11 | 0.135 mg/kg PM01183 1.5 mg/kg Temozolomide | | 98.7 | 102.4 | 62.7 | 42.0 | 30.3 | 29.1 | 29.0 | 30.9 |
| G12 | 0.09 mg/kg PM01183 1.0 mg/kg Temozolomide | | 96.2 | 101.0 | 79.3 | 76.1 | 49.8 | 51.2 | 57.6 | 56.5 |
| G13 | 0.045 mg/kg PM01183 0.75 mg/kg Temozolomide | | 101 | 106.0 | 67.4 | 73.0 | 57.8 | 59.0 | 69.3 | 72.2 |

Placebo: as disclosed in table 13.

According to this assay it was found that:
a. The combination treatment of PM01183 and temozolomide was effective in the inhibition of the growth of the U87-MG brain tumor cells, resulting in a statistically significant (P<0.01) tumor reduction compared to the control group with T/C values of 17.4% and 30.9% (Day 16) in the H460 cells were grown at 37° C. with 5% $CO_2$ in Dulbecco's modified Eagle's medium (DMEM). Each animal was subcutaneously implanted on the right flank, using 26G needle and a 1 cc syringe, with 5×10⁶ H460 cells, from in vitro passage 10, in 0.05 mL suspension of 50% Matrigel and 50% serum free medium, without antibiotics.

Tumor measurements and treatment tolerability were performed and determined as disclosed in Example 13.

When tumors reached a volume of about 177 mm$^3$, mice were randomly allocated into the treatments and control groups (N=5-7/group) based on body weight and tumor volumen measurements by using NewLab Oncology Software (version 2.25.06.00).

PM01183 was provided in the form of vials of lyophilized PM01183 cake which was reconstituted with water for infusion to a concentration of 0.2 mg/mL. The PM01183 stock solution was further diluted in 5% glucose solution for injection to the dosing formulation concentrations. Irinotecan was provided in the form of a solution prepared by diluting the product with 5% glucose solution for injection to the target final concentration.

In these experiments, PM01183 and irinotecan treatments, as well as placebo, were intravenously administered as follows: PM01183 once per week up to 2 consecutive weeks, on Days 0 and 7, irinotecan was dosed every 4 days, on Days 0, 4 and 8, and placebo was administered following the same schedule as those provided for PM01183 and irinotecan. Dose level groups were administered either as single agents or in combination.

Comparison of the median tumor volume in the treatment groups (T) to the median tumor volume in the control group (T/C×100%) was used for evaluation of the antitumor efficacy. In addition, potentiation and combination index (CI) were determined as disclosed in Example 13.

Figure 270:
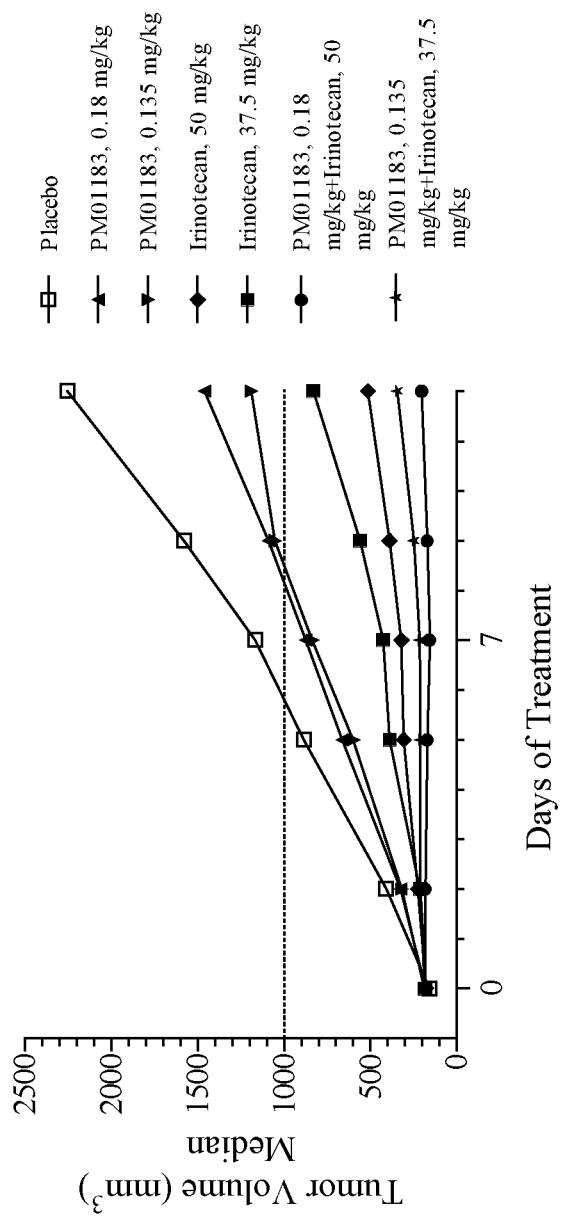
FIG. 270. Tumor volume evaluation of H460 tumors in mice treated with placebo, PM01183, irinotecan and PM01183 plus irinotecan.

Table 20 reports the % T/C values obtained with PM01183 and irinotecan both administered as single agents and in combination for each dose level, and FIG. 270 shows the tumor volume evaluation of H460 tumors in mice treated with placebo, PM01183, irinotecan, and the corresponding combinations for the groups dosed at the two highest ratios.

37.5 mg/kg). Specifically, the TC (%) values of the combination (50 mg/kg irinotecan+0.18 mg/kg PM01183) vs irinotecan alone (50 mg/kg irinotecan) were 19.4 vs 34.7 (day 5), 13.4 vs 27.5 (day 7), 10.9 vs 24.8 (day 9), and 9.0 vs 22.9 (day 12), and the TC (%) values of the combination (37.5 mg/kg irinotecan+0.135 mg/kg PM01183) vs irinotecan alone (37.5 mg/kg irinotecan) were 23.8 vs 44.0 (day 5), 18.4 vs 36.7 (day 7), 15.7 vs 35.6 (day 9), and 15.3 vs 37.0 (day 12). Therefore, when PM01183 is combined with irinotecan a potentiation of the antitumor activity is clearly observed.

Additionally, based on the median-effect principle, the combination of PM01183 and irinotecan resulted in CI values less than 1 (at Fa higher than 0.8), indicating synergism or strong synergism in mice bearing lung H460 xenografted tumors.

Example 18. In Vivo Studies to Determine the Effect of PM01183 in Combination with Dacarbazine in Human Fibrosarcoma Xenografts The aim of these studies was to evaluate the ability of PM01183 to potentiate the antitumor activity of temozolomide by using a xenograft model of human fibrosarcoma.

Female athymic nude mice (Harlan Laboratories Models, S.L. (Barcelona, Spain) were utilized for all experiments. Animals were housed in individually ventilated cages, up to ten per cage in a 12-hour light-dark cycle at 21-23° C. and 40-60% humidity. The mice were allowed free access to irradiated standard rodent diet and sterilized water. Animals were acclimated for at least 5 days prior to tumor implantation with a tumor cell suspension.

The tumor model used in these studies was HT1080 cell line, which was obtained from the American Type Culture Collection (ATCC CCL-121™).

TABLE 20

| Group | Dose | Test materials | % T/C on day 0 | 2 | 5 | 7 | 9 | 12 |
|---|---|---|---|---|---|---|---|---|
| G01 (Control group) | 10 ml/kg | Placebo | — | — | — | — | — | — |
| G02 | 0.18 mg/kg | PM01183 | 114.4 | 79.6 | 74.7 | 75.0 | 69.1 | 64.9 |
| G03 | 0.135 mg/kg | PM01183 | 117.6 | 77.4 | 67.5 | 71.7 | 66.7 | 52.9 |
| G04 | 0.09 mg/kg | PM01183 | 116.9 | 83.1 | 83.9 | 76.9 | 80.6 | 84.9 |
| G05 | 0.045 mg/kg | PM01183 | 108.3 | 78.7 | 61.2 | 67.2 | 78.8 | 87.9 |
| G06 | 50.0 mg/kg | Irinotecan | 112.1 | 54.9 | 34.7 | 27.5 | 24.8 | 22.9 |
| G07 | 37.5 mg/kg | Irinotecan | 114.9 | 51.9 | 44.0 | 36.7 | 35.6 | 37.0 |
| G08 | 25.0 mg/kg | Irinotecan | 112.0 | 55.6 | 54.9 | 49.6 | 53.1 | 51.8 |
| G09 | 12.5 mg/kg | Irinotecan | 97.5 | 50.3 | 44.4 | 48.6 | 50.0 | 51.5 |
| G10 | 0.18 mg/kg PM01183 50.0 mg/kg Irinotecan | | 117.1 | 44.3 | 19.4 | 13.4 | 10.9 | 9.0 |
| G11 | 0.135 mg/kg PM01183 37.5 mg/kg Irinotecan | | 111.2 | 51.7 | 23.8 | 18.4 | 15.7 | 15.3 |
| G12 | 0.09 mg/kg PM01183 25.0 mg/kg Irinotecan | | 110.0 | 53.2 | 38.1 | 26.6 | 28.0 | 27.1 |
| G13 | 0.045 mg/kg PM01183 12.5 mg/kg Irinotecan | | 109.0 | 60.4 | 60.1 | 56.5 | 60.0 | 58.5 |

Placebo: as disclosed in table 13.

According to this assay it was found that:
a. The combination treatment of PM01183 and irinotecan was effective in the inhibition of the growth of the H460 lung cells, resulting in a statistically significant (P<0.01) tumor reduction compared to the control group with T/C values of 9.0% and 15.3% (Day 12) in the two highly-dosed groups. Moreover, the combination of PM01183 and irinotecan produced lower T/C values than the more active single agent in this experiment (irinotecan at doses of 50 mg/kg and HT1080 cells were grown at 37° C. with 5% $CO_2$ in Minimum Essential Medium Eagle (MEME). Each animal was orthotopically implanted into gastroecnemius muscle by an intramuscular injection using 26G needle and a 1 cc syringe, with 5×10$^6$ HT1080 cells, from in vitro passage 9, suspended in serum free medium, without antibiotics.

Total diameter (tumor+leg) measurements were determined by using digital caliper (Fowler Sylvac, S235PAT).

This total diameter and animal body weights were measured 2-3 times per week starting from the first day of treatment.

Treatment tolerability was assessed by monitoring body weight evolution, clinical signs as well as evidences of local damage in the injection site.

When total diameter reached a length of about 11.3 mm, mice were randomly allocated into the treatments and control groups (N=5-7/group) based on body weight and tumor measurements by using NewLab Oncology Software (version 2.25.06.00).

PM01183 was provided in the form of vials of lyophilized PM01183 cake which was reconstituted with water for infusion to a concentration of 0.2 mg/mL. The PM01183 stock solution was further diluted in 5% glucose solution for injection to the dosing formulation concentrations. Dacarbazine was provided in the form of a solution prepared by diluting the product with 5% glucose solution for injection to the target final concentration.

In these experiments, PM01183 and dacarbazine treatments, as well as placebo, were intravenously administered once per week up to 2 consecutive weeks, on Days 0 and 7. Dose level groups were administered either as single agents or in combination.

Comparison of the median total diameter (tumor+leg) in the treatment groups (T) to the median total diameter (tumor+leg) in the control group (T/C×100%) was used for evaluation of the antitumor efficacy. In addition, potentiation and combination index (CI) were determined as disclosed in Example 13.

Figure 271:
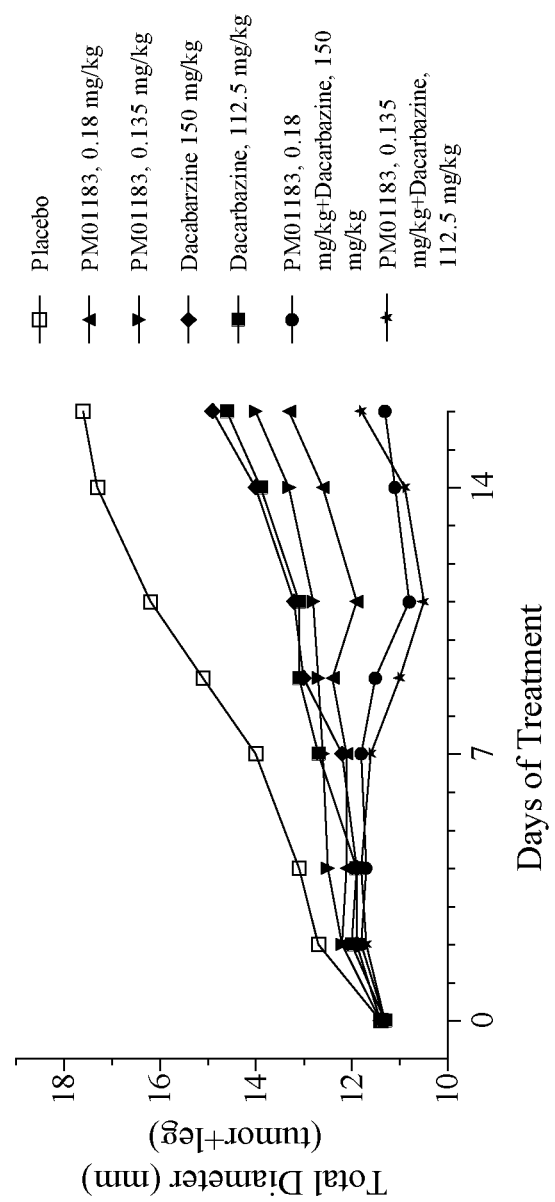
FIG. 271. Tumor volume evaluation of HT1080 tumors in mice treated with placebo, PM01183, dacarbazine and PM01183 plus dacarbazine.

Table 21 reports the % T/C values obtained with PM01183 and dacarbazine both administered as single agents and in combination for each dose level, and FIG. 271 shows the total diameter (tumor+leg) evaluation of HT1080 tumors in mice treated with placebo, PM01183, dacarbazine, and the corresponding combinations for the groups dosed at the two highest ratios.

nation of PM01183 and dacarbazine produced lower T/C values than the more active single agent in this experiment (PM01183 at doses of 0.18 mg/kg and 0.135 mg/kg). Specifically, the TC (%) values of the combination (150 mg/kg dacarbazine+0.18 mg/kg PM01183) vs PM01183 alone (0.18 mg/kg PM01183) were 4.0 vs 26.7 (day 9), 10.4 vs 11.5 (day 11), −4.2 vs 21.2 (day 14), and 1.0 vs 30.6 (day 16), and the TC (%) values of the combination (112.5 mg/kg dacarbazine+0.135 mg/kg PM01183) vs PM01183 alone (0.135 mg/kg PM01183) were −8.0 vs 36.0 (day 9), −17.7 vs 30.2 (day 11), −6.8 vs 33.0 (day 14), and 7.3 vs 41.9 (day 16). Therefore, when PM01183 is combined with dacarbazine a potentiation of the antitumor activity is clearly observed.

Additionally, based on the median-effect principle, the combination of PM01183 and dacarbazine resulted in CI values of 0.28 (at Fa equal to 0.97), indicating strong synergism in mice fibrosarcoma HT1080 orthotopically implanted tumors.

Example 19. In Vivo Studies to Determine the Effect of PM01183 in Combination with Irinotecan in Human Colorectal Tumor Xenografts The aim of these studies was to evaluate the ability of PM01183 to potentiate the antitumor activity of irinotecan by using a xenograft model of human colorectal carcinoma.

Female athymic nude mice (Harlan Laboratories Models, S.L. (Barcelona, Spain) were utilized for all experiments. Animals were housed in individually ventilated cages, up to ten per cage in a 12-hour light-dark cycle at 21-23° C. and 40-60% humidity. The mice were allowed free access to irradiated standard rodent diet and sterilized water. Animals were acclimated for at least 5 days prior to tumor implantation with a tumor cell suspension.

TABLE 21

| Group | Dose | Test materials | % T/C on day | | | | | | | |
|---|---|---|---|---|---|---|---|---|---|---|
| | | | 0 | 2 | 4 | 7 | 9 | 11 | 14 | 16 |
| G01 (Control group) | 10 ml/kg | Placebo | — | — | — | — | — | — | — | — |
| G02 | 0.18 mg/kg | PM01183 | 100 | 59.3 | 40.0 | 26.9 | 26.7 | 11.5 | 21.2 | 30.6 |
| G03 | 0.135 mg/kg | PM01183 | 100 | 63.0 | 62.9 | 48.1 | 36.0 | 30.2 | 33.0 | 41.9 |
| G04 | 0.09 mg/kg | PM01183 | 100 | 66.7 | 57.1 | 65.4 | 48.0 | 42.7 | 45.8 | 56.4 |
| G05 | 0.045 mg/kg | PM01183 | 100 | 77.8 | 74.3 | 94.2 | 80.0 | 74.0 | 80.5 | 91.1 |
| G06 | 150.0 mg/kg | Dacarbazine | 100 | 40.7 | 28.6 | 30.8 | 44.0 | 37.5 | 44.9 | 57.3 |
| G07 | 112.5 mg/kg | Dacarbazine | 100 | 48.1 | 34.3 | 53.8 | 48.0 | 37.5 | 43.2 | 53.2 |
| G08 | 75.0 mg/kg | Dacarbazine | 100 | 74.1 | 65.7 | 69.2 | 58.7 | 45.8 | 46.6 | 51.6 |
| G09 | 37.5 mg/kg | Dacarbazine | 100 | 51.8 | 54.3 | 65.4 | 61.3 | 47.9 | 55.1 | 62.1 |
| G10 | 0.18 mg/kg 150.0 mg/kg | PM01183 Dacarbazine | 100 | 37.0 | 22.9 | 17.3 | 4.0 | 10.4 | −4.2 | 1.0 |
| G11 | 0.135 mg/kg 112.5 mg/kg | PM01183 Dacarbazine | 100 | 29.6 | 25.7 | 11.5 | −8.0 | −17.7 | −6.8 | 7.3 |
| G12 | 0.09 mg/kg 75.0 mg/kg | PM01183 Dacarbazine | 100 | 37.0 | 31.4 | 28.8 | 52.0 | 43.7 | 50.8 | 64.5 |
| G13 | 0.045 mg/kg 37.5 mg/kg | PM01183 Dacarbazine | 100 | 55.6 | 51.4 | 67.3 | 70.7 | 62.5 | 59.3 | 62.1 |

Placebo: as disclosed in table 13.

According to this assay it was found that:
a. The combination treatment of PM01183 and dacarbazine was effective in the inhibition of the growth of the HT1080 fibrosarcoma cells, resulting in a statistically significant (P<0.01) reduction of total diameter (tumor+leg) compared to the control group with T/C values of 1.0% and 7.3% (Day 16) in the two highly-dosed groups. Moreover, the combi- The tumor model used in these studies was HT-29 cell line, which was obtained from the American Type Culture Collection (ATCC ref. HTB-38™).

HT-29 cells were grown at 37° C. with 5% $CO_2$ in Dulbecco's modified Eagle's medium (DMEM). Each animal was subcutaneously implanted on the right flank, using 26G needle and a 1 cc syringe, with 5×10⁶ HT-29 cells, from in vitro passage 10, in 0.05 mL of 0.9% Sodium Chloride for injection.

Tumor measurements and treatment tolerability were performed and determined as disclosed in Example 13. Treatment tolerability was assessed by monitoring body weight evolution, clinical signs as well as evidences of local damage in the injection site.

When tumors reached a volume of about 180 mm$^3$, mice were randomly allocated into the treatments and control groups (N=5-7/group) based on body weight and tumor volumen measurements by using NewLab Oncology Software (version 2.25.06.00).

PM01183 was provided in the form of vials of lyophilized PM01183 cake which was reconstituted with water for infusion to a concentration of 0.2 mg/mL. The PM01183 stock solution was further diluted in 5% glucose solution for injection to the dosing formulation concentrations. Irinotecan was provided in the form of a solution prepared by diluting the product with 5% glucose solution for injection to the target final concentration.

In these experiments, PM01183 and irinotecan treatments, as well as placebo, were intravenously administered as follows: PM01183 once per week up to 3 consecutive weeks, on Days 0, 7 and 14, irinotecan was dosed every 4 days, on Days 0, 4, 8, 12 and 16, and placebo was administered following the same schedule as those provided for PM01183 and irinotecan. Dose level groups were administered either as single agents or in combination.

Comparison of the median tumor volume in the treatment groups (T) to the median tumor volume in the control group (T/C×100%) was used for evaluation of the antitumor efficacy. In addition, potentiation was determined as disclosed in Example 13.

Figure 272:
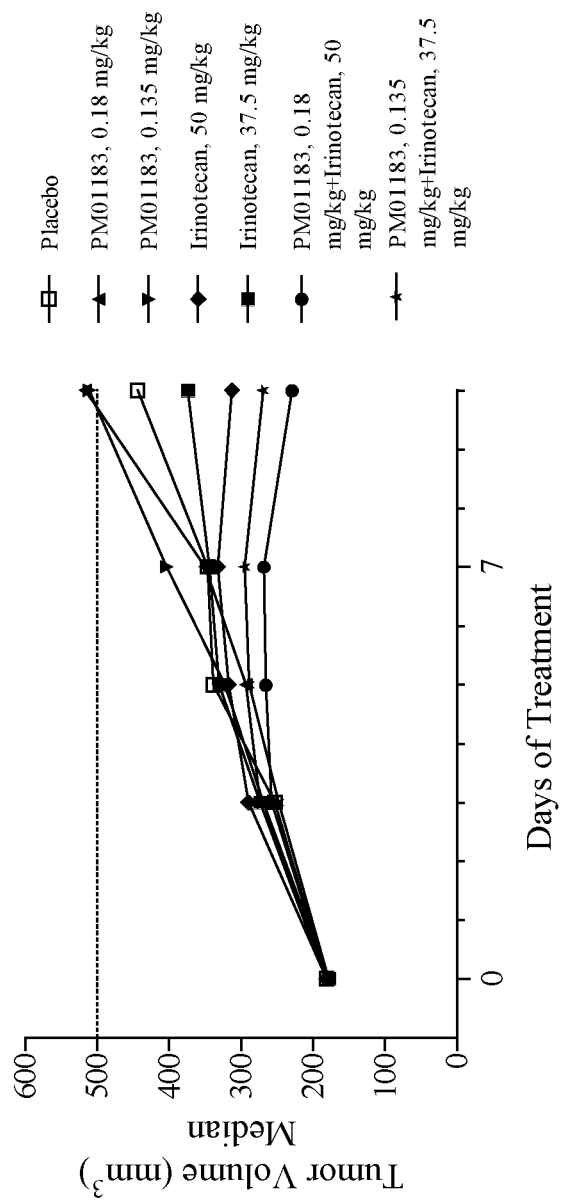
FIG. 272. Tumor volume evaluation of HT-29 tumors in mice treated with placebo, PM01183, irinotecan and PM01183 plus irinotecan.
Figure 273:
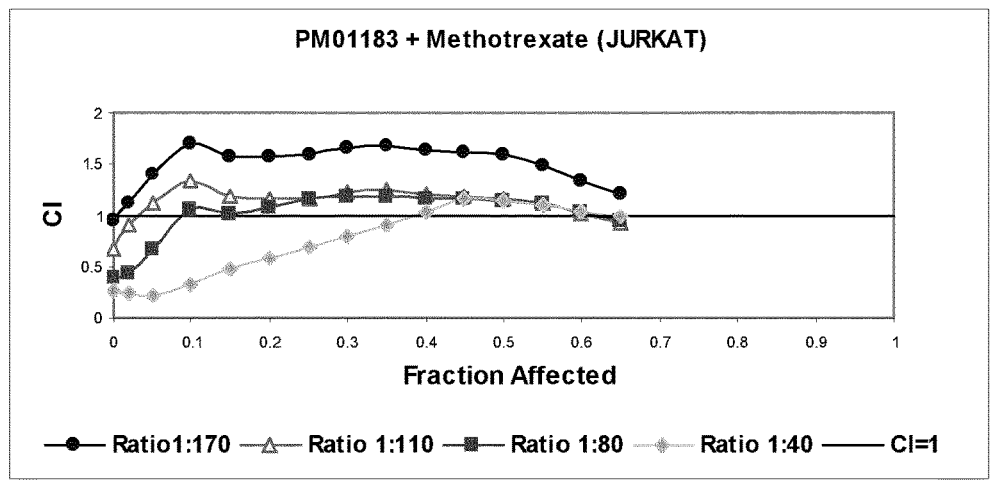
FIG. 273. Effects of the combination of PM01183 with methotrexate in JURKAT cell line.
Figure 274:
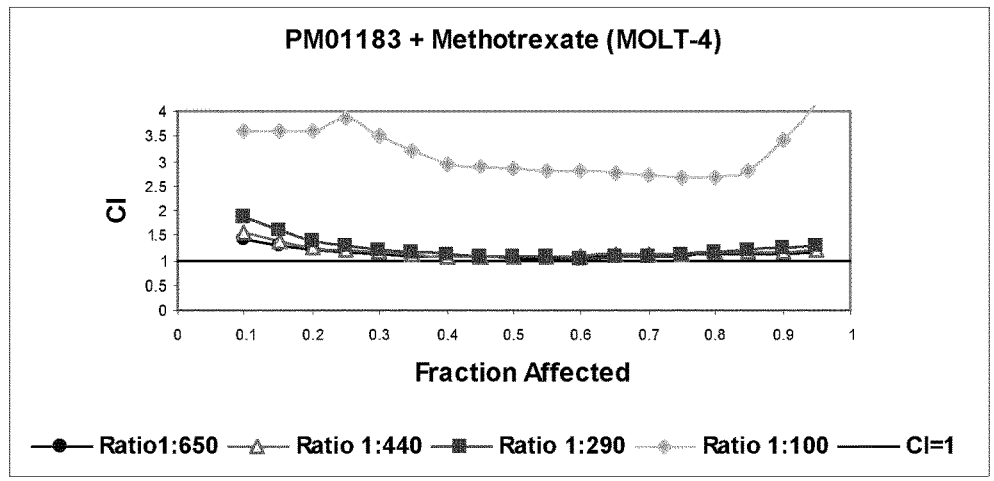
FIG. 274. Effects of the combination of PM01183 with methotrexate in MOLT-4 cell line.
Figure 275:
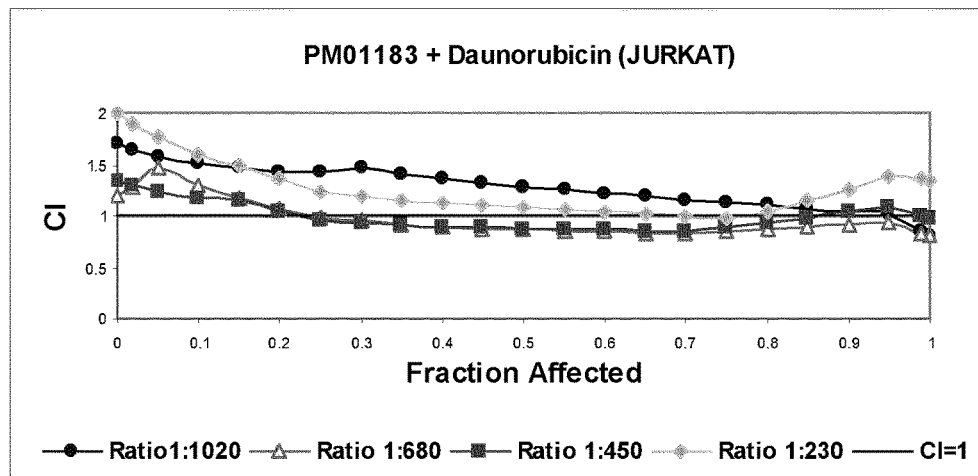
FIG. 275. Effects of the combination of PM01183 with daunorubicin in JURKAT cell line.
Figure 276:
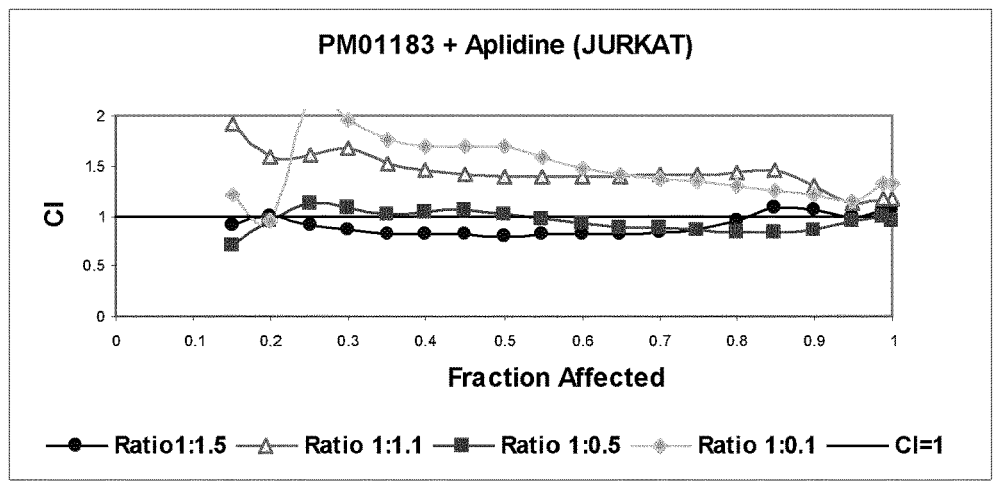
FIG. 276. Effects of the combination of PM01183 with aplidine in JURKAT cell line.
Figure 277:
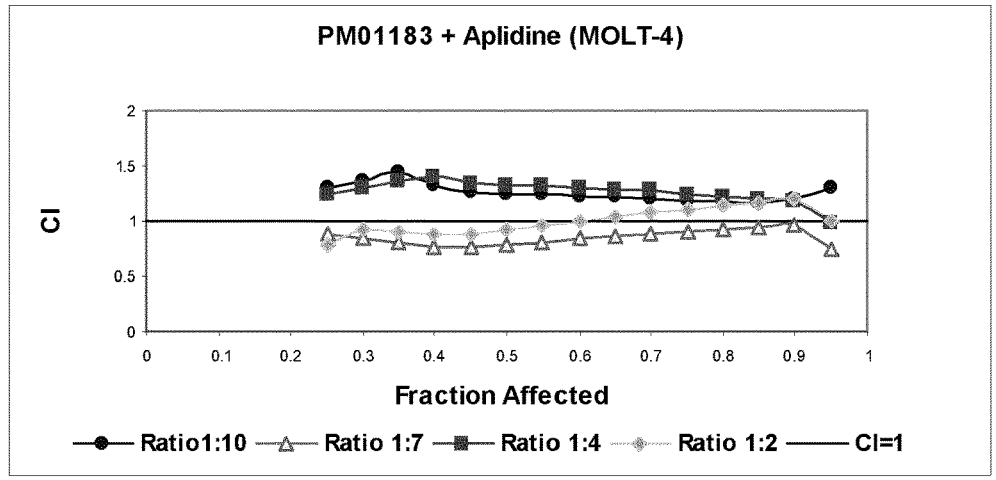
FIG. 277. Effects of the combination of PM01183 with aplidine in MOLT-4 cell line.
Figure 278:
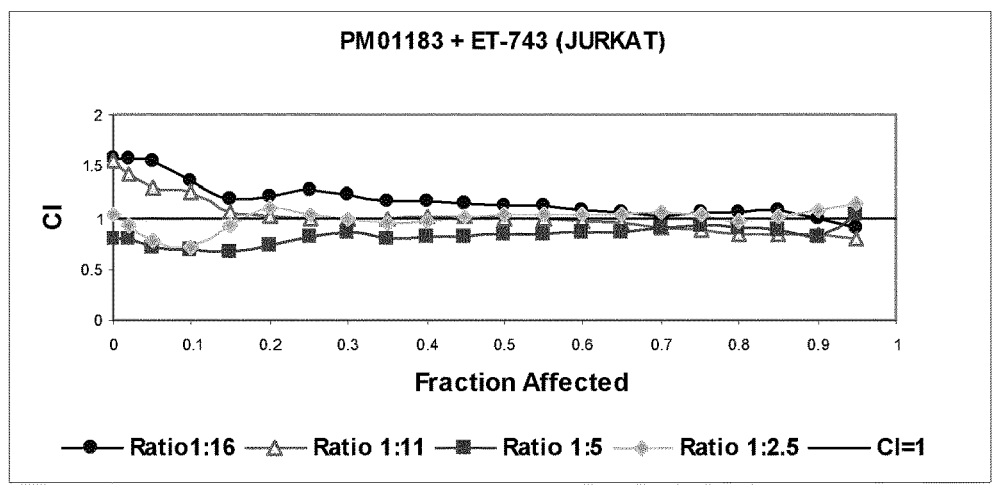
FIG. 278. Effects of the combination of PM01183 with ET-743 in JURKAT cell line.
Figure 279:
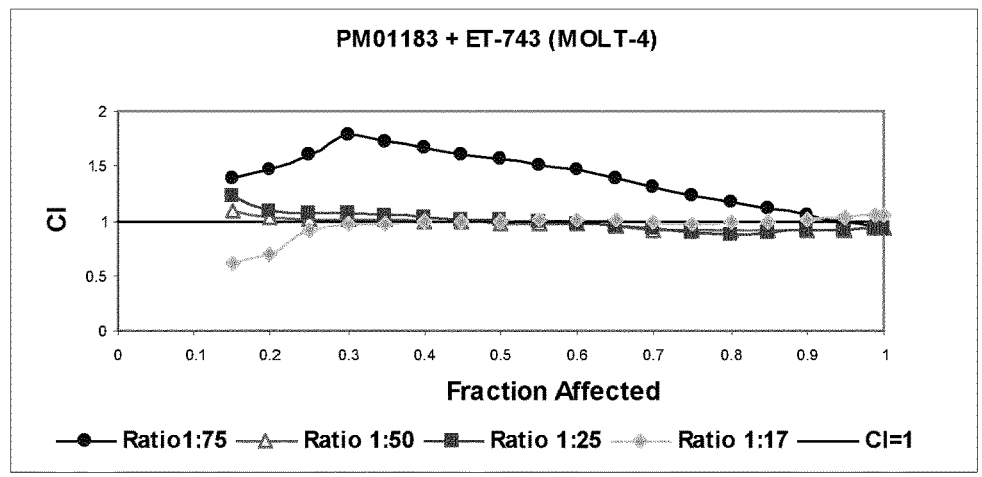
FIG. 279. Effects of the combination of PM01183 with ET-743 in MOLT-4 cell line.
Figure 280:
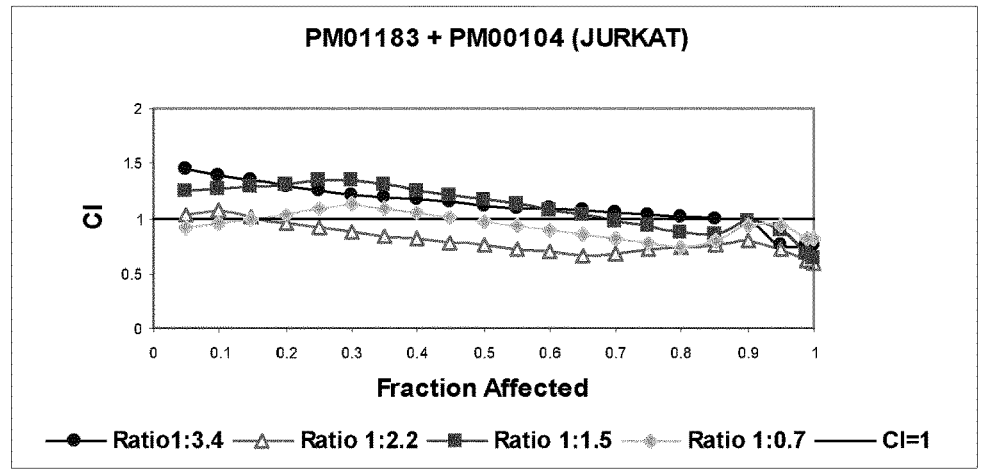
FIG. 280. Effects of the combination of PM01183 with PM00104 in JURKAT cell line.
Figure 281:
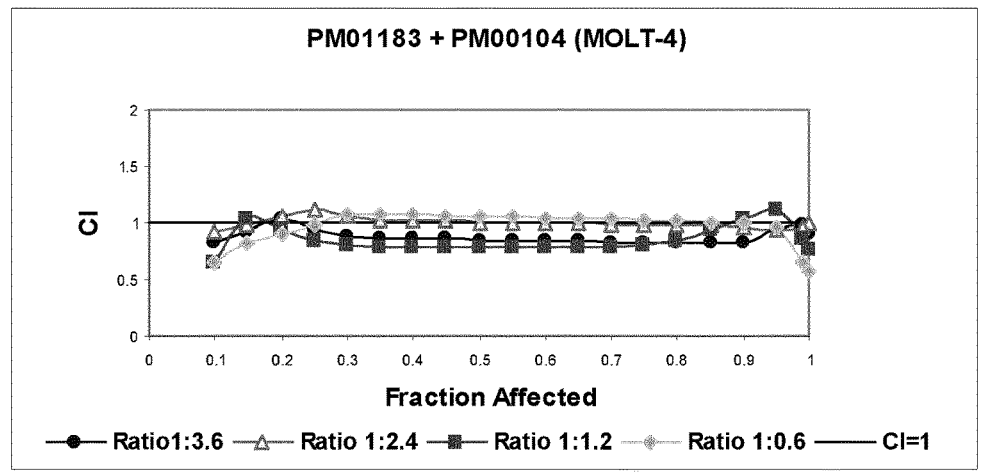
FIG. 281. Effects of the combination of PM01183 with PM00104 in MOLT-4 cell line.
Figure 282:
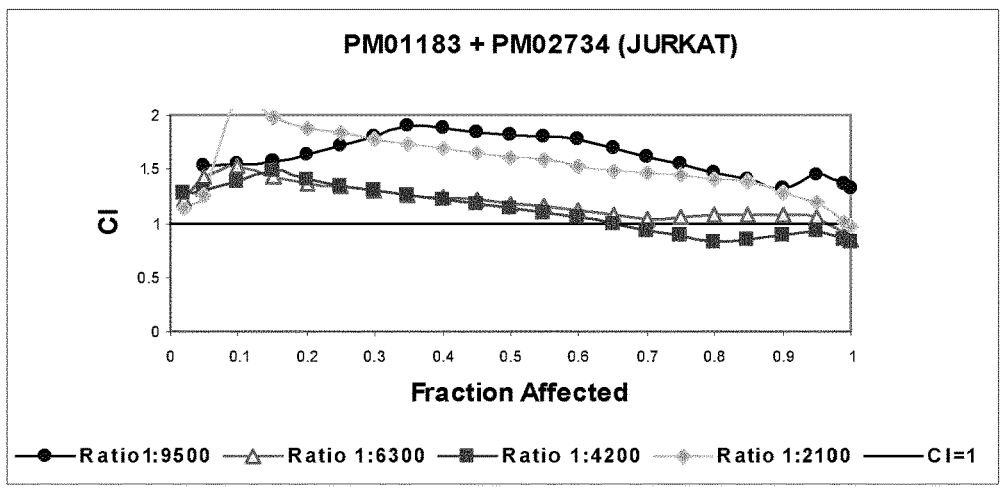
FIG. 282. Effects of the combination of PM01183 with PM02734 in JURKAT cell line.
Figure 283:
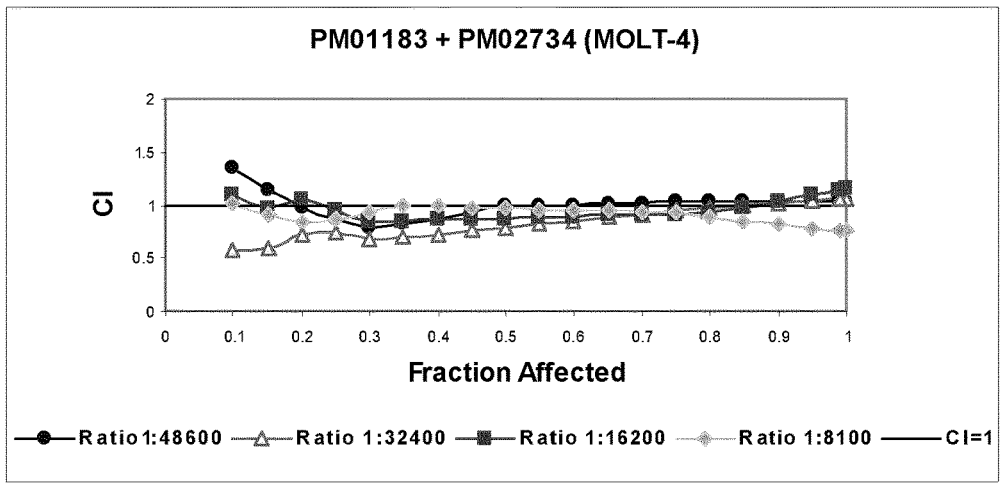
FIG. 283. Effects of the combination of PM01183 with PM02734 in MOLT-4 cell line.
Figure 284:
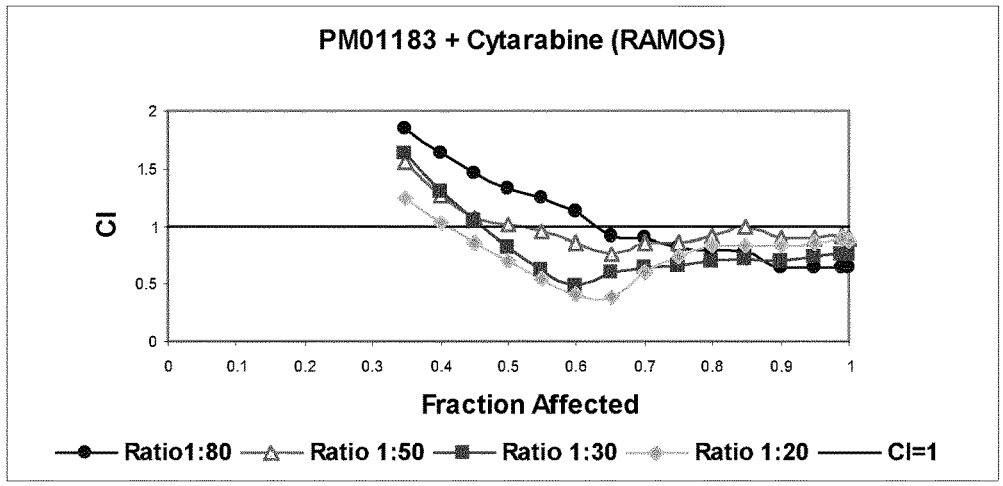
FIG. 284. Effects of the combination of PM01183 with cytarabine in RAMOS cell line.
Figure 285:
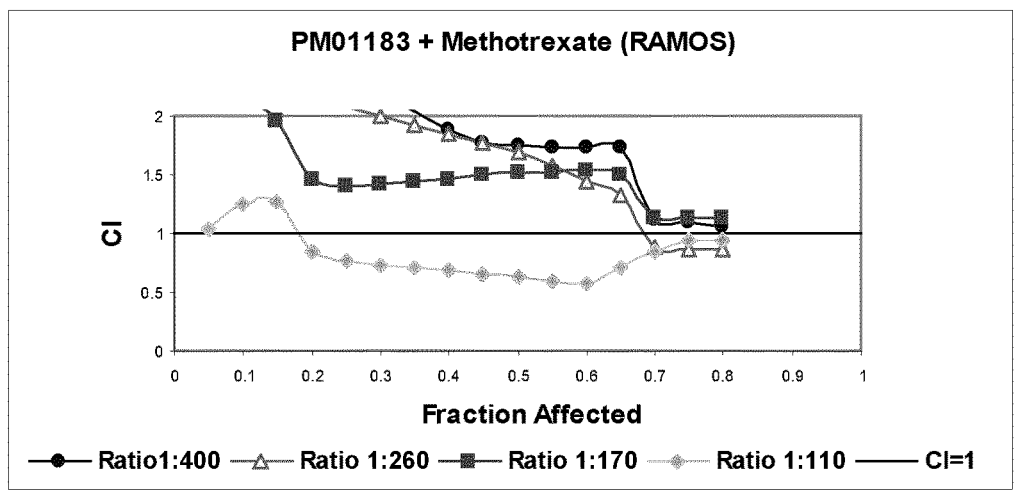
FIG. 285. Effects of the combination of PM01183 with methotrexate in RAMOS cell line.
Figure 286:
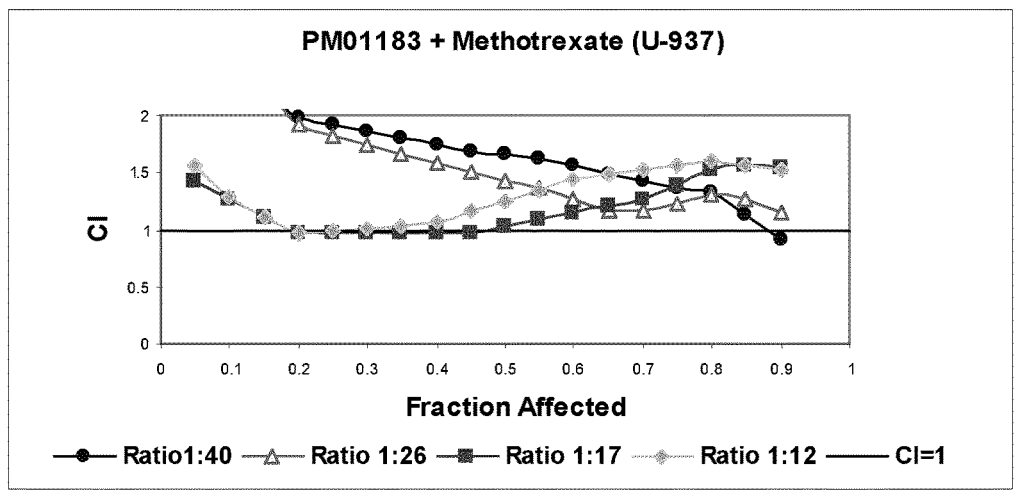
FIG. 286. Effects of the combination of PM01183 with methotrexate in U-937 cell line.
Figure 287:
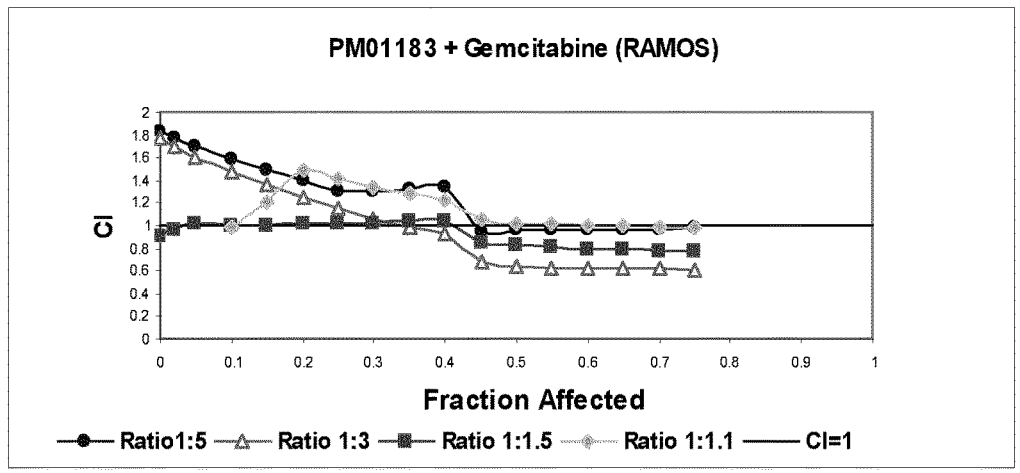
FIG. 287. Effects of the combination of PM01183 with gemcitabine in RAMOS cell line.
Figure 288:
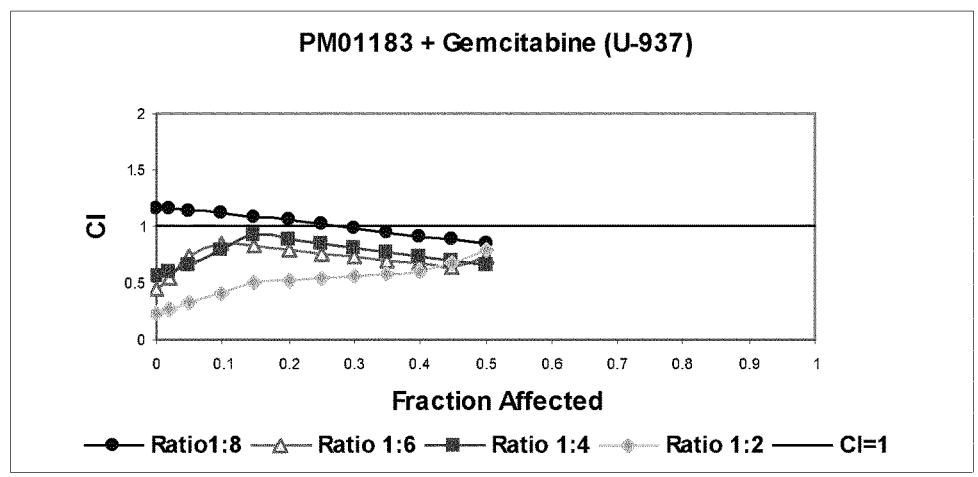
FIG. 288. Effects of the combination of PM01183 with gemcitabine in U-937 cell line.
Figure 289:
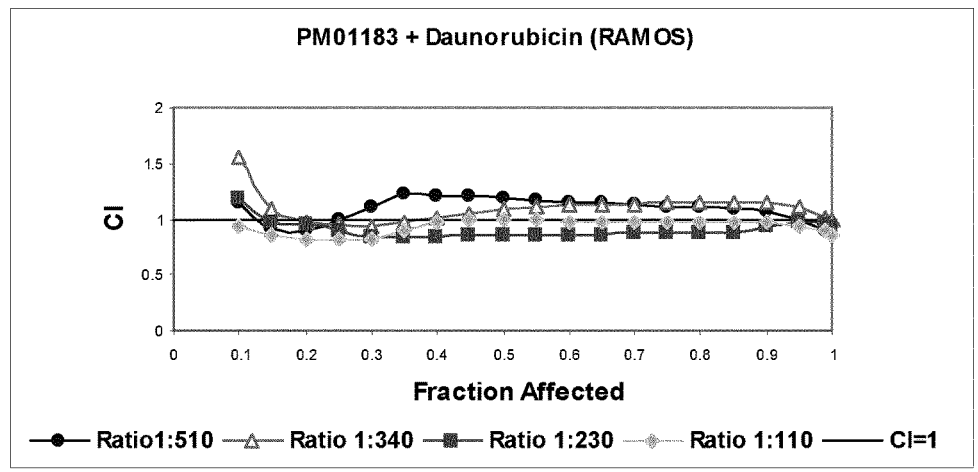
FIG. 289. Effects of the combination of PM01183 with daunorubicin in RAMOS cell line.
Figure 290:
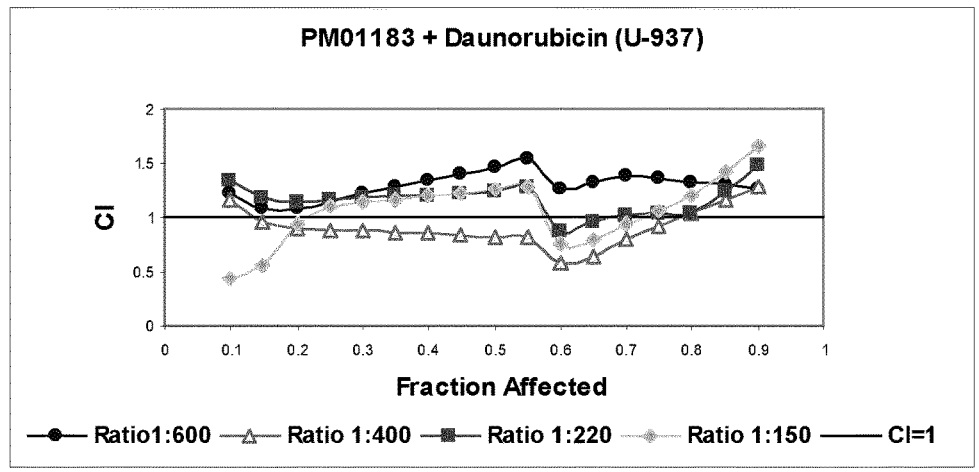
FIG. 290. Effects of the combination of PM01183 with daunorubicin in U-937 cell line.
Figure 291:
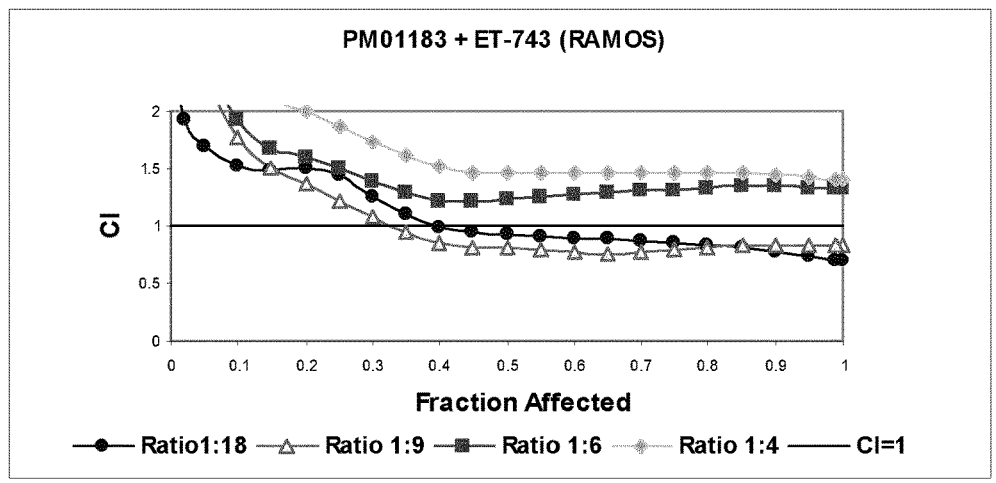
FIG. 291. Effects of the combination of PM01183 with ET-743 in RAMOS cell line.
Figure 292:
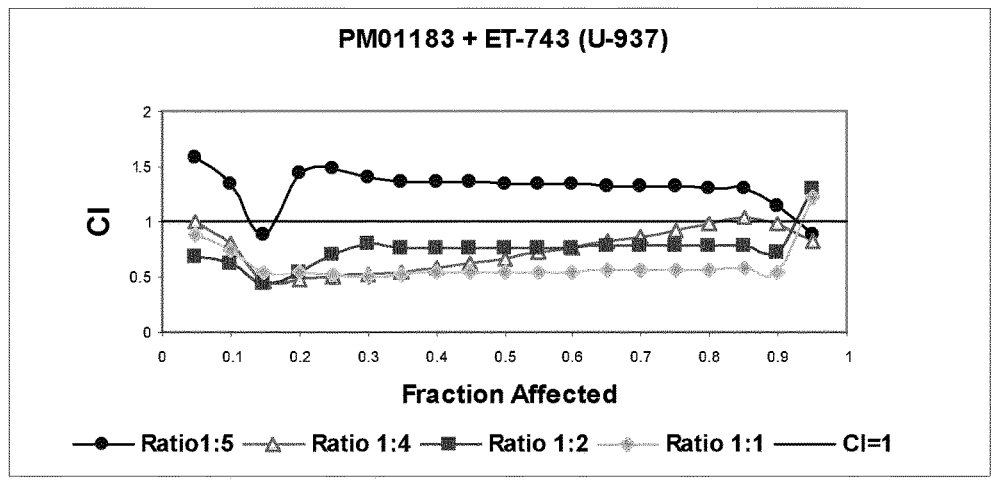
FIG. 292. Effects of the combination of PM01183 with ET-743 in U-937 cell line.
Figure 293:
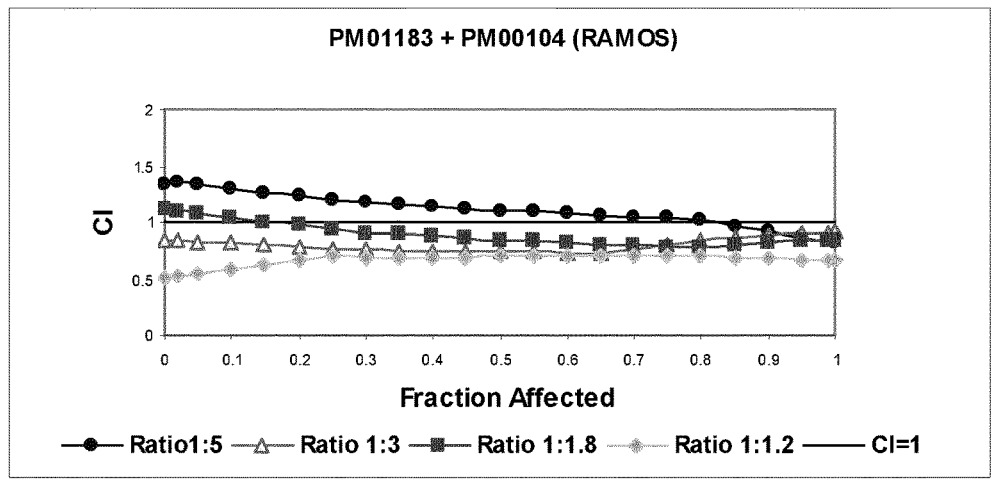
FIG. 293. Effects of the combination of PM01183 with PM00104 in RAMOS cell line.
Figure 294:
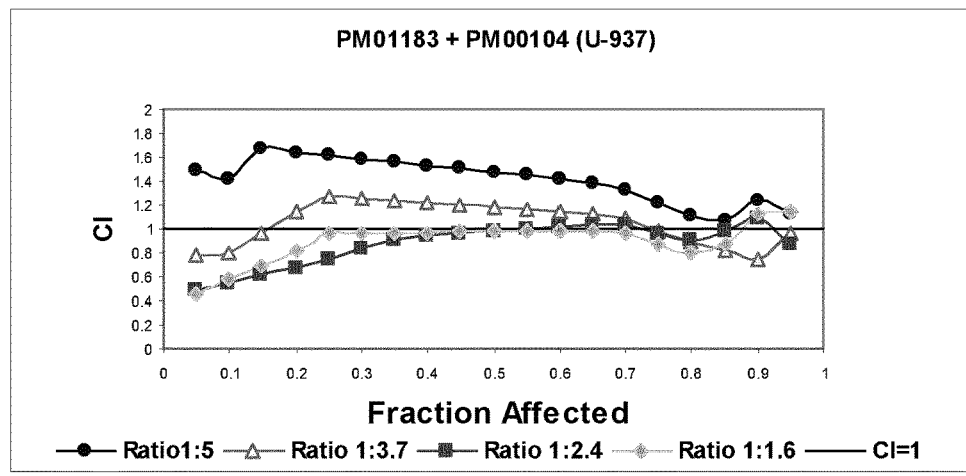
FIG. 294. Effects of the combination of PM01183 with PM00104 in U-937 cell line.
Figure 295:
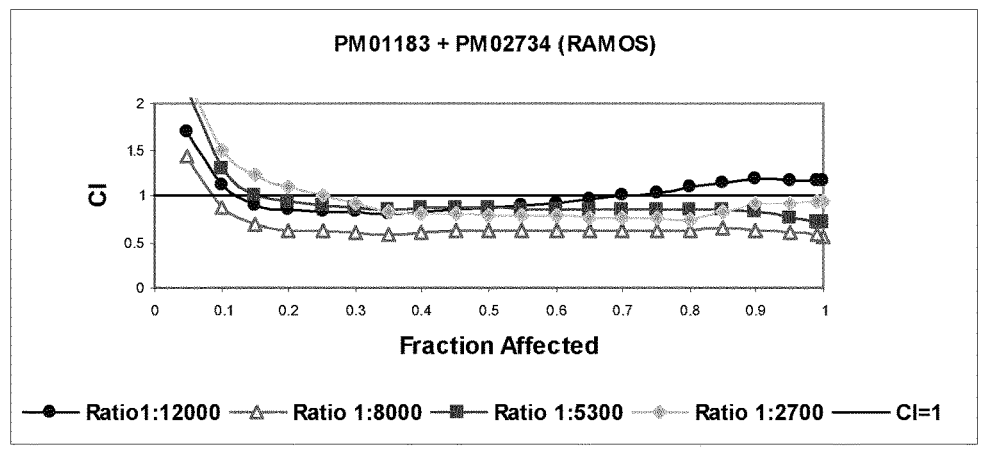
FIG. 295. Effects of the combination of PM01183 with PM02734 in RAMOS cell line.
Figure 296:
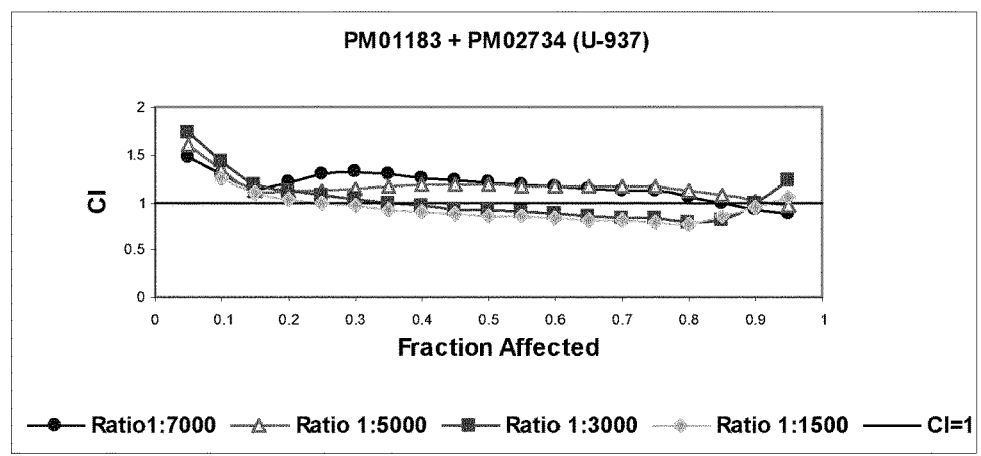
FIG. 296. Effects of the combination of PM01183 with PM02734 in U-937 cell line.

Table 22 reports the % T/C values obtained with PM01183 and irinotecan both administered as single agents and in combination for each dose level, and FIG. 272 shows the tumor volume evaluation of HT-29 tumors in mice treated with placebo, PM01183, irinotecan, and the corresponding combinations for the groups dosed at the two highest ratios.

TABLE 22

| Group | Dose | Test materials | % T/C on day 0 | 3 | 5 | 7 | 10 |
|---|---|---|---|---|---|---|---|
| G01 (Control group) | 10 ml/kg | Placebo | — | — | — | — | — |
| G02 | 0.18 mg/kg | PM01183 | 100.4 | 108.4 | 86.5 | 101.1 | 116.5 |
| G03 | 0.135 mg/kg | PM01183 | 98.4 | 106.4 | 95.3 | 116.6 | 115.2 |
| G04 | 0.09 mg/kg | PM01183 | 98.4 | 100.9 | 88.7 | 121.9 | 129.8 |
| G05 | 0.045 mg/kg | PM01183 | 99.8 | 103.7 | 100.6 | 111.1 | 135.8 |
| G06 | 50.0 mg/kg | Irinotecan | 100.1 | 114.7 | 93.7 | 96.1 | 70.5 |
| G07 | 37.5 mg/kg | Irinotecan | 98.4 | 108.1 | 97.5 | 99.2 | 84.3 |
| G08 | 25.0 mg/kg | Irinotecan | 98.8 | 108.6 | 97.2 | 101.4 | 96.5 |
| G09 | 12.5 mg/kg | Irinotecan | 99.0 | 99.1 | 90.6 | 97.4 | 92.7 |
| G10 | 0.18 mg/kg 50.0 mg/kg | PM01183 Irinotecan | 99.5 | 101.8 | 78.3 | 77.5 | 51.6 |
| G11 | 0.135 mg/kg 37.5 mg/kg | PM01183 Irinotecan | 98.4 | 98.0 | 85.2 | 85.4 | 60.7 |
| G12 | 0.09 mg/kg 25.0 mg/kg | PM01183 Irinotecan | 99.7 | 96.4 | 71.7 | 77.0 | 62.7 |
| G13 | 0.045 mg/kg 12.5 mg/kg | PM01183 Irinotecan | 100.7 | 104.8 | 104.3 | 116.0 | 98.8 |

TABLE 22-continued

| Group | Dose | Test materials | % T/C on day 12 | 14 | 17 | 20 |
|---|---|---|---|---|---|---|
| G01 (Control group) | 10 ml/kg | Placebo | — | — | — | — |
| G02 | 0.18 mg/kg | PM01183 | 115.4 | 123.4 | 86.7 | 77.5 |
| G03 | 0.135 mg/kg | PM01183 | 119.1 | 121.5 | 133.1 | 105.2 |
| G04 | 0.09 mg/kg | PM01183 | 114.1 | 109.4 | 116.1 | 93.4 |
| G05 | 0.045 mg/kg | PM01183 | 125.1 | 109.3 | | |
| G06 | 50.0 mg/kg | Irinotecan | 61.7 | 51.7 | 41.4 | 33.3 |
| G07 | 37.5 mg/kg | Irinotecan | 77.4 | 65.0 | 58.4 | 49.4 |
| G08 | 25.0 mg/kg | Irinotecan | 79.3 | 82.5 | 76.3 | 60.3 |
| G09 | 12.5 mg/kg | Irinotecan | 90.8 | 89.4 | 102.6 | 93.4 |
| G10 | 0.18 mg/kg 50.0 mg/kg | PM01183 Irinotecan | 43.8 | 30.4 | 21.7 | 15.6 |
| G11 | 0.135 mg/kg 37.5 mg/kg | PM01183 Irinotecan | 51.9 | 40.1 | 39.2 | 28.7 |
| G12 | 0.09 mg/kg 25.0 mg/kg | PM01183 Irinotecan | 57.7 | 50.1 | 47.2 | 40.7 |
| G13 | 0.045 mg/kg 12.5 mg/kg | PM01183 Irinotecan | 85.5 | 90.5 | 88.1 | 76.5 |

Placebo: as disclosed in table 13

According to this assay it was found that:

a. The combination treatment of PM01183 and irinotecan was effective in the inhibition of the growth of the U87-MG brain tumor cells, resulting in a statistically significant (P<0.01) tumor reduction compared to the control group with T/C values of 15.6% and 28.7% (Day 20) in the two highly-dosed groups. Moreover, the combination of PM01183 and irinotecan produced lower T/C values than the more active single agent in this experiment (irinotecan at doses of 50 mg/kg and 37.5 mg/kg). Specifically, the TC (%) values of the combination (50 mg/kg irinotecan+0.18 mg/kg PM01183) vs irinotecan alone (50 mg/kg irinotecan) were 30.4 vs 51.7 (day 14), 21.7 vs 41.4 (day 17), and 15.6 vs 33.3 (day 20), and the TC (%) values of the combination (37.5 mg/kg irinotecan+0.135 mg/kg PM01183) vs irinotecan alone (37.5 mg/kg irinotecan) were 40.1 vs 65.0 (day 14), 39.2 vs 58.4 (day 17), and 28.7 vs 49.4 (day 20). Therefore, when PM01183 is combined with irinotecan a potentiation of the antitumor activity is clearly observed.

Example 20. In Vitro Studies to Determine the Effect of PM01183 in Combination with Chemotherapeutic Agents on Human Leukemia Cell Lines The following agents were evaluated in combination with PM01183: methotrexate, daunorubicin, aplidine, ET-743, PM02734 and PM00104 (stock solutions of these compounds prepared in pure DMSO and stored at −20° C.). Additional serial dilutions were prepared in serum-free culture medium to achieve a final 4× concentration. Aliquots of 50 μL of each diluted compound were added per well.

JURKAT and MOLT-4 were the human leukemia cell lines selected for this assay, which were obtained from the American Type Culture Collection (ATCC). JURKAT and MOLT-4 cells were grown in phenol red-free RPMI medium supplemented with 10% Fetal Bovine Serum (FBS), 2 mM L-glutamine and 100 units/mL of Penicillin-Streptomycin, at 37° C., 5% CO2 and 95% humidity.

The screening was performed in two parts:

a. In the first set of assays, the relative potency of each compound against the different cell lines was determined using a 72 hours exposure in vitro cytotoxicity assay.

Briefly, cells were seeded in 96 well microtiter plates at a density of 50000 cells per well in 150 µL of culture medium and incubated for 4-6 hours in drug-free medium before treatment with vehicle alone or test compounds for 72 hours.

After incubation, the cytotoxic effect was evaluated using a MTT reduction assay. 50 µL of MTT solution (1 mg/mL) were added to the wells and incubated for 15-17 hours at 37° C. until formazan crystals were formed. After gently removing the culture medium, DMSO was added to dissolve the insoluble purple formazan product into a colored solution. The absorbance of the wells was quantified by measuring the optical density at 540 nm. Results were expressed as percentage of control cell growth. The EC50 values (half-maximal effective concentration) used for the combination studies were calculated using Prism v5.02 software (Graph-Pad). EC50 was expressed as molar concentration and represented the mean of at least three independent assays.

The individual EC50 values obtained for each drug are shown in tables 23 and 24.

TABLE 23

EC50 values in molar concentration (M) for each of the agents for the JURKAT tumor cell line.

| Compound | EC50 (M) | Compound | EC50 (M) | Compound | EC50 (M) |
|---|---|---|---|---|---|
| Methotrexate | 1.45E−07 | Daunorubicin | 7.92E−07 | Aplidine | 1.38E−08 |
| ET-743 | 6.96E−09 | PM00104 | 4.83E−09 | PM01183 | 1.55E−09 |
| PM02734 | 5.50E−06 | | | | |

TABLE 24

EC50 values in molar concentration (M) for each of the agents for the MoLT-4 tumor cell line.

| Compound | EC50 (M) | Compound | EC50 (M) | Compound | EC50 (M) |
|---|---|---|---|---|---|
| Methotrexate | 4.39E−08 | Aplidine | 1.27E−09 | ET-743 | 3.84E−09 |
| PM00104 | 1.55E−09 | PM01183 | 8.57E−10 | PM02734 | 1.44E−05 | b. In a second set of experiments, concentration-response curves for the agents tested, both alone and in two-drug combination, were performed, using the same methodology described in the previous paragraph.

Given the significant differences between the respective EC50 values for PM01183 and the other standard drugs in this study, different ratios of fixed concentrations for the two drugs were used. Normally, the selection of the fixed ratios of concentrations were the equipotent ratio (1:1) at the EC50 value for each drug, and some other ratios representing different percentages of the corresponding EC50 values for each drug above or below it. Using these starting concentrations, constant serial dilutions were performed to generate the concentration-response curves for each set of drugs, alone and in combination.

The effect of the two-drug combination, as compared with the effect of each drug alone, on the viability of tumor cells, was evaluated using the Chou and Talalay method which is based on the median-effect principle (Chou and Talalay, Adv. Enzyme Regul. 1984, 22, 27-55). The median-effect equation: $f_a/f_u=(C/C_m)^m$ (where C is the drug concentration, $C_m$ the median-effect concentration (i.e., IC50, ED50, or LD50, that inhibits the system under study by 50%), $f_a$ the cell fraction affected by the drug concentration C, $f_u$ the unaffected fraction, and m the sigmoidicity coefficient of the concentration-response curve), describes the relationship between the concentration and the effect of a drug on a given biological system.

Based on this equation, the term "combination index" (CI) is used as a quantitative measure of the degree of drug interactions. The combination index (CI) is determined by the equation:

$$CI=(C)_1/(C_x)_1+(C)_2/(C_x)_2$$

where $(C_x)_1$ is the concentration of drug 1 alone that inhibits an x percentage of a system, $(C_x)_2$ the concentration of drug 2 alone that inhibits the same x percentage of the system, and $(C_1)+(0)_2$ the concentrations of drug 1 and drug 2 that in combination also inhibits an X percentage of the system. CI values were calculated by solving the equation for different values of $f_a$ (i.e., for different degrees of cell groth inhibition). CI values of <1 indicate synergy, the value of 1 indicates additive effects, and values >1 indicate antagonism.

Data were analyzed using CalcuSyn software (Biosoft, Cambridge, UK). For statistical analysis and graphs Prism software (GraphPad, San Diego, USA) was used. All the results represent the mean of at least three independent experiments.

The effect of the tested drug combinations on cell proliferation is shown in FIGS. 273-283:

Combination of PM01183 with methotrexate. The combination of PM01183 with methotrexate in JURKAT (FIG. 273) cell line resulted in some synergistic effects (CI<1) at determined concentrations of both drugs. The effects of PM01183 in combination with methotrexate in MOLT-4 (FIG. 274) cell line were mostly additive.

Combination of PM01183 with daunorubicin. The combination of PM01183 with daunorubicin in JURKAT (FIG. 275) cell line was additive or synergistic (CI<1) at determined concentrations of the compounds.

Combination of PM01183 with aplidine. The combinations of PM01183 with aplidine in JURKAT (FIG. 276) and MOLT-4 (FIG. 277) cell lines resulted in some synergistic effects (CI<1) at determined concentrations of both drugs.

Combination of PM01183 with ET-743. The combination of PM01183 with ET-743 in JURKAT (FIG. 278) cell line was additive or synergistic (CI<1) at determined concentrations of both drugs. The combination of PM01183 with ET-743 in MOLT-4 (FIG. 279) cell line was mostly additive.

Combination of PM01183 with PM00104. The combination of PM01183 with PM00104 in JURKAT (FIG. 280) cell line was at least additive resulting in some synergistic effects (CI<1). The combination of PM01183 with PM00104 in MOLT-4 (FIG. 281) cell line resulted in synergistic effects (CI<1).

Combination of PM01183 with PM02734. The combination of PM01183 with PM02734 in JURKAT (FIG. 282) cell line was mostly additive, resulting in some synergistic effects (CI<1) at determined concentrations of both drugs. The combination of PM01183 with ET-743 in MOLT-4 (FIG. 283) cell line resulted in synergistic effects (CI<1).

Example 21. In Vitro Studies to Determine the Effect of PM01183 in Combination with Chemotherapeutic Agents on Human Lymphoma Cell Lines The following agents were evaluated in combination with PM01183: gemcitabine, cytarabine, methotrexate, daunorubicin, ET-743, PM02734 and PM00104 (stock solutions of these compounds prepared in pure DMSO and stored at −20° C.). Additional serial dilutions were prepared in serum-free culture medium to achieve a final 4× concentration. Aliquots of 50 μL of each diluted compound were added per well.

RAMOS and U-937 were the human lymphoma cell lines selected for this assay, which were obtained from the American Type Culture Collection (ATCC). RAMOS and U-937 cells were grown in phenol red-free RPMI medium supplemented with 10% Fetal Bovine Serum (FBS), 2 mM L-glutamine and 100 units/mL of Penicillin-Streptomycin, at 37° C., 5% CO2 and 95% humidity.

The screening was performed in two parts, as previously described in example 20.

In the first set of assays, the individual EC50 values were determined for each drug as shown in tables 25 and 26.

TABLE 25

EC50 values in molar concentration (M) for each of the agents for the RAMOS tumor cell line.

| Compound | EC50 (M) | Compound | EC50 (M) | Compound | EC50 (M) |
|---|---|---|---|---|---|
| Gemcitabine | 2.51E−08 | Cytarabine | 3.64E−08 | Methotrexate | 5.02E−06 |
| Daunorubicin | 3.15E−07 | ET-743 | 9.55E−09 | PM00104 | 4.35E−09 |
| PM01183 | 1.39E−09 | PM02734 | 1.36E−05 | | |

TABLE 26

EC50 values in molar concentration (M) for each of the agents for the U-937 tumor cell line.

| Compound | EC50 (M) | Compound | EC50 (M) | Compound | EC50 (M) |
|---|---|---|---|---|---|
| Gemcitabine | 3.27E−08 | Methotrexate | 2.63E−08 | Daunorubicin | 3.04E−07 |
| ET-743 | 8.62E−09 | PM00104 | 4.50E−09 | PM01183 | 1.03E−09 |
| PM02734 | 6.85E−06 | | | | |

In the second set of assays, concentration-response curves for the agents tested, both alone and in two-drug combination, were performed. The effects of the drug combinations were evaluated using the Chou and Talalay method as described in the example 20

The effect of the tested drug combinations on cell proliferation is shown in FIGS. 284-296:

Combination of PM01183 with cytarabine. The combination of PM01183 with cytarabine in RAMOS (FIG. 284) cell line resulted in some synergistic effects (CI<1).

Combination of PM01183 with methotrexate. The combination of PM01183 with methotrexate in RAMOS (FIG. 285) cell line resulted in some synergistic effects (CI<1) at determined concentrations of both drugs. The effects of PM01183 in combination with methotrexate in U-937 (FIG. 286) cell line resulted in some synergistic effects at determined concentrations.

Combination of PM01183 with gemcitabine. The combination of PM01183 with gemcitabine in RAMOS (FIG. 287) cell line was additive or synergistic (CI<1) at determined concentrations of both drugs. The combination of PM01183 with gemcitabine in U-937 (FIG. 288) cell line resulted in synergistic effects (CI<1).

Combination of PM01183 with daunorubicin. The combinations of PM01183 with daunorubicin in RAMOS (FIG. 289) and U-937 (FIG. 290) cell lines were at least additive resulting in some synergistic effects (CI<1).

Combination of PM01183 with ET-743. The combinations of PM01183 with ET-743 in RAMOS (FIG. 291) and U-937 (FIG. 292) cell lines resulted in synergistic effects (CI<1) at determined concentrations of the compounds.

Combination of PM01183 with PM00104. The combination of PM01183 with PM00104 in RAMOS (FIG. 293) resulted in synergistic effects (CI<1). The combination of PM01183 with PM00104 in U-937 (FIG. 294) cell line resulted in some synergistic effects (CI<1) at determined concentrations of both drugs.

Combination of PM01183 with PM02734. The combination of PM01183 with PM02734 in RAMOS (FIG. 295) cell line resulted in synergistic effects (CI<1), while the combination of PM01183 with ET-743 in U-937 (FIG. 296) cell line was at least additive, resulting in some synergistic effects (CI<1) at high concentrations of both drugs.

What is claimed is:

1. A method of treating cancer comprising administering to a patient in need of such treatment an amount of PM01183, or a pharmaceutically acceptable salt thereof, with an amount of irinotecan that together are therapeutically effective and wherein the cancer to be treated is lung cancer.

2. The method of treating cancer according to claim 1, wherein PM01183, or a pharmaceutically acceptable salt thereof, and irinotecan form part of the same medicament.

3. The method of treating cancer according to claim 1, wherein PM01183, or a pharmaceutically acceptable salt thereof, and irinotecan are provided as separate medicaments for administration at the same time or at different times.

4. The method of treating cancer according to claim 3, wherein PM01183, or a pharmaceutically acceptable salt thereof, and irinotecan are provided as separate medicaments for administration at different times.

5. The method of treating cancer according to claim 1, wherein the cancer is refractory to previous therapy.

6. The method of treating cancer according to claim 5, wherein the patient is relapsing with progressive disease after previous treatment for lung cancer.

7. The method of treating cancer according to claim 1, wherein the cancer is metastatic.

8. The method of treating cancer according to claim 1, wherein the cancer is advanced.

9. The method of treating cancer according to claim 1, wherein administration is every three to four weeks.

10. The method of treating cancer according to claim 9, wherein administration is every three weeks.

11. The method of treating cancer according to claim 1, wherein the dose of PM01183 administered in combination with irinotecan in lung cancer is lower than an effective dose of PM01183 administered as a monotherapy in lung cancer.

12. The method of treating cancer according to claim 1, wherein PM01183 is administered in synergistic combination with irinotecan.

13. The method of treating cancer according to claim 1, wherein the combination treatment increases the efficacy of the therapeutic effect for treating the lung cancer in said patient or minimizes or delays the development of drug resistance.

14. A method of inhibiting cancer cell growth comprising contacting cancer cells with PM01183, or a pharmaceutically acceptable salt thereof, in synergistic combination with irinotecan, wherein the cancer cells are lung cancer cells.

15. A method of increasing or potentiating the therapeutic efficacy of PM01183 monotherapy in the treatment of lung cancer, which comprises administering to a patient in need thereof a therapeutically effective amount of PM01183, or a pharmaceutically acceptable salt thereof, in conjunction with irinotecan.

* * * * *